US012617786B2

(12) United States Patent
Norman et al.

(10) Patent No.: US 12,617,786 B2
(45) **Date of Patent: *May 5, 2026**

(54) DIHYDRO-CYCLOPENTA-ISOQUINOLINE SULFONAMIDES DERIVATIVES

(71) Applicant: UCB Biopharma SRL, Brussels (BE)

(72) Inventors: Timothy John Norman, Slough (GB); Zhaoning Zhu, Slough (GB); Selvaratnam Suganthan, Abingdon (GB); Konstantinos Rampalako, Abingdon (GB); James Madden, Abingdon (GB); Jag Paul Heer, Slough (GB); Richard Jeremy Franklin, Slough (GB); Rickki Lee Connelly, Abingdon (GB); Thierry Demaude, Abingdon (GB); Gregory William Haslett, Slough (GB); Benedicte Lallemand, Slough (GB); Nathaniel Julius Thomas Monck, Abingdon (GB); Julian Hugh Rowley, Slough (GB); Giancarlo Trani, Abingdon (GB)

(73) Assignee: UCB Biopharma SRL, Brussels (BE)

( * ) Notice: Subject to any disclaimer, the term of this patent is extended or adjusted under 35 U.S.C. 154(b) by 691 days.

This patent is subject to a terminal disclaimer.

(21) Appl. No.: 17/786,387

(22) PCT Filed: Dec. 22, 2020

(86) PCT No.: PCT/EP2020/087683

§ 371 (c)(1),
(2) Date: Jun. 16, 2022

(87) PCT Pub. No.: WO2021/130257

PCT Pub. Date: Jul. 1, 2021

(65) Prior Publication Data

US 2024/0092773 A1 Mar. 21, 2024

(30) Foreign Application Priority Data

Dec. 23, 2019 (GB) ..................................... 1919212

(51) Int. Cl.

| | |
|---|---|
| ***C07D 471/04*** | (2006.01) |
| ***C07D 217/02*** | (2006.01) |
| ***C07D 237/30*** | (2006.01) |
| ***C07D 401/04*** | (2006.01) |
| ***C07D 401/12*** | (2006.01) |
| ***C07D 401/14*** | (2006.01) |
| ***C07D 403/12*** | (2006.01) |

(Continued)

(52) U.S. Cl.

CPC ......... *C07D 471/04* (2013.01); *C07D 217/02* (2013.01); *C07D 237/30* (2013.01); *C07D 401/04* (2013.01); *C07D 401/12* (2013.01); *C07D 401/14* (2013.01); *C07D 403/12* (2013.01); *C07D 403/14* (2013.01); *C07D 413/14* (2013.01); *C07D 417/12* (2013.01); *C07D 491/04* (2013.01)

(58) Field of Classification Search

CPC .. C07D 471/04; C07D 217/02; C07D 237/30; C07D 401/04; C07D 401/12; C07D 401/14; C07D 403/12; C07D 403/14; C07D 413/14; C07D 417/12; C07D 491/04; C07D 221/06; A61P 11/00

See application file for complete search history.

(56) References Cited

U.S. PATENT DOCUMENTS

| | | | |
|---|---|---|---|
| 4,857,301 | A | 8/1989 | Czarniecki et al. |
| 5,340,811 | A | 8/1994 | Kajihara et al. |

(Continued)

FOREIGN PATENT DOCUMENTS

| | | | |
|---|---|---|---|
| CN | 1050183 | A | 3/1991 |
| EP | 0418071 | A2 | 3/1991 |

(Continued)

OTHER PUBLICATIONS

Tarun K. Sarkar, Niranjan Panda, and Sankar Basak The Journal of Organic Chemistry 2003 68 (18), 6919-6927. (Year: 2003).*

(Continued)

*Primary Examiner* — Clinton A Brooks
*Assistant Examiner* — Izabela Schmidt
(74) *Attorney, Agent, or Firm* — McDonnell Boehnen Hulbert & Berghoff LLP

(57) ABSTRACT

The present invention relates to dihydro-cyclopenta-isoquinoline derivatives of formula (I): processes for preparing them, pharmaceutical compositions containing them and their use in treating disorders caused by IgE (such as allergic responses, non-allergic mast cell responses or certain auto-immune responses), and in particular, disorders caused by the interaction of IgE with the FcεRI receptor.

(I)

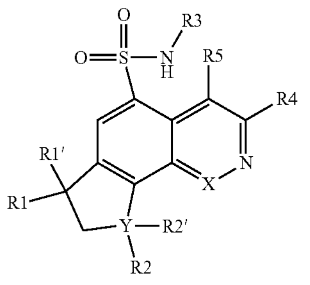

19 Claims, No Drawings

(51) Int. Cl.

| | |
|---|---|
| ***C07D 403/14*** | (2006.01) |
| ***C07D 413/14*** | (2006.01) |
| ***C07D 417/12*** | (2006.01) |
| ***C07D 491/04*** | (2006.01) |

(56) References Cited

U.S. PATENT DOCUMENTS

| | | | |
|---|---|---|---|
| 5,962,634 | A | 10/1999 | Jameson et al. |
| 12,410,161 | B2 | 9/2025 | Norman et al. |
| 2007/0027184 | A1 | 2/2007 | Malecha et al. |
| 2009/0156642 | A1 | 6/2009 | Nishida et al. |
| 2023/0050670 | A1 | 2/2023 | Norman et al. |
| 2023/0192646 | A1 | 6/2023 | Norman et al. |
| 2023/0303517 | A1 | 9/2023 | Norman et al. |

FOREIGN PATENT DOCUMENTS

| | | | | |
|---|---|---|---|---|
| EP | 0 419 676 | | 4/1991 | |
| EP | 0419676 | A1 * | 4/1991 | ........... C07C 323/21 |
| GB | 2270689 | | 3/1994 | |
| JP | 2007 099676 | | 4/2007 | |
| JP | 2017-501215 | | 1/2017 | |
| WO | 1996/01643 | | 1/1996 | |
| WO | 199828293 | A1 | 7/1998 | |
| WO | WO 2004/058709 | | 7/2004 | |
| WO | 2008059368 | A2 | 5/2008 | |
| WO | WO 2008/129276 | | 10/2008 | |
| WO | 2009041705 | A2 | 4/2009 | |
| WO | 2015080707 | A1 | 6/2015 | |
| WO | 2019/243550 | | 12/2019 | |
| WO | 2021/130255 | | 7/2021 | |
| WO | 2021/130259 | | 7/2021 | |
| WO | 2021/130260 | | 7/2021 | |
| WO | 2021/130262 | | 7/2021 | |

OTHER PUBLICATIONS

Kohno J, Sakurai M, Kameda N, Nishio M, Kawano K, Kishi N, Okuda T, Komatsubara S. Production, isolation and biological properties of TMC-120A, B and C, novel inhibitors of eosinophil survival from Aspergillus ustus TC 1118. J Antibiot (Tokyo). Oct. 1999;52(10):913-6. (Year: 1999).*

Sarkar Tarun K. et al., "A Sequential Pummerer-Diels-Alder Route for the Generation and Trapping of Furo[3,4-c]pyridines: Synthesis of Heterocyclic Analogues of 1-Arylnaphthalene Lignans", Journal of Organic Chemisgtry, vol. 68, No. 18, Sep. 1, 2003, p. 6919-6927.

Kohno Jun et al, "The Journal of Antibiotics Production, Isolation and Biological Properties Novel Inhibitors of Eosinophil Survival from Aspergillus ustus TC 1118", Journal of Antibiotics, vol. 52, No. 10, Oct. 1, 1999, pp. 913-916.

International Search Report dated Mar. 2, 2021 for International Application No. PCT/EP2020/087683, 3 pages.

Parisi, Gluseppe Fablo et al. "Omalizumab treatment in a 12 year-old girl with chronic spontaneous urticaria" The Journal of Dermatological Treatment (2018) vol. 29, pp. 10-11.

Hay, Michael P. et al. "Tricyclic 1-18 [1,2,4]triazine 1,4-dioxides as hypoxia selective cytotoxins" Journal of Medicinal Chemistry (2008) vol. 51(21), pp. 6853-6865.

Kitagaki, Shinji et al. "Intermolecular [4 + 2] Cycloaddition of o -Quinodimethanes Derived from Ene-Bis (sulfinylallenes)" Journal of Organic Chemistry (2006) vol. 71(18), pp. 6908-6914.

* cited by examiner

DIHYDRO-CYCLOPENTA-ISOQUINOLINE SULFONAMIDES DERIVATIVES

TECHNICAL FIELD

The present invention relates to dihydro-cyclopenta-isoquinoline derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

BACKGROUND OF THE INVENTION

IgE (immunoglobulin E) is a member of the immunoglobulin family and mediates allergic responses such as asthma, food allergies, type 1 hypersensitivity and the familiar sinus inflammation.

IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII). Upon exposure of a mammal to an allergen, B-cells are clonally amplified which synthesize IgE that binds the allergen. This IgE in turn is released into the circulation by the B-cells where it is bound by B-cells (through FcεRII) and by mast cells and basophils through the so-called high affinity receptor (FcεRI) found on the surface of the mast cells and basophils. Such mast cells and basophils are thereby sensitized for allergen. The next exposure to the allergen cross-links the FcεRI on these cells and thus activate their release of histamine and other factors which are responsible for clinical hypersensitivity and anaphylaxis.

Currently, allergic diseases, urticaria, and asthma are usually treated with one or more of the following drugs: (1) antihistamines and antileukotrienes which antagonize the inflammatory mediators histamine and leukotrienes, (2) local or systemic (oral or injectable) corticosteroids or immunosuppressants which suppress a broad spectrum of inflammatory mechanisms, (3) short or long-acting bronchodilators which relax smooth muscle of constricted airway in asthma, or (4) mast cell stabilizers which inhibit the degranulation of mast cells that is normally triggered by IgE-binding at FcεRI, (5) biologicals which prevent the binding of IgE at FcεRI. There has been also attempts to use peptides that modulate IgE binding to FcεRI. As an example, WO96/01643 describes peptides that consist of 4-50 amino to treat immediate allergic responses.

However, there is still a need to identify compounds which have therapeutic utility in the treatment or prevention of disorders caused by IgE, particularly disorders caused by the interaction of IgE with the FcεRI receptor.

SUMMARY OF THE INVENTION

It has been found that compounds of formula (I) and their pharmaceutically acceptable salts can be used for this purpose.

DETAILED DESCRIPTION

The present invention provides compounds of formula (I) and pharmaceutically acceptable salts thereof:

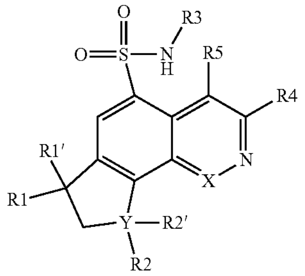

Wherein:

X is C or N,

Y is C or O,

When Y is O, R1 is hydrogen or hydroxy, R1' is hydrogen and R2, R2' is absent;

R1 represents

Hydrogen,

Hydroxy;

An oxo group;

Amino;

C1-6-alkyl;

C1-6-alkylamino;

C(O)OH;

C(O)NH-Heteroaryl;

NH—C1-6-alkyl-C3-6-cycloalkyl;

NH—C1-6-alkyl-C(O)OH optionally substituted with an amino group

—NH-cycloalkyl optionally substituted with one or more group chosen amongst halogen; oxo; C1-6-alkyl; C1-6-alkylamino; C1-6-alkyl-C1-4-alkylamino; C3-8-cycloalkyl-C1-6-alkylamino; heteroaryl; heteroarylamino optionally substituted with one or more C1-6-alkyl;

Heteroaryl optionally substituted with one or more groups chosen amongst Halogen; hydroxy; oxo; amino; cyano; —C(O)—C1-6-alkyl; C1-6-alkyl; C1-6-alkylamino; C1-6-alkoxy; —NH—(C1-6-alkyl)-heterocycloalkyl; —NH—(C1-6-alkyl)-heteroaryl optionally substituted with one or more C1-6-alkyl; —NH—C1-6-alkyl-cycloalkyl; —NH—C(O)-cycloalkyl; —NH-heteroaryl substituted with one or more C1-6-alkyl; —NH—C1-6-alkyl-C(O)OH;

Heteroaryl substituted with heteroarylamino optionally substituted with C1-6-alkyl; C1-6-alkoxy; C3-6-cycloalkyl; C1-6-haloalkoxy, C1-6-haloalkyl; CN, halogen; C(O)OH, —C(O)O—C1-6-alkyl;

—NH—C(S)—NH—$Ra^1$;

NH—SO2-$Rb^1$;

—NH-heteroaryl optionally substituted with one or more groups chosen amongst oxo; C1-6-alkyl; C1-6-alkylamino; heteroaryl optionally substituted with one or more oxo; C1-6-alkyl; —C(O)—NHNH—C(O)CH3; aryl; heteroarylamino; C1-6-alkoxy; C3-6-cycloalkyl; C1-6-haloalkoxy, C1-6-haloalkyl; CN, halogen; C(O)OH, —C(O)O—C1-6-alkyl;

—NH-heterocycloalkyl optionally substituted with one or more groups chosen amongst Halogen; C1-6-alkyl; oxo; heteroaryl; C(O)O$Rb^1$; C1-6-alkyl-N$Rb^1Rb^1$; NHC(O)-aryl; NHC(O)-heteroaryl;

—NH—C1-6-Alkyl substituted with one heteroaryl group optionally substituted with one or more groups chosen amongst C1-6-alkyl; amino;

—NH—C(O)O—$Rb^1$;

—NH—C(NCN)—NH—$Ra^1$;

—NH—C(NCN)—NH-Heteroaryl;

—NH—C(O)—C3-8-heterocycloalkyl-C(O)O—$Rb^1$;
—C(O)NH—C1-6-alkyl;
—NH—C(O)NH—C1-6-alkyl optionally substituted with one or more C3-8-heterocycloalkyl;
—NH—C(O)NH-heterocycloalkyl-C1-6-alkyl;
—NH—C1-6-alkyl-C(O)—C1-6-alkylamino;
Heteroaryloxy;
—NH—C(O)-aryl;
—NH—C(O)-heteroaryl;
—NH—C(O)-heterocycloalkyl;
—NH—C(O)—C1-6-alkyl optionally substituted with one or more amino group;
—NH—C(O)—C1-6-alkyl-C(O)O$Rb^1$ optionally substituted with a group chosen amongst amino; —NH—C(O)O$Rb^1$
Heterocycloalkyl optionally substituted with one or more groups chosen amongst amino; —C(O)NH—$Rb^1$; —C(O)O$Rb^1$; —NHC(O)-heteroaryl optionally substituted with one or more C1-6-alkyl; —NHC(O)—C1-6-alkyl optionally substituted with an amino group; —NHC(O)O—C1-6-alkyl; —NH—C(O)$Rb^1$;
—C2-6-alkene group optionally substituted with one or more groups chosen amongst halogen; =NH group;

$Ra^1$ represents
C1-6-alkyl; or
Aryl optionally substituted with one or more C1-6-alkyl; or
Heteroaryl optionally substituted with one or more C1-6-alkyl;

$Rb^1$ represents
Hydrogen; or
C1-6-alkyl; or
Aryl optionally substituted with one or more halogen; C1-6-alkyl; hydroxy;

R1' represents
hydrogen;
hydroxy;

R2 represents
hydrogen;
Halogen;
A hydroxy group;
An oxo group;
C1-6-alkyl;
C3-8-heterocycloalkyl optionally substituted with one or more hydroxy; Halogen; amino; amino-C-1-6-alkyl; C1-6-alkyl; C(O)O—C1-6-alkyl; C(O)NH2;
Heteroaryl optionally substituted with one or more groups chosen amongst C1-6-alkylamino; heteroaryl optionally substituted with one or more C1-6-alkyl; halogen;
Heteroaryl optionally substituted with —NH-heteroaryl optionally substituted with one or more C1-6-alkyl; halogen; cyano; —C(O)OH; —C(O)O—C1-6-alkyl, C1-6-haloalkyl; C1-6-alkoxy; C1-6-haloalkoxy; C3-6-cycloalkyl;
—NH-cycloalkyl optionally substituted with one or more group chosen amongst halogen; oxo; C1-6-alkyl; C1-6-alkylamino; C1-6-alkyl-C1-4-alkylamino; C3-8-cycloalkyl-C1-6-alkylamino; aryl; heteroaryl; heteroarylamino optionally substituted with one or more C1-6-alkyl;
—NH-heteroaryl optionally substituted with one or more groups chosen amongst hydroxy; halogen; oxo; C1-6-alkyl; C1-6-alkoxy; heteroaryl optionally substituted with one or more hydroxy; Halogen; oxo; C1-6-alkyl; C(O)O—C1-6-alkyl; C(O)OH; C1-6-haloalkyl; C1-6-alkoxy; C1-6-haloalkoxy; C3-6-cycloalkyl; C1-6-alkylamino; cyano; heterocycloalkyl substituted with one or more hydroxy Halogen; oxo group;
—NH—C1-6-Alkyl substituted with one heteroaryl group optionally substituted with one or more groups chosen amongst C1-6-alkyl;
—NH—SO2-Heteroaryl optionally substituted with one or more group chosen amongst halogen;
—NHC(O)—C1-6-alkyl optionally substituted with one or more halogen; C1-6-alkoxy; amino; C3-8-cycloalkyl; C3-8-heterocycloalkyl; heteroaryl;
—NHC(O)-heteroaryl optionally substituted with one or more group chosen amongst halogen; hydroxy; oxo; C1-6-alkyl; heteroaryl; C1-6-alkylamino; S(O)2-C1-3-alkyl; —NHC(O)—C1-6-alkyl;
—NHC(O)—C3-8-heterocycloalkyl optionally substituted with one or more oxo; C1-6-alkyl;
—NHC(O)O—C1-6-alkyl;
—NHC(O)O—C1-6-alkyl-$Ra^2$;
—NHC(O)O-aryl;
—NHC(O)NH—$Ra^2$
NHC(O)NH—C1-6-alkyl-$Ra^2$
NH—C(NCN)—NH—$Ra^1$;
—NHC(O)—C3-8-cycloalkyl;
—NH—SO2-$Rb^2$;
—NH—C(S)—NH—$Rb^2$;
—NH—C3-8-heterocycloalkyl optionally substituted with one or more groups chosen amongst oxo; C1-6-alkyl;
An Aryloxy group;
Heteroaryloxy group;

$Ra^2$ represents
Hydrogen;
Aryl optionally substituted with one or more group chosen amongst halogen; hydroxy; oxo; C1-6-alkyl;
Heteroaryl optionally substituted with one or more group chosen amongst halogen; hydroxy; oxo; C1-6-alkyl;

$Rb^2$ represents
C1-6-alkyl;
Heteroaryl;

R2' represents
hydrogen;
hydroxy;

R3 represents a group chosen amongst:
C1-6-alkyl optionally substituted with one or more group chosen amongst R3';
C1-3-alkanediyl-C3-6-cycloalkyl optionally substituted with one or more R3';
C1-3-alkanediyl-C3-6-heterocycloalkyl optionally substituted with one or more R3';
C3-6-heterocycloalkyl optionally substituted with one or more R3';
C3-6-cycloalkyl optionally substituted with one or more R3';
R3' represents a group chosen amongst hydrogen Halogen, C1-2-alkyl; hydroxy; C1-2-alkoxy R4 represents a group chosen amongst:
C3-6-cycloalkyl optionally substituted with one or more R4' group; or C1-6-alkanediyl-C3-6-cycloalkyl optionally substituted with one or more R4' group; or C1-6-alkanediyl-C3-6-heterocycloalkyl optionally substituted with one or more R4' group;
R4' represents a group chosen amongst hydroxy; Halogen; C1-2-alkyl.

R5 represents
Hydrogen, methyl or halogen;

With the provisio that:

- when R1' is hydroxy, then R1 is chosen amongst pyridyl, C1-6-alkyl;
- when R2' is hydroxy, then R2 is chosen amongst pyridyl, C1-6-alkyl;
- when R1, is different than hydrogen, then R2 and R2' is hydrogen;
- when R2, is different than hydrogen, then R1 and R1' is hydrogen;
- when R1 is oxo, R1' is absent;
- when R2 is oxo, R2' is absent;

The compounds of formula (I) may contain one or more asymmetric carbon atoms. They can therefore exist as enantiomers or diastereoisomers. These enantiomers, diastereoisomers, and mixtures thereof, include racemic mixtures, forming part of the invention.

The compounds of formula (I) may exist in the form of bases or addition salts with acids. Such addition salts are part of the invention. These salts are advantageously prepared with pharmaceutically acceptable acids. Salts of other acids that are useful, for example, for the purification or the isolation of the compounds of formula (I) are also part of the present invention In the frame of the present invention:

- Ct-z represents a carbon chain which may have from t to z carbon atoms, for example a C1-7 carbon chain which may have from 1 to 7 carbon atoms;
- Alkyl is a saturated, linear or branched aliphatic group; for example, a C1-6-alkyl group represents a carbon chain of 1 to 6 carbon atoms, linear or branched, for example a methyl, ethyl, propyl, isopropyl, butyl, isobutyl, tertbutyl, pentyl, hexyl. Alkyl encompass deuterated groups, where one or more hydrogen atoms are replaced with deuterium atom $^2$H.
- Alkylamino refers to one or more alkyl groups substituted on an amino radical. As examples of alkylamino one can mention methylamino; ethylamino; tertbutylamino; dimethylamino;
- acyl, an alkyl-C(O)— group;
- hydroxy is a —OH group;
- alkoxy, —O-alkyl group;
- halogen atom, a fluorine, chlorine, bromine or iodine atom;
- haloalkyl is an alkyl group of which one or more hydrogen atom has been substituted with a halogen atom;
- haloalkoxy is an alkoxy group of which one or more hydrogen atom has been substituted with a halogen atom;
- oxo is an oxygen showing a double bond, such as =0;
- cycloalkyl refers to a mono or bicyclic aliphatic group that may comprise a double bond without being aromatic and comprising between 3 and 14 atoms, preferably 3 to 9 atoms in the group. As an example of cycloalkyl one can mention cyclopropyl; cyclobutyl, cyclobutenyl; cyclopentyl; cyclohexyl; spiro[2.2]pentanyl; spiro-undecanyl;
- heterocycloalkyl refers to a mono or bicyclic saturated group comprising between 3 and 14 atoms, preferably 3 to 9 atoms in the group that may comprise a double bond without being aromatic and wherein one or more carbon atom is replaced with an atom chosen amongst nitrogen; oxygen; sulfur. As an example of heterocycloalkyl one can mention aziridinyl; pyrrolidinyl; piperidyl; oxetane; oxa-spiro-undecanyl;
- aryl refers to a mono- or bicyclic aromatic group comprising between 6 and 14 carbon atoms wherein at least one ring in the group is aromatic. As examples of an aryl group one can mention phenyl or naphthyl groups;
- Heteroaryl refers to a mono- or bicyclic group comprising from 5 to 14 atoms, preferably 3 to 9 atoms wherein at least one ring in the group is aromatic and wherein at least one atom in the group is chosen amongst nitrogen; oxygen; sulfur. As examples of heteroaryl group one can mention triazolyl; furanyl; pyrrolyl; chromanyl; isoquinolinyl;
- Heteroarylamino refers to an amino group —NH2 substituted with a heteroaryl group. Example of heteroaryl group can be pyridinylamino;
- Aryloxy refers to an aryl substituted with an oxygen radical. As an example of aryloxy one can cite phenoxy;
- Heteroaryloxy is a heteroaryl group substituted with an oxygen radical. As an example of heteroaryloxy one can cite pyridyloxy.

The term "pharmaceutically acceptable salt" according to the invention embraces salts of the compounds of formula (I) with a pharmaceutically acceptable acid or base, in particular an acid addition salt. The acid addition salt form of a compound of formula (I) that occurs in its free form as a base can be obtained by treating the free base with an appropriate acid such as an inorganic acid, for example, a hydrohalic acid such as hydrochloric acid or hydrobromic acid, sulfuric acid, nitric acid, phosphoric acid and the like; or an organic acid, such as, for example, acetic acid, trifluoroacetic acid, oxalic acid, hydroxyacetic acid, propanoic acid, lactic acid, pyruvic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and the like.

The invention also relates to all stereoisomeric forms such as enantiomeric and diastereoisomeric forms of the compounds of formula (I) or mixtures thereof (including all possible mixtures of stereoisomers such as racemates). With respect to the present invention reference to a compound or compounds is intended to encompass that compound in each of its possible isomeric forms and mixtures thereof, unless the particular isomeric form is referred to specifically.

Some of the compounds of formula (I) may also exist in tautomeric forms. Such forms although not explicitly indicated in the above formula are intended to be included within the scope of the present invention.

It is to be understood that each individual atom present in formula (I), or in formulae depicted herein, may in fact be present in the form of any of its naturally occurring isotopes, with the most abundant isotope(s) being preferred. Thus, by way of example, each individual hydrogen atom present in formula (I), or in the formulae depicted herein, may be present as a 1H, 2H (deuterium) or 3H (tritium) atom, preferably 1H. Similarly, by way of example, each individual carbon atom present in formula (I), or in the formulae depicted herein, may be present as a 12C, 13C or 14C atom, preferably 12C.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The present invention also includes within its scope prodrug of the compounds of formula (I) above. The term "prodrug" means a compound metabolised in vivo to a compound of the invention or its salt. A prodrug may be identified by administering the prodrug to a mammal, such as rat, mouse, monkey or man, and identifying the compound or its salt, for example in blood or urine.

Another embodiment of the present invention concerns a pharmaceutical composition comprising a detectable amount of a compound of formula (I) or a pharmaceutically acceptable salt, solvate or co-crystal thereof in combination with a pharmaceutically acceptable diluent or carrier.

In yet another embodiment, the present invention concerns a compound of formula (I) a pharmaceutically acceptable salt, solvate or co-crystal thereof for use as a medicament, in particular for use in a method for the treatment or prevention of disorders caused by IgE, including allergy, type 1 hypersensitivity, familiar sinus inflammation, urticaria or related conditions, such as airway constriction in asthma, local inflammation in eczema, increased mucus secretion in allergic rhinitis, increased vascular permeability, eosinophilic granulomatosis with polyangiitis (also known as "Churg Strauss syndrome"), aspirin exacerbated respiratory disease, or cutaneous T-cell lymphoma.

In a further embodiment, the present invention concerns a method for the treatment or prevention of allergy, type 1 hypersensitivity, familiar sinus inflammation, urticaria or related conditions, which comprises the administration of a compound of formula (I) in a therapeutically effective amount.

According to an embodiment, compounds of the invention are characterized by the formula (I) wherein R4 represents cyclopropyl or spiro[2.2]pentanyl; optionally substituted with one or more group chosen independently from hydroxy;

Chloro, Fluoro, Bromo;

Methyl;

According to an embodiment, compounds of the invention are characterized by the formula (I) wherein R4 represents cyclopropyl.

According to an embodiment, compounds of the invention are characterized by the formula (I) wherein R1 represents -Heteroaryl-NH—$Ra^1$ and R2 represents NH-Heteroaryl optionally substituted with one or more group chosen amongst heteroaryl; C1-6-alkyl; —C(O)OH wherein $Ra^1$ is C1-6-alkyl or heteroaryl optionally substituted with one or more C1-6-alkyl.

According to an embodiment, compounds of the invention are characterized by the formula (I) wherein:

R1 represents:

Hydrogen; methoxyimidazopyridinyl; carboxy group; cyclopropyl-methyl-carbamoyl-amino; pyridine-carbonylamino; hydroxy(pyridyl); [(fluorocarbonimidoyl) propenyl]; [(cyclopropylmethylamino)imidazolyl]; [[(cyclopropylmethyl)imidazolyl]amino]; [(dimethylpyrazolyl)carbamothioylamino]; [[(dimethylpyrazolyl)-triazolyl]amino]; (pyridylamino); (tert-butoxycarbonylamino); Amino; [(cyclopropylmethylamino)-triazolyl]; pyridylcarbamoyl; [(cyclopropanecarbonylamino)pyrazolyl]; (aminotetrazolyl); [[(methyltetrazolyl)pyridyl]amino]; [(methylpyrazolopyridinyl)amino]; [[(methyl-oxadiazolyl)-pyridyl]amino]; Oxo; hydroxy(methyl); ethylcarbamothioylamino); [(ethylamino)-triazolyl]; [[(ethylamino)-dioxo-cyclobutenyl]amino]; [[(ethylamino)-dioxo-thiadiazolyl]amino]; [[N'-cyano-N-(p-tolyl)carbamimidoyl]amino]; [(tert-butoxycarbonylazetidine-carbonyl)amino]; [aminopiperidyl]; [(methylcarbamoyl)pyrrolidinyl]; [[(dimethylpyrazolearbonyl)amino]azetidinyl]; [(dimethyl-oxo-cyclobutenyl)amino]; (indolylmethylamino); Methanesulfonamido; [[dioxo(pyridylamino)cyclobutenyl]amino]; ethylcarbamoylamino; [[(dimethylpyrazolyl)amino]-triazolyl]; [[(methyl-pyridyl)amino]-triazolyl]; [[(pyridyl)-triazolyl]amino]; [(pyridylamino)-triazolyl]; (benzimidazolylamino); pyridyloxy; (pyridylcarbamothioylamino);

According to an embodiment, compounds of the invention are characterized by the formula (I) wherein:

R2 represents:

Hydrogen; [(methylbenzotriazolyl)-triazolyl]methyl; [[(methylpyrazolyl)-triazolyl]amino]; [[(methylpyrazolyl)amino]-triazolyl]; [[(fluoro-pyridyl)-triazolyl] amino]; [[(fluoro-pyridyl)amino]-triazolyl]; (pyridylmethylamino); (pyridylsulfonylamino); [(fluoroindolecarbonyl)amino]; [(methylbenzimidazolyl) amino]; [(methoxycarbonyl-pyridyl)amino]; [(carboxypyridyl)amino]; [(methyl-pyrazole-carbonyl) amino]; (pyridine-carbonylamino); [(methylcyclopropanecarbonyl)amino]; (pyrimidinylamino); [(oxoindolinyl)amino]; [(methoxypyridyl)amino]; (pyridylamino); [(methylpyrazolopyridinyl)amino]; Benzyloxycarbonylamino; [(bromophenyl)carbamoylamino]; [(dimethylpyrazolyl)methylcarbamoylamino]; Hydroxy; Oxo; Methyl; Fluorine; [[(ethylamino)-dioxo-thiadiazolyl]amino]; [(cyanomethylpyrazolyl)amino]; (isoquinolylamino); [[N'-cyano-N-(p-tolyl)carbamimidoyl]amino]; Methanesulfonamido; Ethylcarbamothioylamino; [(ethylamino)-triazolyl]; [(ethyl-triazolyl)amino]; (pyridylcarbamothioylamino); [[(pyridyl)-triazolyl]amino]; [[(methyltetrazolyl)-pyridyl]amino]; [[dioxo-(pyridylamino)cyclobutenyl]amino]; [[(ethylamino)-dioxo-cyclobutenyl]amino]; (benzimidazolylamino); pyridyloxy.

According to an embodiment, compounds of the invention are characterized by the formula (I) wherein:

R1 represents:

Hydrogen; (7-methoxyimidazo[4,5-b]pyridin-3-yl); Carboxy group; cyclopropyl-methyl-carbamoyl-amino; pyridine-3-carbonylamino; hydroxy(3-pyridyl); [1-(fluorocarbonimidoyl)prop-1-enyl]; [2-(cyclopropylmethylamino)imidazol-1-yl]; [[1-(cyclopropylmethyl) imidazol-2-yl]amino]; [(2,5-dimethylpyrazol-3-yl) carbamothioylamino]; [[4-(2,5-dimethylpyrazol-3-yl)-1,2,4-triazol-3-yl]amino]; (3-pyridylamino); (tert-butoxycarbonylamino); Amino; [3-(cyclopropylmethylamino)-1,2,4-triazol-4-yl]; 3-pyridylcarbamoyl; [5-(cyclopropanecarbonylamino) pyrazol-1-yl]; (5-aminotetrazol-1-yl); [[6-(2-methyltetrazol-5-yl)-3-pyridyl]amino]; [(1-methylpyrazolo[3,4-c]pyridin-4-yl)amino]; [[6-(5-methyl-1,3,4-oxadiazol-2-yl)-3-pyridyl]amino]; oxo; hydroxy(methyl); (ethylcarbamothioylamino); [3-(ethylamino)-1,2,4-triazol-4-yl]; [[2-(ethylamino)-3,4-dioxo-cyclobuten-1- yl]amino]; [[4-(ethylamino)-1,1-dioxo-1,2,5-thiadiazol-3-yl]amino]; [[N'-cyano-N-(p-tolyl)carbamimidoyl]amino]; [(1-tert-butoxycarbonylazetidine-3-carbonyl)amino]; [3-amino-1-piperidyl]; [(2R)-2-(methylcarbamoyl)pyrrolidin-1-yl]; [3-[(2,5-dimethylpyrazole-3-carbonyl)amino]azetidin-1-yl]; [(4,4-dimethyl-3-oxo-cyclobuten-1-yl)amino]; (1H-indol-2-ylmethylamino); Methanesulfonamido; [[3,4-dioxo-2-(3-pyridylamino)cyclobuten-1-yl]amino]; ethylcarbamoylamino; [3-[(2,5-dimethylpyrazol-3-yl)amino]-1,2,4-triazol-4-yl]; [3-[(5-methyl-3-pyridyl)amino]-1,2,4-triazol-4-yl]; [[4-(3-pyridyl)-1,2,4-triazol-3-yl]amino]; [3-(3-pyridylamino)-1,2,4-triazol-4-yl]; (1H-benzimidazol-2-ylamino); 3-pyridyloxy; (3-pyridylcarbamothioylamino).

According to an embodiment, compounds of the invention are characterized by the formula (I) wherein:

R2 represents:

Hydrogen; [4-(1-methylbenzotriazol-4-yl)-1,2,4-triazol-3-yl]methyl; [[4-(2-methylpyrazol-3-yl)-1,2,4-triazol-3-yl]amino]; [3-[(2-methylpyrazol-3-yl)amino]-1,2,4-triazol-4-yl]; [[4-(5-fluoro-3-pyridyl)-1,2,4-triazol-3-yl]amino]; [3-[(5-fluoro-3-pyridyl)amino]-1,2,4-triazol-4-yl]; (3-pyridylmethylamino); (3-pyridylsulfonylamino); [(6-fluoro-1H-indole-3-carbonyl)amino]; [(1-methylbenzimidazol-2-yl)amino]; [(6-methoxycarbonyl-3-pyridyl)amino]; [(6-carboxy-3-pyridyl)amino]; [(5-methyl-1H-pyrazole-3-carbonyl)amino]; (pyridine-3-carbonylamino); [(2-methylcyclopropanecarbonyl)amino]; (pyrimidin-5-ylamino); (2-oxoindolin-5-yl)amino]; [(5-methoxy-3-pyridyl)amino]; (3-pyridylamino); [(1-methylpyrazolo[3,4-c]pyridin-4-yl)amino]; Benzyloxycarbonylamino; [(4-bromophenyl)carbamoylamino]; [(2,5-dimethylpyrazol-3-yl)methylcarbamoylamino]; Hydroxy oxo; Methyl; fluorine; [[4-(ethylamino)-1,1-dioxo-1,2,5-thiadiazol-3-yl]amino]; [(4-cyano-1-methyl-pyrazol-3-yl)amino]; (4-isoquinolylamino); [[N'-cyano-N-(p-tolyl)carbamimidoyl]amino]; Methanesulfonamido; Ethylcarbamothioylamino; [3-(ethylamino)-1,2,4-triazol-4-yl]; [(4-ethyl-1,2,4-triazol-3-yl)amino]; (3-pyridylcarbamothioylamino); [[4-(3-pyridyl)-1,2,4-triazol-3-yl]amino]; [[6-(2-methyltetrazol-5-yl)-3-pyridyl]amino]; [[3,4-dioxo-2-(3-pyridylamino)cyclobuten-1-yl]amino]; 15 [[2-(ethylamino)-3,4-dioxo-cyclobuten-1-yl]amino]; (1H-benzimidazol-2-ylamino); 3-pyridyloxy.

According to an embodiment compounds of the invention are chosen amongst:

3-cyclopropyl-N-(2-fluoro-2-methylpropyl)-7-(7-methoxy-imidazo[4,5-b]pyridin-3-yl)-8,9-dihydro-7H-cyclopenta[h]isoquinoline-5-sulfonamide;

3-cyclopropyl-N-isobutyl-9-[[4-(1-methylbenzotriazol-4-yl)-1,2,4-triazol-3-yl]amino]-8,9-dihydro-7H-cyclopenta[h]isoquinoline-5-sulfonamide;

3-cyclopropyl-N-isobutyl-9-[[4-(2-methylpyrazol-3-yl)-1,2,4-triazol-3-yl]amino]-8,9-dihydro-7H-cyclopenta[h]isoquinoline-5-sulfonamide;

3-cyclopropyl-N-isobutyl-9-[3-[(2-methylpyrazol-3-yl)amino]-1,2,4-triazol-4-yl]-8,9-dihydro-7H-cyclopenta[h]isoquinoline-5-sulfonamide;

3-cyclopropyl-9-[[4-(5-fluoro-3-pyridyl)-1,2,4-triazol-3-yl]amino]-N-isobutyl-8,9-dihydro-7H-cyclopenta[h]isoquinoline-5-sulfonamide;

3-cyclopropyl-9-[3-[(5-fluoro-3-pyridyl)amino]-1,2,4-triazol-4-yl]-N-isobutyl-8,9-dihydro-7H-cyclopenta[h]isoquinoline-5-sulfonamide;

3-cyclopropyl-5-[(2-fluoro-2-methylpropyl)sulfamoyl]-8,9-dihydro-7H-cyclopenta[h]isoquinoline-7-carboxylic acid;

1-(cyclopropylmethyl)-3-[(7R*)-3-cyclopropyl-5-[(2-fluoro-2-methylpropyl)sulfamoyl]-8,9-dihydro-7H-cyclopenta[h]isoquinolin-7-yl]urea [* or S];

N-[(7R*)-3-cyclopropyl-5-[(2-fluoro-2-methylpropyl)sulfamoyl]-8,9-dihydro-7H-cyclopenta[h]isoquinolin-7-yl]pyridine-3-carboxamide [* or S];

3-cyclopropyl-N-(2-fluoro-2-methylpropyl)-7-hydroxy-7-pyridin-3-yl-8,9-dihydrocyclopenta[h]isoquinoline-5-sulfonamide;

3-cyclopropyl-N-(2-fluoro-2-methylpropyl)-7-(2-fluoro-pyridin-3-yl)-8,9-dihydro-7H-cyclopenta[h]isoquinoline-5-sulfonamide;

(7R*)-3-cyclopropyl-7-[2-(cyclopropylmethylamino)imidazol-1-yl]-N-(2-fluoro-2-methylpropyl)-8,9-dihydro-7H-cyclopenta[h]isoquinoline-5-sulfonamide [* or S];

(7R*)-3-cyclopropyl-7-[[1-(cyclopropylmethyl)imidazol-2-yl]amino]-N-(2-fluoro-2-methylpropyl)-8,9-dihydro-7H-cyclopenta[h]isoquinoline-5-sulfonamide [* or S];

3-cyclopropyl-N-(2-methylpropyl)-9-(pyridin-3-ylmethylamino)-8,9-dihydro-7H-cyclopenta[h]isoquinoline-5-sulfonamide;

3-cyclopropyl-N-(2-methylpropyl)-9-(pyridin-3-ylsulfonylamino)-8,9-dihydro-7H-cyclopenta[h]isoquinoline-5-sulfonamide;

6-fluoro-N-[(9R*)-3-cyclopropyl-5-[(2-fluoro-2-methylpropyl)sulfamoyl]-8,9-dihydro-7H-cyclopenta[h]isoquinolin-9-yl]-1H-indole-3-carboxamide [* or S];

3-cyclopropyl-N-(2-fluoro-2-methylpropyl)-9-[(1-methylbenzimidazol-2-yl)amino]-8,9-dihydro-7H-cyclopenta[h]isoquinoline-5-sulfonamide;

methyl 5-[[3-cyclopropyl-5-(2-methylpropyisulfamoyl)-8,9-dihydro-7H-cyclopenta[h]isoquinolin-9-yl]amino]pyridine-2-carboxylate;

5-[[3-cyclopropyl-5-(2-methylpropyisulfamoyl)-8,9-dihydro-7H-cyclopenta[h]isoquinolin-9-yl]amino]pyridine-2-carboxylic acid;

5-methyl-N-[(9R*)-3-cyclopropyl-5-(2-methylpropylsulfamoyl)-8,9-dihydro-7H-cyclopenta[h]isoquinolin-9-yl]-1H-pyrazole-3-carboxamide [* or S];

N-[(9R*)-3-cyclopropyl-5-(2-methylpropylsulfamoyl)-8,9-dihydro-7H-cyclopenta[h]isoquinolin-9-yl]pyridine-3-carboxamide [* or S];

3-cyclopropyl-N-(2-methylpropyl)-8,9-dihydro-7H-cyclopenta[h]cinnoline-5-sulfonamide;

1-[3-cyclopropyl-5-[(2-fluoro-2-methylpropyl)sulfamoyl]-8,9-dihydro-7H-cyclopenta[h]cinnolin-7-yl]-3-(2,5-dimethylpyrazol-3-yl)thiourea;

3-cyclopropyl-7-[[4-(2,5-dimethylpyrazol-3-yl)-1,2,4-triazol-3-yl]amino]-N-(2-fluoro-2-methylpropyl)-8,9-dihydro-7H-cyclopenta[h]cinnoline-5-sulfonamide;

(7R*)-3-cyclopropyl-7-[3-[(2,5-dimethylpyrazol-3-yl)amino]-1,2,4-triazol-4-yl]-N-(2-fluoro-2-methylpropyl)-8,9-dihydro-7H-cyclopenta[h]cinnoline-5-sulfonamide [* or S];

N-[3-cyclopropyl-5-[(2-fluoro-2-methylpropyl)sulfamoyl]-8,9-dihydro-7H-cyclopenta[h]isoquinolin-9-yl]-2-methylcyclopropane-1-carboxamide;

3-cyclopropyl-N-(2-fluoro-2-methylpropyl)-9-(pyrimidin-5-ylamino)-8,9-dihydro-7H-cyclopenta[h]isoquinoline-5-sulfonamide;

3-cyclopropyl-N-(2-fluoro-2-methylpropyl)-9-[(2-oxo-1,3-dihydroindol-5-yl)amino]-8,9-dihydro-7H-cyclopenta[h]isoquinoline-5-sulfonamide;

3-cyclopropyl-N-(2-fluoro-2-methylpropyl)-9-[(5-methoxypyridin-3-yl)amino]-8,9-dihydro-7H-cyclopenta[h]isoquinoline-5-sulfonamide;

3-cyclopropyl-N-(2-fluoro-2-methylpropyl)-7-(pyridin-3-ylamino)-8,9-dihydro-7H-cyclopenta[h]isoquinoline-5-sulfonamide;

3-cyclopropyl-N-(2-fluoro-2-methylpropyl)-9-(pyridin-3-ylamino)-8,9-dihydro-7H-cyclopenta[h]isoquinoline-5-sulfonamide;

tert-butyl N-[3-cyclopropyl-5-[(1,1-dideuterio-2-methylpropyl)sulfamoyl]-8,9-dihydro-7H-cyclopenta[h]isoquinolin-7-yl]carbamate;

7-amino-3-cyclopropyl-N-(1,1-dideuterio-2-methylpropyl)-8,9-dihydro-7H-cyclopenta[h]isoquinoline-5-sulfonamide;

3-cyclopropyl-7-[3-(cyclopropylmethylamino)-1,2,4-triazol-4-yl]-N-(1,1-dideuterio-2-methylpropyl)-8,9-dihydro-7H-cyclopenta[h]isoquinoline-5-sulfonamide;

7-cyclopropyl-N-(2-fluoro-2-methylpropyl)-3-hydroxy-2,3-dihydrofuro[3,2-h]isoquinoline-5-sulfonamide;

(7R*)-3-cyclopropyl-5-[(2-fluoro-2-methylpropyl)sulfamoyl]-N-pyridin-3-yl-8,9-dihydro-7H-cyclopenta[h]isoquinoline-7-carboxamide [* or S];

N-[2-[3-cyclopropyl-5-[(2-fluoro-2-methylpropyl)sulfamoyl]-8,9-dihydro-7H-cyclopenta[h]isoquinolin-7-yl]pyrazol-3-yl]cyclopropanecarboxamide;

7-(5-aminotetrazol-1-yl)-3-cyclopropyl-N-(2-fluoro-2-methylpropyl)-8,9-dihydro-7H-cyclopenta[h]isoquinoline-5-sulfonamide;

3-cyclopropyl-N-(2-fluoro-2-methylpropyl)-7-[[6-(2-methyltetrazol-5-yl)pyridin-3-yl]amino]-8,9-dihydro-7H-cyclopenta[h]isoquinoline-5-sulfonamide;

3-cyclopropyl-N-(2-fluoro-2-methylpropyl)-7-[(1-methylpyrazolo[3,4-c]pyridin-4-yl)amino]-8,9-dihydro-7H-cyclopenta[h]isoquinoline-5-sulfonamide;

3-cyclopropyl-N-(2-fluoro-2-methylpropyl)-7-[[6-(5-methyl-1,3,4-oxadiazol-2-yl)pyridin-3-yl]amino]-8,9-dihydro-7H-cyclopenta[h]isoquinoline-5-sulfonamide;

3-cyclopropyl-N-(2-fluoro-2-methylpropyl)-9-[(1-methylpyrazolo[3,4-c]pyridin-4-yl)amino]-8,9-dihydro-7H-cyclopenta[h]isoquinoline-5-sulfonamide;

benzyl N-[3-cyclopropyl-5-(2-methylpropylsulfamoyl)-8,9-dihydro-7H-cyclopenta[h]isoquinolin-9-yl]carbamate;

1-(4-bromophenyl)-3-[3-cyclopropyl-5-(2-methylpropylsulfamoyl)-8,9-dihydro-7H-cyclopenta[h]isoquinolin-9-yl]urea;

1-[3-cyclopropyl-5-(2-methylpropylsulfamoyl)-8,9-dihydro-7H-cyclopenta[h]isoquinolin-9-yl]-3-[(2,5-dimethylpyrazol-3-yl)methyl]urea;

3-cyclopropyl-7-hydroxy-N-(2-methylpropyl)-8,9-dihydro-7H-cyclopenta[h]isoquinoline-5-sulfonamide;

3-cyclopropyl-N-(2-methylpropyl)-7-oxo-8,9-dihydrocyclopenta[h]isoquinoline-5-sulfonamide;

3-cyclopropyl-7-hydroxy-7-methyl-N-(2-methylpropyl)-8,9-dihydrocyclopenta[h]isoquinoline-5-sulfonamide;

7-amino-3-cyclopropyl-N-(2-methylpropyl)-8,9-dihydro-7H-cyclopenta[h]isoquinoline-5-sulfonamide;

1-[3-cyclopropyl-5-(2-methylpropyisulfamoyl)-8,9-dihydro-7H-cyclopenta[h]isoquinolin-7-yl]-3-ethylthiourea;

(7R*)-3-cyclopropyl-7-[3-(ethylamino)-1,2,4-triazol-4-yl]-N-(2-methylpropyl)-8,9-dihydro-7H-cyclopenta[h]isoquinoline-5-sulfonamide (* or S);

(7R*)-3-cyclopropyl-7-[[2-(ethylamino)-3,4-dioxocyclobuten-1-yl]amino]-N-(2-methylpropyl)-8,9-dihydro-7H-cyclopenta[h]isoquinoline-5-sulfonamide (* or S);

3-cyclopropyl-7-[[4-(ethylamino)-1,1-dioxo-1,2,5-thiadiazol-3-yl]amino]-N-(2-methylpropyl)-8,9-dihydro-7H-cyclopenta[h]isoquinoline-5-sulfonamide;

2-cyano-1-[3-cyclopropyl-5-(2-methylpropylsulfamoyl)-8,9-dihydro-7H-cyclopenta[h]isoquinolin-7-yl]-3-(4-methylphenyl)guanidine;

tert-butyl 3-[[(7R*)-3-cyclopropyl-5-[(2-fluoro-2-methylpropyl)sulfamoyl]-8,9-dihydro-7H-cyclopenta[h]isoquinolin-7-yl]carbamoyl]azetidine-1-carboxylate [* or S];

7-[(3R)-3-aminopiperidin-1-yl]-3-cyclopropyl-N-(2-fluoro-2-methylpropyl)-8,9-dihydro-7H-cyclopenta[h]isoquinoline-5-sulfonamide;

(2R)-1-[(7R*)-3-cyclopropyl-5-[(2-fluoro-2-methylpropyl)sulfamoyl]-8,9-dihydro-7H-cyclopenta[h]isoquinolin-7-yl]-N-methylpyrrolidine-2-carboxamide [* or S];

N-[1-[3-cyclopropyl-5-[(2-fluoro-2-methylpropyl)sulfamoyl]-8,9-dihydro-7H-cyclopenta[h]isoquinolin-7-yl]azetidin-3-yl]-2,5-dimethylpyrazole-3-carboxamide;

3-cyclopropyl-7-[(4,4-dimethyl-3-oxocyclobuten-1-yl)amino]-N-(2-fluoro-2-methylpropyl)-8,9-dihydro-7H-cyclopenta[h]isoquinoline-5-sulfonamide;

3-cyclopropyl-N-(2-fluoro-2-methylpropyl)-7-(1H-indol-2-ylmethylamino)-8,9-dihydro-7H-cyclopenta[h]isoquinoline-5-sulfonamide;

3-cyclopropyl-9-hydroxy-N-(2-methylpropyl)-8,9-dihydro-7H-cyclopenta[h]isoquinoline-5-sulfonamide;

3-cyclopropyl-N-(2-methylpropyl)-9-oxo-7,8-dihydrocyclopenta[h]isoquinoline-5-sulfonamide;

3-cyclopropyl-9-hydroxy-9-methyl-N-(2-methylpropyl)-7,8-dihydrocyclopenta[h]isoquinoline-5-sulfonamide;

3-cyclopropyl-9-fluoro-N-(2-methylpropyl)-8,9-dihydro-7H-cyclopenta[h]isoquinoline-5-sulfonamide;

3-cyclopropyl-9-[[4-(ethylamino)-1,1-dioxo-1,2,5-thiadiazol-3-yl]amino]-N-(2-methylpropyl)-8,9-dihydro-7H-cyclopenta[h]isoquinoline-5-sulfonamide;

9-[(4-cyano-1-methylpyrazol-3-yl)amino]-3-cyclopropyl-N-(2-fluoro-2-methylpropyl)-8,9-dihydro-7H-cyclopenta[h]isoquinoline-5-sulfonamide;

3-cyclopropyl-N-(2-fluoro-2-methylpropyl)-9-(isoquinolin-4-ylamino)-8,9-dihydro-7H-cyclopenta[h]isoquinoline-5-sulfonamide;

2-cyano-1-[3-cyclopropyl-5-(2-methylpropylsulfamoyl)-8,9-dihydro-7H-cyclopenta[h]isoquinolin-9-yl]-3-(4-methylphenyl)guanidine;

3-cyclopropyl-9-(methanesulfonamido)-N-(2-methylpropyl)-8,9-dihydro-7H-cyclopenta[h]isoquinoline-5-sulfonamide;

1-[3-cyclopropyl-5-(2-methylpropylsulfamoyl)-8,9-dihydro-7H-cyclopenta[h]isoquinolin-9-yl]-3-ethylthiourea;

3-cyclopropyl-9-[3-(ethylamino)-1,2,4-triazol-4-yl]-N-(2-methylpropyl)-8,9-dihydro-7H-cyclopenta[h]isoquinoline-5-sulfonamide;

(9R*)-3-cyclopropyl-9-[(4-ethyl-1,2,4-triazol-3-yl)amino]-N-(2-methylpropyl)-8,9-dihydro-7H-cyclopenta[h]isoquinoline-5-sulfonamide [* or S];

1-[3-cyclopropyl-5-(2-methylpropylsulfamoyl)-8,9-dihydro-7H-cyclopenta[h]isoquinolin-9-yl]-3-pyridin-3-ylthiourea;

3-cyclopropyl-N-(2-methylpropyl)-9-[(4-pyridin-3-yl-1,2,4-triazol-3-yl)amino]-8,9-dihydro-7H-cyclopenta[h]isoquinoline-5-sulfonamide;

3-cyclopropyl-N-(2-fluoro-2-methylpropyl)-9-[[6-(5-methyl-1,3,4-oxadiazol-2-yl)pyridin-3-yl]amino]-8,9-dihydro-7H-cyclopenta[h]isoquinoline-5-sulfonamide;

3-cyclopropyl-N-(2-fluoro-2-methylpropyl)-9-[[6-(2-methyltetrazol-5-yl)pyridin-3-yl]amino]-8,9-dihydro-7H-cyclopenta[h]isoquinoline-5-sulfonamide;

3-cyclopropyl-9-[[3,4-dioxo-2-(pyridin-3-ylamino)cyclobuten-1-yl]amino]-N-(2-methylpropyl)-8,9-dihydro-7H-cyclopenta[h]isoquinoline-5-sulfonamide;

(9R*)-3-cyclopropyl-9-[[2-(ethylamino)-3,4-dioxocyclobuten-1-yl]amino]-N-(2-methylpropyl)-8,9-dihydro-7H-cyclopenta[h]isoquinoline-5-sulfonamide [* or S];

(9R*)-9-(1H-benzimidazol-2-ylamino)-3-cyclopropyl-N-(2-methylpropyl)-8,9-dihydro-7H-cyclopenta[h]isoquinoline-5-sulfonamide [* or S];

3-cyclopropyl-7-[3-(cyclopropylmethylamino)-1,2,4-triazol-4-yl]-N-(3,3-difluorocyclobutyl)-8,9-dihydro-7H-cyclopenta[h]isoquinoline-5-sulfonamide;

3-cyclopropyl-7-[3-(cyclopropylmethylamino)-1,2,4-triazol-4-yl]-N-(3-fluorocyclobutyl)-8,9-dihydro-7H-cyclopenta[h]isoquinoline-5-sulfonamide;

3-cyclopropyl-7-(methanesulfonamido)-N-(2-methylpropyl)-8,9-dihydro-7H-cyclopenta[h]isoquinoline-5-sulfonamide;

3-cyclopropyl-7-[[3,4-dioxo-2-(pyridin-3-ylamino)cyclobuten-1-yl]amino]-N-(2-methylpropyl)-8,9-dihydro-7H-cyclopenta[h]isoquinoline-5-sulfonamide;

1-ethyl-3-[(7R*)-3-cyclopropyl-5-(2-methylpropylsulfamoyl)-8,9-dihydro-7H-cyclopenta[h]isoquinolin-7-yl] urea [* or S];

(7R*)-3-cyclopropyl-7-[3-[(2,5-dimethylpyrazol-3-yl) amino]-1,2,4-triazol-4-yl]-N-(2-fluoro-2-methylpropyl)-8,9-dihydro-7H-cyclopenta[h]isoquinoline-5-sulfonamide [* or S];

(7R*)-3-cyclopropyl-7-[3-[(2,5-dimethylpyrazol-3-yl) amino]-1,2,4-triazol-4-yl]-N-(2-methylpropyl)-8,9-dihydro-7H-cyclopenta[h]isoquinoline-5-sulfonamide [* or S];

3-cyclopropyl-7-[[4-(2,5-dimethylpyrazol-3-yl)-1,2,4-triazol-3-yl]amino]-N-(2-methylpropyl)-8,9-dihydro-7H-cyclopenta[h]isoquinoline-5-sulfonamide;

(7R*)-3-cyclopropyl-N-(2-methylpropyl)-7-[3-[(5-methylpyridin-3-yl)amino]-1,2,4-triazol-4-yl]-8,9-dihydro-7H-cyclopenta[h]isoquinoline-5-sulfonamide [* or S];

3-cyclopropyl-N-(2-methylpropyl)-7-[(4-pyridin-3-yl-1,2,4-triazol-3-yl)amino]-8,9-dihydro-7H-cyclopenta[h]isoquinoline-5-sulfonamide;

3-cyclopropyl-N-(2-methylpropyl)-7-[3-(pyridin-3-ylamino)-1,2,4-triazol-4-yl]-8,9-dihydro-7H-cyclopenta[h]isoquinoline-5-sulfonamide;

7-(1H-benzimidazol-2-ylamino)-3-cyclopropyl-N-(2-methylpropyl)-8,9-dihydro-7H-cyclopenta[h]isoquinoline-5-sulfonamide;

3-cyclopropyl-N-(2-fluoro-2-methylpropyl)-9-pyridin-3-yloxy-8,9-dihydro-7H-cyclopenta[h]isoquinoline-5-sulfonamide;

3-cyclopropyl-N-(2-fluoro-2-methylpropyl)-7-pyridin-3-yloxy-8,9-dihydro-7H-cyclopenta[h]isoquinoline-5-sulfonamide;

1-[3-cyclopropyl-5-(isobutylsulfamoyl)-8,9-dihydro-7H-cyclopenta[h]isoquinolin-7-yl]-3-(3-pyridyl)thiourea.

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

Abbreviations

DCM Dichloromethane
MTBE tert-Butylmethyl ether
$Et_2O$ Diethyl ether
THF Tetrahydrofuran
EtOAc Ethyl acetate
MeCN Acetonitrile
MeOH Methanol
broad s Broad singlet
M Mass or Molar
Brine Saturated sodium chloride solution
HPLC High performance liquid chromatography
LCMS Liquid Chromatography Mass Spectrometry
DIPEA N,N-di-iso-propylethylamine
RT Retention time
DMF N,N'-dimethylformamide
NaOH Sodium hydroxide
DMAP 4-Dimethylaminopyridine
TFA Trifluoroacetic acid
DMSO Dimethyl sulfoxide
TBTU 2-(1H-Benzotriazole-1-yl)-1,1,3,3-tetramethylaminium tetrafluoroborate
EtOH Ethanol
sat. saturated
aq. aqueous
BOC tert-Butoxycarbonyl
tBuXPhos Pd G3 [(2-Di-tert-butylphosphino-2',4',6'-triisopropyl-1,1'-biphenyl)-2-(2'-amino-1,1' biphenyl)] palladium(II) methanesulfonate
HATU 1-[Bis(dimethylamino)methylene]-1H-1,2,3-triazolo[4,5-b]pyridinium 3-oxid hexafluorophosphate
hrs hours
IPA Isopropyl alcohol
conc. concentrated
TBDMSCl tert-Butyldimethylsilyl chloride
equiv. equivalents
TBAB tetra-n-butyl ammonium bromide
NBS N-bromosuccinimide
NIS N-iodosuccinimide
SCX Biotage® ISOLUTE® SCX-2 Propylsulfonic acid functionalized silica
SFC Supercritical fluid chromatography

LCMS Methods

Method 1:

| | |
|---|---|
| Stationary phase: | X-Bridge C18 Waters 2.1 × 20 mm, 2.5 μM column |
| Mobile Phase A: | 10 mM Ammonium formate in water + 0.1% Ammonia solution |
| Mobile Phase B: | Acetonitrile + 5% water + 0.1% Ammonia Solution |
| Flow rate: | 1 mL/min |

| Gradient program: | Time | A % | B % |
|---|---|---|---|
| | 0.00 | 95.00 | 5.00 |
| | 1.50 | 5.00 | 95.00 |
| | 2.25 | 5.00 | 95.00 |
| | 2.50 | 95.00 | 5.00 |

Method 2:

| | | | |
|---|---|---|---|
| Stationary phase: | X-Bridge C18 Waters 2.1 × 20 mm, 2.5 μM column | | |
| Mobile Phase A: | 10 mM Ammonium formate in water + 0.1% Ammonia solution | | |
| Mobile Phase B: | Acetonitrile + 5% water + 0.1% Ammonia Solution | | |
| Flow rate: | 1 mL/min | | |
| Gradient program: | Time | A % | B % |
| | 0.00 | 95.00 | 5.00 |
| | 1.50 | 5.00 | 95.00 |
| | 2.25 | 5.00 | 95.00 |
| | 2.50 | 95.00 | 5.00 |

Method 3:

| | | | | | | |
|---|---|---|---|---|---|---|
| Stationary phase: | X-Bridge C18 Waters 2.1 × 20 mm, 2.5 μM column | | | | | |
| Mobile Phase A: | 10 mM Ammonium formate in water + 0.1% Ammonia solution | | | | | |
| Mobile Phase B: | Acetonitrile + 5% water + 0.1% Ammonia solution | | | | | |
| Flow rate: | Pump 1: 1 mL/min, Pump 2: 0.5 mL/min | | | | | |
| | Gradient program: | | | | | |
| | Pump 1: | | | Pump 2: | | |
| | Time | A % | B % | Time | A % | B % |
| | 0.00 | 95.10 | 4.90 | 0.10 | 5.00 | 95.00 |
| | 4.00 | 5.00 | 95.00 | 1.00 | 5.00 | 95.00 |
| | 5.00 | 5.00 | 95.00 | 1.10 | 95.00 | 5.00 |
| | 5.10 | 95.10 | 4.90 | | | |

Method 4:

| | | | |
|---|---|---|---|
| Stationary phase: | X-Bridge C18 Waters 2.1 × 20 mm, 2.5 μM column | | |
| Mobile Phase A: | 10 mM Ammonium formate in water + 0.1% ammonia solution | | |
| Mobile Phase B: | Acetonitrile + 5% water + 0.1% Ammonia Solution | | |
| Flow rate: | 1 mL/min | | |
| Gradient program: | Time | A % | B % |
| | 0.00 | 95.00 | 5.00 |
| | 4.00 | 5.00 | 95.00 |
| | 5.00 | 5.00 | 95.00 |
| | 5.10 | 95.00 | 5.00 |

Method 5:

| | | | |
|---|---|---|---|
| Stationary phase: | X-Bridge C18 Waters 2.1 × 20 mm, 2.5 μM column | | |
| Mobile Phase A: | 10 mM Ammonium formate in water + 0.1% Ammonia solution | | |
| Mobile Phase B: | Acetonitrile + 5% water + 0.1% Ammonia Solution | | |
| Flow rate: | 1 mL/min | | |
| Gradient program: | Time | A % | B % |
| | 0.00 | 95.00 | 5.00 |
| | 1.50 | 5.00 | 95.00 |
| | 2.25 | 5.00 | 95.00 |
| | 2.50 | 95.00 | 5.00 |

Method 6:

-continued

| | | | |
|---|---|---|---|
| Stationary phase: | X-Bridge C18 Waters 2.1 × 20 mm, 2.5 μM column | | |
| Mobile Phase A: | 10 mM Ammonium formate in water + 0.1% ammonia solution | | |
| Mobile Phase B: | Acetonitrile + 5% water + 0.1% Ammonia Solution | | |
| Flow rate: | 1 mL/min | | |
| Gradient program: | Time | A % | B % |
| | 0.00 | 95.00 | 5.00 |
| | 4.00 | 5.00 | 95.00 |
| | 5.00 | 5.00 | 95.00 |
| | 5.10 | 95.00 | 5.00 |

Method 7:

| | | | |
|---|---|---|---|
| Stationary phase: | X-Bridge C18 Waters 2.1 × 20 mm, 2.5 μM column | | |
| Mobile Phase A: | 10 mM Ammonium formate in water + 0.1% ammonia solution | | |
| Mobile Phase B: | Acetonitrile + 5% water + 0.1% Ammonia Solution | | |
| Flow rate: | 1 mL/min | | |
| Gradient program: | Time | A % | B % |
| | 0.00 | 95.00 | 5.00 |
| | 4.00 | 5.00 | 95.00 |
| | 5.00 | 5.00 | 95.00 |
| | 5.10 | 95.00 | 5.00 |

Method 8:

| | | | |
|---|---|---|---|
| X-Bridge C18 Waters 2.1 × 20 mm, 2.5 μM column | | | |
| Column Temperature | 40° C. | | |
| Mobile Phase A: | 10 mM Ammonium formate in water + 0.1% formic acid | | |
| Mobile Phase B: | Acetonitrile + 5% water + 0.1% Formic acid | | |
| Gradient program: | Flow rate 1 mL/min | | |
| | Time | A % | B % |
| | 0.00 | 95.00 | 5.00 |
| | 4.00 | 5.00 | 95.00 |
| | 5.00 | 5.00 | 95.00 |
| | 5.10 | 95.00 | 5.00 |

Method 9:

| | |
|---|---|
| X-Bridge C18 Waters 2.1 × 20 mm, 2.5 μM column | |
| Column Temperature | 40° C. |
| Mobile Phase A: | 10 mM Ammonium formate in water + 0.1% formic acid |

-continued

| | |
|---|---|
| Mobile Phase B: | Acetonitrile + 5% water + 0.1% formic acid |
| Gradient program: | Flow rate 1 mL/min |

| | Time | A % | B % |
|---|---|---|---|
| | 0.00 | 95.00 | 5.00 |
| | 1.50 | 5.00 | 95.00 |
| | 2.25 | 5.00 | 95.00 |
| | 2.50 | 95.00 | 5.00 |

Method 10:

| | |
|---|---|
| Stationary phase: | X-Bridge C18 Waters 2.1 × 20 mm, 2.5 μM column |
| Mobile Phase A: | 10 mM Ammonium formate in water + 0.1% Formic acid |
| Mobile Phase B: | Acetonitrile + 5% water + 0.1% Formic acid |
| Flow rate: | Pump 1: 1 mL/min, Pump 2: 0.5 mL/min |

| | Gradient program: | | | | | |
|---|---|---|---|---|---|---|
| | Pump 1: | | | Pump 2: | | |
| | Time | A % | B % | Time | A % | B % |
| | 0.00 | 95.10 | 4.90 | 0.10 | 5.00 | 95.00 |
| | 4.00 | 5.00 | 95.00 | 1.00 | 5.00 | 95.00 |
| | 5.00 | 5.00 | 95.00 | 1.10 | 95.00 | 5.00 |
| | 5.10 | 95.10 | 4.90 | | | |

Method 11:

| | |
|---|---|
| Stationary phase: | Waters Acquity UPLC BEH C18 2.1 × 50 mm, 1.7 μM column |
| Mobile Phase A: | 10 mM Ammonium formate in water + 0.1% Ammonia solution |
| Mobile Phase B: | Acetonitrile + 5% water + 0.1% Ammonia Solution |
| Flow rate: | 1.5 mL/min |

| Gradient program: | Time | A % | B % |
|---|---|---|---|
| | 0.00 | 95.00 | 5.00 |
| | 0.10 | 95.00 | 5.00 |
| | 3.50 | 5.00 | 95.00 |
| | 4.00 | 5.00 | 95.00 |
| | 4.05 | 95.00 | 5.00 |

Method 12:

| | |
|---|---|
| Mobile Phase A: | 0.1% Formic Acid in water |
| Mobile Phase B: | 0.1% Formic Acid in Acetonitrile |
| Phenomenex, Kinetex-XB C18, 2.1 mm × 100 mm, 1.7 μm column | |
| Flow rate: | 0.6 mL/min |
| Column temperature: | 40° C. |
| Injection volume: | 1 μL |

| Gradient: | Time (minutes): | % A | % B |
|---|---|---|---|
| | 0.00 | 95 | 5 |
| | 5.30 | 0 | 100 |
| | 5.80 | 0 | 100 |
| | 5.82 | 95 | 5 |
| | 7.00 | 95 | 5 |

UV 215 nM, PDA spectrum 200-400 nm, step: 1 nm
MSD Scan Positive 150-850

Method 13:

| | |
|---|---|
| Column: | Waters UPLC X Bridge BEH (C18, 2.1 × 50 mm, 2.5 μm) |
| Temperature: | 45° C. |
| Injection volume: | 1.0 μL |
| Flow rate: | 1.00 mL/minute |
| Detection: | Mass spectrometry - +/−detection in the same run |
| PDA: | 210 to 400 nm |
| Solvent A: | 10 mM ammonium formate in water + 0.1% ammonia |
| Solvent B: | 95% acetonitrile + 5% H2O + 0.1% ammonia 10 |

| Time | % A | % B |
|---|---|---|
| 0 | 95 | 5 |
| 0.1 | 95 | 5 |
| 2.1 | 5 | 95 |
| 2.35 | 5 | 95 |
| 2.80 | 95 | 5 |

Method 14:

| | |
|---|---|
| Column: | Waters UPLC X Bridge BEH (C18, 2.1 × 50 mm, 2.5 μm) 20 |
| Temperature: | 45° C. |
| Injection volume: | 1.0 μL |
| Flow rate: | 1.00 mL/minute |
| Detection: | Mass spectrometry - +/−detection in the same run |
| PDA: | 210 to 400 nm 25 |
| Solvent A: | 10 mM ammonium formate in water + 0.1% formic acid |
| Solvent B: | 95% acetonitrile + 5% H2O + 0.1% formic acid |

| Time | % A | % B |
|---|---|---|
| 0 | 95 | 5 |
| 0.1 | 95 | 5 |
| 2.1 | 5 | 95 |
| 2.35 | 5 | 95 |
| 2.80 | 95 | 5 |

Method 15:

| | |
|---|---|
| Column: | Waters XBridge MS C18 column (3.5 μm, 100 × 4.6 mm) |
| Temperature: | 45° C. |
| Injection volume: | 5.0 μL |
| Flow rate: | 1.9 to 2.4 mL/minute |
| Detection: | Mass spectrometry - positive detection |
| PDA: | 210 to 400 nm |
| Solvent A: | water |
| Solvent B: | Acetonitrile |
| Solvent D: | Ammonium Formate in water 630 mg/L + 500 μL/L $NH_4OH$ 30% (pH~8.5) |

| Time (min) | A (%) | B (%) | D (%) | Flow (mL/min) |
|---|---|---|---|---|
| 0 | 90 | 0 | 10 | 1.9 |
| 1 | 90 | 0 | 10 | 1.9 |
| 5.5 | 2 | 88 | 10 | 2.4 |
| 8 | 2 | 88 | 10 | 2.4 |
| 8.05 | 90 | 0 | 10 | 1.9 |
| 9.90 | 90 | 0 | 10 | 1.9 |

Method 16:

| | |
|---|---|
| Stationary phase: | Waters Acquity UPLC BEH, C18, 2.1 × 50 mm, 1.7 μM |
| Mobile Phase A: | 10 mM Ammonium Formate in water + 0.1% Ammonia Solution |
| Mobile Phase B: | Acetonitrile + 5% water + 0.1% Ammonia Solution |
| Flow rate: | 0.7 mL/min |
| Temp: | 40° C. |

-continued

| Gradient program: | Time | A % | B % |
|---|---|---|---|
| | 0.00 | 98.00 | 2.00 |
| | 4.00 | 5.00 | 95.00 |
| | 5.00 | 5.00 | 95.00 |
| | 5.10 | 98.00 | 2.00 |

Method 17:

| | |
|---|---|
| Mobile Phase A: | 0.1% Formic Acid in water |
| Mobile Phase B: | 0.1% Formic Acid in Acetonitrile |
| Kinetex Core-Shell C18 50 × 2.1 mm, 5 μm column protected by Phenomenex 'Security Guard' column. | |
| Flow rate: | 1.2 mL/min |
| Column temperature: | 40° C. |
| Injection volume: | 3 μL |

| Gradient: | Time (minutes): | % A | % B |
|---|---|---|---|
| | 0.00 | 95 | 5 |
| | 1.20 | 0 | 100 |
| | 1.30 | 0 | 100 |
| | 1.31 | 95 | 5 |

UV 215 nM, PDA spectrum 210-420 nm, step: 1 nm
MSD Scan Positive 100-1000

GENERAL PROCEDURES

General Procedure 1

A solution of mercuric chloride (2 equiv.) and formic acid hydrazide (3 equiv.) in anhydrous N,N-dimethylformamide (1 mL) was added to the thiourea intermediate. Triethylamine (3 equiv.) was added and the reaction heated to 80° C. with stirring for 8 h. Reactions were filtered through celite, washing with MeCN (2-3 mL). Solvents were removed in vacuo and products purified by column chromatography.

General Procedure 2

To a solution of the aryl chloride (1 equiv.) in 1,4-dioxane (20 mL/g) was added cyclopropane boronic acid (3 equiv.), tricyclohexylphosphonium tetrafluoroborate (2 equiv.) and $Pd(OAc)_2$ (0.1 equiv.). The mixture was degassed with a stream of $N_2$ gas for 5 min prior to addition of $K_3PO_4$ (1 equiv.). The mixture was degassed with a stream of $N_2$ gas for a further 5 min, sealed and heated to 110° C. until reaction was deemed complete by LCMS. The reaction was cooled and diluted with EtOAc (20 mL/g) and washed with sat. aq. $NaHCO_3$ (20 mL/g). The organic extracts were dried over $Na_2SO_4$ and concentrated in vacuo.

General Procedure 3

To a solution of amine (1 equiv.), sodium tert-butoxide (3 equiv.), aryl halide (2.5 equiv.) and tBuXPhos Pd G3 (0.15 equiv.) was added anhydrous 1,4-dioxane (20 mL/g). The mixture was degassed with 3 cycles of vacuum/$N_2$ then sealed and heated to 100° C. with stirring until the reaction was deemed complete by LCMS. The reaction was diluted with EtOAc (20 mL/g) and washed with water (10 mL/g). The aqueous layer was reextracted with EtOAc (20 mL/g) and the combined organic extracts dried over $Na_2SO_4$ and concentrated in vacuo.

General Procedure 4

To a stirred suspension of the relevant intermediate (1 equivalent) in dichloromethane (40 mL) was added N,N-diisopropylethylamine (1.5 equivalents) and the relevant isothiocyanate (1.5 equivalents) unless otherwise stated. The mixture was stirred at room temperature for 1 to 3 days. The reaction mixture was evaporated under vacuum and the residue dry loaded onto silica and purified by column chromatography.

General Procedure 5

To a stirred solution of the relevant thiourea in N,N-dimethylformamide (15 mL) was added formic acid hydrazide (~3 equivalents) followed by mercuric chloride (~2 equivalents). The mixture was stirred for 5 minutes at room temperature before the addition of triethylamine (~3 equivalents). The resulting reaction mixture was stirred at 80° C. for 16 hours. The cooled reaction mixture was diluted with acetonitrile, filtered through a pad of celite which was then washed with acetonitrile (30 mL×3). The filtrate was evaporated, and the residue purified via column chromatography to give the desired product.

INTERMEDIATES

Intermediate 1

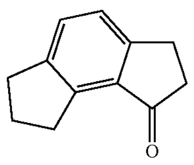 [SMILES: O=C1CCc2ccc3c(c21)CCC3]

3,6,7,8-tetrahydro-2H-as-indacen-1-one 3-indan-5-ylpropanoic acid (100 g, 526 mol, commercially available from Angene, CAS number: 23291-98-7) in polyphosphoric acid (320 mL) was heated to 140° C. for 6 minutes then cooled to 10° C. and quenched by the addition of ice-water (500 mL). The resulting mixture was extracted with DCM (25 L followed by 15 L). The combined organic extracts were dried over $Na_2SO_4$, filtered and concentrated in vacuo. The residue was purified by column chromatography on $SiO_2$ to give the title compound as a brown solid (4.5 g, 5% yield). $\delta_H$ (400 MHz, CDCl3) 7.42 (m, 1H), 7.23 (m, 1H), 3.21 (m, 2H), 3.10 (m, 2H), 2.94 (m, 2H), 2.66 (m, 2H), 2.14 (m, 2H).

Intermediate 2

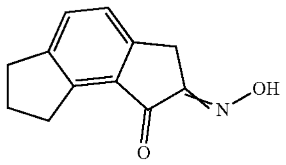 [SMILES: O=C1C(=NO)Cc2ccc3c(c21)CCC3]

2-hydroxyimino-3,6,7,8-tetrahydro-as-indacen-1-one

A solution of intermediate 1 (85 g, 493 mmol) in MTBE (1.27 L) was treated with HCl (12 M in EtOH, 20.6 mL), cooled to 0° C. and treated with a solution of isopentyl nitrite (100 mL, 740 mol) in ethanol (600 mL) [added dropwise over 5 minutes]. The resulting mixture was stirred at 0° C. for 0.4 hours then the solid was collected by filtration and washed with MTBE and dried, to yield the title compound as a brown solid (80 g, 81% yield). MS m/z=202 $[M+H]^+$. $\delta_H$ (400 MHz, DMSO-d6) 7.55 (d, 1H), 7.34 (d, 1H), 3.70 (s, 2H), 3.12 (t, 2H), 2.86 (t, 2H), 2.04-2.11 (m, 2H) [OH proton not visible].

Intermediate 3

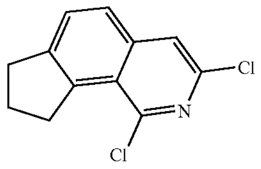 [SMILES: Clc1cc2ccc3c(c2c(Cl)n1)CCC3]

1,3-dichloro-8,9-dihydro-7H-cyclopenta[h]Isoquinoline

A solution of intermediate 2 (83 g, 412.5 mol) in $POCl_3$ (1.25 L) was cooled to 0° C. and treated with $PCl_5$ (94.5 g, 454 mol). The resulting mixture was treated with HCl (gas) until the reaction was saturated and stirred at 65° C. for 1 h. After this time the mixture was treated with further PCls (34.4 g, 165 mmol) and stirred for a further 15 h. The mixture was concentrated in vacuo and treated with water, the resulting solid was collected by filtration and dried to give the title compound (80 g, 81% yield). MS m/z=238 $[M+H]^+$ $\delta_H$ (400 MHz, $CDCl_3$) 7.64-7.56 (m, 3H), 3.75 (m, 2H), 3.09 (m, 2H), 2.19-2.26 (m, 2H).

Intermediate 4

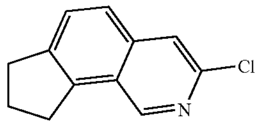 [SMILES: Clc1cc2ccc3c(c2cn1)CCC3]

3-chloro-8,9-dihydro-7H-cyclopenta[h]Isoquinoline

A solution of intermediate 3 (80 g, 6 mol) in EtOAc (666 mL) was treated with red phosphorous (27.4 g, 806.4 mmol) and HI (155 mL, 57% wt aqueous solution, 1.18 mol) and stirred at 120° C. for 4 h. The resulting mixture was filtered whilst hot and concentrated in vacuo. The residue was dissolved in water, basified by the addition of ammonia solution and the resulting solid collected by filtration. The solid was dissolved in DCM, washed with brine, dried over $Na_2SO_4$ and concentrated and purified by column chromatography on $SiO_2$ to give the title compound as a white solid (38.5 g, 56% yield). MS m/z=204 $[M+H]^+$. Ne (400 MHz, $CDCl_3$) 9.04 (s, 1H), 7.70 (s, 1H), 7.56-7.63 (m, 2H), 3.34 (m, 2H), 3.11 (m, 2H), 2.34-2.27 (m, 2H).

Intermediate 5

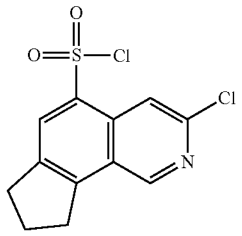 [SMILES: O=S(=O)(Cl)c1cc2c(c3cnc(Cl)cc13)CCC2]

3-chloro-8,9-dihydro-7H-cyclopenta[h]Isoquinoline-5-sulfonyl chloride

Intermediate 4 (10 g, 49 mmol) was charged in a sealed 250 mL round bottom pressure flask and chlorosulfonic acid (35 mL, 520 mmol) was added (evolution of hydrogen chloride gas was observed upon addition). The resulting dark red/brown solution was purged under a flow of nitrogen for 5 minutes. The flask was sealed and heated at 80° C. for 3 hours. The reaction mixture was diluted with dichloromethane (100 mL) and then added carefully to stirred ice-water (500 mL) over 45 minutes. The two phases were separated, and the aqueous layer further extracted into dichloromethane (200 mL×2), combined organic extracts were washed with brine (200 mL), dried over sodium sulfate and evaporated down to give the title compound (14.6 g, 98% Yield). $^1H$ NMR (300 MHz, Chloroform-d) $\delta_H$ 9.20 (d, J=0.9 Hz, 1H), 8.57 (d, J=0.8 Hz, 1H), 8.46 (s, 1H), 3.48 (tt, J=8.0, 1.2 Hz, 2H), 3.29-3.14 (m, 2H), 2.50-2.32 (m, 2H). LCMS $[M+H]^+$ 302/304, RT 1.33 min (Method 1).

Intermediate 6

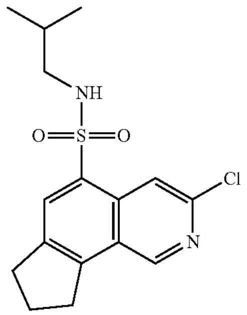 [SMILES: CC(C)CNS(=O)(=O)c1cc2c(c3cnc(Cl)cc13)CCC2]

3-chloro-N-isobutyl-8,9-dihydro-7H-cyclopenta[h] isoquinoline-5-sulfonamide

To a stirred solution of Intermediate 5 (14.6 g, 48 mmol) in anhydrous DCM (125 mL) under nitrogen was added isobutylamine (12 mL, 120 mmol) dropwise (evolution of gas was observed). The reaction mixture was stirred at room temperature for 3 days. The reaction mixture was washed with water (125 mL). The aqueous layer separated and further extracted into dichloromethane (125 mL×2), combined organic extracts washed with brine (150 mL), dried over sodium sulfate and evaporated to dryness. The crude was purified by chromatography (gradient of 0% to 100% ethyl acetate in iso-hexane) to give the title compound (10.7 g, 65% Yield). $^1$H NMR (300 MHz, Chloroform-d) $\delta_H$ 9.14 (d, J=0.9 Hz, 1H), 8.48 (d, J=0.9 Hz, 1H), 8.36 (s, 1H), 4.67 (t, J=6.4 Hz, 1H), 3.50-3.35 (m, 2H), 3.18 (t, J=7.4 Hz, 2H), 2.78-2.65 (m, 2H), 2.45-2.28 (m, 2H), 1.69 (dq, J=13.4, 6.7 Hz, 1H), 0.81 (d, J=6.7 Hz, 6H). LCMS $[M+H]^+$ 339/341, RT 1.26 min (Method 1).

Intermediates 7 & 8

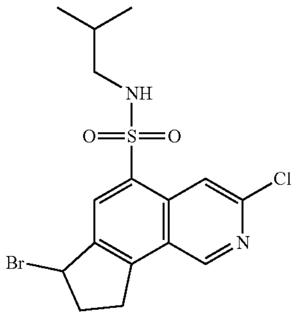

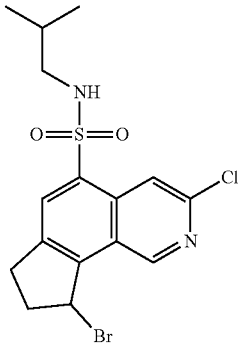

7-bromo-3-chloro-N-isobutyl-8,9-dihydro-7H-cyclopenta[h]isoquinoline-5-sulfonamide (7)

9-bromo-3-chloro-N-isobutyl-8,9-dihydro-7H-cyclopenta[h]isoquinoline-5-sulfonamide (8)

To a stirred solution of intermediate 6 (4.77 g, 14.1 mmol) in EtOAc (250 mL), 2,2'-azobis(2-methylpropionitrile) (240 mg, 1.4 mmol) and N-bromosuccinimide (3.3 g, 18 mmol) were added. The reaction mixture was stirred at 90° C. in the dark for 2.5 hours. The reaction mixture was evaporated to give a crude 1:1 mixture of the title compounds (9.24 g) which was used in the next step without further purification.

Intermediate 9 & 10

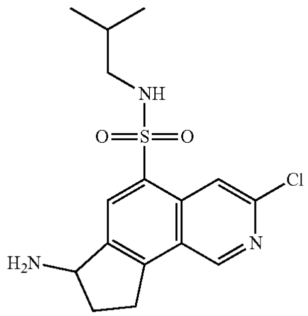

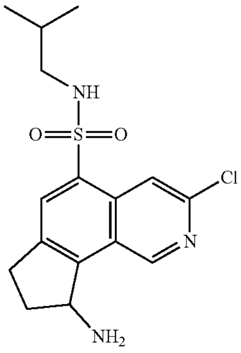

7-amino-3-chloro-N-isobutyl-8,9-dihydro-7H-cyclopenta[h]isoquinoline-5-sulfonamide (9)

9-amino-3-chloro-N-isobutyl-8,9-dihydro-7H-cyclopenta[h]isoquinoline-5-sulfonamide (10)

Two batches of a crude 1:1 mixture of Intermediates 7 & 8 (2.31 g, 6 mmol) were dissolved in 0.4 M ammonia in THF (400 mL, 200 mmol) in round bottom pressure flasks. The sealed reaction mixtures were heated at 70° C. for 16 hours. The two reaction mixtures were cooled and evaporated down. The resulting residues were resubmitted to the reaction conditions above using half the amount of ammonia in THF for 21 hours. The reaction mixtures were cooled, combined and evaporated down to give a ~1:1 ratio of the title compounds (4.7 g) which was used in the next step without further purification.

Intermediate 11 & 12

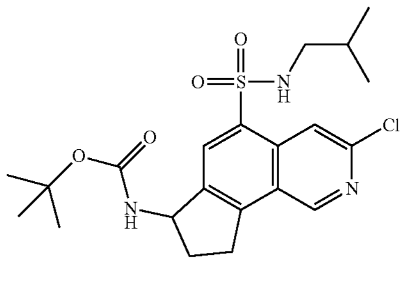

-continued

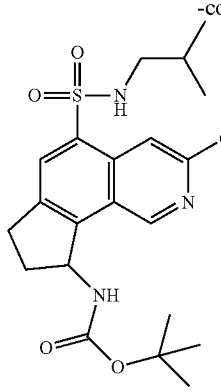

tert-butyl N-[3-chloro-5-(isobutylsulfamoyl)-8,9-dihydro-7H-cyclopenta[h]isoquinolin-7-yl]carbamate (11)

tert-butyl N-[3-chloro-5-(isobutylsulfamoyl)-8,9-dihydro-7H-cyclopenta[h]isoquinolin-9-yl]carbamate (12)

To a stirred ~1:1 mixture of intermediates 9 & 10 (2.88 g, 8.14 mmol) in dichloromethane (60 mL) was added di-tert-butyl dicarbonate (1.86 g, 8.52 mmol) followed by triethylamine (2.26 mL, 16.3 mmol). The reaction mixture was stirred at room temperature for 2 hours. The reaction mixture was evaporated to dryness and the crude purified by column chromatography (gradient of 0% to 100% ethyl acetate in iso-hexane) to give the title compounds.

Intermediate 11 (877 mg, 39% Yield); LCMS $[M+H]^+$ 454/456, RT 1.28 min(Method 1). $^1H$ NMR (300 MHz, Chloroform-d) $\delta_H$ 9.15 (d, J=0.8 Hz, 1H), 8.51 (d, J=0.9 Hz, 1H), 8.42 (s, 1H), 5.40 (m, 1H), 4.88 (m, 1H), 4.72 (t, J=6.4 Hz, 1H), 3.54 (ddd, J=17.1, 9.1, 3.3 Hz, 1H), 3.35-3.17 (m, 1H), 2.95-2.63 (m, 3H), 2.17-1.98 (m, 1H), 1.77-1.66 (m, 1H), 1.51 (s, 9H), 0.83 (dd, J=6.7, 3.8 Hz, 6H).

Intermediate 12 (1.00 g, 46% Yield); LCMS $[M+H]^+$ 454/456, RT 1.31 min (Method 1). $^1H$ NMR (300 MHz, Chloroform-d) $\delta_H$ 9.40 (d, J=0.8 Hz, 1H), 8.48 (d, J=0.8 Hz, 1H), 8.33 (s, 1H), 5.86 (s, 1H), 4.94 (m, J=9.5 Hz, 1H), 4.77 (t, J=6.4 Hz, 1H), 3.27 (dt, J=15.8, 7.6 Hz, 1H), 3.07 (ddd, J=16.8, 9.0, 4.6 Hz, 1H), 2.85-2.65 (m, 3H), 2.20 (m, 1H), 1.76-1.67 (m, 1H), 1.46 (s, 9H), 0.83 (dd, J=6.7, 1.8 Hz, 6H).

Intermediate 13

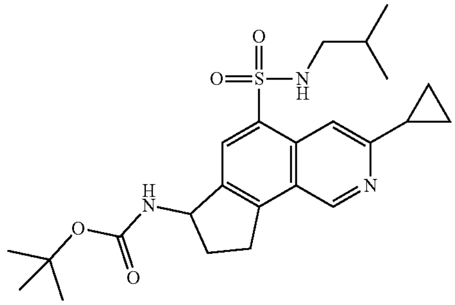 [SMILES: CC(C)CNS(=O)(=O)c1cc2c(c3cnc(C4CC4)cc13)CCC2NC(=O)OC(C)(C)C]

tert-butyl N-[3-cyclopropyl-5-(isobutylsulfamoyl)-8,9-dihydro-7H-cyclopenta[h]isoquinolin-7-yl]carbamate A mixture of intermediate 11 (910 mg, 2.0 mmol), cyclopropylboronic acid (540 mg, 6.0 mmol) and caesium carbonate (1.6 g, 4.9 mmol) in 1,4-dioxane (20 mL) was charged in a round bottom pressure flask under an atmosphere of nitrogen. Chloro($\eta^2$—P,C-tris(2,4-di-tert-butylphenyl)phosphite)(tricyclohexylphosphine)palladium(II) (210 mg, 0.20 mmol) was added and the sealed reaction mixture heated at 100° C. for 17 hours. The cooled reaction mixture was evaporated down. The resulting residue was partitioned between dichloromethane (50 mL) and water (25 mL). The aqueous layer was separated and further extracted into dichloromethane (50 mL×2), combined organic extracts were washed with brine (50 mL), dried over sodium sulfate and evaporated to dryness. The crude was purified by chromatography (gradient of 0% to 100% ethyl acetate in iso-hexane) to give the title compound (694 mg, 75% Yield). $^1H$ NMR (300 MHz, Chloroform-d) δ 9.21 (d, J=0.9 Hz, 1H), 8.34 (s, 1H), 8.26 (d, J=0.9 Hz, 1H), 5.39 (m, 1H), 4.85 (m, 1H), 4.66 (t, J=6.4 Hz, 1H), 3.49 (ddd, J=17.1, 9.1, 3.5 Hz, 1H), 3.23 (dt, J=16.8, 8.1 Hz, 1H), 2.93-2.62 (m, 3H), 2.24 (ddd, J=13.2, 8.1, 4.8 Hz, 1H), 2.12-1.93 (m, 1H), 1.72 (m, 1H), 1.51 (s, 9H), 1.18-1.01 (m, 4H), 0.84 (dd, J=6.7, 4.4 Hz, 6H). LCMS $[M+H]^+$ 460, RT 1.38 min (Method 1).

Intermediate 14

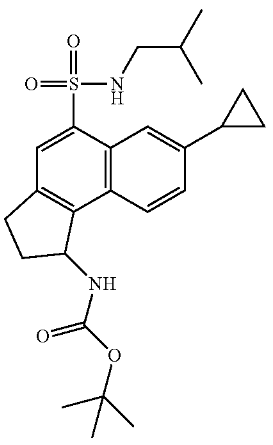 [SMILES: CC(C)CNS(=O)(=O)c1cc2c(c3ccc(C4CC4)cc13)C(NC(=O)OC(C)(C)C)CC2]

tert-butyl N-[7-cyclopropyl-5-(isobutylsulfamoyl)-2,3-dihydro-1H-cyclopenta[a]naphthalen-1-yl]carbamate A mixture of intermediate 12 (500 mg, 1.10 mmol), cyclopropylboronic acid (299 mg, 3.304 mmol) and cesium carbonate (906 mg, 2.753 mmol) in anhydrous 1,4-dioxane (5 mL) was degassed and filled with nitrogen. Chloro($\eta^2$—P,C-tris(2,4-di-tert-butylphenyl)phosphite)(tricyclohexylphosphine)palladium(II) (117.6 mg, 0.11 mmol) was added and the reaction mixture heated at 120° C. for 1.5 hours in the microwave. The reaction mixture was concentrated under reduced pressure, then partitioned between DCM and water. Organic phase washed with brine, passed through a phase separator cartridge and evaporated. The crude was purified by column chromatography (eluting with 20-70% EtOAc in ipahexane) to give the title compound (332 mg, 66% Yield). LCMS $[M+H-tBu]^+$ 404.0, RT 2.73 min (Method 3).

Intermediate 15

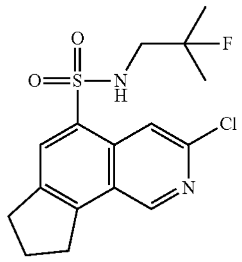 [SMILES: CC(C)(F)CNS(=O)(=O)c1cc2c(c3cnc(Cl)cc13)CCC2]

3-chloro-N-(2-fluoro-2-methyl-propyl)-8,9-dihydro-7H-cyclopenta[h]isoquinoline-5-sulfonamide To a stirred solution of intermediate 5 (11.5 g, 38.1 mmol) in DCM (200 mL) was added 2-fluoro-2-methyl-propan-1-amine hydrochloride (5.83 g, 45.7 mmol) followed by triethylamine (13.2 mL, 95.1 mmol). The reaction mixture was stirred at room temperature for 1 h. The reaction was washed with water (200 mL). The organic layer was partitioned and washed with more water (200 mL). The organic layer was dried and concentrated in vacuo to afford 11.8 g of green/black solid. This was triturated with hot IPA and filtered to give the title compound (10.4 g, 77% Yield) as a grey powder. $^1H$ NMR (300 MHz, Chloroform-d) $\delta_H$ 9.14 (d, J=0.9 Hz, 1H), 8.46 (d, J=0.8 Hz, 1H), 8.34 (s, 1H), 4.98 (t, J=6.5 Hz, 1H), 3.49-3.37 (m, 2H), 3.17 (t, J=7.5 Hz, 2H), 3.04 (dd, J=19.8, 6.5 Hz, 2H), 2.45-2.29 (m, 2H), 1.31 (d, J=21.4 Hz, 6H). LCMS $[M+H]^+$357, RT 1.92 min (Method 2).

Intermediates 16 and 17

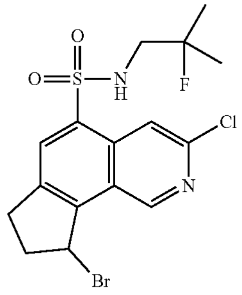

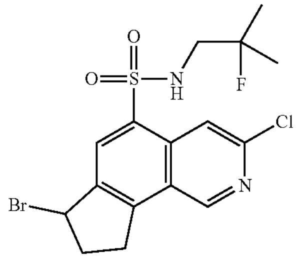

9-bromo-3-chloro-N-(2-fluoro-2-methyl-propyl)-8,9-dihydro-7H-cyclopenta[h]isoquinoline-5-sulfonamide (16)

7-bromo-3-chloro-N-(2-fluoro-2-methyl-propyl)-8,9-dihydro-7H-cyclopenta[h]isoquinoline-5-sulfonamide (17)

To a stirred solution of Intermediate 15 (3.0 g, 8.4 mmol) in ethyl acetate (180 mL) under nitrogen was added 2,2'-azobis(2-methylpropionitrile) (140 mg, 0.84 mmol) and N-bromosuccinimide (2.0 g, 11 mmol). The mixture was stirred at 90° C. in the dark for 1.5 hours. The reaction mixture was evaporated down under vacuum to afford crude product as a 1:1 mixture of the title compound 16 (1.65 g, 44% yield) and title compound 17 (1.65 g, 44% yield). LCMS $[M+H]^+$ 435/437/439, RT 1.56 min (Method 5).

Intermediate 18

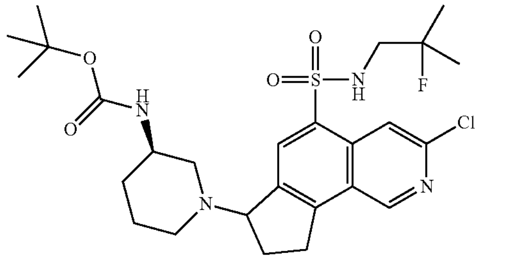 [SMILES: CC(C)(F)CNS(=O)(=O)c1cc2c(c3cnc(Cl)cc13)CCC2N1CCC[C@@H](NC(=O)OC(C)(C)C)C1]

tert-butyl N-[(3R)-1-[3-chloro-5-[(2-fluoro-2-methyl-propyl)sulfamoyl]-8,9-dihydro-7H-cyclopenta[h]isoquinolin-7-yl]-3-piperidyl]carbamate To a solution of intermediate 17 (200 mg, 0.46 mmol) in DMF (2 mL) was added potassium carbonate (128 mg, 0.92 mmol) followed by (R)-3-boc-aminopiperidine (190 mg, 0.95 mmol). The mixture was stirred for 18 hours. Water (10 mL) and EtOAc (20 mL) were added to the mixture. The organic layer was separated and washed further with water (2×5 mL). The organic layer was passed through a phase separator and the solvent was removed to give a brown oil. The oil was purified by flash column chromatography eluting with a gradient of 0 to 100% EtOAc in heptane to afford the title compound as a brown gum (240 mg, 94% yield). LCMS $[M+H]^+$ 555/557, RT 2.54 minutes (Method 4).

Intermediate 19

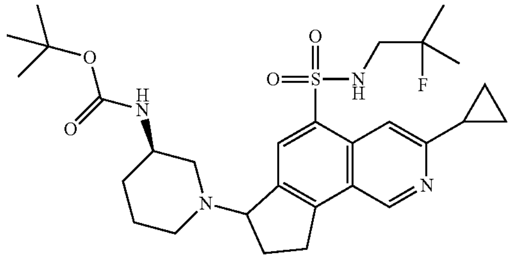 [SMILES: CC(C)(F)CNS(=O)(=O)c1cc2c(c3cnc(C4CC4)cc13)CCC2N1CCC[C@@H](NC(=O)OC(C)(C)C)C1]

tert-butyl N-[(3R)-1-[3-cyclopropyl-5-[(2-fluoro-2-methyl-propyl)sulfamoyl]-8,9-dihydro-7H-cyclopenta[h]isoquinolin-7-yl]-3-piperidyl]carbamate To a solution of intermediate 18 (240 mg, 0.43 mmol) in a mixture of toluene (2 mL) and 1,4-dioxane (3 mL) was added cyclopropylboronic acid (117 mg, 1.30 mmol) followed by palladium (II) acetate (4.8 mg, 0.022 mmol). Nitrogen gas was bubbled through the mixture for 2 minutes then tricyclohexylphosphonium tetrafluoroborate (25 mg, 0.065 mmol) and potassium phosphate tribasic (230 mg, 1.08 mmol) were added. Nitrogen was bubbled through for 5 minutes then the microwave vial was capped and heated at 130° C. for 18 hours in a microwave. Saturated aq. $NaHCO_3$ solution (10 mL) and EtOAc (10 mL) were added to the mixture. The organic layer was separated and passed through a phase separator and the solvent was removed to give a green oil. The oil was purified by flash column chromatography eluting with a gradient of 0 to 100% EtOAc in heptane followed by a gradient of 0 to 10% MeOH in EtOAc to afford the title compound as a brown gum (231 mg, 95% yield). LCMS $[M+H]^+$ 561, RT 2.63 minutes (Method 4).

Intermediate 20

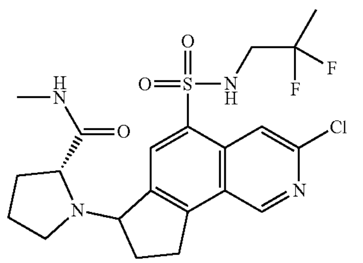 [SMILES: CNC(=O)[C@H]1CCCN1C1CCc2c1cc(S(=O)(=O)NCC(C)(F)F)c1cc(Cl)ncc21]

To a solution of intermediate 17 (100 mg, 0.23 mmol) in DMF (2 mL) was added potassium carbonate (96.1 mg, 0.69 mmol) followed by (2R)—N-methylpyrrolidine-2-carboxamide (59 mg, 0.46 mmol). The mixture was left to for 18 hours. Water (10 mL) and EtOAc (20 mL) were added to the mixture. The organic layer was separated and washed further with water (2×10 mL). The organic layer was passed through a phase separator and the solvent was removed to give a brown oil. The oil was purified by flash column chromatography eluting with a gradient of 0 to 100% EtOAc in heptane followed by a 0-10% MeOH in EtOAc gradient to afford the title compound as a mixture of two diastereoisomers (96 mg, 87% yield). LCMS $[M+H]^+$ 483/485, RT 1.89 and 1.94 minutes (Method 4).

Intermediate 21

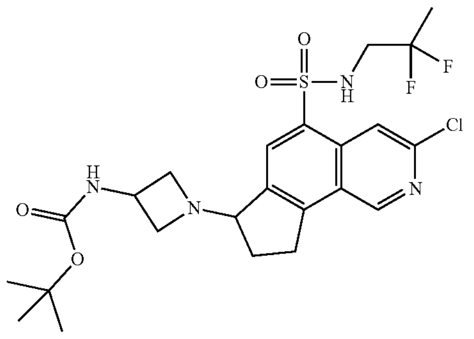 [SMILES: CC(F)(F)CNS(=O)(=O)c1cc2c(c3cnc(Cl)cc13)CCC2N1CC(NC(=O)OC(C)(C)C)C1]

tert-butyl N-[1-[3-chloro-5-[(2-fluoro-2-methyl-propyl)sulfamoyl]-8,9-dihydro-7H-cyclopenta[h]isoquinolin-7-yl]azetidin-3-yl]carbamate To a solution of Intermediate 17 (160 mg, 0.37 mmol) in DMF (2 mL) was added 3-N-Boc-aminoazetidine (130 mg, 0.73 mmol) followed by potassium carbonate (154 mg, 1.10 mmol). The mixture was stirred for 18 hours. Ethyl acetate (15 mL) was added to the mixture. The suspension was washed with water (2×15 mL) and brine (15 mL). The combined organic layers were then passed through a phase separator and concentrated under reduced pressure. The residue was purified by flash column chromatography eluting with a 0-100% EtOAc in heptane gradient followed by a 0-20% MeOH in EtOAc gradient to afford the title compound as a light brown glass (119 mg, 61% Yield). LCMS $[M+H]^+$ 527/529, RT 2.29 minutes (Method 4).

Intermediate 22

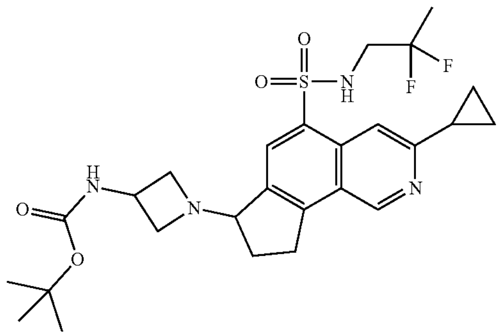 [SMILES: CC(F)(F)CNS(=O)(=O)c1cc2c(c3cnc(C4CC4)cc13)CCC2N1CC(NC(=O)OC(C)(C)C)C1]

tert-butyl N-[1-[3-cyclopropyl-5-[(2-fluoro-2-methyl-propyl)sulfamoyl]-8,9-dihydro-7H-cyclopenta[h]isoquinolin-7-yl]azetidin-3-yl]carbamate A mixture of intermediate 21 (119 mg, 0.23 mmol), cyclopropylboronic acid (61 mg, 0.67 mmol), palladium (II) acetate (2.5 mg, 0.011 mmol), tricyclohexylphosphonium tetrafluoroborate (13 mg, 0.034 mmol), potassium phosphate tribasic (120 mg, 0.57 mmol) and water (20 μL) were suspended in toluene (2 mL). The mixture was purged with nitrogen before being heated to 120° C. for 14 hours. The reaction mixture was diluted with water (5 mL) and DCM (10 mL). The biphasic layer was separated, and the aqueous layer extracted with DCM (2×10 mL). The combined organic layers were passed through a phase separator and concentrated under reduced pressure to give an oil. The oil was purified by flash column chromatography eluting with a 0-100% EtOAc in isohexane gradient followed by a 0-20% MeOH in EtOAc gradient to afford the title compound as a light brown glass (55 mg, 46% Yield). LCMS $[M+H]^+$ 533, RT 1.96 minutes (Method 4).

Intermediate 23

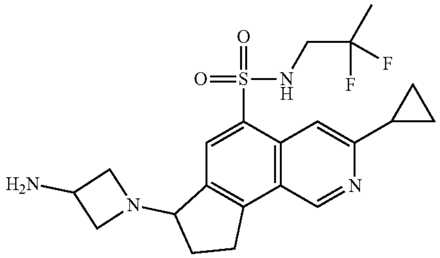 [SMILES: CC(F)(F)CNS(=O)(=O)c1cc2c(c3cnc(C4CC4)cc13)CCC2N1CC(N)C1]

7-(3-aminoazetidin-1-yl)-3-cyclopropyl-N-(2-fluoro-2-methyl-propyl)-8,9-dihydro-7H-cyclopenta[h]isoquinoline-5-sulfonamide To a solution of intermediate 22 (47 mg, 0.088 mmol) in DCM (2 mL) was added TFA (2 mL). The solution was stirred for 1 hour. The solvent was removed and the excess TFA azeotroped using a 1:1 mixture of DCM and isohexane. The brown gum obtained was purified by SCX column chromatography eluting with a gradient of 0 to 100% 7 M ammonia in MeOH to afford the title compound as a pale brown solid (36 mg, 94% yield). LCMS $[M+H]^+$ 433, RT 1.64 minutes (Method 4).

Intermediate 24

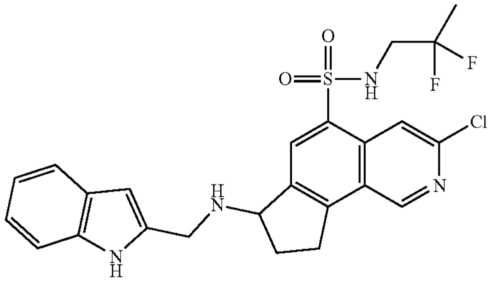 [SMILES: CC(F)(F)CNS(=O)(=O)c1cc2c(c3cnc(Cl)cc13)CCC2NCc1cc2ccccc2[nH]1]

3-chloro-N-(2-fluoro-2-methyl-propyl)-7-(1H-indol-2-ylmethylamino)-8,9-dihydro-7H-cyclopenta[h]isoquinoline-5-sulfonamide To a solution of intermediate 17 (100 mg, 0.23 mmol) in DMF (2 mL) was added potassium carbonate (64 mg, 0.46 mmol) followed by (1H-indol-2-ylmethyl)amine (69 mg, 0.46 mmol). The mixture was left to stir for 18 hours. Water (5 mL) and EtOAc (10 mL) were added to the mixture. The organic layer was separated and washed further with water (2×5 mL). The organic layer was passed through a phase separator and the solvent was removed to give a green oil. The oil was purified by flash column chromatography eluting with a gradient of 0 to 100% EtOAc in isohexane to afford the title compound as a brown foam (95 mg, 82% yield). LCMS $[M+H]^+$ 501/503, RT 2.46 minutes (Method 4).

Intermediates 25 & 26

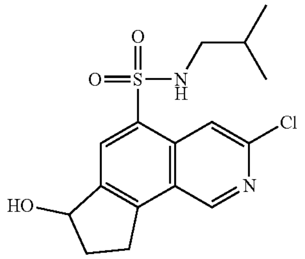

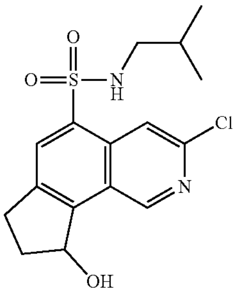

3-chloro-7-hydroxy-N-isobutyl-8,9-dihydro-7H-cyclopenta[h]isoquinoline-5-sulfonamide (25)
3-chloro-9-hydroxy-N-isobutyl-8,9-dihydro-7H-cyclopenta[h]isoquinoline-5-sulfonamide (26)

To a mixture of intermediate 7 and 8 (1480 mg, 3.54 mmol) in THF (6 mL)/water (3 mL) was added silver carbonate (1973 mg, 7.09 mmol). The reaction was stirred vigorously for 18 hours. The mixture was filtered through Celite to remove the silver salts washing with EtOAc (20 mL) and water (5 mL). The organic layer was separated and passed through a phase separator. The solvent was removed to give a brown gum. The gum was purified by flash column chromatography eluting with a gradient of 0 to 50% EtOAc in isohexane to afford the intermediate 26 (280 mg, 22% yield), intermediate 25 (200 mg, 16% yield), and a 1:1 mixture of intermediates 25 and 26 (113 mg, 9% yield).

Intermediate 25; LCMS $[M+H]^+$ 355, RT 2.10 minutes (Method 4).

Intermediate 26; LCMS $[M+H]^+$ 355, RT 2.16 minutes (Method 4).

Intermediate 27

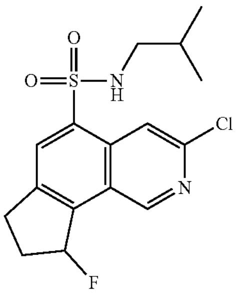 [SMILES: CC(C)CNS(=O)(=O)c1cc2c(c3cnc(Cl)cc13)C(F)CC2]

3-chloro-9-fluoro-N-isobutyl-8,9-dihydro-7H-cyclopenta[h]isoquinoline-5-sulfonamide To a solution of Intermediate 26 (48 mg, 0.14 mmol) in DCM (2 mL) at 0° C. was added DAST (44 mg, 0.27 mmol). The mixture was stirred at 0° C. for 10 minutes then room temperature for 1 hour. Saturated aqueous $NaHCO_3$ solution (5 mL) was added and the organic layer was separated and passed through a phase separator. The solvent was removed to give a gum. The gum was purified by flash column chromatography eluting with a gradient of 0 to 50% EtOAc in iso-hexane to afford the title compound as a white solid (43 mg, 89% yield). LCMS $[M+H]^+$ 357, RT 2.41 minutes (Method 4).

Intermediate 28

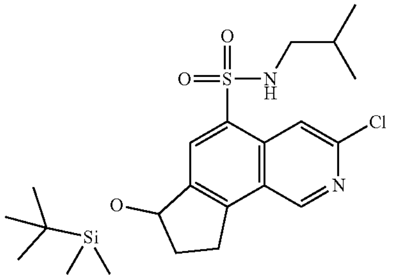

7-[tert-butyl(dimethyl)silyl]oxy-3-chloro-N-isobutyl-8,9-dihydro-7H-cyclopenta[h]isoquinoline-5-sulfonamide To a solution of intermediate 25 (200 mg, 0.56 mmol) in DMF (3 mL) was added imidazole (78 mg, 1.13 mmol), 4-dimethylaminopyridine (3.4 mg, 0.028 mmol) and TBDMSCl (127 mg, 0.85 mmol). The mixture was stirred for 6 hours and 4-dimethylaminopyridine (0.1 equivalent) was added and the reaction was heated at 40° C. for 18 hours. Another portion of TBDMSCl (127 mg, 0.85 mmol) and imidazole (3.4 mg, 0.028 mmol) were added and the mixture was heated for 5 hours. Water (10 mL) and EtOAc (20 mL) were added to the mixture. The organic layer was separated, washed with water (10 mL) and passed through a phase separator. The solvent was removed to give a brown gum. The gum was purified by flash column chromatography eluting with a gradient of 0 to 20% EtOAc in isohexane to afford the title product as a white solid (190 mg, 72% yield). LCMS $[M+H]^+$ 469/471, RT 3.66 minutes (Method 4).

Intermediate 29

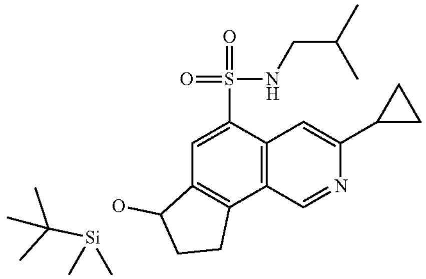

7-[tert-butyl(dimethyl)silyl]oxy-3-cyclopropyl-N-isobutyl-8,9-dihydro-7H-cyclopenta[h]isoquinoline-5-sulfonamide In a microwave vial, Intermediate 28 (135 mg, 0.29 mmol) was suspended in 1,4-dioxane (3 mL) and caesium carbonate (237 mg, 0.72 mmol) followed by cyclopropylboronic acid (78 mg, 0.86 mmol) were added. The flask was evacuated and placed under a nitrogen atmosphere for 5 minutes. Chloro($\eta^2$—P,C-tris(2,4-di-tert-butylphenyl)phosphite)(tricyclohexylphosphine)palladium(II) (31 mg, 0.029 mmol) was then added and the flask was again evacuated and placed under a nitrogen atmosphere. The reaction was then heated at 120° C. for 2.5 hours. The solvent was removed, and the residue was partitioned between water (10 mL) and EtOAc (15 mL). The organic layer was separated and passed through a phase separator. The solvent was removed to give a brown oil. The oil was purified by flash column chromatography eluting with a gradient of 0 to 20% EtOAc in isohexane to afford the title product as an off-white solid (74 mg, 54% yield). LCMS $[M+H]^+$ 475, RT 3.68 minutes (Method 3).

Intermediate 30

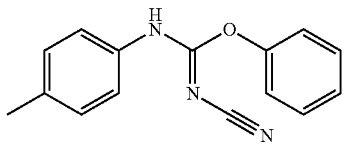 [SMILES: Cc1ccc(N/C(=N/C#N)Oc2ccccc2)cc1]

3-cyano-2-phenyl-1-(p-tolyl)isourea

Diphenyl N-cyanocarbonimidate (500 mg, 2.10 mmol) and p-toluidine (240 mg, 2.24 mmol) were dissolved in dichloromethane (70 mL). N,N-Diisopropylethylamine (397 mg, 3.15 mmol) and 2-propanol (2 mL) were added. The mixture was stirred at room temperature overnight. The solvent was evaporated. The residue was triturated with EtOAc and filtered off, washing with EtOAc three times, to give the title compound as a white solid, (210 mg, 40% yield). LCMS $[M+H]^+$252, RT 1.90 min (Method 6).

Intermediates 31 and 32

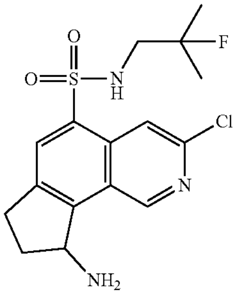

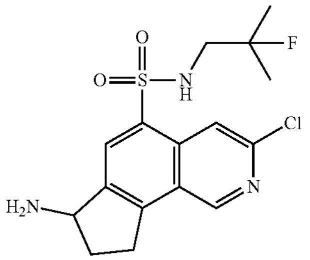

9-amino-3-chloro-N-(2-fluoro-2-methyl-propyl)-8,9-dihydro-7H-cyclopenta[h]isoquinoline-5-sulfonamide (31)

7-amino-3-chloro-N-(2-fluoro-2-methyl-propyl)-8,9-dihydro-7H-cyclopenta[h]isoquinoline-5-sulfonamide (32)

A crude mixture containing Intermediate 16 (1.65 g, 3.79 mmol) and intermediate 17 (1.65 g, 3.79 mmol) was dissolved in tetrahydrofuran (200 mL) and the mixture charged into a sealed 500 mL round bottom pressure flask. Ammonia gas was bubbled through the reaction mixture for 5 minutes. The sealed mixture was heated at 70° C. for 2 days. The cooled reaction mixture was evaporated down under vacuum to give crude product containing a 1:1 mixture of the title compound 31 (1.71 g/quantitative yield, 3.79 mmol) and the title compound 32 (1.71 g/quantitative yield, 3.79 mmol). LCMS $[M+H]^+$ 372/374, RT 1.89 & 1.92 minutes (Method 6).

Intermediates 33 and 34

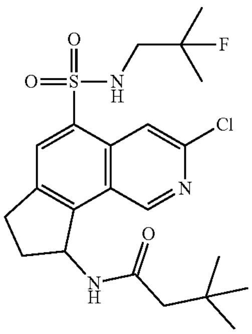

-continued

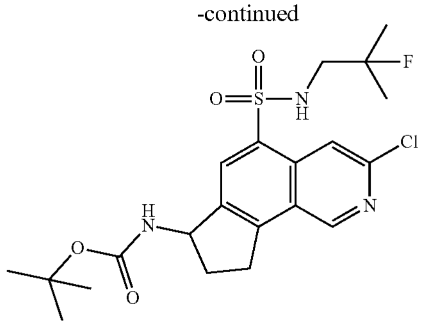

tert-butyl N-[3-chloro-5-[(2-fluoro-2-methyl-propyl)sulfamoyl]-8,9-dihydro-7H-cyclopenta[h]isoquinolin-9-yl]carbamate (33)

tert-butyl N-[3-chloro-5-[(2-fluoro-2-methyl-propyl)sulfamoyl]-8,9-dihydro-7H-cyclopenta[h]isoquinolin-7-yl]carbamate (34)

To a stirred crude mixture of intermediate 31 (3.79 mmol) and intermediate 32 (3.79 mmol) in dichloromethane (100 mL) was added di-tert-butyl dicarbonate (2.1 g, 9.5 mmol) followed by triethylamine (2.5 mL, 18 mmol). The mixture was stirred at room temperature under nitrogen for 3 hours. The reaction mixture was evaporated under vacuum and purified via column chromatography, using a gradient of 0-40% ethyl acetate in iso-hexane.

Intermediate 33 (1.2 g, 85% purity, 2.16 mmol, 57% yield) was isolated as a yellow foam. $\delta_H$ (300 MHz, d-Chloroform) 9.40 (d, J=0.8 Hz, 1H), 8.46 (d, J=0.9 Hz, 1H), 8.31 (s, 1H), 5.86 (m, 1H), 5.01 (t, J=6.4 Hz, 1H), 4.98-4.88 (m, 1H), 3.34-3.19 (m, 1H), 3.06 (m, 3H), 2.87-2.66 (m, 1H), 2.21 (ddt, J=13.7, 8.9, 4.0 Hz, 1H), 1.48 (s, 9H), 1.36 (d, J=6.0 Hz, 3H), 1.31-1.27 (m, 3H). LCMS $[M+H]^+$ 472/474, RT 2.55 min (Method 6).

Intermediate 34 (877 mg, 1.86 mmol, 49% yield) was isolated as a yellow solid. $\delta_H$ (300 MHz, d-Chloroform) 9.15 (d, J=0.9 Hz, 1H), 8.49 (d, J=0.8 Hz, 1H), 8.41 (s, 1H), 5.41 (m, 1H), 5.03 (t, J=6.4 Hz, 1H), 4.89 (d, J=8.9 Hz, 1H), 3.54 (ddd, J=17.1, 9.2, 3.2 Hz, 1H), 3.37-2.79 (m, 4H), 2.15-1.98 (m, 1H), 1.51 (s, 9H), 1.41-1.23 (m, 6H). LCMS $[M+H]^+$ 472/474, RT 2.52 min (Method 6).

Intermediate 35

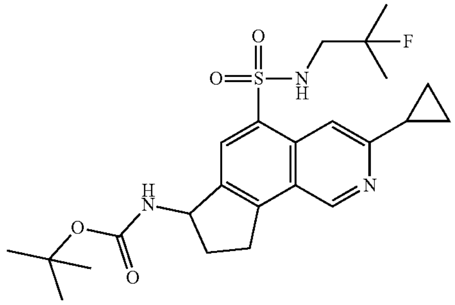 [SMILES: CC(C)(F)CNS(=O)(=O)c1cc2c(c3cnc(C4CC4)cc13)CCC2NC(=O)OC(C)(C)C]

tert-butyl N-[3-cyclopropyl-5-[(2-fluoro-2-methyl-propyl)sulfamoyl]-8,9-dihydro-7H-cyclopenta[h]isoquinolin-7-yl]carbamate A mixture of intermediate 34 (870 mg, 1.8 mmol), cyclopropylboronic acid (500 mg, 5.5 mmol) and caesium carbonate (1.5 g, 4.6 mmol) in anhydrous 1,4-dioxane (20 mL) was charged in a 50 mL pressure flask and purged out under a flow of nitrogen for 5 minutes. Chloro($\eta^2$—P,C-tris(2,4-di-tert-butylphenyl)phosphite)(tricyclohexylphosphine)palladium(II) (200 mg, 0.19 mmol) was added and the sealed mixture heated at 100° C. for 16 hours. The cooled reaction mixture was evaporated under vacuum and the resulting residue partitioned between dichloromethane (100 mL) and water (50 mL). The aqueous layer was separated and further extracted into dichloromethane (2×100 mL), combined organic extracts washed with brine (100 mL), dried over sodium sulfate and evaporated under vacuum. The residue was and purified via column chromatography, using a gradient of 0-80% ethyl acetate in iso-hexane to afford the title compound (571 mg, 65% Yield). $\delta_H$ (300 MHz, d-Chloroform) 9.22 (d, J=0.9 Hz, 1H), 8.33 (s, 1H), 8.23 (d, J=1.0 Hz, 1H), 5.39 (m, 1H), 4.95 (t, J=6.5 Hz, 1H), 4.84 (d, J=8.9 Hz, 1H), 3.50 (ddd, J=17.1, 9.1, 3.4 Hz, 1H), 3.23 (dt, J=17.0, 8.3 Hz, 1H), 3.13-2.76 (m, 3H), 2.25 (ddd, J=13.3, 8.2, 4.9 Hz, 1H), 2.08-1.98 (m, 1H), 1.51 (s, 9H), 1.43-1.24 (m, 6H), 1.13 (m, 4H). LCMS $[M+H]^+$ 478, RT 1.23 min (Method 1).

Intermediate 36

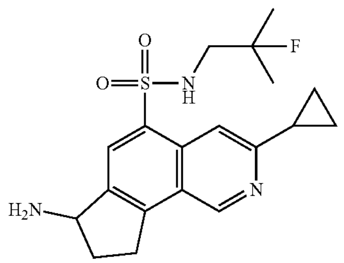

7-amino-3-cyclopropyl-N-(2-fluoro-2-methyl-propyl)-8,9-dihydro-7H-cyclopenta[h]isoquinoline-5-sulfonamide A solution of intermediate 35 (570 mg, 1.2 mmol) in 4 M hydrochloric acid in dioxane solution (15 mL) was stirred at room temperature for 1 hour. The reaction mixture was evaporated under vacuum and the residue purified via an SCX column eluting with 100% methanol followed by 7N ammonia in methanol solution to afford the title compound (438 mg, 97% Yield). $\delta_H$ (300 MHz, d-Chloroform) 9.21 (s, 1H), 8.38 (s, 1H), 8.21 (s, 1H), 5.05 (m, 1H), 4.60 (m, 1H), 3.59-3.51 (m, 1H), 3.29-3.12 (m, 1H), 3.03 (m, 2H), 2.76 (m, 1H), 2.22 (m, 1H), 1.94 (m, 1H), 1.38-1.23 (m, 6H), 1.10 (m, 4H). $NH_2$ protons missing. LCMS $[M+H]^+$ 378, RT 1.31 min (Method 5).

Intermediates 37 and 38

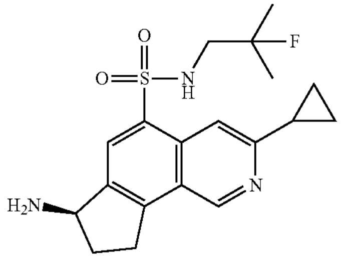

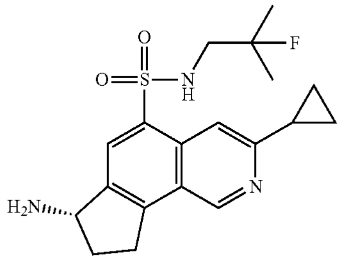 [SMILES: CC(C)(F)CNS(=O)(=O)c1cc2c(c3cnc(C4CC4)cc13)CCC2N]

(7R)-7-amino-3-cyclopropyl-N-(2-fluoro-2-methyl-propyl)-8,9-dihydro-7H-cyclopenta[h]isoquinoline-5-sulfonamide (75)-7-amino-3-cyclopropyl-N-(2-fluoro-2-methyl-propyl)-8,9-dihydro-7H-cyclopenta[h]isoquinoline-5-sulfonamide The title compounds were obtained by separation of Intermediate 36 by chiral HPLC using the following conditions: a LUX Cellulose-4, 250×21.2 mm, 5 μM column with a flow rate of 10 mL/min. Column Temp: 40° C., Mobile Phase: MeOH+0.1% $NH_4OH$. Run Time: 20 mins Note: In intermediates 37 and 38 one is the R-enantiomer and the other is the S-enantiomer, we have not assigned which enantiomer is which intermediate.

Intermediate 37: Chiral RT**=2.50 min; LCMS $[M+H]^+$ 378.2, RT 1.67 min (Method 3).

Intermediate 38: Chiral RT**=2.77 min; LCMS $[M+H]^+$ 378.2, RT 1.74 min (Method 3).

**Chiral analysis was carried out by polar organic mode, using a Lux Cellulose-4 4.6×150 mm, 3 μm column, flow rate 1 mL/min eluting with Methanol (0.1% ammonium hydroxide) using a 10 min run time on an Agilent 1100 UV directed system.

Intermediate 39

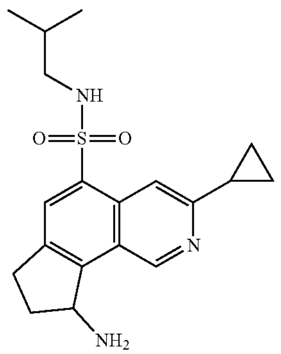 [SMILES: CC(C)CNS(=O)(=O)c1cc2c(c3cnc(C4CC4)cc13)C(N)CC2]

9-amino-3-cyclopropyl-N-isobutyl-8,9-dihydro-7H-cyclopenta[h]isoquinoline-5-sulfonamide Hydrochloride 9-amino-3-cyclopropyl-N-isobutyl-8,9-dihydro-7H-cyclopenta[h]isoquinoline-5-sulfonamide Intermediate 14 (1.81 g, 3.47 mmol) was dissolved in 4 M hydrochloric acid in dioxane (20 mL) and stirred at ambient temperature for 30 min. The reaction was concentrated in vacuo to afford the title compound as a hydrochloride salt. It was then dissolved in MeOH (10 mL) and absorbed onto a SCX cartridge washing first with MeOH (50 mL) and then eluting with 7N $NH_3$ in MeOH (75 mL). The methanol ammonia was removed in vacuo to afford the title compound as the free base (1.18 g, 95% Yield). $\delta_H$ (300 MHz, d-Methanol) 9.47 (s, 1H), 8.37 (d, J=0.9 Hz, 1H), 8.28 (s, 1H), 5.05 (dd, J=7.5, 2.5 Hz, 1H), 3.43-3.32 (m, 1H), 3.03 (ddd, J=16.4, 9.0, 3.1 Hz, 1H), 2.68-2.50 (m, 3H), 2.30 (tt, J=7.9, 5.3 Hz, 1H), 2.12 (ddt, J=13.6, 8.1, 2.8 Hz, 1H), 1.62 (dp, J=13.4, 6.7 Hz, 1H), 1.18-1.01 (m, 4H), 0.78 (d, J=6.7 Hz, 6H).

Intermediates 40-42

Intermediates 40-42 were synthesized according to the following procedure: To a solution of Intermediate 39 (50 mg, 0.14 mmol) in DCM (1 mL) and THF (1 mL) was added isothiocyanate (1.2 equiv.). Reactions were stirred at ambient temperature overnight, concentrated in vacuo and then purified using column chromatography to afford the title compounds. LCMS data given in the table below was obtained using Method 5.

| Int. | Structure | Name | Reagent | RT | Mass |
|---|---|---|---|---|---|
| 40 | 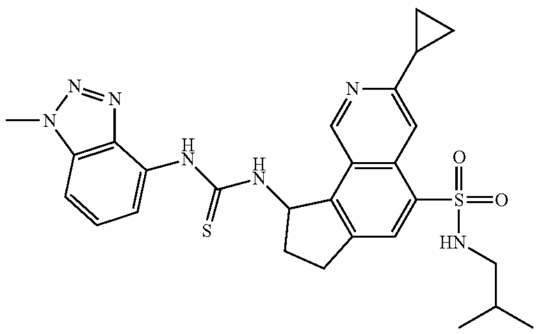 [SMILES: CC(C)CNS(=O)(=O)c1cc2c(c3cnc(C4CC4)cc13)C(NC(=S)Nc1cccc3c1nnn3C)CC2] | 1-[3-cyclopropyl-5-(isobutylsulfamoyl)-8,9-dihydro-7H-cyclopenta[h]isoquinolin-9-yl]-3-(1-methylbenzotriazol-4-yl)thiourea | 4-isothiocyanato-1-methyl-benzotriazole | 1.58 min | 550 |
| 41 | 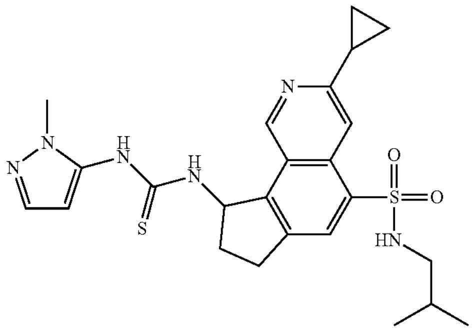 [SMILES: CC(C)CNS(=O)(=O)c1cc2c(c3cnc(C4CC4)cc13)C(NC(=S)Nc1ccnn1C)CC2] | 1-[3-cyclopropyl-5-(isobutylsulfamoyl)-8,9-dihydro-7H-cyclopenta[h]isoquinolin-9-yl]-3-(2-methylpyrazol-3-yl)thiourea | 5-isothiocyanato-1-methyl-pyrazole | 1.47 min | 499 |

-continued

| Int. | Structure | Name | Reagent | RT | Mass |
|---|---|---|---|---|---|
| 42 | 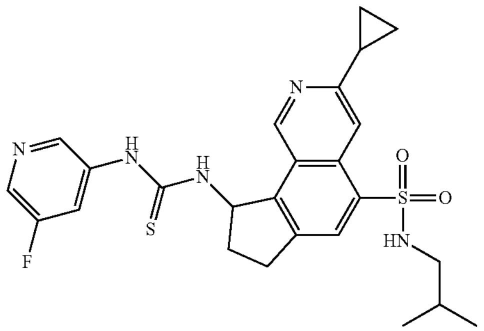 [SMILES: CC(C)CNS(=O)(=O)c1cc2c(c3cnc(C4CC4)cc13)C(NC(=S)Nc1cncc(F)c1)CC2] | 1-[3-cyclopropyl-5-(isobutylsulfamoyl)-8,9-dihydro-7H-cyclopenta[h]isoquinolin-9-yl]-3-(5-fluoro-3-pyridyl)thiourea | 3-fluoro-5-isothiocyanato-pyridine | 1.57 min | 514 |

Intermediate 43

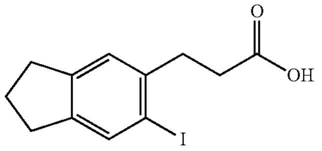 [SMILES: O=C(O)CCc1cc2c(cc1I)CCC2]

3-(6-iodoindan-5-yl)propanoic acid

To a mixture of 3-indan-5-ylpropanoic acid (5.14 kg, 27 mol) and TFA (6.9 L) in DCM (26 L) at 0-10° C. was added N-iodosuccinimide (1.0 equivalents). The solution was stirred for 20 hours at 10-15° C. and then poured over ice. The aqueous mixture was extracted with DCM and washed with a 10% aqueous solution of $Na_2S_2O_3$. The dichloromethane solution was taken directly into the subsequent step. Assumed quantitative yield (8.5 kg, mw=315.1).

Intermediate 44

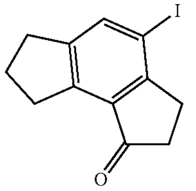 [SMILES: O=C1CCc2c(I)cc3c(c21)CCC3]

4-iodo-3,6,7,8-tetrahydro-2H-as-indacen-1-one

A solution of intermediate 43 (8.5 kg, 27 mol) in DCM (127 L) at 0° C. was treated with DMF followed by oxalyl chloride (6.8 kg, 54 mol) and the reaction mixture stirred at 10-15° C. for 3 hours. The mixture was concentrated in vacuo, dissolved in DCM (127 L), cooled to 0° C. and treated with $AlCl_3$ (10.8 kg, 81 mol). The mixture was stirred at 0'C for 2 hours then quenched by the addition of ice-water (85 L) and extracted with DCM (85 L). The organic extract was concentrated in vacuo and purified by column chromatography to give the title compound (approx. 750 g, ~12% Yield). $\delta_H$ (300 MHz, DMSO-d6) 7.92 (s, 1H), 3.03 (t, J=7.5 Hz, 2H) 2.85 (t, J=5.8 Hz, 4H), 2.69-2.56 (m, 2H), 2.04 (p, J=7.5 Hz, 2H). LCMS $[M+H]^+$299, RT 2.51 min (Method 3).

Intermediate 45

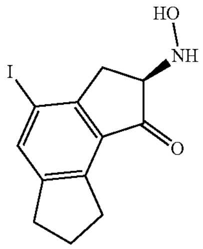 [SMILES: O=C1c2c(c(I)cc3c2CCC3)C[C@H]1NO]

2-hydroxyimino-4-iodo-3,6,7,8-tetrahydro-as-indacen-1-one

Intermediate 44 (100 g, 335 mmol) was suspended in a mixture of $Et_2O$ (800 mL) and EtOH (100 mL). HCl (4 mol/L) in 1,4-dioxane (16 mL) was added at room temperature, followed by butyl nitrite (58 mL, 471 mmol), which was added at 0° C. The ice bath was removed, and the reaction mixture left to warm up while stirring overnight. A white solid precipitate was collected by filtration, rinsed with MeOH and EtOAc and dried under vacuum to afford the title compound (109 g, 99% yield). $^1H$ NMR (300 MHz, DMSO-$d_6$) δ 12.69 (s, 1H), 7.99 (d, J=0.9 Hz, 1H), 3.50 (s, 2H), 3.10 (t, J=7.5 Hz, 2H), 2.88 (t, J=7.5 Hz, 2H), 2.07 (p, J=7.6 Hz, 2H). LCMS $[M+H]^+$328, RT 1.13 min (Method 1).

Intermediate 46

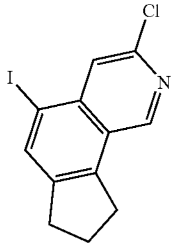 [SMILES: Clc1cc2c(I)cc3c(c2cn1)CCC3]

3-chloro-5-iodo-8,9-dihydro-7H-cyclopenta[h]isoquinoline

The title compound was obtained using the following two steps:

Step 1: To a suspension of intermediate 45 (50 g, 152 mmol) in phosphoryl chloride (280 mL, 3010 mmol) at room temperature was added phosphorus pentachloride (36 g, 172 mmol). After a few minutes most of the precipitates in the reaction mixture had dissolved and a dark orange suspension was obtained (small amount of gas evolution was noted). Keeping the reaction mixture at room temperature, HCl (produced in situ from step-wise addition of sulfuric acid to NaCl) was bubbled through the reaction mixture for 30 min. The mixture was then heated to 80° C. Slow but steady gas evolution was noted. After 15 minutes the evolution of gas ceased. NOTE: After the first hour of heating, more phosphorus pentachloride (6 g, 28.8 mmol) was added. After a total of about 4 hours of heating, the mixture was concentrated under reduced pressure. The residue (green solid) was cooled in an ice/water bath and treated with water (~80 mL). The grey precipitate was collected by filtration.

Step 2: To a solution of the grey precipitate from step 1 above (50 g, 137 mmol) in AcOH was added HCl (70 mL, 514 mmol, 57 mass %) followed by red phosphorus (9.5 g, 310 mmol). The mixture was heated to 110° C. for approx. 15 hours. Volatiles were evaporated, and the crude was suspended in water. Concentrated ammonium hydroxide solution was added to adjust the pH to 8-9. DCM and water were added to the slurry and the layers were separated. Organics were dried with sodium sulfate and evaporated to afford the title compound (33 g, 62% yield). $^1$H NMR (300 MHz, Chloroform-d) δ 8.95 (d, J=0.8 Hz, 1H), 8.20 (s, 1H), 7.95 (d, J=0.7 Hz, 1H), 3.34 (t, J=7.5 Hz, 2H), 3.11 (t, J=7.5 Hz, 2H), 2.39-2.22 (m, 21H). LCMS $[M+H]^+$330, RT 3.08 min (Method 4).

Intermediates 47 and 48

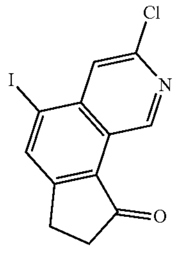
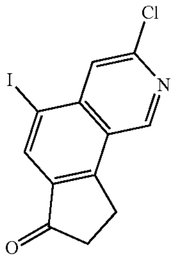

3-chloro-5-iodo-7,8-dihydrocyclopenta[h]isoquinolin-9-one (47)

3-chloro-5-iodo-8,9-dihydrocyclopenta[h]isoquinolin-7-one (48)

Intermediate 46 (47 mmol, 15.5 g) was suspended in DCM (500 mL). Chromium (VI) oxide (5 mmol, 500 mg) and 70% aqueous t-butyl hydroperoxide (930 mmol, 120 mL) were added at room temperature and the reaction was stirred vigorously overnight. The reaction mixture was then quenched with a saturated aqueous solution of $Na_2S_2O_5$ at 0° C. The two layers were then separated, and the organic layer washed with water, dried with sodium sulfate and evaporated to dryness. The resulting residue was dry loaded onto silica and purified by column chromatography eluting with a 0 to 20% EtOAc in toluene gradient to give the title compounds:

Intermediate 47 (5.9 g, 37% yield); $^1$H NMR (300 MHz, Chloroform-d) δ 10.19 (d, J=0.9 Hz, 1H), 8.46 (s, 1H), 8.03 (d, J=0.8 Hz, 1H), 3.41-3.16 (m, 2H), 3.04-2.73 (m, 2H). LCMS $[M+H]^+$ 344, RT 1.47 min (Method 5).

Intermediate 48 (3.4 g, 21% Yield); $^1$H NMR (300 MHz, Chloroform-d) δ 9.22 (d, J=0.8 Hz, 1H), 8.54 (s, 1H), 8.10 (d, J=0.7 Hz, 1H), 3.77-3.36 (m, 2H), 3.21-2.74 (m, 2H). LCMS $[M+H]^+$ 344, RT 1.43 min (Method 5).

Intermediate 49

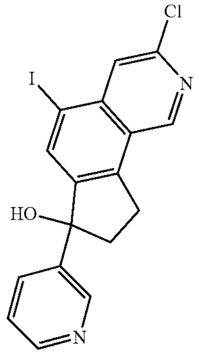 [SMILES: OC1(c2cccnc2)CCc2c1cc(I)c1cc(Cl)ncc21]

3-chloro-5-iodo-7-(3-pyridyl)-8,9-dihydrocyclopenta[h]isoquinolin-7-ol

To a stirred solution of 3-bromopyridine (0.1 g, 0.63 mmol) in anhydrous THF (2 mL) at −78° C. under an atmosphere of $N_2$ was added 2.5 M N-butyllithium (0.30 mL, 0.75 mmol) in hexanes. The reaction mixture was stirred at −78° C. for 20 min and then a solution of Intermediate 48 (217 mg, 0.63 mmol) in anhydrous THF (3 mL) was added dropwise over 10 min. Upon completion of addition, the cooling bath was removed, and the reaction allowed to warm to ambient temperature overnight. The reaction was quenched by addition of saturated aqueous $NH_4Cl$ (3 mL) and diluted with a mixture of water (5 mL) and EtOAc (5 mL). The organic layer was partitioned, dried over $Na_2SO_4$ and concentrated in vacuo. The crude product was purified by column chromatography to afford the title compound (53 mg, 20% yield). LCMS $[M+H]^+$ 423/425, RT 1.09 min (Method 1).

Intermediate 50

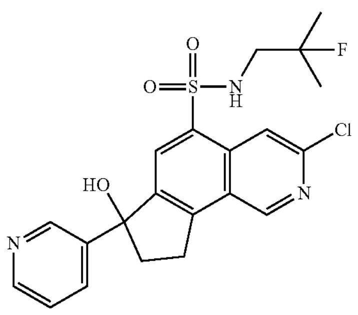 [SMILES: CC(C)(F)CNS(=O)(=O)c1cc2c(c3cnc(Cl)cc13)CCC2(O)c1cccnc1]

3-chloro-N-(2-fluoro-2-methyl-propyl)-7-hydroxy-7-(3-pyridyl)-8,9-dihydrocyclopenta[h]isoquinoline-5-sulfonamide Intermediate 49 (53 mg, 0.12 mmol), 1,4-diazabicyclo [2.2.2]octane bis(sulfur dioxide) adduct (19 mg, 0.08 mmol), palladium(II) acetate (1.5 mg, 0.006 mmol) and butyl di-1-adamantylphosphine (3.4 mg, 0.009 mmol) were charged to a sealed tube. Triethylamine (52 μL, 0.38 mmol) and anhydrous IPA (2 mL) were added and the reaction sealed and heated to 75° C. overnight. The reaction was treated with 2-fluoro-2-methylpropan-1-amine HCl (51 mg, 0.38 mmol) and aq. sodium hypochlorite solution (0.16 mL, 0.25 mmol) and stirred at ambient temperature for 3 h. The reaction was diluted with EtOAc (5 mL) and washed with water (5 mL). The organic phase was dried over $Na_2SO_4$ and concentrated in vacuo. The crude product was purified by column chromatography to afford the title compound (11 mg, 10% yield). LCMS $[M+H]^+$ 450/452, RT 0.98 min (Method 1).

Intermediate 51

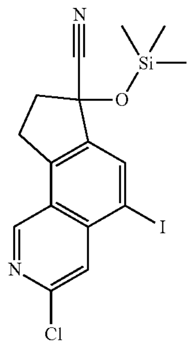 [SMILES: C[Si](C)(C)OC1(C#N)CCc2c1cc(I)c1cc(Cl)ncc21]

3-chloro-5-iodo-7-trimethylsilyloxy-8,9-dihydrocyclopenta[h]isoquinoline-7-carbonitrile To a solution of Intermediate 48 (1.2 g, 3.5 mmol) in toluene (20 mL) and acetonitrile (10 mL) was added zinc iodide (110 mg, 0.35 mmol) and trimethylsilyl cyanide (1.3 mL, 10 mmol). The reaction was heated to 75° C. overnight with stirring then treated with trimethylsilyl cyanide (2.0 mL) and heated at 75° C. for 4.5 hours. The reaction was cooled and quenched with sat. aq. $NaHCO_3$ (25 mL) and extracted with EtOAc (100 mL). The organic phase was partitioned, dried over $Na_2SO_4$ and concentrated in vacuo. Purification by column chromatography gave the title compound (694 mg, 45% Yield). $^1H$ NMR (300 MHz, Chloroform-d) δ 9.02 (d, J=0.8 Hz, 1H), 8.35 (s, 1H), 8.03 (d, J=0.8 Hz, 1H), 3.62-3.31 (m, 2H), 3.02 (ddd, J=13.5, 7.8, 4.6 Hz, 1H), 2.61 (ddd, J=13.5, 8.3, 6.3 Hz, 1H), 0.32 (s, 9H).

Intermediate 52

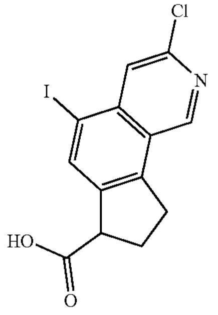 [SMILES: O=C(O)C1CCc2c1cc(I)c1cc(Cl)ncc21]

3-chloro-5-iodo-8,9-dihydro-7H-cyclopenta[h]isoquinoline-7-carboxylic Acid

Stannous chloride (1.69 g, 8.70 mmol) was added to Intermediate 51 (967 mg, 2.18 mmol) followed by glacial acetic acid (4.0 mL) and then conc. aq. hydrochloric acid (4.0 mL). The reaction vessel was sealed and placed in a pre-heated block (140° C.) for 2.5 hours with vigorous stirring. The reaction was cooled, diluted with water (10 mL) and extracted with 10% MeOH in DCM (3×20 mL). The combined organic extracts were dried over $Na_2SO_4$ and concentrated in vacuo to afford the title compound (0.58 g, 50% Yield). LCMS $[M+H]^+$374, RT 1.39 min (Method 1).

Intermediate 53

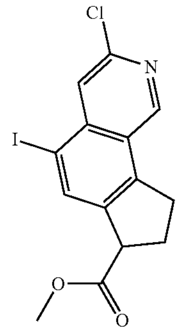 [SMILES: COC(=O)C1CCc2c1cc(I)c1cc(Cl)ncc21]

methyl 3-chloro-5-iodo-8,9-dihydro-7H-cyclopenta[h]isoquinoline-7-carboxylate

To an ice-cold suspension of intermediate 52 (0.58 g, 0.93 mmol) in methanol (10 mL) was added dropwise thionyl chloride (0.14 mL, 1.9 mmol). Upon completion of addition, the ice bath was removed, and the reaction allowed to warm to ambient temperature for 2 hours. The reaction was concentrated in vacuo and the crude product was purified by column chromatography to afford the title compound (125 mg, 35% Yield). $^1H$ NMR (300 MHz, Chloroform-d) δ 8.95 (d, J=0.8 Hz, 1H), 8.31 (s, 1H), 7.96 (d, J=0.7 Hz, 1H), 4.23 (dd, J=8.7, 5.8 Hz, 1H), 3.78 (s, 3H), 3.59-3.42 (m, 1H), 3.40-3.23 (m, 1H), 2.76-2.47 (m, 2H). LCMS $[M+H]^+$ 388/390, RT 1.36 min (Method 1).

Intermediate 54

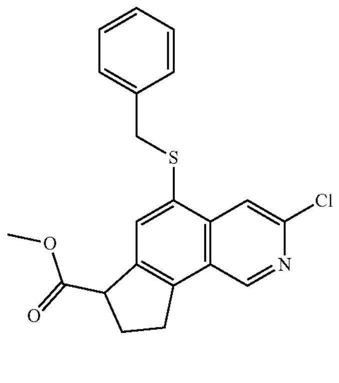 [SMILES: COC(=O)C1CCc2c1cc(SCc1ccccc1)c1cc(Cl)ncc21]

methyl 5-benzylsulfanyl-3-chloro-8,9-dihydro-7H-cyclopenta[h]isoquinoline-7-carboxylate A mixture of intermediate 53 (125 mg, 0.32 mmol), 4,5-bis(diphenylphosphino)-9,9-dimethylxanthene (23 mg, 0.039 mmol), tris(dibenzylideneacetone)dipalladium(0) (18 mg, 0.019 mmol) and N,N-diisopropylethylamine (135 µL, 0.77 mmol) in 1,4-dioxane (2 mL) was purged with nitrogen for 5 minutes before addition of benzyl mercaptan (61 mg, 0.48 mmol). The mixture was heated to 85° C. with stirring for 1.5 hours. The mixture was cooled, diluted with DCM (10 mL) and washed with sat. aq. $NaHCO_3$ (5 mL). The organic layer was passed through a phase separator and the volatiles removed in vacuo. The crude product was purified by column chromatography to afford the title compound (102 mg, 76% Yield); $^1$H NMR (300 MHz, Chloroform-d) δ 9.02 (d, J=0.8 Hz, 1H), 8.18 (d, J=0.8 Hz, 1H), 7.74 (s, 1H), 7.25-7.10 (m, 5H), 3.71 (s, 3H), 3.59-3.42 (m, 1H), 3.40-3.23 (m, 1H), 2.74-2.44 (m, 2H), 2.04 (s, 3H).

Intermediate 55

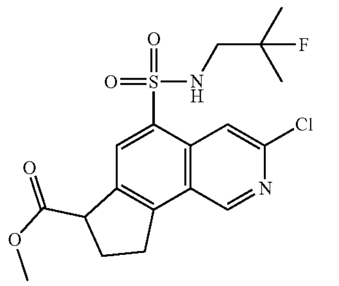 [SMILES: COC(=O)C1CCc2c1cc(S(=O)(=O)NCC(C)(C)F)c1cc(Cl)ncc21]

methyl 3-chloro-5-[(2-fluoro-2-methyl-propyl)sulfamoyl]-8,9-dihydro-7H-cyclopenta[h]isoquinoline-7-carboxylate To an ice-cold solution of Intermediate 54 (350 mg, 0.87 mmol) in a mixture of acetonitrile (6 mL), water (0.100 mL) and acetic acid (0.06 mL) was added 1,3-dichloro-5,5-dimethylhydantoin (380 mg, 1.93 mmol) and the reaction stirred for 10 min. 2-Fluoro-2-methyl-propan-1-amine hydrochloride (232 mg, 1.82 mmol) was added followed by N,N-diisopropylethylamine (0.60 mL, 3.5 mmol). The mixture was stirred at ambient temperature for 15 min then concentrated in vacuo. The crude residue was purified by column chromatography to afford title compound (160 mg, 42% Yield). LCMS [M+H]$^+$ 415, RT 1.49 min (Method 5).

Intermediate 56

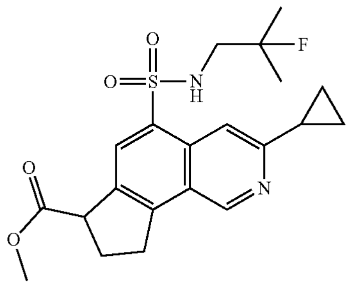 [SMILES: COC(=O)C1CCc2c1cc(S(=O)(=O)NCC(C)(C)F)c1cc(C3CC3)ncc21]

methyl 3-cyclopropyl-5-[(2-fluoro-2-methyl-propyl)sulfamoyl]-8,9-dihydro-7H-cyclopenta[h]isoquinoline-7-carboxylate To a solution of intermediate 55 (65 mg, 0.16 mmol) in 1,4-dioxane (1 mL) was added cyclopropylboronic acid (42 mg, 0.47 mmol), Chloro($\eta^2$—P,C-tris(2,4-di-tert-butylphenyl)phosphite)(tricyclohexylphosphine)palladium(II) (17 mg, 0.016 mmol), and caesium carbonate (128 mg, 0.39 mmol). The mixture was degassed under a stream of $N_2$ for 5 min and sealed and heated to 120° C. for 2 hours. The reaction was diluted with EtOAc (5 mL) and washed with sat. aq. $NaHCO_3$ (2.5 mL). The organic layer was dried over $Na_2SO_4$ and concentrated in vacuo. The crude product was purified by flash chromatography to afford title compound (3 mg, 4.5% Yield). $^1$H NMR (400 MHz, Chloroform-d) δ 9.21 (d, J=1.0 Hz, 1H), 8.38 (s, 1H), 8.23 (d, J=1.0 Hz, 1H), 4.96 (t, J=6.5 Hz, 1H), 4.32-4.21 (m, 1H), 3.71 (s, 3H), 3.63-3.47 (m, 1H), 3.38 (ddd, J=17.0, 9.0, 5.9 Hz, 1H), 3.03 (ddd, J=19.7, 6.6, 2.0 Hz, 2H), 2.80-2.55 (m, 2H), 2.24 (tt, J=8.1, 4.8 Hz, 1H), 1.29 (d, J=3.4 Hz, 6H), 0.73-0.36 (m, 4H).

Intermediate 57

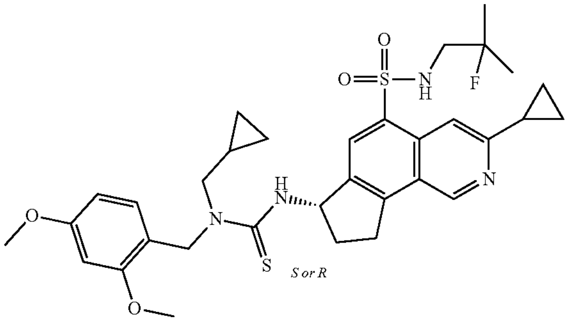 [SMILES: COc1ccc(CN(CC2CC2)C(=S)N[C@H]2CCc3c2cc(S(=O)(=O)NCC(C)(C)F)c2cc(C4CC4)ncc32)c(OC)c1]

1-(cyclopropylmethyl)-1-[(2,4-dimethoxyphenyl)methyl]-3-[(7S*)-3-cyclopropyl-5-[(2-fluoro-2-methyl-propyl)sulfamoyl]-8,9-dihydro-7H-cyclopenta[h]isoquinolin-7-yl]thiourea [* or R]

To a stirred solution of Intermediate 38 (75 mg, 0.20 mmol) in dichloromethane (1 mL) was added 1,1'-thiocarbonyldiimidazole (43 mg, 0.22 mmol). The reaction mixture was stirred at room temperature for 1.5 hours. N-(cyclopropylmethyl)-1-(2,4-dimethoxyphenyl)methanamine (66 mg, 0.30 mmol) was then added and the reaction stirred for a further hour. The reaction mixture was diluted with DCM (1 mL) and washed with sat. aq. $NH_4Cl$ (1 mL) and 0.5 M aqueous HCl (1 mL) to afford the title compound (168 mg, 60% purity, 79%). LCMS $[M+H]^+$ 641, RT 2.95 min (Method 7).

Intermediate 58

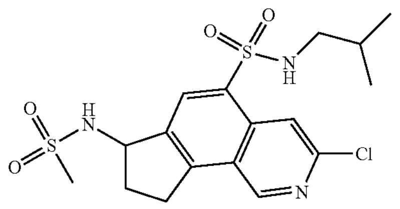 [SMILES: CC(C)CNS(=O)(=O)c1cc2c(c3cnc(Cl)cc13)CCC2NS(C)(=O)=O]

3-chloro-N-isobutyl-7-(methanesulfonamido)-8,9-dihydro-7H-cyclopenta[h]isoquinoline-5-sulfonamide To a stirred solution of intermediate 9 (330 mg, 0.61 mmol, 65%) in anhydrous DCM (10 mL) were added DIPEA (0.32 mL, 1.87 mmol) and methanesulfonyl chloride (87.2 μl, 1.12 mmol). The reaction mixture was stirred at room temperature for 15 hours. The reaction mixture was then washed with water (10 mL) and brine (10 mL), dried ($MgSO_4$), filtered and concentrated in vacuo. The crude material was purified by column chromatography using a gradient of 2-20% MeOH in DCM to give title compound (0.26 g, 62% Yield) as a beige foam. LCMS $[M+H]^+$ 432, RT 1.10 min (Method 17).

Intermediates 59 & 60

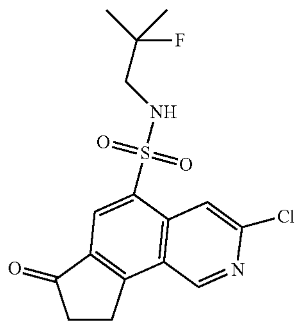

-continued

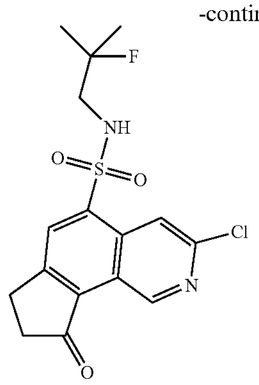

3-chloro-N-(2-fluoro-2-methyl-propyl)-7-oxo-8,9-dihydrocyclopenta[h]isoquinoline-5-sulfonamide (59)

3-chloro-N-(2-fluoro-2-methyl-propyl)-9-oxo-7,8-dihydrocyclopenta[h]isoquinoline-5-sulfonamide (60)

To a solution of potassium tetrachloroaurate(III) (2.6 mg, 7.0 μmol) in pyridine (0.2 mL, 2 mmol) was added intermediate 15 (50 mg, 0.14 mmol) followed by tert-butyl hydroperoxide (0.05 mL, 0.28 mmol). The reaction was sealed and heated to 90° C. with stirring for 1 hour. The reaction was cooled and purified by column chromatography to afford the title compounds:

Intermediate 59 (15 mg, 29% yield): $^1H$ NMR (300 MHz, Chloroform-d) δ 9.39 (d, J=0.8 Hz, 1H), 8.63-8.56 (m, 2H), 5.40 (t, J=6.4 Hz, 1H), 3.69-3.61 (m, 2H), 3.12 (dd, J=20.2, 6.4 Hz, 2H), 2.99-2.91 (m, 2H), 1.32 (d, J=21.4 Hz, 6H).

Intermediate 60 (15 mg, 29% yield): $^1H$ NMR (300 MHz, Chloroform-d) δ 10.30 (d, J=0.9 Hz, 1H), 8.52-8.45 (m, 2H), 5.53 (t, J=6.3 Hz, 1H), 3.38-3.31 (m, 2H), 3.15 (dd, J=20.0, 6.4 Hz, 2H), 2.96-2.89 (m, 2H), 1.32 (d, J=21.4 Hz, 6H).

Intermediate 61

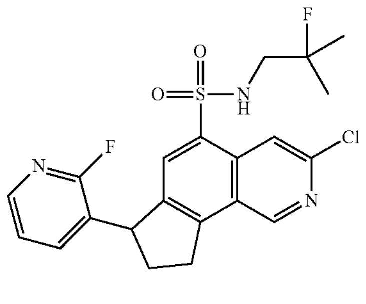 [SMILES: CC(C)(F)CNS(=O)(=O)c1cc2c(c3cnc(Cl)cc13)CCC2c1cccnc1F]

3-chloro-N-(2-fluoro-2-methyl-propyl)-7-(2-fluoro-3-pyridyl)-8,9-dihydro-7H-cyclopenta[h]isoquinoline-5-sulfonamide Intermediate 59 (270 mg, 0.73 mmol) and 4-methylbenzenesulfonohydrazide (140 mg, 0.73 mmol) were suspended in anhydrous 1,4-dioxane (7.0 mL) and the mixture heated to 80° C. for 45 min. Potassium carbonate (251 mg, 1.82 mmol) and 2-fluoropyridine-3-boronic acid hydrate (177 mg, 1.09 mmol) were added and heating continued at 110° C. for 4 hours. The reaction was cooled, diluted with EtOAc (25 mL) and washed with sat. aq. $NaHCO_3$ (25 mL). The aqueous phase was extracted with EtOAc (25 mL) and the combined organic extracts dried over $Na_2SO_4$ and concentrated in vacuo. Purification by column chromatography gave the title compound (122 mg, 32% Yield); $^1$H NMR (300 MHz, Chloroform-d) δ 9.23 (d, J=0.9 Hz, 1H), 8.51 (d, J=0.9 Hz, 1H), 8.17 (dt, J=4.8, 1.5 Hz, 1H), 8.07 (s, 1H), 7.44 (ddd, J=9.7, 7.4, 2.0 Hz, 1H), 7.17 (ddd, J=7.1, 4.9, 1.8 Hz, 1H), 4.94 (t, J=6.4 Hz, 1H), 4.83 (t, J=8.2 Hz, 1H), 3.74-3.59 (m, 1H), 3.55-3.39 (m, 1H), 3.13-2.86 (m, 3H), 2.52-2.26 (m, 1H), 1.27 (dd, J=21.4, 5.0 Hz, 6H).

Intermediate 62

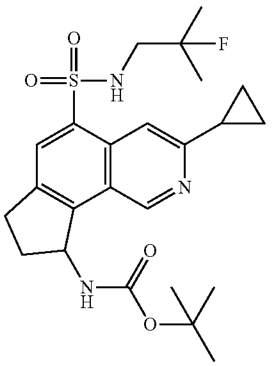 [SMILES: CC(C)(F)CNS(=O)(=O)c1cc2c(c3cnc(C4CC4)cc13)C(NC(=O)OC(C)(C)C)CC2]

tert-butyl N-[3-cyclopropyl-5-[(2-fluoro-2-methyl-propyl)sulfamoyl]-8,9-dihydro-7H-cyclopenta[h]isoquinolin-9-yl]carbamate A mixture of intermediate 33 (1140 mg, 2.41 mmol), cyclopropylboronic acid (652 mg, 7.214 mmol) and palladium(II) acetate (27 mg, 0.120 mmol) in toluene (10 mL) was degassed and placed under an atmosphere of nitrogen. Tricyclohexylphosphonium tetrafluoroborate (137 mg, 0.361 mmol) and a solution of potassium phosphate tribasic (1280 mg, 6.01 mmol) in water (1 mL) were added, the mixture was degassed and placed under an atmosphere of nitrogen. The reaction mixture was heated at 120° C. for 2 hours in the microwave. The reaction mixture was cooled and then diluted with EtOAc, washed with water then brine, passed through a phase separator and evaporated. The crude material was purified by flash chromatography eluting with a gradient of 10-60% EtOAc in hexane to afford the title compound as an off-white solid (938 mg, 82% yield). LCMS [M+H]$^+$ 478, RT 2.70 min (Method 3).

Intermediates 63 & 64

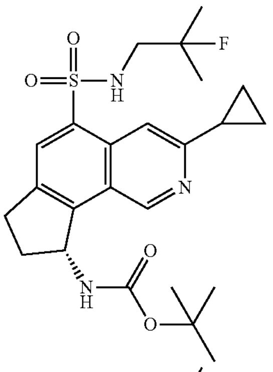

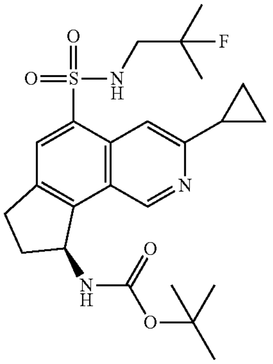

tert-butyl N-[(9R)-3-cyclopropyl-5-[(2-fluoro-2-methyl-propyl)sulfamoyl]-8,9-dihydro-7H-cyclopenta[h]isoquinolin-9-yl]carbamate tert-butyl N-[(9S)-3-cyclopropyl-5-[(2-fluoro-2-methyl-propyl)sulfamoyl]-8,9-dihydro-7H-cyclopenta[h]isoquinolin-9-yl]carbamate The title compounds were obtained by separation of intermediate 62 using chiral SFC with the following conditions: Column—Chir AS 265×50 mm, 5 μM. Flow rate—360 ml/min. Column Temp—30° C. Mobile Phase—10% EtOH in $CO_2$. Run Time—10 mins.

Note: In intermediates 63 and 64 one is the R-enantiomer and the other is the S-enantiomer, we have not assigned which enantiomer is which intermediate.

Intermediate 63: Chiral RT**=2.55 min; $^1$H NMR (300 MHz, Chloroform-d) δ 9.44 (d, J=0.9 Hz, 1H), 8.24 (s, 1H), 8.20 (d, J=0.9 Hz, 1H), 5.86-5.71 (m, 1H), 4.96 (t, J=6.5 Hz, 1H), 4.86 (d, J=8.9 Hz, 1H), 3.32-3.16 (m, 1H), 3.11-2.93 (m, 3H), 2.80-2.62 (m, 1H), 2.29-2.14 (m, 2H), 1.47 (s, 9H), 1.33 (dd, J=21.5, 6.9 Hz, 6H), 1.21-1.03 (m, 4H).

Intermediate 64: Chiral RT** 1.92 min; $^1$H NMR (300 MHz, Chloroform-d) δ 9.43 (d, J=0.9 Hz, 1H), 8.24 (s, 1H), 8.20 (d, J=0.9 Hz, 1H), 5.89-5.67 (m, 1H), 4.97 (t, J=6.5 Hz, 1H), 4.86 (d, J=9.0 Hz, 1H), 3.34-3.18 (m, 1H), 3.13-2.93 (m, 3H), 2.82-2.62 (m, 1H), 2.31-2.13 (m, 2H), 1.47 (s, 9H), 1.33 (dd, J=21.5, 6.9 Hz, 6H), 1.21-0.99 (m, 4H).

** Chiral analysis was carried out by Normal Phase using a Lux Cellulose-2, 4.6×150 mm, 3 μm column, flow rate 1.5 mL/min eluting with 50% ethanol: 50% n-heptane (+0.1% diethylamine), using an 8 min run time on an Agilent 1290 Infinity UV directed system.

Intermediate 65

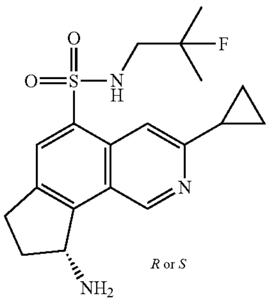 [SMILES: CC(C)(F)CNS(=O)(=O)c1cc2c(c3cnc(C4CC4)cc13)[C@H](N)CC2]

(9R*)-9-amino-3-cyclopropyl-N-(2-fluoro-2-methyl-propyl)-8,9-dihydro-7H-cyclopenta[h]isoquinoline-5-sulfonamide [* or S]

Intermediate 63 (200 mg, 0.42 mmol) was dissolved in dichloromethane (2.0 mL) and trifluoroacetic acid (1.0 mL) was added. The reaction was stirred at ambient temperature overnight, concentrated in vacuo, then dissolved in MeOH (1.5 mL) and absorbed onto an SCX cartridge. The cartridge was washed with MeOH (10 mL) and the product eluted with 7N MeOH in ammonia (10 mL). The methanolic ammonia was removed in vacuo to afford the title compound (155 mg, 93% Yield). $^1$H NMR (300 MHz, Chloroform-d) δ 9.68 (s, 1H), 8.37-8.34 (m, 2H), 8.14 (s, 1H), 4.93 (dd, J=7.6, 3.7 Hz, 1H), 3.25 (d, J=41.9 Hz, 2H), 3.00-2.83 (m, 4H), 2.56-2.40 (m, 1H), 2.28 (tt, J=7.7, 5.8 Hz, 1H), 1.93 (ddt, J=12.7, 8.3, 4.2 Hz, 1H), 1.23 (d, J=21.4 Hz, 6H), 1.09-0.98 (m, 4H).

Intermediate 66

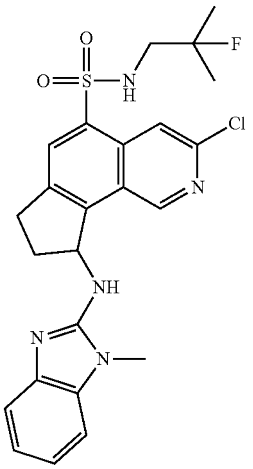 [SMILES: Cn1c(NC2CCc3cc(S(=O)(=O)NCC(C)(C)F)c4cc(Cl)ncc4c32)nc2ccccc21]

3-chloro-N-(2-fluoro-2-methyl-propyl)-9-[(1-methylbenzimidazol-2-yl)amino]-8,9-dihydro-7H-cyclopenta[h]isoquinoline-5-sulfonamide Intermediate 16 (50 mg, 0.12 mmol) and 2-amino-1-methylbenzimidazole (36 mg, 0.24 mmol) were suspended in anhydrous toluene (1 mL) and the mixture heated to 70° C. overnight. The reaction was cooled and diluted with EtOAc (2 mL) and washed with sat. aq. $NaHCO_3$ (1 mL). The organic phase was dried over $Na_2SO_4$ and concentrated in vacuo. The resulting crude product by column chromatography to afford the title compound (13 mg, 23% Yield); $^1$H NMR (400 MHz, Chloroform-d) δ 9.39 (s, 1H), 8.34 (d, J=4.0 Hz, 2H), 7.49 (d, J=7.4 Hz, 1H), 7.15-7.00 (m, 3H), 6.35 (td, J=8.1, 3.9 Hz, 1H), 5.51-5.10 (m, 1H), 4.81 (s, 1H), 3.46 (s, 3H), 3.34 (dt, J=15.7, 7.4 Hz, 1H), 3.24-2.91 (m, 4H), 2.37 (ddt, J=13.3, 8.8, 4.4 Hz, 1H), 1.43-1.26 (m, 6H).

Intermediates 67 & 68

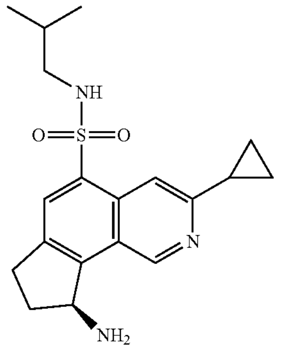

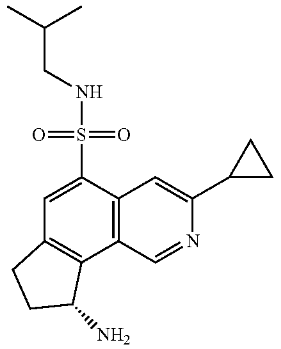

(9S)-9-amino-3-cyclopropyl-N-isobutyl-8,9-dihydro-7H-cyclopenta[h]isoquinoline-5-sulfonamide (9R)-9-amino-3-cyclopropyl-N-isobutyl-8,9-dihydro-7H-cyclopenta[h]isoquinoline-5-sulfonamide The title compounds were obtained by separation of Intermediate 39 using chiral SFC with the following conditions: Column—Chiralcel OJ-H 250×20 mm, 5 μM. Flow rate—100 mL/min. Column Temp—40° C. Mobile Phase—10-25% gradient MeOH+0.1% $NH_4OH$ in $CO_2$. Run Time—6 min.

Note: In intermediates 67 and 68 one is the R-enantiomer and the other is the S-enantiomer, we have not assigned which enantiomer is which intermediate.

Intermediate 67: Chiral SFC RT**=2.28 min

Intermediate 68: Chiral SFC RT**=3.23 min

**Chiral analysis was carried out by SFC, using a Chiralcel OJ-3 4.6×150 mm, 3 μm column, flow rate 3.5 mL/min eluting with 10-25% Methanol (0.1% ammonium hydroxide) using a 6 min run time on a Waters UPC$^2$-SQD system.

Intermediate 69

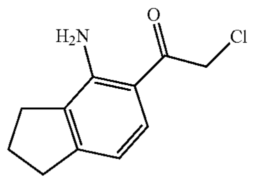 [SMILES: Nc1c(C(=O)CCl)ccc2c1CCC2]

1-(4-aminoindan-5-yl)-2-chloro-ethanone

To an ice-cold solution of boron trichloride-methyl sulfide complex (25.4 g, 140 mmol) in 1,2-dichloroethane (400 mL) was added indan-4-amine (17 g, 128 mmol) dropwise over 5 min. The solution was stirred at 0° C. for 10 min. Chloroacetonitrile (10 mL, 160 mmol) and aluminium chloride (18.7 g, 140 mmol) were added and the reaction warmed to ambient temperature over 10 min and then refluxed for 2 hours. The reaction was cooled to ambient temperature and 2 M HCl (300 mL) was added in portions. The quench was heated to 80° C. for 20 min, cooled and diluted with DCM (250 mL). The organic phase was partitioned, and the aqueous phase extracted with DCM (2×250 mL). The combined organic extracts were dried over $Na_2SO_4$ and the solvents removed in vacuo. The solid was triturated with EtOAc and dried to afford the title compound (7.13 g, 27% Yield). $^1$H NMR (400 MHz, Chloroform-d) δ 7.50 (d, J=8.2 Hz, 1H), 6.62 (d, J=8.2 Hz, 1H), 4.68 (s, 2H), 3.01-2.83 (m, 2H), 2.74 (t, J=7.4 Hz, 2H), 2.15 (p, J=7.6 Hz, 2H). $NH_2$ protons not visible Intermediate 70

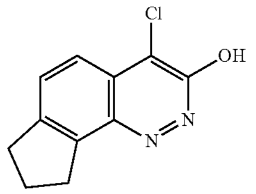 [SMILES: Oc1nnc2c3c(ccc2c1Cl)CCC3]

4-chloro-8,9-dihydro-7H-cyclopenta[h]cinnolin-3-ol

Intermediate 69 (7100 mg, 34 mmol) was dissolved in acetic acid (35 mL) and aqueous hydrochloric acid (1.2 M, 35 mL) and cooled in an ice bath prior to portion-wise addition of sodium nitrite (12 g, 170 mmol). Upon completion of addition, the reaction was stirred at 0° C. for 5 min and then at ambient temperature for 2 hours. Sodium nitrite (5.4 g, 78.4 mmol) was added at ambient temperature and stirring continued for 30 min. The reaction was diluted with water (50 mL) and extracted with 1:1 $CHCl_3$:IPA (3×100 mL). The combined organic extracts were dried ($Na_2SO_4$) and concentrated in vacuo. The product was purified by column chromatography followed by trituration with EtOAc to afford the title compound (0.96 g, 13% Yield); $^1$H NMR (400 MHz, DMSO-d6) δ 7.92 (d, J=8.2 Hz, 1H), 7.40 (d, J=8.3 Hz, 1H), 3.11 (t, J=7.5 Hz, 2H), 3.03 (t, J=7.5 Hz, 2H), 2.19 (p, J=7.6 Hz, 2H). OH proton not visible.

Intermediate 71

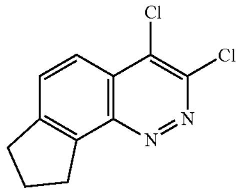 [SMILES: Clc1nnc2c3c(ccc2c1Cl)CCC3]

3,4-dichloro-8,9-dihydro-7H-cyclopenta[h]cinnoline

A slurry of Intermediate 70 (3.6 g, 16.3 mmol) in phosphorus oxychloride (127 mmol, 12.0 mL) was stirred for 45 min at 75° C. The reaction mixture was then cooled and concentrated in vacuo and the residue dissolved in DCM (100 mL) and washed with sat. aq. $NaHCO_3$ (100 mL). The organic layer was partitioned, and the aqueous layer extracted with DCM (50 mL). The combined organic extracts were dried over $Na_2SO_4$ and the solvent removed in vacuo to afford the title compound (3.29 g, 80% Yield); $^1$H NMR (300 MHz, Chloroform-d) δ 8.07-7.90 (m, 1H), 7.78 (d, J=8.6 Hz, 1H), 3.78-3.57 (m, 2H), 3.20 (t, J=7.4 Hz, 2H), 2.37 (p, J=7.7 Hz, 2H).

Intermediate 72

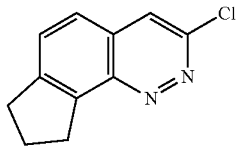 [SMILES: Clc1cc2ccc3c(c2nn1)CCC3]

3-chloro-8,9-dihydro-7H-cyclopenta[h]cinnoline

Intermediate 71 (3.29 g, 13.8 mmol) was dissolved in chloroform (50 mL) and 4-methylbenzenesulfonohydrazide (5280 mg, 27.5 mmol) was added. The reaction was heated at 60° C. overnight then cooled and concentrated in vacuo. The residue was taken up in a mixture of water (150 mL) and 1,4-dioxane (15 mL). Sodium carbonate (13.1 g, 124 mmol) was added and the reaction heated to 95° C. with vigorous stirring for 3 h. The reaction was cooled and extracted with DCM (4×150 mL). The combined organic extracts were dried over $Na_2SO_4$ and the solvents removed in vacuo to afford a brown solid, which was triturated with $Et_2O$ (20 mL), filtered and dried to afford the title compound (1.63 g, 49% Yield); $^1$H NMR (300 MHz, Chloroform-d) δ 7.89 (s, 1H), 7.69 (d, J=8.4 Hz, 1H), 7.59 (d, J=8.3 Hz, 1H), 3.65 (t, J=7.6 Hz, 2H), 3.18 (t, J=7.6 Hz, 2H), 2.35 (p, J=7.6 Hz, 2H).

Intermediate 73

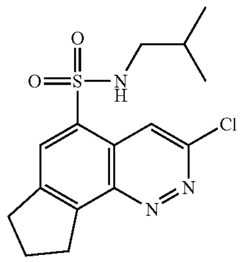 [SMILES: CC(C)CNS(=O)(=O)c1cc2c(c3nnc(Cl)cc13)CCC2]

3-chloro-N-isobutyl-8,9-dihydro-7H-cyclopenta[h]cinnoline-5-sulfonamide

Intermediate 72 (225 mg, 1.1 mmol) was added to a sealed tube prior to addition of chlorosulfonic acid (1.94 g, 16.5 mmol). The reaction was sealed and heated to 120° C. with stirring for 6 hours. The reaction was poured slowly into a mixture of ice and DCM (100 mL) and diluted with a mixture of DCM and brine (100 mL). The organic phase was dried over $Na_2SO_4$ and treated with 2-methylpropan-1-amine (1608 mg, 21.99 mmol) and stirred for 15 min at room temperature. The reaction was concentrated in vacuo and the crude product was purified by column chromatography to afford the title compound (77 mg, 21% Yield) $^1$H NMR (400 MHz, Chloroform-d) δ 8.69 (s, 1H), 8.40 (s, 1H), 4.68 (t, J=6.4 Hz, 1H), 3.78-3.65 (m, 2H), 3.31-3.17 (m, 2H), 2.76 (t, J=6.6 Hz, 2H), 2.41 (p, J=7.7 Hz, 2H), 1.70 (dp, J=13.4, 6.7 Hz, 1H), 0.83 (d, J=6.7 Hz, 6H).

Intermediate 74

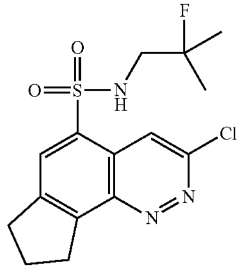 [SMILES: CC(C)(F)CNS(=O)(=O)c1cc2c(c3nnc(Cl)cc13)CCC2]

3-chloro-N-(2-fluoro-2-methyl-propyl)-8,9-dihydro-7H-cyclopenta[h]cinnoline-5-sulfonamide To a sealed pressure tube Intermediate 72 (1.63 g, 7.96 mmol) was added followed by chlorosulfonic acid (8.03 mL, 119 mmol). The flask was sealed and heated at 120° C. overnight. The reaction mixture was diluted with dichloromethane (200 mL) and then added to stirred ice-water (200 mL) over 25 minutes. The organic layer was dried with $Na_2SO_4$ and concentrated in vacuo and then dissolved in DCM (100 mL). 2-Fluoro-2-methylpropan-1-amine HCl (1.28 g, 9.56 mmol) was added followed by dropwise addition of triethylamine (2.01 g, 19.9 mmol). The reaction mixture was stirred at room temperature for 1 hour, washed with water (100 mL) and the organic layer partitioned. The aqueous phase was extracted with DCM (50 mL) and the combined organic extracts dried over $Na_2SO_4$. The solvent was removed in vacuo and the crude product purified by column chromatography to the title compound (480 mg, 17% Yield); $^1$H NMR (300 MHz, Chloroform-d) δ 8.67 (s, 1H), 8.38 (s, 1H), 5.23 (t, J=6.4 Hz, 1H), 3.71 (tt, J=8.4, 1.5 Hz, 2H), 3.31-3.18 (m, 2H), 3.09 (dd, J=19.8, 6.5 Hz, 2H), 2.41 (p, J=7.7 Hz, 2H), 1.31 (d, J=21.4 Hz, 6H).

Intermediates 75 & 76

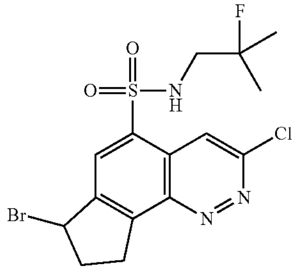

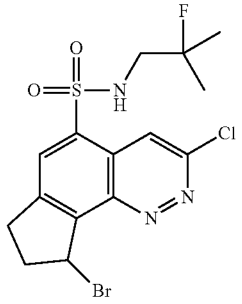

7-bromo-3-chloro-N-(2-fluoro-2-methyl-propyl-8,9-dihydro-7H-cyclopenta[h]cinnoline-5-sulfonamide (75)

9-bromo-3-chloro-N-(2-fluoro-2-methyl-propyl)-8,9-dihydro-7H-cyclopenta[h]cinnoline-5-sulfonamide (76)

To a stirred solution of Intermediate 74 (455 mg, 1.27 mmol) in EtOAc (10 mL) at ambient temperature was added N-bromosuccinimide (294 mg, 1.65 mmol) followed by 2,2'-azobis(2-methylpropionitrile) (21 mg, 0.13 mmol). The reaction was sealed and heated to 70° C. for 1 hour, then cooled and concentrated in vacuo to afford a mixture of the title compounds, intermediates 75 and 76, which was taken onto the next step without further purification. LCMS $[M+H]^+$ 436/438 RT 2.41 & 2.45 min (Method 6).

Intermediates 77 & 78

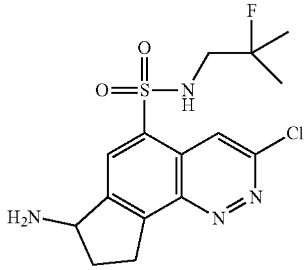

-continued

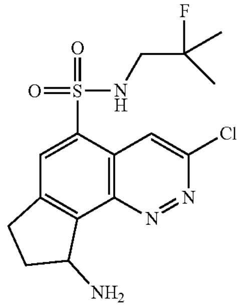

7-amino-3-chloro-N-(2-fluoro-2-methyl-propyl)-8,9-dihydro-7H-cyclopenta[h]cinnoline-5-sulfonamide (77)

9-amino-3-chloro-N-(2-fluoro-2-methyl-propyl)-8,9-dihydro-7H-cyclopenta[h]cinnoline-5-sulfonamide (78)

A crude mixture of Intermediates 75 and 76 (460 mg, 0.53 mmol) was dissolved in ammonia (100 mL, sat. sol in THF). The reaction mixture was sealed and heated at 70° C. The reaction was cooled and concentrated in vacuo to afford a mixture of the title compounds, intermediates 77 and 78 (390 mg), which was taken onto the next step. LCMS $[M+H]^+$373/375, RT 1.72 & 1.74 min (Method 6).

Intermediates 79 & 80

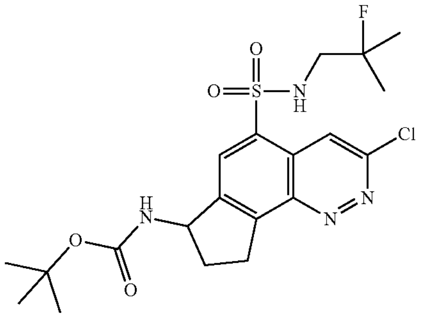

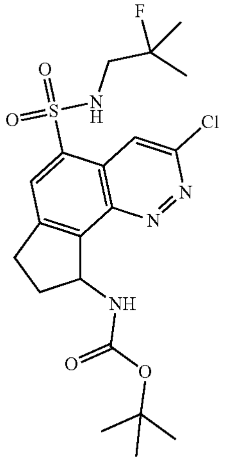

tert-butyl N-[3-chloro-5-[(2-fluoro-2-methyl-propyl)sulfamoyl]-8,9-dihydro-7H-cyclopenta[h]cinnolin-7-yl]carbamate (79)

tert-butyl N-[3-chloro-5-[(2-fluoro-2-methyl-propyl)sulfamoyl]-8,9-dihydro-7H-cyclopenta[h]cinnolin-9-yl]carbamate (80)

To a stirred mixture of intermediates 77 & 78 (390 mg, 0.52 mmol) in DCM (25 mL) was added di-tert-butyl dicarbonate (240 mg, 1.1 mmol) followed by triethylamine (0.29 mL, 2.1 mmol). The reaction mixture was stirred at room temperature overnight and then diluted with DCM (50 mL) and water (50 mL). The aqueous phase was partitioned and extracted with DCM (50 mL). The combined organic extracts were dried over $Na_2SO_4$ and concentrated in vacuo. The crude residue was purified by column chromatography to afford the title compounds:

Intermediate 79 (58 mg, 23% Yield); $^1H$ NMR (300 MHz, Chloroform-d) δ 8.69 (s, 1H), 8.45 (s, 1H), 5.56-5.38 (m, 1H), 5.16 (t, J=6.4 Hz, 1H), 4.95 (d, J=8.8 Hz, 1H), 3.95-3.79 (m, 1H), 3.59-3.40 (m, 1H), 3.29-2.98 (m, 2H), 2.98-2.83 (m, 1H), 2.19-2.06 (m, 1H), 1.51 (s, 9H), 1.42-1.26 (m, 6H). LCMS $[M+H]^+$473/475 RT 2.34 min (Method 6).

Intermediate 80 (57 mg, 23% Yield); $^1H$ NMR (300 MHz, Chloroform-d) δ 8.67 (s, 1H), 8.37 (s, 1H), 5.90-5.78 (m, 1H), 5.78-5.63 (m, 1H), 5.24 (t, J=6.6 Hz, 1H), 3.46-3.32 (m, 1H), 3.23-3.02 (m, 3H), 2.96-2.79 (m, 1H), 2.52-2.33 (m, 1H), 1.42 (s, 9H), 1.36-1.26 (m, 6H). LCMS $[M+H]^+$ 473/475 RT 2.38 min (Method 6).

Intermediate 81

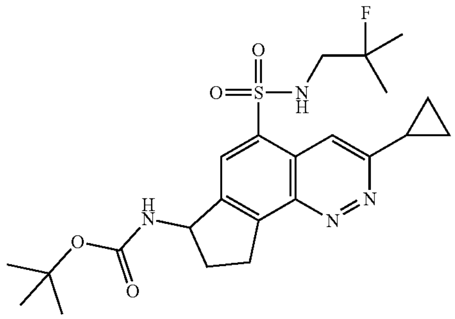 [SMILES: CC(C)(F)CNS(=O)(=O)c1cc2c(c3nnc(C4CC4)cc13)CCC2NC(=O)OC(C)(C)C]

tert-butyl N-[3-cyclopropyl-5-[(2-fluoro-2-methyl-propyl)sulfamoyl]-8,9-dihydro-7H-cyclopenta[h]cinnolin-7-yl]carbamate A slurry of Intermediate 79 (58 mg, 0.13 mmol), cyclopropylboronic acid (33 mg, 0.37 mmol) and palladium(II) acetate (1.4 mg, 6.11 mol) in toluene (1 mL) was degassed under a flow of nitrogen for 5 minutes. Tricyclohexylphosphonium tetrafluoroborate (7 mg, 0.018 mmol) and potassium phosphate tribasic (65 mg, 0.31 mmol) were added and degassing continued for 5 min. The reaction was sealed and heated at 115° C. for 1 hour under microwave irradiation. The reaction was diluted with water (2 mL) and EtOAc (2 mL). The organic phase was partitioned, and the aqueous phase extracted with EtOAc (2 mL). The combined organic extracts were dried over $Na_2SO_4$ and concentrated in vacuo. The crude product was purified by column chromatography to afford the title compound (51 mg, 87% Yield); $^1$H NMR (300 MHz, Chloroform-d) δ 8.37 (d, J=3.2 Hz, 2H), 5.58-5.35 (m, 1H), 5.09 (t, J=6.5 Hz, 1H), 4.92 (d, J=9.0 Hz, 1H), 3.83 (ddd, J=18.4, 9.5, 3.3 Hz, 1H), 3.56-3.35 (m, 1H), 3.25-2.76 (m, 2H), 2.44-2.26 (m, 1H), 2.16-1.95 (m, 1H), 1.51 (s, 9H), 1.44-1.23 (m, 7H), 0.93-0.79 (m, 2H), 0.75-0.48 (m, 2H).

Intermediate 82

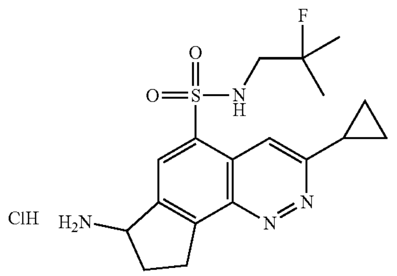 [SMILES: Cl ; CC(C)(F)CNS(=O)(=O)c1cc2c(c3nnc(C4CC4)cc13)CCC2N]

7-amino-3-cyclopropyl-N-(2-fluoro-2-methyl-propyl)-8,9-dihydro-7H-cyclopenta[h]cinnoline-5-sulfonamide Hydrochloride To a stirred solution of Intermediate 81 (51 mg, 0.11 mmol) in DCM (0.5 mL) was added hydrochloric acid (4 mol/L) in 1,4-dioxane (0.11 mL) and the reaction stirred at ambient temperature for 2.5 hours. The reaction was concentrated in vacuo to afford the title compound as an HCl salt (44 mg, quantitative); LCMS $[M+H]^+$ 379, RT 1.01 min (Method 1).

Intermediate 83

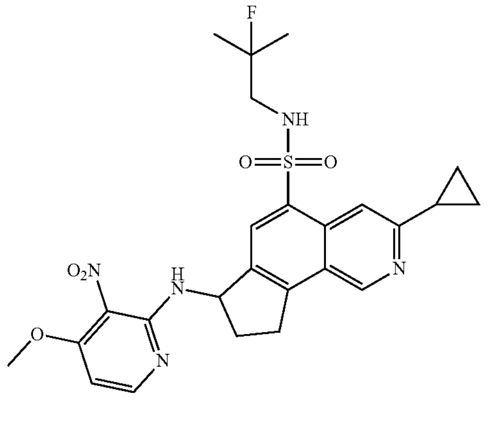 [SMILES: COc1ccnc(NC2CCc3c2cc(S(=O)(=O)NCC(C)(C)F)c2cc(C4CC4)ncc32)c1[N+](=O)[O-]]

3-cyclopropyl-N-(2-fluoro-2-methyl-propyl)-7-[(4-methoxy-3-nitro-2-pyridyl)amino]-8,9-dihydro-7H-cyclopenta[h]isoquinoline-5-sulfonamide Intermediate 36 (0.42 mmol) was suspended in $CH_3CN$ (4 mL), treated with DIPEA (0.183 mL, 1.05 mmol) and stirred at room temperature. The mixture was then treated with 2-chloro-4-methoxy-3-nitropyridine (80 mg, 0.42 mmol) and the reaction was stirred at room temperature overnight.

The reaction was then treated with DIPEA (0.18 mL, 1.05 mmol) and 2-chloro-4-methoxy-3-nitropyridine (80 mg, 0.42 mmol), and heated to 100° C. for 24 hrs. The reaction mixture was cooled to room temperature, dry loaded onto silica and purified by column chromatography using a gradient of ethyl acetate in iso-hexane to give the title compound (34 mg (81% pure by LCMS), 0.052 mmol, 12%); $\delta_H$ (400 MHz, d4-methanol) 9.23 (d, J=1.0 Hz, 1H), 8.39 (d, J=0.9 Hz, 1H), 8.25 (s, 1H), 8.19 (d, J=5.9 Hz, 1H), 6.62 (d, J=5.9 Hz, 1H), 6.04 (t, J=7.6 Hz, 1H), 3.97 (d, J=2.8 Hz, 3H), 3.69-3.54 (m, 1H), 3.36 (dd, J=15.0, 6.9 Hz, 1H), 3.06 (dd, J=19.9, 6.5 Hz, 1H), 2.97 (d, J=19.6 Hz, 2H), 2.93-2.81 (m, 1H), 2.42-2.29 (m, 1H), 2.27-2.15 (m, 1H), 1.27-1.21 (m, 4H), 1.20-1.14 (m, 3H), 1.15-1.05 (m, 2H). LCMS $[M+H]^+$ 530, RT 1.23 min (Method 1).

Intermediate 84

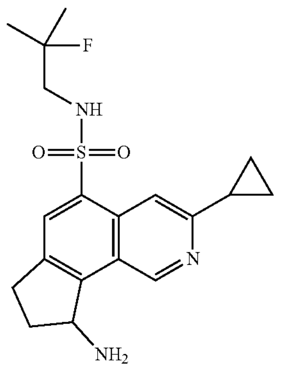 [SMILES: CC(C)(F)CNS(=O)(=O)c1cc2c(c3cnc(C4CC4)cc13)C(N)CC2]

9-amino-3-cyclopropyl-N-(2-fluoro-2-methyl-propyl)-8,9-dihydro-7H-cyclopenta[h]isoquinoline-5-sulfonamide HCl in 1,4-dioxane (4 mol/L, 24 mL, 96 mmol) was added to Intermediate 62 (2 g, 4.18 mmol). MeOH (8 mL, 198 mmol) was then added and the resulting solution was stirred at ambient temperature. After 1 hour the mixture was concentrated under reduced pressure to give a yellow solid which was then dissolved in MeOH (20 mL) and passed through an SCX column eluting first with methanol, then with 7N $NH_3$ in methanol. The methanolic ammonia solution was concentrated under reduced pressure and the resulting solid triturated with diethyl ether to give the title compound as a white solid (1.3 g, 82% yield); $^1$H NMR (300 MHz, DMSO-$d_6$) δ 9.52 (s, 1H), 8.43 (d, J=0.9 Hz, 1H), 8.27 (s, 1H), 5.44 (d, J=7.4 Hz, 1H), 3.17 (s, 1H), 3.14-3.06 (m, 1H), 3.02 (s, 1H), 2.95 (s, 1H), 2.34 (dd, J=12.2, 6.4 Hz, 3H), 1.27 (d, J=2.1 Hz, 3H), 1.19 (d, J=2.1 Hz, 4H), 1.07 (p, J=5.0 Hz, 6H). LCMS $[M+H]^+$ 378, RT 0.95 min (Method 1).

Intermediate 85

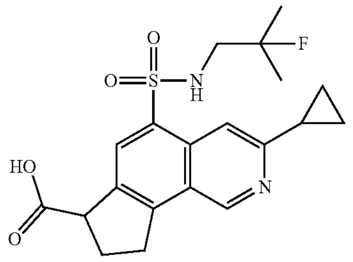 [SMILES: CC(C)(F)CNS(=O)(=O)c1cc2c(c3cnc(C4CC4)cc13)CCC2C(=O)O]

3-cyclopropyl-5-[(2-fluoro-2-methyl-propyl)sulfamoyl]-8,9-dihydro-7H-cyclopenta[h]isoquinoline-7-carboxylic Acid Intermediate 56 (145 mg, 0.33 mmol) was dissolved in THF (3 mL) and water (2 mL) and lithium hydroxide monohydrate (27 mg, 0.64 mmol) was added. The reaction mixture was stirred at room temperature overnight then concentrated under reduced pressure and the resulting residue diluted with water and diethyl ether. The aqueous layer was partitioned, acidified to pH 1 and extracted with EtOAc. The organic layer was dried and evaporated to afford the title compound as a white solid (139 mg, quantitative). LCMS $[M+H]^+$407, RT 0.77 min (Method 5).

Intermediate 86

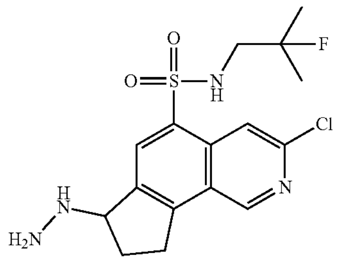 [SMILES: CC(C)(F)CNS(=O)(=O)c1cc2c(c3cnc(Cl)cc13)CCC2NN]

3-chloro-N-(2-fluoro-2-methyl-propyl)-7-hydrazino-8,9-dihydro-7H-cyclopenta[h]isoquinoline-5-sulfonamide Intermediate 17 (320 mg, 0.73 mmol) and hydrazine in THF (1 mol/L, 15 mL, 15 mmol) were heated at 70° C. with stirring for 20 min. The solvent was removed under vacuum and the residue loaded onto an SCX cartridge eluting with MeOH followed by 4N ammonia in MeOH to afford the title compound (298 mg, quantitative). LCMS $[M+H]^+$ 387, RT 1.40 min (Method 1).

Intermediate 87

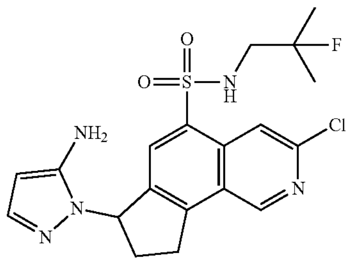 [SMILES: CC(C)(F)CNS(=O)(=O)c1cc2c(c3cnc(Cl)cc13)CCC2n1nccc1N]

7-(5-aminopyrazol-1-yl)-3-chloro-N-(2-fluoro-2-methyl-propyl)-8,9-dihydro-7H-cyclopenta[h]isoquinoline-5-sulfonamide A mixture of intermediate 86 (190 mg, 0.49 mmol) and 3,3-dimethoxypropanenitrile (0.06 mL, 0.5 mmol) was dissolved in EtOH (6 mL) and HCl (0.2 mL, 2 mmol, 37 mass %) was added. The reaction mixture was heated at 80° C. in a sealed tube overnight. The volatiles were evaporated, and the resulting residue diluted with DCM and washed with water. Organics were dried and evaporated to afford a solid, which was triturated with hexanes and purified by reverse phase column chromatography (basic conditions) to afford the title compound (134 mg, 62% Yield) as white solid. LCMS $[M+H]^+$ 438, RT 1.67 min (Method 4).

Intermediate 88

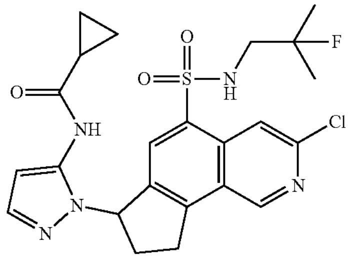 [SMILES: CC(C)(F)CNS(=O)(=O)c1cc2c(c3cnc(Cl)cc13)CCC2n1nccc1NC(=O)C1CC1]

N-[2-[3-chloro-5-[(2-fluoro-2-methyl-propyl)sulfamoyl]-8,9-dihydro-7H-cyclopenta[h]isoquinolin-7-yl]pyrazol-3-yl]cyclopropanecarboxamide Intermediate 87 (135 mg, 0.30 mmol) was dissolved in pyridine (5 mL) and cyclopropanecarbonyl chloride (0.030 mL, 0.32 mmol) was added, followed by DMAP (5 mg, 0.040 mmol). The reaction mixture was stirred at room temperature overnight, then diluted with a mixture of DCM and sat. aq. $NaHCO_3$. The organic layers were dried over sodium sulfate and concentrated under reduced pressure. The resulting residue was purified by column chromatography eluting with a gradient of 0-50% EtOAc in Hexane followed by 0-2% MeOH in DCM to give the title compound (105 mg, 67% Yield); $^1H$ NMR (300 MHz, Chloroform-d) δ 9.21 (s, 1H), 8.53 (s, 1H), 8.16 (s, 1H), 7.46 (s, 1H), 7.33 (s, 1H), 6.17 (s, 1H), 5.94 (s, 1H), 5.10 (s, 1H), 3.77 (d, J=12.5 Hz, 1H), 3.48-3.36 (m, 1H), 3.13-2.84 (m, 3H), 2.74 (s, 1H), 1.30 (dd, J=21.4, 14.2 Hz, 6H), 1.14 (m, 2H), 1.01-0.81 (m, 3H). LCMS $[M+H]^+$ 506, RT 1.96 min (Method 4).

Intermediate 89

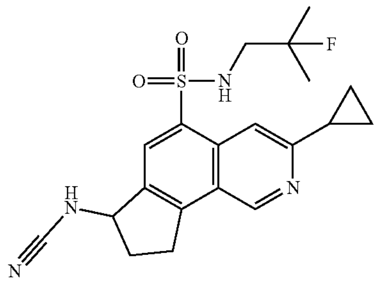 [SMILES: CC(C)(F)CNS(=O)(=O)c1cc2c(c3cnc(C4CC4)cc13)CCC2NC#N]

7-(cyanoamino)-3-cyclopropyl-N-(2-fluoro-2-methyl-propyl)-8,9-dihydro-7H-cyclopenta[h]isoquinoline-5-sulfonamide Intermediate 36 (140 mg, 0.37 mmol) was dissolved in THF (10 mL) and N,N-diisopropylethylamine (0.130 mL, 0.74 mmol) was added, followed by cyanogen bromide (51 mg, 0.48 mmol). After 30 min of stirring at room temperature the reaction mixture was washed with sat. aq. $NaHCO_3$ [Note: partial decomposition was observed by LCMS]. Due to suspected instability, the reaction mixture was taken onto the next step without further purification. LCMS $[M+H]^+$ 403, RT 0.97 min (Method 1).

Intermediate 90

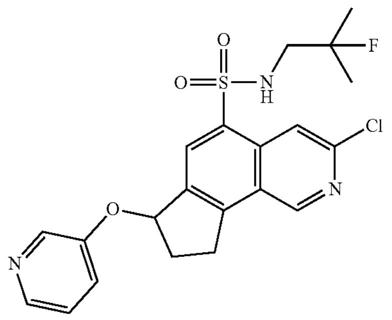 [SMILES: CC(C)(F)CNS(=O)(=O)c1cc2c(c3cnc(Cl)cc13)CCC2Oc1cccnc1]

3-chloro-N-(2-fluoro-2-methyl-propyl)-7-(3-pyridyloxy)-8,9-dihydro-7H-cyclopenta[h]isoquinoline-5-sulfonamide To a solution of Intermediate 17 (95 mg, 0.22 mmol) in anhydrous DMF (5 mL) were added 3-hydroxypyridine (25 mg, 0.26 mmol) and sodium carbonate (28 mg, 0.26 mmol) and the resultant solution stirred at room temperature. After 2 hours, 3-hydroxypyridine (25 mg, 0.26 mmol) was added followed by sodium carbonate (28 mg, 0.26 mmol). After a further 1 hour, the reaction mixture was concentrated in vacuo and purified by column chromatography eluting with a gradient of 0-100% EtOAc in iso-hexane to give the title compound (25 mg, 26% Yield). LCMS $[M+H]^+$ 450, RT 1.12 minutes (Method 1).

Intermediate 91

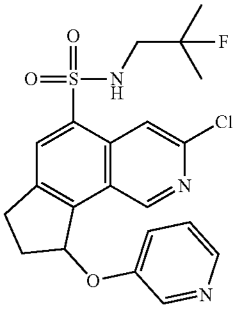 [SMILES: CC(C)(F)CNS(=O)(=O)c1cc2c(c3cnc(Cl)cc13)C(Oc1cccnc1)CC2]

3-chloro-N-(2-fluoro-2-methyl-propyl)-9-(3-pyridyloxy)-8,9-dihydro-7H-cyclopenta[h]isoquinoline-5-sulfonamide Synthesised in the same manner as intermediate 90 using Intermediate 16 (95 mg, 0.22 mmol) and comparable stoichiometries of reagents. Purification by column chromatography eluting with a gradient of 0-100% EtOAc in iso-hexane gave the title compound (37 mg, 38% Yield). LCMS $[M+H]^+$ 450, RT 1.13 minutes (Method 1).

Intermediate 92

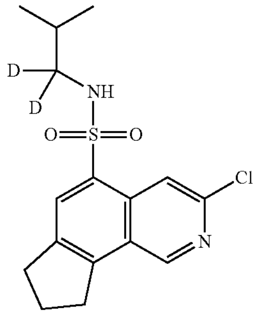 [SMILES: [2H]C([2H])(NS(=O)(=O)c1cc2c(c3cnc(Cl)cc13)CCC2)C(C)C]

3-chloro-N-(1,1-dideuterio-2-methyl-propyl)-8,9-dihydro-7H-cyclopenta[h]isoquinoline-5-sulfonamide To a solution of Intermediate 5 (3.45 g, 11.4 mmol) in dichloromethane (25 mL) was added 1,1-dideuterio-2-methyl-propan-1-amine hydrochloride (1.34 g, 12.0 mmol) followed by triethylamine (6.4 mL, 46 mmol). After 30 minutes the suspension was diluted with water (50 mL) and dichloromethane (20 mL). The aqueous layer was extracted with dichloromethane (2×40 mL). The combined organics were washed with brine (50 mL), passed through a hydrophobic frit and concentrated under reduced pressure. Purification by flash chromatography gave the title compound as a cream solid (3.15 g, 81% Yield). $\delta_H$ (300 MHz, Chloroform-d) 9.15 (d, J=0.9 Hz, 1H), 8.49 (d, J=0.8 Hz, 1H), 8.38

(s, 1H), 4.66 (s, 1H), 3.44 (t, J=7.6 Hz, 2H), 3.19 (t, J=7.5 Hz, 2H), 2.39 (app. p, J=7.7 Hz, 2H), 1.68 (hept, J=6.7, 1H), 0.83 (d, J=6.7 Hz, 6H); LCMS $[M+H]^+$ 341/343, RT 2.40 min (Method 6).

Intermediates 93 & 94

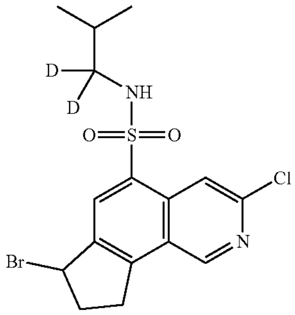

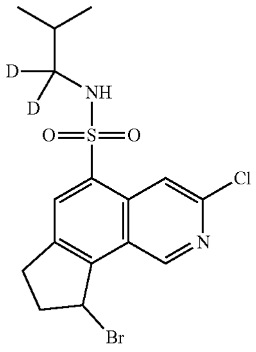

7-bromo-3-chloro-N-(1,1-dideuterio-2-methyl-propyl)-8,9-dihydro-7H-cyclopenta[h]isoquinoline-5-sulfonamide (93)

9-bromo-3-chloro-N-(1,1-dideuterio-2-methyl-propyl)-8,9-dihydro-7H-cyclopenta[h]isoquinoline-5-sulfonamide (94)

To a solution of Intermediate 92 (3.15 g, 9.24 mmol) in ethyl acetate (200 mL) was added 2,2'-azobis(2-methylpropionitrile) (152 mg, 0.92 mmol) and N-bromosuccinimide (recrystallised from water and dried) (1.9 g, 11 mmol). The mixture was heated to 90° C. with the exclusion of light. After 1.5 hours the mixture was concentrated under reduced pressure to give the title compounds as a brown solid, which was used crude in the next step. LCMS $[M+H]^+$ 419/421/423, RT 2.44 min (Method 6).

Intermediates 95 & 96

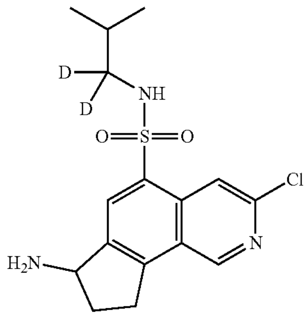

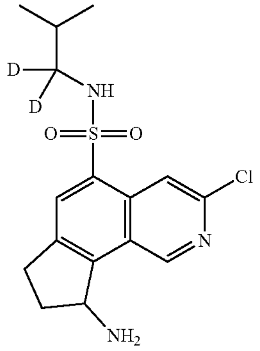

7-amino-3-chloro-N-(1,1-dideuterio-2-methyl-propyl)-8,9-dihydro-7H-cyclopenta[h]isoquinoline-5-sulfonamide (95)

9-amino-3-chloro-N-(1,1-dideuterio-2-methyl-propyl)-8,9-dihydro-7H-cyclopenta[h]isoquinoline-5-sulfonamide (96)

To the crude mixture of Intermediates 93 and 94 was added tetrahydrofuran (200 mL). Gaseous ammonia was passed through the solution for 20 minutes before the mixture was heated to 70° C. in a sealed vessel for 16 hours. The mixture was concentrated under reduced pressure to give a mixture of the title compounds as a green/brown solid, which was used crude in the next step. LCMS $[M+H]^+$ 356/358, RT 1.80 and 1.87 minutes (Method 6).

Intermediates 97 & 98

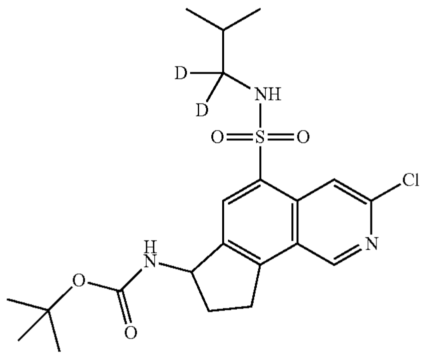

-continued

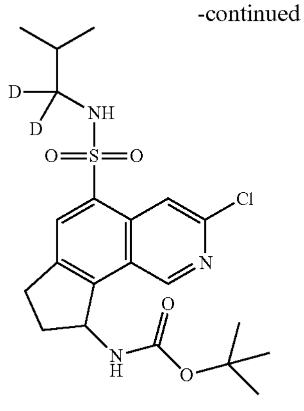

tert-butyl N-[3-chloro-5-[(1,1-dideuterio-2-methyl-propyl)sulfamoyl]-8,9-dihydro-7H-cyclopenta[h]isoquinolin-7-yl]carbamate (97)

tert-butyl N-[3-chloro-5-[(1,1-dideuterio-2-methyl-propyl)sulfamoyl]-8,9-dihydro-7H-cyclopenta[h]isoquinolin-9-yl]carbamate (98)

To the crude mixture of Intermediates 95 and 96 was added dichloromethane (150 mL), triethylamine (3.2 mL, 23 mmol) and di-tert-butyl dicarbonate (3.0 g, 14 mmol). After 72 hours the mixture was washed with saturated ammonium chloride solution (80 mL), passed through a hydrophobic frit and purified by flash chromatography to give the title compounds as cream solids.

Intermediate 97 (1.24 g, 29% Yield); $\delta_H$ (400 MHz, Chloroform-d) 9.15 (s, 1H), 8.51 (s, 1H), 8.42 (s, 1H), 5.47-5.35 (m, 1H), 5.09-4.95 (m, 21H), 3.55 (ddd, J=17.2, 9.2, 3.3 Hz, 1H), 3.33-3.22 (m, 1H), 2.96-2.83 (m, 1H), 2.17-2.03 (m, 1H), 1.76-1.67 (m, 1H), 1.52 (s, 9H), 0.89-0.80 (m, 6H); LCMS $[M+H]^+$ 456/458, RT 2.42 min (Method 6).

Intermediate 98 (66% w/w purity, 2.0 g, 32% Yield); $\delta_H$ (300 MHz, Chloroform-d) 9.38 (d, J=0.8 Hz, 1H), 8.49 (d, J=0.9 Hz, 1H), 8.31 (s, 1H), 5.90-5.79 (m, 1H), 5.32 (s, 1H), 5.03 (d, J=9.6 Hz, 1H), 3.33-3.20 (m, 1H), 3.12-3.00 (m, 1H), 2.84-2.67 (m, 1H), 2.25-2.12 (m, 1H), 1.74-1.66 (m, 1H), 1.47 (s, 9H), 0.85-0.80 (m, 6H); LCMS $[M+H]^+$ 456, 458, RT 2.47 min (Method 6).

Intermediate 99

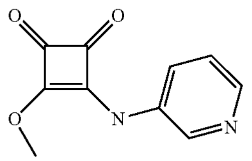

3-Methoxy-4-(3-pyridylamino)cyclobut-3-ene-1,2-dione

To a solution of 3-aminopyridine (500 mg, 5.26 mmol) in DCM (20 mL) was added 3,4-dimethoxy-3-cyclobutene-1,2-dione (822 mg, 5.79 mmol) and N,N-diisopropylethylamine (1020 mg, 7.89 mmol). The mixture was stirred at room temperature overnight. The resultant precipitate was filtered off and the filtrate evaporated. The residue was triturated with 5% MeOH in DCM and the precipitate filtered off, washing with DCM to give the title compound as a yellow solid (382 mg, 36% yield). LCMS $[M+H]^+$ 205, RT 0.57 min (Method 3).

Intermediate 100

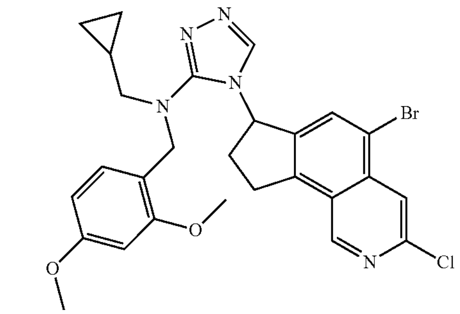 [SMILES: COc1ccc(CN(CC2CC2)c2nncn2C2CCc3c2cc(Br)c2cc(Cl)ncc32)c(OC)c1]

4-(5-bromo-3-chloro-8,9-dihydro-7H-cyclopenta[h]isoquinolin-7-yl)-N-(cyclopropylmethyl)-N-[(2,4-dimethoxyphenyl)methyl]-1,2,4-triazol-3-amine Intermediate 137 (480 mg, 0.83 mmol) was dissolved in dry DMF (8 mL). Formic hydrazide (149.5 mg, 2.49 mmol) and mercury dichloride (676 mg, 2.49 mmol) were added and the reaction stirred for 5 minutes. Triethylamine (0.34 mL, 2.49 mmol) was added and reaction heated to 90° C. with stirring for 2 hours which resulted in a black suspension. Once at room temperature the reaction was diluted with DCM (20 mL) and Kieselguhr added, the mixture stirred for 5 minutes then filtered through a plug of Kieselguhr washing through with DCM. The filtrate was concentrated under vacuum and the residue dissolved in ethyl acetate (50 mL). The solution was washed with saturated $NH_4Cl$ (30 mL), water (30 mL), brine (30 mL), dried (sodium sulphate) and concentrated under vacuum. Purification by column chromatography using a gradient of 0-10% MeOH in DCM afforded the title compound (295 mg, 57% Yield) as a black solid. LCMS $[M+H]^+$ 568/570, RT 2.03 min (Method 9).

Intermediate 101

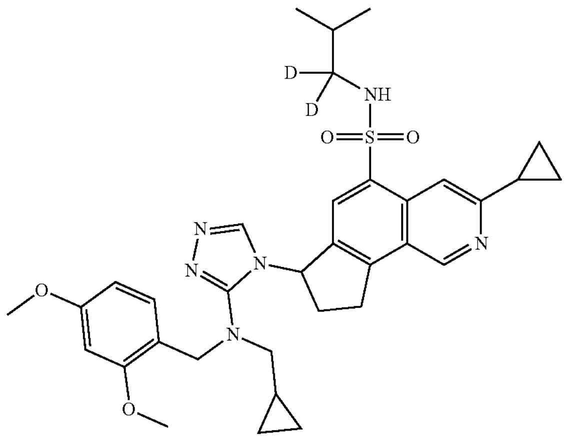 [SMILES: [2H]C([2H])(NS(=O)(=O)c1cc2c(c3cnc(C4CC4)cc13)CCC2n1cnnc1N(Cc1ccc(OC)cc1OC)CC1CC1)C(C)C]

3-cyclopropyl-7-[3-[cyclopropylmethyl-[(2,4-dimethoxyphenyl)methyl]amino]-1,2,4-triazol-4-yl]-N-(1,1-dideuterio-2-methyl-propyl)-8,9-dihydro-7H-cyclopenta[h]isoquinoline-5-sulfonamide To a suspension of Example 34 (420 mg, 1.16 mmol) in dichloromethane (20 mL) was added 1,1'-thiocarbonyldiimidazole (230 mg, 1.16 mmol). After 3 hours N-(cyclopropylmethyl)-1-(2,4-dimethoxyphenyl)methanamine (280 mg, 1.26 mmol) was added as a solution in dichloromethane (5 mL). After 90 minutes the mixture was diluted with dichloromethane (20 mL) and washed successively with water (20 mL), 10% ammonium chloride solution (40 mL, water (40 mL) and brine (40 mL). After concentration under reduced pressure, the residue was dissolved in N,N-dimethylformamide (15 mL). Formic acid hydrazide (210 mg, 3.50 mmol) and mercuric chloride (630 mg, 2.32 mmol) was added. After 5 minutes, triethylamine (0.5 ml, 4 mmol) was added and the mixture was heated to 80° C. After 2 hours 20 minutes the mixture was cooled, filtered through kieselguhr and concentrated under reduced pressure. The residue was taken into ethyl acetate (80 mL), washed with 10% ammonium chloride solution (2×40 mL), brine (50 mL), passed through a hydrophobic frit and concentrated under reduced pressure. Purification by flash chromatography gave the title compound as a yellow glass (407 mg, 55% Yield). $\delta_H$ (300 MHz, Chloroform-d) 9.27 (d, J=1.0 Hz, 1H), 8.31 (d, J=1.0 Hz, 1H), 7.73 (s, 1H), 7.56 (s, 1H), 7.14 (d, J=8.9 Hz, 1H), 6.47-6.39 (m, 2H), 5.93 (t, J=7.4 Hz, 1H), 4.88 (s, 1H), 4.40-4.23 (m, 2H), 3.82 (s, 3H), 3.72 (s, 3H), 3.67-3.54 (m, 1H), 3.43-3.27 (m, 1H), 3.23-3.05 (m, 2H), 2.85-2.66 (m, 1H), 2.33-2.19 (m, 1H), 2.18-2.07 (m, 1H), 1.74-1.55 (m, 2H), 1.21-1.02 (m, 4H), 0.86-0.74 (m, 6H), 0.60-0.44 (m, 2H), 0.22-0.10 (m, 2H); LCMS $[M+H]^+$ 633, RT 2.67 min (Method 6).

Intermediate 102

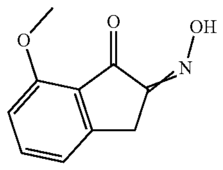

2-hydroxyimino-7-methoxy-indan-1-one

To a suspension of 7-methoxy-1-indanone (4.5 g, 28 mmol) in diethyl ether (80 mL) at 0° C. was added hydrochloric acid (4 mol/L) in 1,4-dioxane (1.7 mL) followed by dropwise addition of 10-20% ethyl nitrite in ethanol (25 mL, 39.6 mmol). After 5 minutes the mixture was warmed to ambient temperature. After 2 hours 10-20% ethyl nitrite in ethanol (5 mL, 7.9 mmol) was added. After 30 minutes diethyl ether (50 mL) was added and the off-white precipitate recovered on a sinter. The title compound was obtained as an off-white solid (3.90 g, 72% Yield). $\delta_H$ (300 MHz, DMSO-d6) 12.40 (s, 1H), 7.66 (dd, J=8.3, 7.5 Hz, 1H), 7.10 (dd, J=7.5, 0.8 Hz, 1H), 7.02 (dd, J=8.4, 0.8 Hz, 1H), 3.88 (s, 3H), 3.69 (s, 2H); LCMS $[M+H]^+$ 192, RT 1.04 min (Method 6).

Intermediate 103

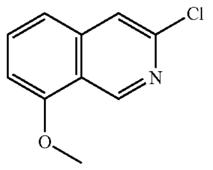

To a suspension of Intermediate 102 (5.2 g, 27 mmol) in phosphoryl chloride (63 mL, 680 mmol) at 0° C. was added phosphorus pentachloride (6.5 g, 31 mmol). After 5 minutes hydrogen chloride was bubbled through the mixture for 20 minutes. After 3 hours, the mixture was cooled to ambient temperature, treated with phosphorus pentachloride (2.2 g, 11 mmol) and heated to 80° C. for 16 hours. The mixture was concentrated under reduced pressure. The residue was suspended in water (60 mL) and ammonium hydroxide was added to adjust the pH to 8-9. Dichloromethane (150 mL) was added and the suspension filtered through kieselguhr. The filtrate was separated using a hydrophobic frit and the organics concentrated under reduced pressure. The residue was purified by flash chromatography to give the title compound as a cream solid (3.0 g, 58% Yield). $\delta_H$ (300 MHz, DMSO-d6) 9.29 (t, J=0.9 Hz, 1H), 7.98 (d, J=0.8 Hz, 1H), 7.82-7.69 (m, 1H), 7.55-7.42 (m, 1H), 7.19-7.00 (m, 1H), 4.02 (s, 3H); LCMS $[M+H]^+$ 194/196 RT 1.19 min (Method 1).

Intermediate 104

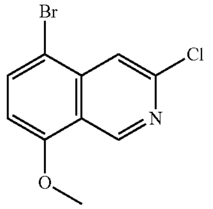

5-bromo-3-chloro-8-methoxy-isoquinoline

Intermediate 103 (1 g, 5.16 mmol) was added in portions to sulfuric acid (15 mL) at 0° C. The mixture was then further cooled to −20° C. before being treated with N-bromosuccinimide (920 mg, 5.17) in portions over 5 minutes. After 30 minutes, ice (30 g) and dichloromethane (50 mL) were added. The pH was adjusted to 7-8 with ammonium hydroxide solution. The aqueous layer was extracted with dichloromethane (2×50 mL). The combined organics were passed through a hydrophobic frit, concentrated and the residue purified by flash chromatography to give the title compound as a pale pink solid (1.02 g, 70% Yield). $\delta_H$ (400 MHz, DMSO-d6) 9.33 (d, J=0.8 Hz, 1H), 8.09 (d, J=8.4 Hz, 1H), 7.87 (d, J=0.7 Hz, 1H), 7.11 (d, J=8.4 Hz, 1H), 4.03 (s, 3H); LCMS $[M+H]^+$ 272/274/276, RT 1.41 min (Method 1).

Intermediate 105

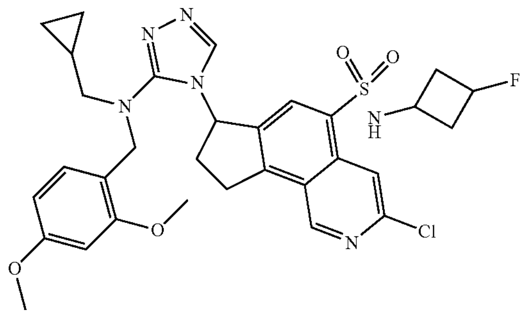

3-chloro-7-[3-[cyclopropylmethyl-[(2,4-dimethoxyphenyl)methyl]amino]-1,2,4-triazol-4-yl]-N-(3-fluorocyclobutyl)-8,9-dihydro-7H-cyclopenta[h]isoquinoline-5-sulfonamide A sealable tube was charged with Intermediate 100 (75 mg, 0.013 mmol), potassium metabisulfite (58 mg, 0.26 mmol), TBAB (46.7 mg, 0.14 mmol), sodium formate (19.7 mg, 0.29 mmol), $Pd(OAc)_2$ (1.48 mg, 0.007 mmol), triphenylphosphine (5.18 mg, 0.02 mmol) and 1,10-phenanthroline (3.56 mg, 0.02 mmol). DMSO (1.0 mL) was added and the suspension de-gassed and placed under an atmosphere of nitrogen. The tube was sealed and heated to 70° C. for 3 hours. Once at room temperature a mixture of 3-fluorocyclobutan-1-amine hydrochloride (33.1 mg, 0.26 mmol) and triethylamine (36.6 µL, 0.26 mmol) in THF (1.5 mL) was added and the reaction cooled to 0° C. A solution of NBS (46.9 mg, 0.26 mmol) in THF (2 mL) was then added dropwise. The reaction was mixture was then stirred for 1 hour, while allowing the reaction to warm to room temperature. The mixture was diluted with ethyl acetate (20 mL) and water (15 mL). The organic layer was washed with water (15 mL), brine (10 mL, dried (magnesium sulphate) and concentrated under reduced pressure. Purification by column chromatography afforded the title compound (65 mg, 38% Yield) as a pale-yellow gum. LCMS $[M+H]^+$ 641, RT 3.06 min (Method 8).

Intermediate 106

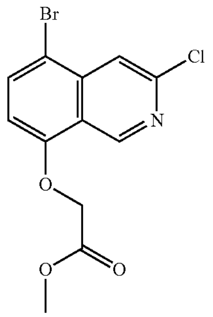 [SMILES: COC(=O)COc1ccc(Br)c2cc(Cl)ncc12]

methyl 2-[(5-bromo-3-chloro-8-isoquinolyl)oxy] acetate

To a −40° C. solution of Intermediate 104 (200 mg, 0.55 mmol) in dichloromethane (5 mL) was added boron tribromide in dichloromethane (1 mol/L, 2.2 mL, 2.2 mmol) dropwise. The mixture was warmed to ambient temperature. After 18 hours boron tribromide in dichloromethane (1 mol/L, 0.5 mL, 0.5 mmol) was added. After a further 24 hours, methanol (3 mL) was added to the solution at 0° C. The mixture was concentrated under reduced pressure to give a yellow solid which was taken up in N,N-dimethylformamide (4 mL). Potassium carbonate (230 mg, 1.74 mmol) was added followed by methyl bromoacetate (75 µL, 0.77 mmol). After 20 hours the mixture was diluted with ethyl acetate (20 mL) and water (20 mL). The organics were washed with brine, passed through a hydrophobic frit and concentrated under reduced pressure. The residue was purified by flash chromatography to give a white solid (220 mg, quantitative). $\delta_H$ (400 MHz, DMSO-d6) 9.41 (d, J=0.8 Hz, 1H), 8.10 (d, J=8.5 Hz, 1H), 7.93 (d, J=0.7 Hz, 1H), 7.12 (d, J=8.5 Hz, 1H), 5.15 (s, 2H), 3.74 (s, 3H); LCMS $[M+H]^+$ 330/332/334, RT 1.30 min (Method 1).

Intermediate 107

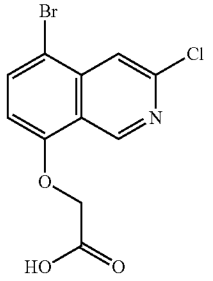 [SMILES: O=C(O)COc1ccc(Br)c2cc(Cl)ncc12]

2-[(5-bromo-3-chloro-8-isoquinolyl)oxy]acetic Acid

To a suspension of Intermediate 106 (580 mg, 1.54 mmol) in tetrahydrofuran (10 mL) was added lithium hydroxide (120 mg, 5.010 mmol) followed by water (1 mL). After 4 hours, the mixture was acidified to pH 2-3 using 2 M HCl. The mixture was extracted with ethyl acetate. The organics were concentrated under reduced pressure to give the crude title compound as a white solid (600 mg, quantitative yield). LCMS $[M+H]^+$ 316/318/320, RT 0.85 min (Method 1).

Intermediate 108 & 109

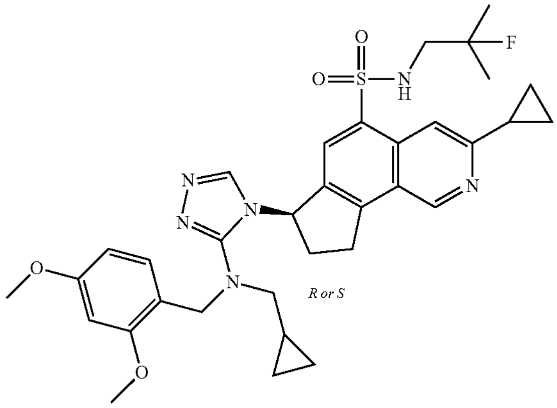

-continued

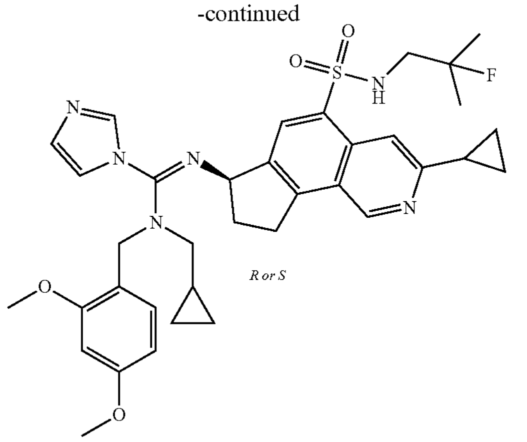

(7R*)-3-cyclopropyl-7-[3-[cyclopropylmethyl-[(2,4-dimethoxyphenyl)methyl]amino]-1,2,4-triazol-4-yl]-N-(2-fluoro-2-methyl-propyl)-8,9-dihydro-7H-cyclopenta[h]isoquinoline-5-sulfonamide [* or S] (108)

N-(cyclopropylmethyl)-N-[(2,4-dimethoxyphenyl)methyl]-N'-[(7R*)-3-cyclopropyl-5-[(2-fluoro-2-methyl-propyl)sulfamoyl]-8,9-dihydro-7H-cyclopenta[h]isoquinolin-7-yl]imidazole-1-carboxamidine [* or S] (109)

The title compounds were prepared according to general procedure 1 using intermediate 57 (60 mg (50% purity), 0.047 mmol). The products were purified using basic reverse phase column chromatography to afford:

Intermediate 108 (7 mg, 23% Yield); $^1$H NMR (300 MHz, Chloroform-d) δ 9.24 (d, J=0.9 Hz, 1H), 8.28 (d, J=1.0 Hz, 1H), 7.68 (s, 1H), 7.55 (s, 1H), 7.16-7.06 (m, 1H), 6.46-6.39 (m, 2H), 5.95-5.85 (m, 1H), 4.37-4.20 (m, 2H), 3.79 (s, 3H), 3.70 (s, 3H), 3.66-3.53 (m, 1H), 3.42-3.26 (m, 1H), 3.21-2.93 (m, 5H), 2.82-2.67 (m, 1H), 2.35-2.21 (m, 1H), 2.19-2.02 (m, 1H), 1.28 (dd, J=21.4, 12.7 Hz, 7H), 1.19-0.95 (m, 4H), 0.56-0.41 (m, 2H), 0.22-0.05 (m, 2H).

Intermediate 109 (12 mg, 38% yield); $^1$H NMR (300 MHz, Chloroform-d) δ 9.14 (d, J=0.9 Hz, 1H), 8.20 (d, J=0.9 Hz, 1H), 8.05 (s, 1H), 7.64 (s, 1H), 7.16 (d, J=1.1 Hz, 1H), 7.12-7.01 (m, 2H), 6.49-6.37 (m, 2H), 4.57-4.23 (m, 2H), 3.89-3.69 (m, 7H), 3.58-3.41 (m, 1H), 3.19-3.02 (m, 1H), 3.02-2.84 (m, 3H), 2.55-2.36 (m, 1H), 2.27-2.07 (m, 2H), 1.24 (dd, J=21.5, 7.2 Hz, 6H), 1.16-0.90 (m, 5H), 0.59-0.35 (m, 2H), 0.21--0.04 (m, 2H).

Intermediate 110

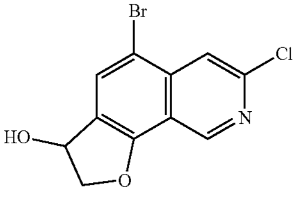 [SMILES: OC1COc2c1cc(Br)c1cc(Cl)ncc21]

5-bromo-7-chloro-2,3-dihydrofuro[3,2-h]isoquinolin-3-ol

To a suspension of Intermediate 107 (450 mg, 1.35 mmol) in 1,2-dichloroethane (4 mL) was added thionyl chloride (8 mL). The mixture was heated to 60° C. for 3 hours and then concentrated under reduced pressure. 1,2-Dichloroethane (9 mL) was added to the residue and cooled to 0° C. The suspension was treated with aluminium chloride (660 mg, 4.95 mmol). After 1.5 hours, aluminium chloride (50 mg, 0.37 mmol) was added and the mixture heated to 45° C. After 15 minutes the mixture was cooled in an ice/water bath, diluted with dichloromethane (50 mL) and quenched with ice (10 g). Saturated Rochelle's salt solution (20 mL) and water (20 mL) were added. Separation using a hydrophobic frit and concentration of the organics under reduced pressure gave a beige solid (406 mg). Methanol (8 mL) and dichloromethane (8 mL) were added and the suspension was cooled to −20° C. Sodium borohydride (50 mg, 1.59 mmol) was added. After 30 minutes the mixture was warmed to ambient temperature and the reaction quenched with water (10 mL). The mixture was diluted with dichloromethane (20 mL) and the aqueous extracted with ethyl acetate (2×10 mL). The combined organics were concentrated under reduced pressure and purified by flash chromatography to give the title compound as an off-white solid (189 mg, 44% Yield). $\delta_H$ (300 MHz, DMSO-d6) 9.23 (d, J=0.8 Hz, 1H), 8.16 (s, 1H), 7.94 (d, J=0.8 Hz, 1H), 5.91 (d, J=5.9 Hz, 1H), 5.55-5.41 (m, 1H), 4.86 (dd, J=10.4, 7.0 Hz, 1H), 4.58 (dd, J=10.4, 3.0 Hz, 1H); LCMS [M+H]$^+$ 300/302/304, RT 1.16 min (Method 1).

Intermediate 111

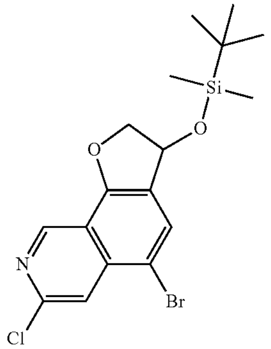 [SMILES: CC(C)(C)[Si](C)(C)OC1COc2c1cc(Br)c1cc(Cl)ncc21]

(5-bromo-7-chloro-2,3-dihydrofuro[3,2-h]isoquinolin-3-yl)oxy-tert-butyl-dimethyl-silane To a solution of Intermediate 110 (189 mg, 0.6 mmol) in N,N-dimethylformamide (4 mL) was added imidazole (82 mg, 1.2 mmol) and tert-butyldimethylchlorosilane (126 mg, 0.84), and the mixture stirred at ambient temperature for 18 hours. Imidazole (50 mg, 0.74 mmol) and tert-butyldimethylchlorosilane (50 mg, 0.33) were added. After a further 1 hour the mixture was diluted with ethyl acetate (20 mL) and water (20 mL). The organics were washed with brine before being passed through a hydrophobic frit and concentrated under reduced pressure. The residue was purified by flash chromatography to give the title compound as a white solid (250 mg, 97% Yield). $\delta_H$ (300 MHz, DMSO-d6) 9.24 (d, J=0.8 Hz, 1H), 8.07 (d, J=0.4 Hz, 1H), 7.95 (d, J=0.8 Hz, 1H), 5.70 (dd, J=6.7, 2.6 Hz, 1H), 4.90 (dd, J=10.5, 6.7 Hz, 1H), 4.59 (dd, J=10.5, 2.6 Hz, 1H), 0.87 (s, 9H), 0.17 (s, 6H); LCMS $[M+H]^+$ 414/416/418, RT 1.77 min (Method 1).

Intermediate 112

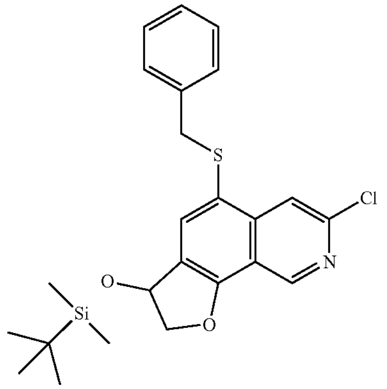

(5-benzylsulfanyl-7-chloro-2,3-dihydrofuro[3,2-h]isoquinolin-3-yl)oxy-tert-butyl-dimethyl-silane To a nitrogen purged solution of Intermediate 111 (250 mg, 0.58 mmol), 4,5-bis(diphenylphosphino)-9,9-dimethylxanthene (42 mg, 0.07 mmol), tris(dibenzylideneacetone)dipalladium(0) (32 mg, 0.035 mmol) and N,N-diisopropylethylamine (0.24 ml, 1.4 mmol) in 1,4-dioxane (3 mL) was added benzyl mercaptan (103 μL, 0.87 mmol). The mixture was heated to 85° C. for 3.5 hours, cooled and filtered through kieselguhr washing with ethyl acetate and then concentrated under reduced pressure. Purification by flash chromatography gave the desired compound as an orange oil (305 mg, 79% Yield). LCMS $[M+H]^+$ 458/460, RT 4.12 min (Method 6).

Intermediate 113

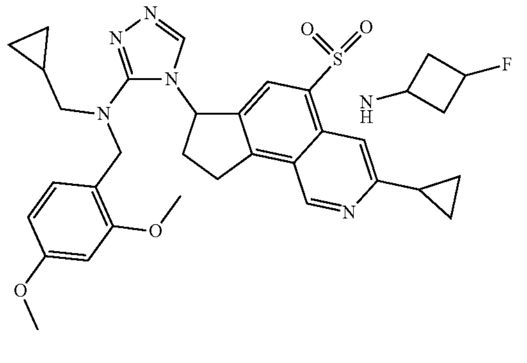

3-cyclopropyl-7-[3-[cyclopropylmethyl-[2,4-dimethoxyphenyl)methyl]amino]-1,2,4-triazol-4-yl]-N-(3-fluorocyclobutyl)-8,9-dihydro-7H-cyclopenta[h]isoquinoline-5-sulfonamide Toluene (5 mL) and water (0.075 mL) were added to a mixture of intermediate 105 (65 mg, 0.101 mmol), cyclopropylboronic acid (21.7 mg, 0.25 mmol), Pd(OAc)2 (1.1 mg, 5.0 μmol), $P(Cy)_3 \cdot HBF_4$ (5.6 mg, 15.2 μmol) and $K_3PO_4$ (53.8 mg, 0.25 mmol). The bi-phasic solution was heated at 120° C. for 5 hrs. The reaction mixture was then diluted with DCM (20 mL), dried ($MgSO_4$) and filtered through celite (washing through with DCM). The filtrate was concentrated under reduced pressure and purified by column chromatography eluting with a gradient of 0% to 10% MeOH in DCM to afford the title compound (46 mg, 33% Yield) as a pale-yellow gum. LCMS $[M+H]^+$ 647, RT 3.15 min (Method 8).

Intermediate 114

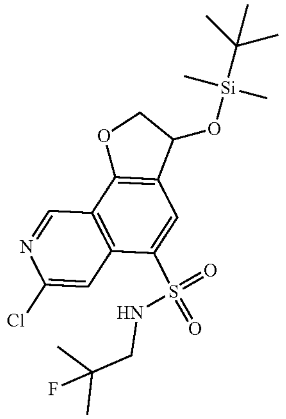 [SMILES: CC(C)(F)CNS(=O)(=O)c1cc2c(c3cnc(Cl)cc13)OCC2O[Si](C)(C)C(C)(C)C]

3-[tert-butyl(dimethyl)silyl]oxy-7-chloro-N-(2-fluoro-2-methyl-propyl)-2,3-dihydrofuro[3,2-h]isoquinoline-5-sulfonamide To a solution of Intermediate 112 (305 mg, 0.46 mmol) in a mixture of acetonitrile (5 mL), acetic acid (30 μL, 0.52 mmol), water (60 μL, 3.3 mmol) and dichloromethane (2 mL) at −20° C., was added 1,3-dichloro-5,5-dimethylhydantoin (181 mg, 0.92 mmol) in portions. After 35 minutes 1,3-dichloro-5,5-dimethylhydantoin (25 mg, 0.13 mmol) was added. After a further 15 minutes, a solution of fluoro isobutylamine hydrochloride (120 mg, 0.94) in a mixture of N,N-diisopropylethylamine (0.4 mL, 2 mmol), acetonitrile (1 mL) and dichloromethane (0.2 mL) was added. After 20 minutes, the mixture was diluted with water (10 mL) and dichloromethane (20 mL). The organics were separated using a hydrophobic frit and concentrated under reduced pressure to give an oil. To the residue was added N,N-dimethylformamide (3 mL), imidazole (63 mg, 0.91 mmol) and tert-butyldimethylchlorosilane (97 mg, 0.64). After 2 hours the mixture was diluted with ethyl acetate (20 mL) and water (10 mL). The organics were washed with brine, passed through a hydrophobic frit and concentrated under reduced pressure. Purification by flash chromatography gave the title compound as a white gum (134 mg, 57% Yield). LCMS $[M+H]^+$ 489/491, RT 3.14 min (Method 6).

Intermediate 115

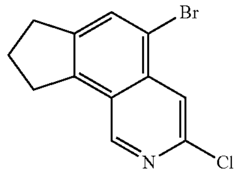 [SMILES: Clc1cc2c(Br)cc3c(c2cn1)CCC3]

5-bromo-3-chloro-8,9-dihydro-7H-cyclopenta[h]isoquinoline

Intermediate 4 (1.0 g, 0.98 mmol) was added in batches to a mixture of sulfuric acid (4.09 mL) and DCM (50 mL) at 0 T. The reaction mixture was cooled at −10° C. and NBS (961 mg, 5.4 mmol) added portion-wise. The reaction mixture was stirred at −10° C. for 2 hrs. NBS (0.2 equivalents) was added and the reaction mixture stirred for 1 hour at room temperature. The reaction mixture was diluted with ice-water (50 mL) and the pH adjusted to 8-10 with concentrated ammonium hydroxide. The resulting solution was extracted with DCM (2×50 mL) and the combined organic layers dried (sodium sulphate) and concentrated under reduced pressure. The residue was purified by column chromatography eluting with a gradient of 0% to 20% EtOAc in heptane to afford the title compound (1.26 g, 75% Yield) as off white solid. LCMS $[M+H]^+$ 282/284, RT 2.13 min (Method 9).

Intermediate 116

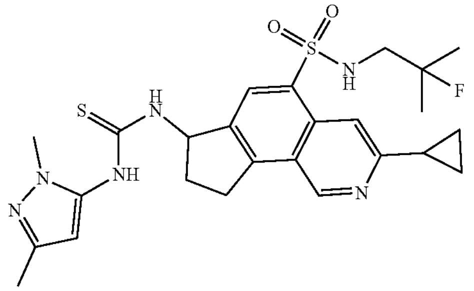 [SMILES: Cc1cc(NC(=S)NC2CCc3c2cc(S(=O)(=O)NCC(C)(C)F)c2cc(C4CC4)ncc32)n(C)n1]

1-[3-cyclopropyl-5-[(2-fluoro-2-methyl-propyl)sulfamoyl]-8,9-dihydro-7H-cyclopenta[h]isoquinolin-7-yl]-3-(2,5-dimethylpyrazol-3-yl)thiourea The title compound was prepared according to general procedure 4 with intermediate 36 (378 mg, 1.00 mmol), 5-isothiocyanato-1,3-dimethyl-1H-pyrazole (250 mg, 1.6 mmol), N,N-diisopropylethylamine (0.26 mL, 1.5 mmol) and dichloromethane (40 mL). Purified via column chromatography, using a gradient of 0-100% ethyl acetate in isohexane followed by 1-30% methanol in ethyl acetate to afford the title compound (416 mg, 78% Yield). $\delta_H$ (300 MHz, d6-DMSO) 9.34 (s, 1H), 9.29 (s, 1H), 8.52-8.31 (m, 2H), 8.23 (s, 1H), 6.17 (m, 1H), 5.93 (s, 1H), 3.54 (m, 4H), 3.25 (m, 2H), 3.01-2.82 (m, 2H), 2.80-2.63 (m, 1H), 2.29 (q, J=6.2 Hz, 1H), 2.07 (m, 4H), 1.26 (d, J=7.3 Hz, 3H), 1.19 (d, J=7.3 Hz, 3H), 1.06 (m, 4H). LCMS $[M+H]^+$ 531, RT 1.17 min (Method 1).

Intermediate 117

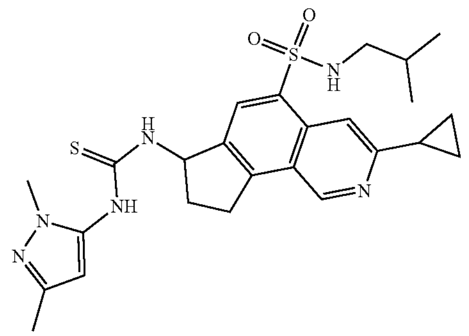 [SMILES: Cc1cc(NC(=S)NC2CCc3c2cc(S(=O)(=O)NCC(C)C)c2cc(C4CC4)ncc32)n(C)n1]

1-[3-cyclopropyl-5-(isobutylsulfamoyl)-8,9-dihydro-7H-cyclopenta[h]isoquinolin-7-yl]-3-(2,5-dimethylpyrazol-3-yl)thiourea The title compound was prepared according to general procedure 4 with Example 50 (100 mg, 0.28 mmol), 5-isothiocyanato-1,3-dimethyl-1H-pyrazole (0.05 mL, 0.4 mmol), N,N-diisopropylethylamine (0.07 mL, 0.4 mmol) and dichloromethane (10 mL). Purified via column chromatography, using a gradient of 0-100% ethyl acetate in isohexane followed by 1-30% methanol in ethyl acetate to afford the title compound (147 mg, 100% Yield). $\delta_H$ (300 MHz, d6-DMSO) 9.36 (s, 1H), 9.28 (d, J=1.0 Hz, 1H), 8.43 (d, J=8.2 Hz, 1H), 8.34 (d, J=1.0 Hz, 1H), 8.23 (s, 1H), 8.07 (t, J=5.9 Hz, 1H), 6.18 (m, 1H), 5.92 (s, 1H), 3.55 (s, 3H), 3.52-3.42 (m, 1H), 3.28-3.15 (m, 1H), 2.70 (m, 1H), 2.55 (m, 2H), 2.29 (p, J=6.5 Hz, 1H), 2.08 (m, 4H), 1.59 (dq, J=13.2, 6.7 Hz, 1H), 1.05 (m, 4H), 0.76 (dd, J=6.6, 1.2 Hz, 6H). LCMS $[M+H]^+$513, RT 1.19 min (Method 1).

Intermediate 118

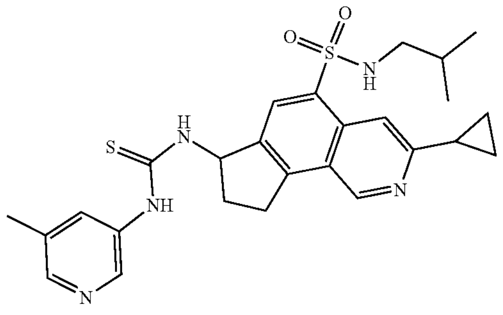 [SMILES: Cc1cncc(NC(=S)NC2CCc3c2cc(S(=O)(=O)NCC(C)C)c2cc(C4CC4)ncc32)c1]

1-[3-cyclopropyl-5-(isobutylsulfamoyl)-8,9-dihydro-7H-cyclopenta[h]isoquinolin-7-yl]-3-(5-methyl-3-pyridyl)thiourea The title compound was prepared according to general procedure 4 with Example 50 (100 mg, 0.28 mmol), 3-isothiocyanato-5-methyl-pyridine (63 mg, 0.42 mmol), N,N-diisopropylethylamine (0.07 mL, 0.4 mmol) and dichloromethane (10 mL). Purified via column chromatography, using a gradient of 0-100% ethyl acetate in iso-hexane followed by 1-20% methanol in ethyl acetate to afford the title compound (140 mg, 99% Yield). $\delta_H$ (300 MHz, d-Chloroform) 9.12 (d, J=1.0 Hz, 1H), 8.92 (s, 1H), 8.35 (s, 1H), 8.31 (d, J=2.3 Hz, 1H), 8.18 (d, J=0.9 Hz, 1H), 8.15-8.01 (m, 2H), 7.33 (d, J=8.1 Hz, 1H), 6.23 (q, J=7.7 Hz, 1H), 5.56 (m, 1H), 3.50-3.36 (m, 1H), 3.20 (dt, J=16.8, 8.2 Hz, 1H), 3.06-2.90 (m, 1H), 2.81 (m, 1H), 2.71-2.62 (m, 1H), 2.31 (s, 3H), 2.20 (td, J=9.0, 8.4, 4.0 Hz, 1H), 2.15-2.05 (m, 1H), 1.67 (dq, J=13.4, 6.7 Hz, 1H), 1.17-1.03 (m, 4H), 0.79 (m, 6H). LCMS $[M+H]^+$ 510, RT 1.35 min (Method 1).

Intermediate 119

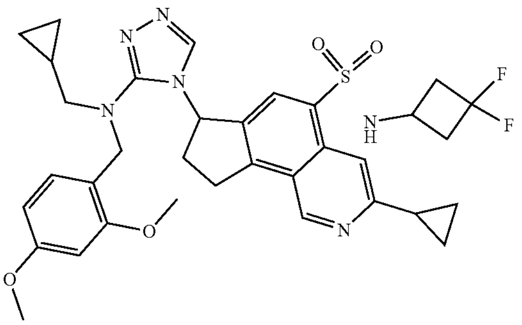

3-cyclopropyl-7-[3-[cyclopropylmethyl-[(2,4-dimethoxyphenyl)methyl]amino]-1,2,4-triazol-4-yl]-N-(3,3-difluorocyclobutyl)-8,9-dihydro-7H-cyclopenta[h]isoquinoline-5-sulfonamide A mixture of intermediate 131 (51 mg, 0.077 mmol), cyclopropylboronic acid (16.6 mg, 0.19 mmol), $Pd(OAc)_2$ (0.87 mg, 3.8 μmol), $P(Cy)_3 \cdot HBF_4$ (4.27 mg, 11.6 μmol) and $K_3PO_4$ (41.0 mg, 0.19 mmol) in a bi-phasic solution of toluene (5 mL) and water (0.075 mL) was heated at 120° C. for 5 hours. The reaction mixture was diluted with DCM (20 mL), dried ($MgSO_4$) and filtered through celite (washing through with DCM). The filtrate was concentrated under reduced pressure and purified by column chromatography eluting with a gradient of 0% to 10% MeOH in DCM to afford the title compound (35 mg, 55% Yield) as a pale yellow gum. LCMS $[M+H]^+$665, RT 1.93 min (Method 9).

Intermediate 120

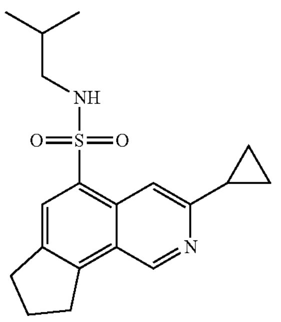 [SMILES: CC(C)CNS(=O)(=O)c1cc2c(c3cnc(C4CC4)cc13)CCC2]

3-cyclopropyl-N-isobutyl-8,9-dihydro-7H-cyclopenta[h]isoquinoline-5-sulfonamide

A mixture of Intermediate 6 (300 mg, 0.886 mmol), cyclopropylboronic acid (240 mg, 2.66 mmol) and caesium carbonate (729 mg, 2.21 mmol) in 1,4-dioxane (5 mL) was degassed and placed under an atmosphere of $N_2$. Chloro($\eta^2$—P,C-tris(2,4-di-tert butylphenyl)phosphite)(tricyclohexylphosphine)palladium(II) (95 mg, 0.0886 mmol) was added and the reaction mixture heated at 120° C. for 90 min in the microwave. The solvent was evaporated, and the residue partitioned between DCM and water. The organic phase was washed with brine, passed through a phase separator and evaporated. The crude material was purified by flash chromatography eluting with a gradient of 20-70% EtOAc in hexane to give the title product as an off-white solid (214 mg, 70% Yield). LCMS $[M+H]^+$ 345, RT 2.60 min (Method 3).

Intermediates 121 & 122

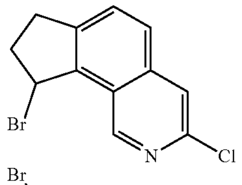

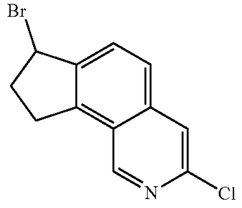

9-bromo-3-chloro-8,9-dihydro-7H-cyclopenta[h]isoquinoline (121)

7-bromo-3-chloro-8,9-dihydro-7H-cyclopenta[h]isoquinoline (122)

Intermediate 4 (2.5 g, 12.2 mmol) was dissolved in EtOAc (150 mL) and NBS (2.4 g, 13.5 mmol) was added. The reaction mixture was irradiated with light for 1 hour. The solvent was removed and the crude title compound mixture (4.9 g) was used in next stage without further purification. LCMS [M+H, —Br, +OH]$^+$ 220, RT 2.04 and 2.18 minutes (Method 8)

Intermediates 123 & 124

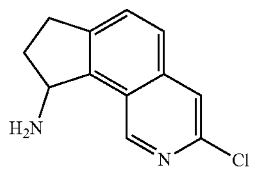

-continued

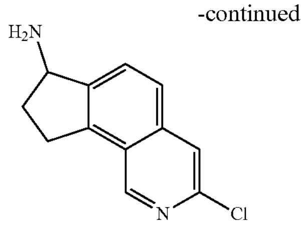

3-chloro-8,9-dihydro-7H-cyclopenta[h]isoquinolin-9-amine (123)

3-chloro-8,9-dihydro-7H-cyclopenta[h]isoquinolin-7-amine (124)

In a pressure flask, a mixture of intermediates 121 & 122 (3.46 g, 12.25 mmol) was dissolved in THF (160 mL). Ammonia gas was bubbled through for 5 min then the reaction mixture was stirred at 60° C. for 3 hrs then at room temperature for 16 hrs. Ammonia gas was bubbled through for~5 min and the reaction mixture heated at 60° C. for 5 hrs then at room temperature for 16 hrs. The solvent was removed under vacuum to give the title compound mixture (3.4 g) as a black gum. The material was used in the next stage without further purification. LCMS $[M+H]^+$219, RT 1.17 and 1.29 minutes (Method 8).

Intermediates 125 & 126

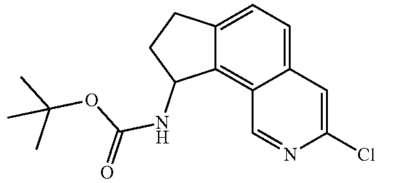

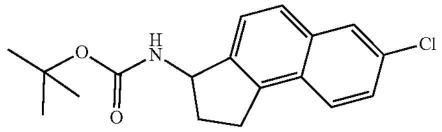

tert-butyl N-[3-chloro-8,9-dihydro-7H-cyclopenta[h]isoquinolin-9-yl)carbamate (125)

tert-butyl N-(3-chloro-8,9-dihydro-7H-cyclopenta[h]isoquinolin-7-yl]carbamate (126)

To a stirred mixture of intermediates 123 and 124 (2.6 g, 11.8 mmol) in DCM (100 mL) was added di-tert-butyl dicarbonate (2.8 g, 13.0 mmol) followed by triethylamine (3.31 mL, 23.7 mmol). The reaction mixture was stirred at room temperature for 16 hours. The reaction mixture was diluted with DCM (100 mL) and washed with water (100 mL). The organic layer dried over sodium sulphate and concentrated under vacuum. Purification by column chromatography using 0-50% ethyl acetate in heptane gave the title compounds:

Intermediate 125 (940 mg, 24% Yield); $\delta_H$ (500 MHz, Chloroform-d) 9.27 (s, 1H), 7.73 (s, 1H), 7.67 (d, J=8.4 Hz, 1H), 7.59 (d, J=8.4 Hz, 1H), 5.86-5.74 (m, 1H), 4.85 (d, J=8.0 Hz, 1H), 3.27-3.14 (m, 1H), 3.06-2.95 (m, 1H), 2.78-2.65 (m, 1H), 2.19-2.09 (m, 1H), 1.48 (s, 9H). LCMS $[M+H]^+$319, RT 3.03 min (Method 8).

Intermediate 126 (1.28 g, 32% Yield); 6 (500 MHz, Chloroform-d) 9.06 (s, 1H), 7.73 (s, 1H), 7.70 (d, J=8.4 Hz, 1H), 7.64 (d, J=8.5 Hz, 1H), 5.44-5.33 (m, 1H), 4.88-4.75 (m, 1H), 3.51-3.39 (m, 1H), 3.26-3.14 (m, 1H), 2.87-2.76 (m, 1H), 2.05-1.93 (m, 1H), 1.50 (s, 9H). LCMS $[M+H]^+$ 319, RT 3.03 min (Method 8).

Intermediate 127

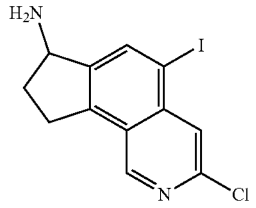 [SMILES: NC1CCc2c1cc(I)c1cc(Cl)ncc21]

3-chloro-5-iodo-8,9-dihydro-7H-cyclopenta[h]isoquinolin-7-amine

Intermediate 126 (1.0 g, 3.13 mmol) was added in batches to a solution of sulphuric acid (2.6 mL) in DCM (50 mL) at 0° C. The reaction mixture was cooled at −10° C. and NIS (847 mg, 3.76 mmol) was added portion-wise. The reaction mixture was stirred at −10° C. for 2 hrs, then stirred at room temperature for 16 hrs. Then, over a period of 32 hours 2 portions of NIS (2 equivalents each) were added. The reaction mixture was diluted with ice water (750 mL) and the pH adjusted to 8-10 with concentrated ammonium hydroxide. The resulting solution was extracted with DCM (2×70 mL) and the combined organic layers were washed with sodium thiosulfate, dried (sodium sulphate) and concentrated under reduced pressure. The crude title compound (650 mg) was used in the next stage without further purification. LCMS $[M+H]^+$ 345, RT 0.93 min (Method 17).

Intermediate 128

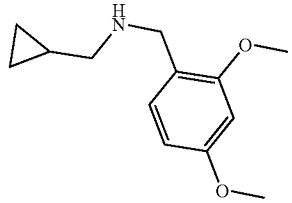 [SMILES: COc1ccc(CNCC2CC2)c(OC)c1]

N-(cyclopropylmethyl)-1-(2,4-dimethoxyphenyl)methanamine 2,4-dimethoxybenzaldehyde (2.0 g, 12.04 mmol), and $MgSO_4$ (400 mg) were added to 1-cyclopropylmethanamine (0.85 g, 12.04 mmol) in ethanol (10 mL). The reaction mixture was stirred at 78° C. for 4 h. The reaction mixture was then cooled to room temperature and sodium borohydride (0.50 g, 13.24 mmol) was added to the reaction mixture. The reaction mixture was stirred overnight at room temperature then concentrated in vacuo. The residue was dissolved in EtOAc (50 mL), wash with sat. aq. $NH_4Cl$, water and brine (30 mL each). The organic layer was dried over $MgSO_4$ and concentrate in vacuo. Purification by flash column chromatography eluting with a gradient of 0% to 20% MeOH in DCM afforded the title compound (2.1 g, 72% Yield) as a colourless oil. LCMS $[M+H]^+$ 222, RT 0.83 min (Method 17).

Intermediate 129

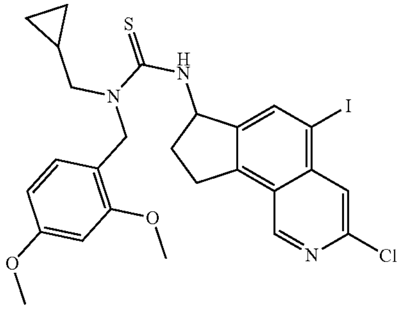 [SMILES: COc1ccc(CN(CC2CC2)C(=S)NC2CCc3c2cc(I)c2cc(Cl)ncc32)c(OC)c1]

3-(3-chloro-5-iodo-8,9-dihydro-7H-cyclopenta[h]isoquinolin-7-yl)-1-(cyclopropylmethyl)-1-[(2,4-dimethoxyphenyl)methyl]thiourea A mixture of intermediate 127 (650 mg, 1.64 mmol, 87% purity) and triethylamine (0.68 mL, 4.9 mmol) in DCM (15 mL) was added dropwise to a stirring solution of phenyl chloromethanethioate (0.25 mL, 1.8 mmol) in DCM (15 mL) at 0° C. The reaction was stirred at 0° C. for 30 minutes. A solution of intermediate 128 (626 mg, 2.83 mmol) in DCM (15 mL) was then added at 0° C. The reaction mixture was allowed to warm to room temperature and stirred for 20 hours. The reaction was diluted with DCM (30 mL) and washed with water (30 mL) followed by saturated aq. $NaHCO_3$ (30 mL). The organic layer was dried over sodium sulphate and concentrated under vacuum. Purification by column chromatography using a gradient of 0-50% ethyl acetate in heptane afforded the title compound (305 mg, 29% Yield) as a pale brown solid. LCMS $[M+H]^+$ 608, RT 2.26 min (Method 9).

Intermediate 130

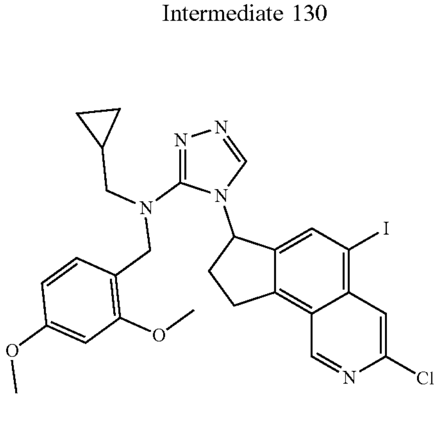

4-(3-chloro-5-iodo-8,9-dihydro-7H-cyclopenta[h]isoquinolin-7-yl)-N-(cyclopropylmethyl)-N-[(2,4-dimethoxyphenyl)methyl]-1,2,4-triazol-3-amine Intermediate 129 (305 mg, 0.48 mmol) was dissolved in dry DMF (7 mL). Formic hydrazide (87.6 mg, 1.46 mmol) and mercury dichloride (396.3 mg, 1.46 mmol) were added and reaction stirred for 5 minutes. Triethylamine (0.20 mL, 1.46 mmol) was added and reaction heated to 90° C. with stirring for 4 hours which resulted in a black suspension. Once at room temperature the reaction was diluted with DCM (20 mL) and Kieselguhr added, the mixture was stirred for 5 minutes then filtered through a plug of Kieselguhr washing through with DCM. The filtrate was concentrated under vacuum and the residue was dissolved in ethyl acetate (50 mL). The organic layer was washed with saturated $NH_4Cl$ (30 mL), water (30 mL) and brine (30 mL), then dried (sodium sulphate) and concentrated under vacuum. Purification by column chromatography using a gradient of 0-10% MeOH in DCM afforded the title compound (175 mg, 54% Yield) as a grey solid. LCMS $[M+H]^+$ 616, RT 2.05 min (Method 9).

Intermediate 131

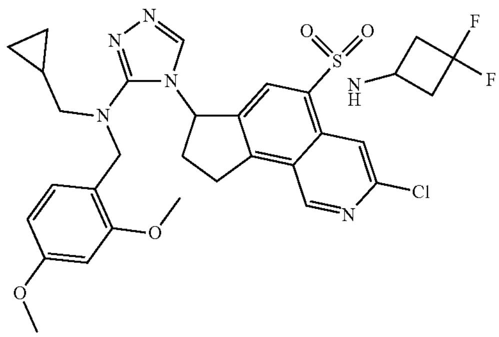

3-chloro-7-[3-[cyclopropylmethyl-[(2,4-dimethoxyphenyl)methyl]amino]-1,2,4-triazol-4-yl]-N-(3,3-difluorocyclobutyl)-8,9-dihydro-7H-cyclopenta[h]isoquinoline-5-sulfonamide A sealable tube was charged with intermediate 130 (90 mg, 0.14 mmol), potassium metabisulfite (64.9 mg, 0.29 mmol), TBAB (51.8 mg, 0.16 mmol), sodium formate (21.8 mg, 0.32 mmol), Pd(OAc)2 (1.6 mg, 0.007 mmol), triphenylphosphine (5.7 mg, 0.022 mmol) and 1,10-phenanthroline (3.9 mg, 0.022 mmol). The mixture was suspended in DMSO (1.0 mL), de-gassed and placed under an atmosphere of nitrogen. The tube was sealed and heated to 70° C. for 2 hours. Once at room temperature a solution of 3,3-difluorocyclobutan-1-amine hydrochloride (41.9 mg, 0.29 mmol) and triethylamine (40.5 mL, 0.29 mmol) in THF (1.5 mL) was added and the reaction was cooled to 0° C. A solution of NBS (52.0 mg, 0.29 mmol) in THF (2 mL) was added dropwise and the reaction allowed to warm to room temperature. After 1 hour the mixture was diluted with ethyl acetate (20 mL) and water (15 mL). The organic layer was washed with water (15 mL) and brine (10 mL), dried (magnesium sulfate) and concentrated under reduced pressure. Purification by flash column chromatography gave the title compound (51 mg, 50%) as a thin film. LCMS [M+H]$^+$ 659, RT 1.94 min (Method 9).

Intermediates 132 & 133

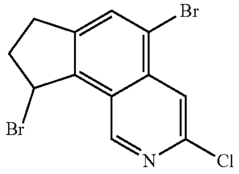

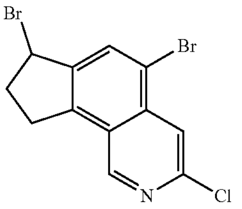

5,9-dibromo-3-chloro-8,9-dihydro-7H-cyclopenta[h] isoquinoline (132)

5,7-dibromo-3-chloro-8,9-dihydro-7H-cyclopenta[h] isoquinoline (133)

Intermediate 115 (200 mg, 0.70 mmol) was dissolved in EtOAc (13 mL) and NBS (132.2 mg, 0.74 mmol) followed by azobisisobutyronitrile (11.6 mg, 0.07 mmol) were added. The reaction mixture was irradiated with light for 1 hour. Due to suspected instability of the product, the solvent was removed and the crude title compound (310 mg) was used in next stage without further purification. LCMS [M+H]$^+$362, RT 3.18 min (Method 8).

Intermediates 134 & 135

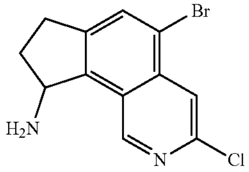

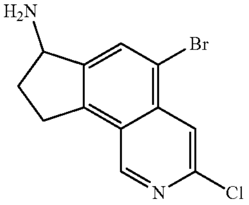

5-bromo-3-chloro-8,9-dihydro-7H-cyclopenta[h] isoquinolin-9-amine (134)

5-bromo-3-chloro-8,9-dihydro-7H-cyclopenta[h] isoquinolin-7-amine (135)

Mixture of intermediate 132 & 133 (1.61 g, 4.4 mmol) was dissolved in THF (95 mL) in a sealed tube. Ammonia gas was bubbled through for 5 min and the reaction mixture stirred at 60° C. for 16 hrs. The solvent was removed and the crude title compound (1.6 g) used in the next stage without further purification. LCMS [M+H]$^+$297/299, RT 1.87 and 2.00 min (Method 8)

Intermediates 136 & 137

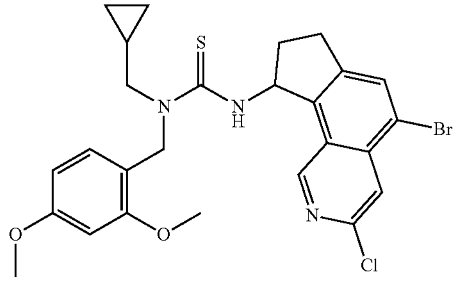

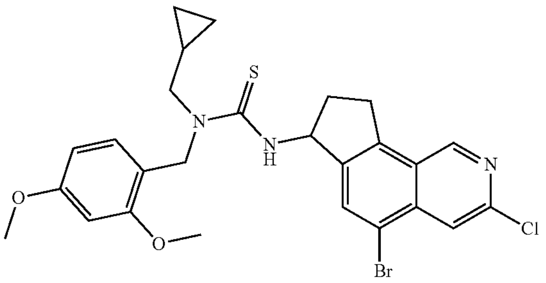

3-(5-bromo-3-chloro-8,9-dihydro-7H-cyclopenta[h] isoquinolin-9-yl)-1-(cyclopropylmethyl)-1-[(2,4-dimethoxyphenyl)methyl]thiourea (136)

3-(5-bromo-3-chloro-8,9-dihydro-7H-cyclopenta[h] isoquinolin-7-yl)-1-(cyclopropylmethyl)-1-[(2,4-dimethoxyphenyl)methyl]thiourea (137)

A mixture of intermediate 134 & 135 (788 mg, 2.64 mmol) and triethylamine (1.10 mL, 7.94 mmol) in DCM (20 mL) was added dropwise to a stirring solution of phenyl chloromethanethioate (0.404 mL, 2.91 mmol) in DCM (20 mL) at 0° C. The reaction was stirred at 0° C. for 30 minutes. A solution of Intermediate 128 (879 mg, 3.92 mmol) in DCM (20 mL) was then added and the reaction mixture allowed to warm to room temperature. After 20 hours the reaction was diluted with DCM (30 mL) and washed with water (30 mL), saturated aq. $NaHCO_3$ (30 mL), dried over sodium sulphate and concentrated under vacuum. Purification by column chromatography using a gradient of 0-50% ethyl acetate in heptane gave the title compounds:

Intermediate 136 (770 mg, 52% Yield); LCMS $[M+H]^+$ 560/562, RT 3.85 min (Method 8)

Intermediate 137 (480 mg, 31% Yield); LCMS $[M+H]^+$ 560/562, RT 3.90 min (Method 8)

EXAMPLES

Example 1

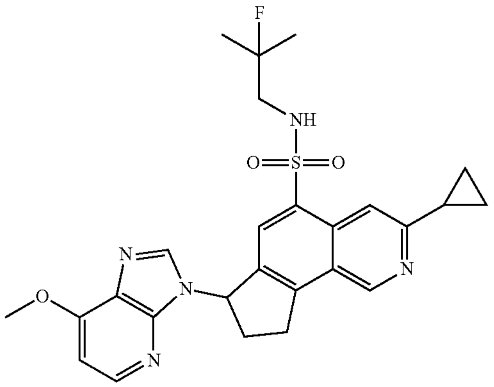 [SMILES: COc1ccnc2c1ncn2C1CCc2c1cc(S(=O)(=O)NCC(C)(C)F)c1cc(C3CC3)ncc21]

3-cyclopropyl-N-(2-fluoro-2-methylpropyl)-7-(7-methoxyimidazo[4,5-b]pyridin-3-yl)-8,9-dihydro-7H-cyclopenta[h]isoquinoline-5-sulfonamide Intermediate 83 (34 mg 0.052 mmol) was dissolved in acetic acid (0.5 mL) and treated with iron powder (25 mg, 0.44 mmol). The resulting mixture was stirred at room temperature for 1 hour. Acetic acid (0.5 mL), MeOH (1 mL) and a second portion of iron powder (25 mg, 0.44 mol) were then added and the mixture heated at 80° C. for 8 hours. A third portion of iron powder (35 mg, 0.63 mmol) was added and the reaction heated at 80° C. for 3 hours. The reaction was diluted with water (20 mL) and EtOAc (30 mL), the layers were separated, and the aqueous layer extracted with EtOAc. Combined organic layers were washed with sat. aq. $NaHCO_3$, dried ($Na_2SO_4$), filtered and concentrated in vacuo. Purification by column chromatography using a gradient of ethyl acetate in iso-hexane gave the title compound (4 mg); $\delta_H$ (300 MHz, d4-methanol) 9.33 (d, J=0.9 Hz, 1H), 8.42 (d, J=0.9 Hz, 1H), 8.24 (d, J=5.7 Hz, 1H), 8.13 (s, 1H), 7.98 (s, 1H), 6.93 (d, J=5.7 Hz, 1H), 6.55-6.46 (m, 1H), 4.10 (s, 3H), 3.93-3.79 (m, 1H), 3.64-3.49 (m, 1H), 3.19-3.01 (m, 1H), 2.87 (dd, J=19.8, 10.3 Hz, 2H), 2.79-2.67 (m, 1H), 2.39-2.28 (m, 1H), 1.17-1.04 (m, 10H). LCMS $[M+H]^+$ 510, RT 2.22 min (Method 4).

Example 2

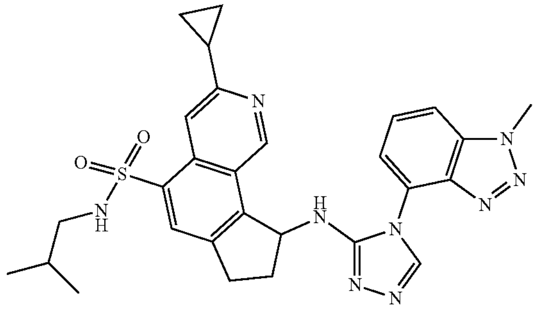 [SMILES: CC(C)CNS(=O)(=O)c1cc2c(c3cnc(C4CC4)cc13)C(Nc1nncn1-c1cccc3c1nnn3C)CC2]

3-cyclopropyl-N-isobutyl-9-[[4-(1-methylbenzotriazol-4-yl)-1,2,4-triazol-3-yl]amino]-8,9-dihydro-7H-cyclopenta[h]isoquinoline-5-sulfonamide General procedure 1 using intermediate 40 (71 mg) gave the title compound (13 mg, 19% Yield). $^1H$ NMR (300 MHz, Methanol-d4) δ 9.38 (d, J=0.9 Hz, 1H), 8.42 (s, 1H), 8.30 (d, J=1.0 Hz, 1H), 8.22 (s, 1H), 7.76 (dd, J=8.4, 0.9 Hz, 1H), 7.66-7.50 (m, 1H), 7.46 (dd, J=7.4, 0.8 Hz, 1H), 5.99 (dd, J=7.9, 3.6 Hz, 1H), 4.30 (s, 3H), 3.29-3.21 (m, 1H), 3.17-3.00 (m, 1H), 2.95-2.77 (m, 1H), 2.63 (dd, J=6.9, 2.7 Hz, 2H), 2.52-2.35 (m, 1H), 2.32-2.15 (m, 1H), 1.63 (dt, J=13.5, 6.8 Hz, 1H), 1.11-1.01 (m, 4H), 0.78 (dd, J=6.7, 2.6 Hz, 6H). LCMS $[M+H]^+$ 558, RT 1.89 min (Method 3).

Examples 3 & 4

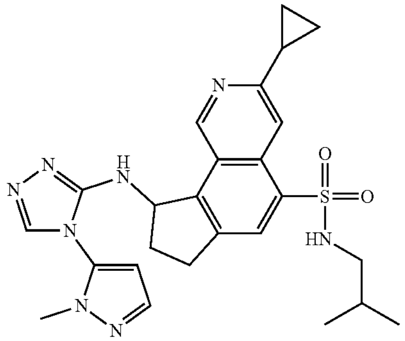

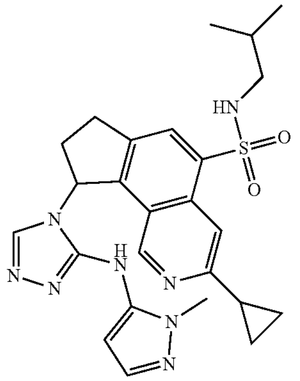

3-cyclopropyl-N-isobutyl-9-[[4-(2-methylpyrazol-3-yl)-1,2,4-triazol-3-yl]amino]-8,9-dihydro-7H-cyclopenta[h]isoquinoline-5-sulfonamide (3)

3-cyclopropyl-N-isobutyl-9-[3-[(2-methylpyrazol-3-yl)amino]-1,2,4-triazol-4-yl]-8,9-dihydro-7H-cyclopenta[h]isoquinoline-5-sulfonamide (4)

General procedure 1 using intermediate 41 (30 mg) gave the title compounds:

Example 3 (5 mg, 16% Yield); $^1$H NMR (300 MHz, Methanol-d4) δ 9.33 (d, J=0.9 Hz, 1H), 8.55 (s, 1H), 8.38 (d, J=1.0 Hz, 1H), 8.27 (s, 1H), 8.22 (s, 1H), 7.49 (d, J=2.1 Hz, 1H), 6.45 (d, J=2.1 Hz, 1H), 5.96 (dd, J=8.2, 3.9 Hz, 1H), 3.61 (s, 3H), 3.29-3.21 (m, 1H), 3.17-3.01 (m, 1H), 2.93-2.75 (m, 1H), 2.62 (d, J=6.9 Hz, 2H), 2.34-2.17 (m, 2H), 1.61 (dq, J=13.4, 6.8 Hz, 1H), 1.08 (d, J=7.0 Hz, 4H), 0.79 (dd, J=6.7, 1.1 Hz, 6H). LCMS $[M+H]^+$507.2 RT 1.76 min (Method 3).

Example 4 (7.5 mg, 25% Yield); $^1$H NMR (300 MHz, Methanol-d4) δ 9.27-8.68 (m, 1H), 8.43 (s, 1H), 8.39 (s, 1H), 7.77-7.57 (m, 1H), 7.56-7.28 (m, 1H), 6.67-6.32 (m, 1H), 6.30-5.82 (m, 1H), 3.80-3.67 (m, 3H), 3.61-3.43 (m, 1H), 3.29-3.21 (m, 1H), 3.06-2.89 (m, 1H), 2.70 (d, J=6.9 Hz, 2H), 2.52-2.37 (m, 1H), 2.34-2.21 (m, 1H), 1.64 (dp, J=13.4, 6.7 Hz, 1H), 1.13-0.99 (m, 4H), 0.79 (d, J=6.7 Hz, 6H). LCMS $[M+H]^+$ 507.2 RT 1.74 min (Method 3).

Example 5 and 6

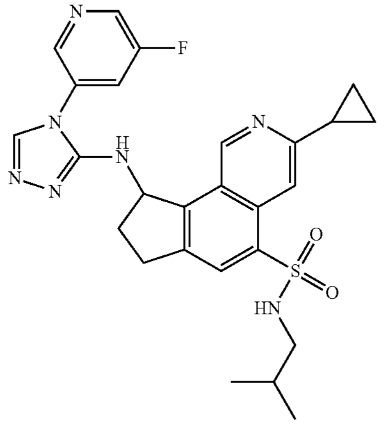

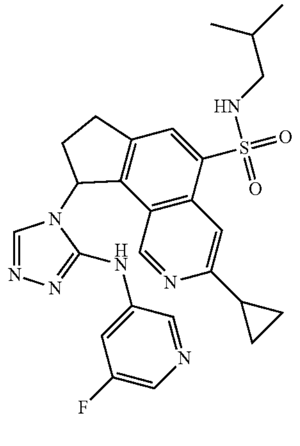

3-cyclopropyl-9-[[4-(5-fluoro-3-pyridyl)-1,2,4-triazol-3-yl]amino]-N-isobutyl-8,9-dihydro-7H-cyclopenta[h]isoquinoline-5-sulfonamide (5)

3-cyclopropyl-9-[3-[(5-fluoro-3-pyridyl)amino]-1,2,4-triazol-4-yl]-N-isobutyl-8,9-dihydro-7H-cyclopenta[h]isoquinoline-5-sulfonamide (6)

General procedure 1 using intermediate 42 (15 mg) gave the title compounds:

Example 5 (5 mg, 33% Yield). $^1$H NMR (300 MHz, Methanol-d4) δ 9.40 (d, J=0.9 Hz, 1H), 8.56-8.49 (m, 2H), 8.38 (d, J=1.0 Hz, 1H), 8.33 (s, 1H), 8.26 (s, 1H), 8.07 (s, 1H), 7.85 (dt, J=8.9, 2.3 Hz, 1H), 5.96 (dd, J=8.1, 3.9 Hz, 1H), 3.29-3.22 (m, 1H), 3.19-3.03 (m, 1H), 2.94-2.78 (m, 1H), 2.62 (d, J=6.9 Hz, 2H), 2.35-2.19 (m, 2H), 1.62 (dp, J=13.7, 6.8 Hz, 1H), 1.14-1.04 (m, 4H), 0.78 (dd, J=6.7, 1.0 Hz, 6H). LCMS $[M+H]^+$ 522, RT 1.86 min (Method 3)

Example 6 (4 mg, 27% Yield). $^1$H NMR (300 MHz, Methanol-d4) δ 8.79 (d, J=1.0 Hz, 1H), 8.48-8.44 (m, 1H), 8.43 (d, J=0.9 Hz, 1H), 8.40 (s, 1H), 8.06 (s, 2H), 7.92 (dt, J=11.1, 2.4 Hz, 1H), 7.82 (s, 1H), 6.52 (dd, J=8.5, 3.4 Hz, 1H), 3.60-3.41 (m, 1H), 3.28-3.23 (m, 1H), 3.10-2.96 (m, 1H), 2.71 (d, J=6.9 Hz, 2H), 2.53-2.36 (m, 1H), 2.36-2.19 (m, 1H), 1.73-1.57 (m, 1H), 1.12-0.96 (m, 4H), 0.80 (dd, J=6.7, 1.0 Hz, 6H). LCMS $[M+H]^+$522, RT 1.88 min (Method 3)

Example 7

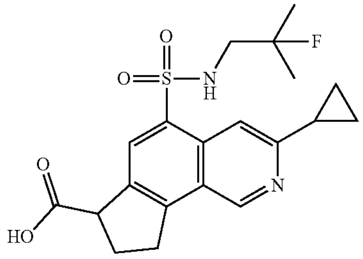 [SMILES: CC(C)(F)CNS(=O)(=O)c1cc2c(c3cnc(C4CC4)cc13)CCC2C(=O)O]

3-cyclopropyl-5-[(2-fluoro-2-methylpropyl)sulfamoyl]-8,9-dihydro-7H-cyclopenta[h]isoquinoline-7-carboxylic Acid Intermediate 56 (3 mg, 7.1 μmol) was dissolved in a mixture of tetrahydrofuran (1.0 mL) and water (0.5 mL). Lithium hydroxide (5 mg, 21.4 μmol) was added and the reaction stirred at ambient temp for 1 hour. The reaction was concentrated to remove organic solvent and diluted with $Et_2O$ (2 mL). The ethereal layer was partitioned and discarded, and the pH of the aqueous layer adjusted to 1 using aq. HCl (0.5 M). The acidic aqueous layer was extracted with EtOAc (2 mL). The organic solvent was removed in vacuo to afford the title compound (0.8 mg, 30% Yield). $^1$H (400 MHz, Methanol-d4) δ 9.22 (d, J=0.9 Hz, 1H), 8.44 (s, 1H), 8.42 (d, J=0.9 Hz, 1H), 4.44-4.17 (m, 1H), 3.68-3.36 (m, 2H), 3.03 (d, J=19.2 Hz, 2H), 2.64 (q, J=7.5 Hz, 2H), 2.33 (tt, J=8.1, 5.2 Hz, 1H), 1.23 (dd, J=21.1, 7.4 Hz, 6H), 1.12 (tt, J=8.2, 2.5 Hz, 4H).

Example 8

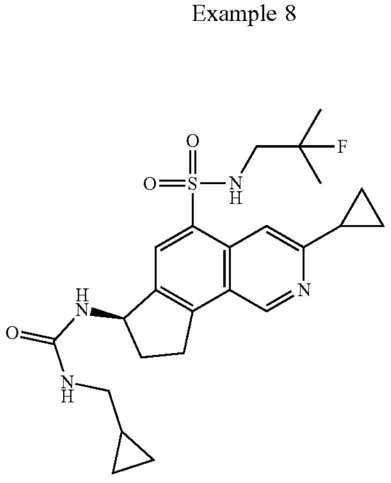

R or S 1-(cyclopropylmethyl)-3-[(7R*)-3-cyclopropyl-5-[(2-fluoro-2-methylpropyl)sulfamoyl]-8,9-dihydro-7H-cyclopenta[h]isoquinolin-7-yl]urea [* or S]

Intermediate 109 (12 mg, 0.018 mmol) was dissolved in dichloromethane (0.225 mL) and trifluoroacetic acid (0.025 mL, 0.32 mmol) was added and the reaction stirred overnight at ambient temperature. The reaction was concentrated in vacuo and the crude product was purified using reverse phase column (acidic conditions) to afford the title compound (1.4 mg, 17% Yield). $^{1}$H (300 MHz, Methanol-d4) δ 9.20 (d, J=1.0 Hz, 1H), 8.39 (d, J=1.0 Hz, 1H), 8.29 (s, 1H), 5.45 (t, J=7.7 Hz, 1H), 3.62-3.44 (m, 1H), 3.28-3.18 (m, 1H), 3.13-2.93 (m, 4H), 2.86-2.70 (m, 1H), 2.32 (tt, J=7.9, 5.3 Hz, 1H), 2.07-1.96 (m, 1H), 1.30-1.15 (m, 6H), 1.14-1.05 (m, 4H), 1.06-0.93 (m, 1H), 0.54-0.45 (m, 2H), 0.22 (td, J=5.6, 4.2 Hz, 2H). LCMS [M+H]+ 475, RT 2.08 min (Method 3).

Example 9

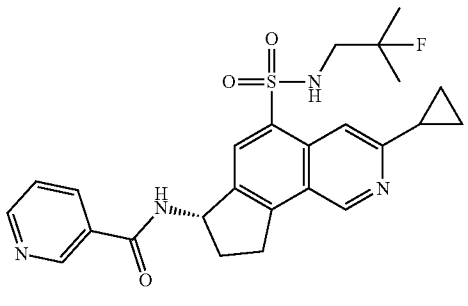

R or S

N-[(7R*)-3-cyclopropyl-5-[(2-fluoro-2-methylpropyl)sulfamoyl]-8,9-dihydro-7H-cyclopenta[h]isoquinolin-7-yl]pyridine-3-carboxamide [* or S]

To a stirred solution of Intermediate 38 (50 mg, 0.13 mmol), nicotinic acid (20 mg, 0.16 mmol) and N,N-diisopropylethylamine (69 μl, 0.40 mmol) in anhydrous N,N-dimethylformamide (1 mL) was added HATU (78 mg, 0.199 mmol). The reaction mixture stirred at room temperature overnight. The reaction mixture was purified by column chromatography to afford the title compound (35 mg, 55%). $^{1}$H (300 MHz, DMSO-d6) δ 9.32 (d, J=0.9 Hz, 1H), 9.15 (d, J=8.1 Hz, 1H), 9.06 (dd, J=2.3, 0.9 Hz, 1H), 8.72 (dd, J=4.9, 1.7 Hz, 1H), 8.45-8.34 (m, 1H), 8.25 (dt, J=8.0, 1.9 Hz, 1H), 8.15 (s, 1H), 7.52 (ddd, J=8.0, 4.8, 0.8 Hz, 1H), 5.77 (q, J=7.6 Hz, 1H), 3.67-3.49 (m, 1H), 3.38-3.24 (m, 1H), 2.95 (t, J=5.3 Hz, 1H), 2.92-2.83 (m, 1H), 2.80-2.64 (m, 1H), 2.37-2.25 (m, 1H), 2.25-2.11 (m, 1H), 1.19 (dd, J=21.4, 6.7 Hz, 6H), 1.06 (d, J=6.5 Hz, 4H). LCMS $[M+H]^{+}$483, RT 1.92 min (Method 3).

Example 10

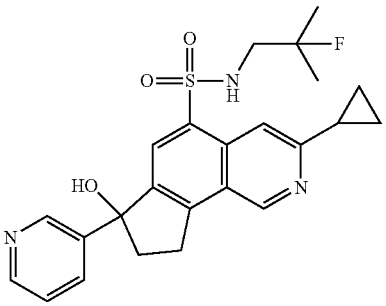 [SMILES: CC(C)(F)CNS(=O)(=O)c1cc2c(c3cnc(C4CC4)cc13)CCC2(O)c1cccnc1]

3-cyclopropyl-N-(2-fluoro-2-methylpropyl)-7-hydroxy-7-pyridin-3-yl-8,9-dihydrocyclopenta[h]isoquinoline-5-sulfonamide General Procedure 2 using intermediate 50 (10 mg, 0.011 mmol) and reverse phase HPLC (basic conditions) for product purification, gave the title compound (0.3 mg, 6% Yield). $^{1}$H (400 MHz, Methanol-d4) δ 9.32 (d, J=1.0 Hz, 1H), 8.59 (dd, J=2.4, 0.8 Hz, 1H), 8.46 (dd, J=4.9, 1.6 Hz, 1H), 8.43 (d, J=1.0 Hz, 1H), 7.99 (s, 1H), 7.82 (ddd, J=8.1, 2.3, 1.6 Hz, 1H), 7.43 (ddd, J=8.1, 4.9, 0.9 Hz, 1H), 3.74-3.49 (m, 2H), 3.09-2.81 (m, 2H), 2.73 (dd, J=7.5, 6.3 Hz, 2H), 2.40-2.28 (m, 1H), 1.25-1.05 (m, 10H). LCMS $[M+H]^{+}$456, RT 1.75 min (Method 3).

Example 11

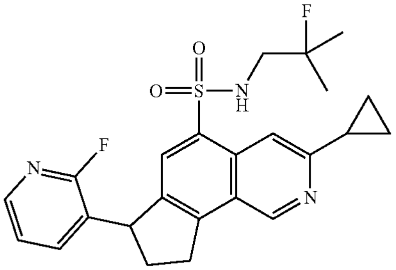 [SMILES: CC(C)(F)CNS(=O)(=O)c1cc2c(c3cnc(C4CC4)cc13)CCC2c1cccnc1F]

3-cyclopropyl-N-(2-fluoro-2-methylpropyl)-7-(2-fluoropyridin-3-yl)-8,9-dihydro-7H-cyclopenta[h]isoquinoline-5-sulfonamide General Procedure 2 using intermediate 61 (110 mg, 0.24 mmol) and reverse phase HPLC (basic conditions) for product purification gave the title compound (40 mg, 36% Yield). $^1$H NMR (400 MHz, DMSO-d6) δ 9.38-9.32 (m, 1H), 8.64-8.36 (m, 1H), 8.21-8.13 (m, 1H), 7.97-7.82 (m, 1H), 7.72-7.60 (m, 1H), 7.35-7.27 (m, 1H), 4.94-4.76 (m, 1H), 3.70-3.55 (m, 1H), 3.52-3.36 (m, 1H), 2.98-2.74 (m, 3H), 2.36-2.27 (m, 1H), 2.26-2.15 (m, 1H), 1.20-1.09 (m, 6H), 1.09-0.99 (m, 4H). LCMS $[M+H]^+$ 458, RT 2.42 min (Method 3).

Example 12 & 13

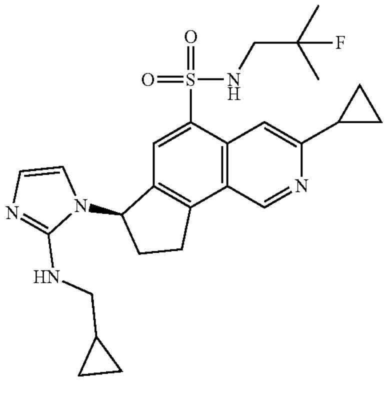

*R or S*

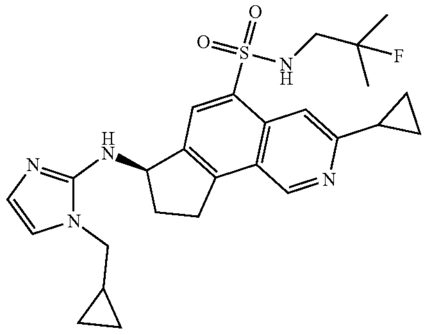

*R or S*

(7R*)-3-cyclopropyl-7-[2-(cyclopropylmethylamino)imidazol-1-yl]-N-(2-fluoro-2-methylpropyl)-8,9-dihydro-7H-cyclopenta[h]isoquinoline-5-sulfonamide [* or S] (12)

(7R*)-3-cyclopropyl-7-[[1-(cyclopropylmethyl)imidazol-2-yl]amino]-N-(2-fluoro-2-methylpropyl)-8,9-dihydro-7H-cyclopenta[h]isoquinoline-5-sulfonamide [* or S] (13)

To a stirred solution of intermediate 57 (134 mg, 0.21 mmol) in DMF (1.0 mL) was added aminoacetaldehyde diethyl acetal (84 mg, 0.63 mmol) followed by mercuric chloride (113.5 mg, 0.42 mmol). The mixture was stirred for 5 minutes at room temperature before the addition of triethylamine (63 mg, 0.63 mmol). The resulting reaction mixture was stirred at 80° C. for 1 h. The reaction was diluted with EtOAc (5 mL) and washed with sat aq. $NaHCO_3$ (3 mL). The aqueous phase was re-extracted with EtOAc (3 mL) and the combined organic extracts filtered through a pad of celite & $Na_2SO_4$. The solvents were removed in vacuo to afford crude material which was subjected to reverse phase HPLC (basic conditions) purification to afford the title compounds:

Example 12 (5 mg, 5% Yield); $^1$H (400 MHz, Methanol-d4) δ 9.27 (d, J=0.9 Hz, 1H), 8.42 (d, J=0.9 Hz, 1H), 8.03 (s, 1H), 6.54 (d, J=1.8 Hz, 1H), 6.25 (d, J=1.8 Hz, 1H), 6.03-5.79 (m, 1H), 3.75-3.59 (m, 1H), 3.48-3.36 (m, 1H), 3.25-3.13 (m, 2H), 3.01-2.89 (m, 3H), 2.39-2.25 (m, 2H), 1.23-1.07 (m, 11H), 0.58-0.47 (m, 2H), 0.33-0.23 (m, 2H).

Example 13 (4 mg, 4% Yield); $^1$H (400 MHz, Methanol-d4) δδ 9.22 (d, J=1.0 Hz, 1H), 8.39 (d, J=1.1 Hz, 1H), 8.33 (s, 1H), 6.76 (d, J=1.7 Hz, 1H), 6.62 (d, J=1.7 Hz, 1H), 5.48 (t, J=7.4 Hz, 1H), 3.61 (d, J=6.9 Hz, 2H), 3.60-3.52 (m, 1H), 3.06-2.83 (m, 4H), 2.37-2.25 (m, 1H), 2.22-2.07 (m, 1H), 1.22 (dd, J=21.1, 15.2 Hz, 6H), 1.17-1.02 (m, 5H), 0.64-0.50 (m, 2H), 0.42-0.14 (m, 2H).

Example 14

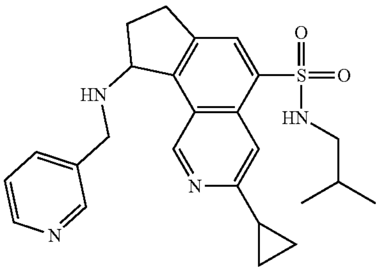 [SMILES: CC(C)CNS(=O)(=O)c1cc2c(c3cnc(C4CC4)cc13)C(NCc1cccnc1)CC2]

3-cyclopropyl-N-(2-methylpropyl)-9-(pyridin-3-ylmethylamino)-8,9-dihydro-7H-cyclopenta[h]isoquinoline-5-sulfonamide Intermediate 39 in its hydrochloride salt form (50 mg, 0.13 mmol) was suspended in 1,2-dichloroethane (1 mL) prior to addition of N,N-diisopropylethylamine (44 μL, 0.25 mmol), 3-pyridinecarboxaldehyde (14 mg, 0.13 mmol) and acetic acid (1 drop). The reaction was stirred at ambient temperature for 1 hour. Sodium borohydride (48 mg, 1.26 mmol) was added along with a few drops of MeOH and the reaction stirred at ambient temp overnight. The reaction was diluted with MeOH (1 mL) and sat. aq. $NaHCO_3$ (2 mL). The organic layer was separated, and the aqueous layer extracted with DCM (2 mL). The combined organic extracts were dried over $Na_2SO_4$ and concentrated in vacuo. The product was purified using reverse phase HPLC (basic conditions) to afford the title compound (8 mg, 14% Yield); $^1$H (300 MHz, DMSO-d6) δ 9.64 (d, J=0.9 Hz, 1H), 8.56 (d, J=2.2 Hz, 1H), 8.43 (dd, J=4.8, 1.7 Hz, 1H), 8.31 (d, J=0.9 Hz, 1H), 8.15 (s, 1H), 8.02 (s, 1H), 7.77 (dt, J=7.8, 2.0 Hz, 1H), 7.34 (dd, J=7.9, 4.6 Hz, 1H), 4.85 (dd, J=7.6, 3.7 Hz, 1H), 3.83 (s, 2H), 3.27-3.13 (m, 1H), 3.06-2.90 (m, 1H), 2.59-2.53 (m, 2H), 2.46-2.32 (m, 1H), 2.30-2.10 (m, 2H), 1.59 (dt, J=13.4, 6.7 Hz, 1H), 1.10-0.99 (m, 4H), 0.75 (dd, J=6.7, 1.0 Hz, 6H).

Example 15

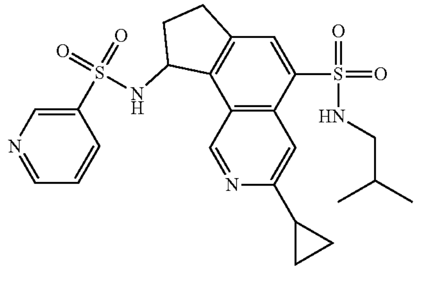 [SMILES: CC(C)CNS(=O)(=O)c1cc2c(c3cnc(C4CC4)cc13)C(NS(=O)(=O)c1cccnc1)CC2]

3-cyclopropyl-N-(2-methylpropyl)-9-(pyridin-3-ylsulfonylamino)-8,9-dihydro-7H-cyclopenta[h]isoquinoline-5-sulfonamide Intermediate 39 (50 mg, 0.14 mmol) was dissolved in dichloromethane (2 mL) and N,N-diisopropylethylamine (45 mg, 0.3477 mmol). Pyridine-3-sulfonyl chloride (34 mg, 0.18 mmol) was added and the reaction stirred at room temperature for 2 hours. The reaction was diluted with DCM (2 mL) and MeOH (1 mL) and washed with water (2 mL). The solvents were removed in vacuo and the product purified by reverse phase HPLC (basic conditions) to afford the title compound (21 mg, 30% Yield); $^{1}$H (300 MHz, DMSO-d6) δ 9.48 (d, J=0.9 Hz, 1H), 9.02 (dd, J=2.4, 0.8 Hz, 1H), 8.85 (dd, J=4.8, 1.6 Hz, 1H), 8.56 (s, 1H), 8.34 (d, J=0.9 Hz, 1H), 8.24 (dt, J=8.1, 1.8 Hz, 1H), 8.15 (s, 1H), 8.09 (t, J=5.9 Hz, 1H), 7.66 (ddd, J=8.0, 4.9, 0.8 Hz, 1H), 5.58 (d, J=7.6 Hz, 1H), 3.21-3.02 (m, 1H), 2.96-2.77 (m, 1H), 2.55 (t, J=6.2 Hz, 2H), 2.34-2.09 (m, 2H), 1.59 (dp, J=12.2, 6.2, 5.5 Hz, 2H), 1.14-1.00 (m, 4H), 0.75 (dd, J=6.7, 1.2 Hz, 6H).

Example 16

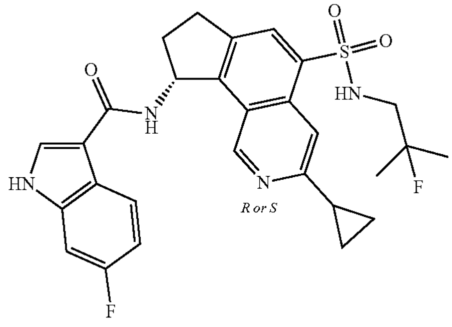 [SMILES: CC(C)(F)CNS(=O)(=O)c1cc2c(c3cnc(C4CC4)cc13)[C@H](NC(=O)c1c[nH]c3cc(F)ccc13)CC2]

6-fluoro-N-[(9R*)-3-cyclopropyl-5-[(2-fluoro-2-methylpropyl)sulfamoyl]-8,9-dihydro-7H-cyclopenta[h]isoquinolin-9-yl]-1H-indole-3-carboxamide [* or S]

6-Fluoro-1H-indole-3-carboxylic acid (12 mg, 0.064 mmol) was dissolved in a solution of DMF (0.25 mL) containing N,N-diisopropylethylamine (0.13 mmol, 0.023 mL) and N,N,N',N'-Tetramethyl-O-(1H-benzotriazol-1-yl) uronium hexafluorophosphate, O-(Benzotriazol-1-yl)-N,N,N',N'-tetramethyluronium hexafluorophosphate (31 mg, 0.079 mmol). The reaction was stirred for 10 min prior to addition of a solution of intermediate 65 (20 mg, 0.053 mmol) in DMF (0.25 mL). The reaction was stirred at ambient temperature overnight, diluted with water (2 mL) and extracted with EtOAc (2×2 mL). The combined organic extracts were dried over $Na_2SO_4$ and concentrated in vacuo. The product was purified reverse phase HPLC (basic conditions) to afford the title compound (4 mg, 14% Yield); $^{1}$H (300 MHz, Methanol-d4) δ 9.41 (d, J=0.9 Hz, 1H), 8.41 (d, J=1.0 Hz, 1H), 8.32 (s, 1H), 8.16 (dd, J=8.8, 5.4 Hz, 1H), 7.82 (s, 1H), 7.15-7.07 (m, 1H), 6.94 (ddd, J=9.7, 8.8, 2.4 Hz, 1H), 6.33 (dd, J=8.6, 4.5 Hz, 1H), 3.47-3.33 (m, 1H), 3.20-3.08 (m, 1H), 3.02 (d, J=19.4 Hz, 2H), 2.93-2.77 (m, 1H), 2.34-2.20 (m, 2H), 1.24 (dd, J=21.1, 5.8 Hz, 6H), 1.09-0.99 (m, 4H). LCMS [M+H]$^{+}$539, RT 2.23 min (Method 3).

Example 17

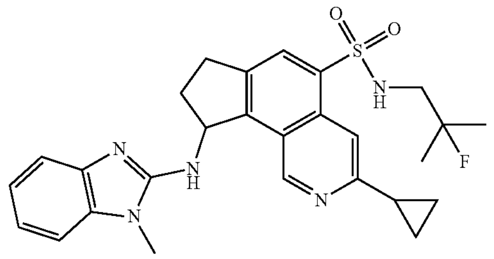 [SMILES: Cn1c(NC2CCc3cc(S(=O)(=O)NCC(C)(C)F)c4cc(C5CC5)ncc4c32)nc2ccccc21]

3-cyclopropyl-N-(2-fluoro-2-methylpropyl)-9-[(1-methylbenzimidazol-2-yl)amino]-8,9-dihydro-7H-cyclopenta[h]isoquinoline-5-sulfonamide General Procedure 2 using intermediate 66 (13 mg, 0.026 mmol) and reverse phase column chromatography (basic condition) gave the title compound (0.5 mg, 4% Yield). $^{1}$H (400 MHz, Methanol-d4) δ 9.35 (d, J=0.9 Hz, 1H), 8.43 (d, J=0.9 Hz, 1H), 8.34 (s, 1H), 7.45-7.35 (m, 1H), 7.22-7.15 (m, 1H), 7.14-7.03 (m, 2H), 6.20 (dd, J=8.2, 4.3 Hz, 1H), 3.47 (s, 3H), 3.46-3.32 (m, 1H), 3.20-3.10 (m, 1H), 3.03 (d, J=19.4 Hz, 2H), 2.91 (dtd, J=14.5, 8.7, 6.2 Hz, 1H), 2.37-2.22 (m, 2H), 1.25 (dd, J=21.1, 8.4 Hz, 6H), 1.12-0.99 (m, 4H). LCMS [M+H]$^{+}$ 508, RT 2.26 min (Method 7).

Example 18

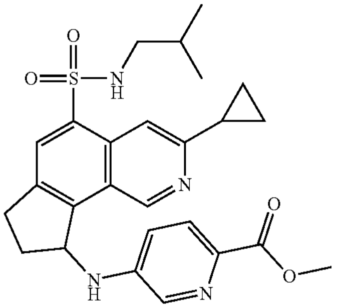 [SMILES: COC(=O)c1ccc(NC2CCc3cc(S(=O)(=O)NCC(C)C)c4cc(C5CC5)ncc4c32)cn1]

methyl 5-[[3-cyclopropyl-5-(2-methylpropylsulfamoyl)-8,9-dihydro-7H-cyclopenta[h]isoquinolin-9-yl]amino]pyridine-2-carboxylate General Procedure 3 using intermediate 39 (50 mg, 0.14 mmol), methyl 5-bromopyridine-2-carboxylate (77 mg, 0.35 mmol) and column chromatography for purification gave the title compounds (28 mg, 39% Yield); $^1$H (400 MHz, DMSO-d6) δ 9.21 (s, 1H), 8.37 (d, J=0.9 Hz, 1H), 8.25 (s, 1H), 8.15-8.07 (m, 2H), 7.88 (d, J=8.7 Hz, 1H), 7.30 (d, J=8.2 Hz, 1H), 7.18 (dd, J=8.8, 2.8 Hz, 1H), 5.86-5.76 (m, 1H), 3.79 (s, 3H), 3.30-3.20 (m, 1H), 3.17-3.04 (m, 1H), 2.72-2.61 (m, 1H), 2.58 (t, J=6.5 Hz, 2H), 2.32-2.20 (m, 1H), 2.14-1.99 (m, 1H), 1.62 (hept, J=6.7 Hz, 1H), 1.07-0.91 (m, 4H), 0.78 (dd, J=6.7, 4.4 Hz, 6H). LCMS $[M+H]^+$ 495, RT 2.09 min (Method 7).

Example 19

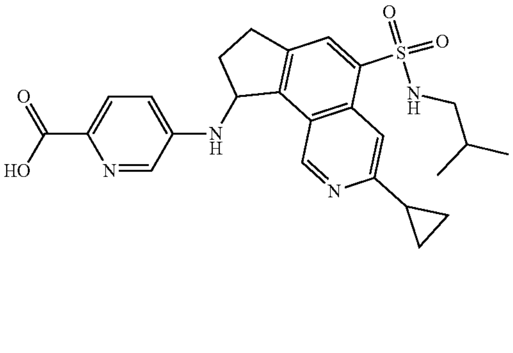 [SMILES: CC(C)CNS(=O)(=O)c1cc2c(c3cnc(C4CC4)cc13)C(Nc1ccc(C(=O)O)nc1)CC2]

5-[[3-cyclopropyl-5-(2-methylpropylsulfamoyl)-8,9-dihydro-7H-cyclopenta[h]isoquinolin-9-yl]amino] pyridine-2-carboxylic Acid Example 18 (26 mg, 0.053 mmol) was dissolved in a mixture of tetrahydrofuran (0.75 mL) and water (0.5 mL). Lithium hydroxide monohydrate (8.5 mg, 0.20 mmol) was added and the reaction heated at 50° C. with stirring for 1 hour. The reaction was cooled and concentrated in vacuo and the crude residue purified by basic reverse phase column chromatography to afford the title compound (11 mg, 45% Yield); $^1$H (400 MHz, DMSO-d6) δ 12.06 (s, 1H), 9.26-9.16 (m, 1H), 8.37 (d, J=0.9 Hz, 1H), 8.25 (s, 1H), 8.16-8.05 (m, 2H), 7.87 (d, J=8.6 Hz, 1H), 7.23 (d, J=8.2 Hz, 1H), 7.19 (dd, J=8.8, 2.8 Hz, 1H), 5.86-5.73 (m, 1H), 3.28-3.21 (m, 1H), 3.15-3.04 (m, 1H), 2.73-2.61 (m, 1H), 2.61-2.55 (m, 2H), 2.31-2.22 (m, 1H), 2.12-2.00 (m, 1H), 1.62 (hept, J=6.7 Hz, 1H), 1.11-0.92 (m, 4H), 0.78 (dd, J=6.7, 4.5 Hz, 6H). LCMS $[M+H]^+$481, RT 1.58 min (Method 7).

Example 20

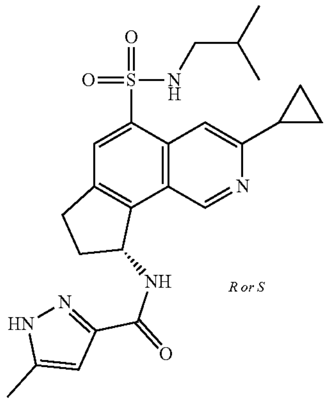 [SMILES: Cc1cc(C(=O)N[C@@H]2CCc3cc(S(=O)(=O)NCC(C)C)c4cc(C5CC5)ncc4c32)n[nH]1]

R or S 5-methyl-N-[(9R*)-3-cyclopropyl-5-(2-methylpropylsulfamoyl)-8,9-dihydro-7H-cyclopenta[h]isoquinolin-9-yl]-1H-pyrazole-3-carboxamide [* or S]

HATU (82 mg, 0.21 mmol) was added to a stirred solution of the hydrochloride salt form of Intermediate 39 (50 mg, 0.14 mmol), 5-methyl-1 h-pyrazole-3-carboxylic acid (21 mg, 0.167 mmol) and N,N-diisopropylethylamine (54 mg, 0.42 mmol) in anhydrous N,N-dimethylformamide (1 mL). The reaction mixture stirred at room temperature for 45 min. The reaction mixture was then purified using reverse phase column chromatography (acidic conditions) followed by reverse phase HPLC (basic conditions) to afford the title compound (39 mg, 60% Yield) as a mixture of enantiomers; The mixture was separated using chiral SFC to give the title compound as a single isomer (2 mg); Chiral SFC RT**=2.31 min. $^1$H (300 MHz, DMSO-d6) δ 12.89 (s, 1H), 9.27 (s, 1H), 8.87-8.68 (m, 1H), 8.34 (d, J=0.9 Hz, 1H), 8.18 (s, 1H), 8.06 (s, 1H), 6.52-6.34 (m, 1H), 6.14 (td, J=9.0, 4.2 Hz, 1H), 3.44-3.35 (m, 1H), 3.10-2.90 (m, 1H), 2.75-2.53 (m, 3H), 2.31-2.04 (m, 5H), 1.62 (dp, J=13.5, 6.7 Hz, 1H), 1.09-0.90 (m, 4H), 0.78 (dd, J=6.7, 2.1 Hz, 6H). LCMS $[M+H]^+$ 468, RT 2.07 min (Method 7).

**Chiral analysis was carried out by SFC, using a Chiralcel OJ-3 150×4.6 mm, 3 μM column, flow rate 3.5 ml/min eluting with 10-25% MeOH (+0.1% $NH_4OH$) using a 6 min run time on a Waters UPC$^2$-SQD2 system.

Example 21

R or S

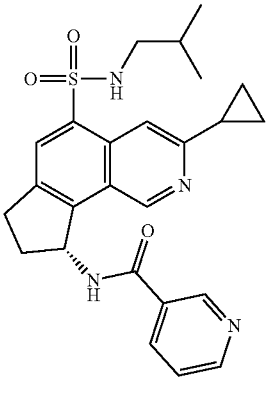

N-[(9R*)-3-cyclopropyl-5-(2-methylpropylsulfamoyl)-8,9-dihydro-7H-cyclopenta[h]isoquinolin-9-yl]pyridine-3-carboxamide [* or S]

HATU (16 mg, 0.042 mmol) was added to a stirred solution of Intermediate 67 (10 mg, 0.028 mmol), nicotinic acid (4 mg, 0.033 mmol) and N,N-diisopropylethylamine (15 μL, 0.084 mmol) in anhydrous N,N-dimethylformamide (0.2 mL, 3 mmol). The reaction mixture was stirred at room temperature for 1 hour. Then purified by basic reverse phase column chromatography to afford the title compound (8 mg, 60% Yield); $^1H$ (300 MHz, DMSO-d6) δ 9.33-9.21 (m, 2H), 9.00 (dd, J=2.3, 0.9 Hz, 1H), 8.69 (dd, J=4.8, 1.7 Hz, 1H), 8.35 (d, J=0.9 Hz, 1H), 8.23 (s, 1H), 8.20 (dt, J=8.0, 2.0 Hz, 1H), 8.15-8.03 (m, 1H), 7.49 (ddd, J=8.0, 4.8, 0.9 Hz, 1H), 6.21 (dt, J=8.5, 4.4 Hz, 1H), 3.45-3.33 (m, 1H), 3.16-3.00 (m, 1H), 2.78-2.53 (m, 2H), 2.31-2.07 (m, 3H), 1.63 (dt, J=13.4, 6.7 Hz, 1H), 1.07-0.90 (m, 4H), 0.78 (dd, J=6.7, 2.5 Hz, 6H). LCMS $[M+H]^+$ 465, RT 2.11 min (Method 4).

Example 22

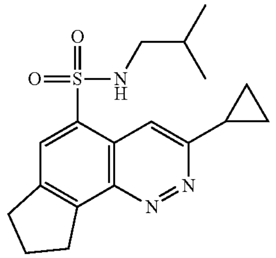 [SMILES: CC(C)CNS(=O)(=O)c1cc2c(c3nnc(C4CC4)cc13)CCC2]

3-cyclopropyl-N-(2-methylpropyl)-8,9-dihydro-7H-cyclopenta[h]cinnoline-5-sulfonamide A mixture of intermediate 73 (77 mg, 0.23 mmol), cyclopropylboronic acid (61 mg, 0.68 mmol) and caesium carbonate (186 mg, 0.57 mmol) in anhydrous 1,4-dioxane (1.5 mL) was sparged with nitrogen for 5 minutes. Chloro(η$^2$—P,C-tris(2,4-di-tert-butylphenyl)phosphite)(tricyclohexylphosphine)palladium(II) (24 mg, 0.023 mmol) was added and the reaction mixture heated in a microwave for 1 hour at 120° C. The reaction was diluted with DCM (3 mL) and washed with water (1 mL). The organic phase was dried over $Na_2SO_4$ and concentrated in vacuo. The product was purified by column chromatography to afford the title compound (21 mg, 27% Yield). $^1H$ (400 MHz, Chloroform-d) δ 8.39 (s, 1H), 8.32 (s, 1H), 4.69 (t, J=6.4 Hz, 1H), 3.69 (t, J=7.6 Hz, 2H), 3.21 (t, J=7.5 Hz, 2H), 2.74 (t, J=6.6 Hz, 2H), 2.45-2.30 (m, 3H), 1.68 (dh, J=13.2, 6.6 Hz, 1H), 1.46-1.38 (m, 2H), 1.27-1.17 (m, 2H), 0.82 (d, J=6.7 Hz, 6H). LCMS $[M+H]^+$ 346, RT 2.41 min (Method 3).

Example 23

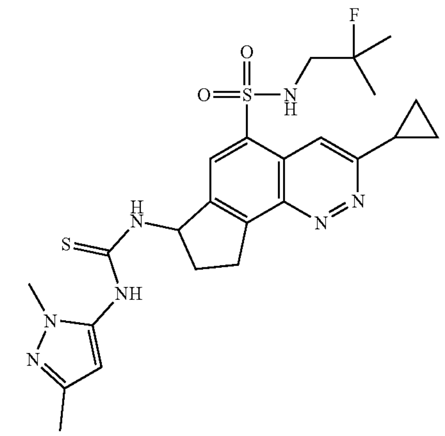 [SMILES: Cc1cc(NC(=S)NC2CCc3c2cc(S(=O)(=O)NCC(C)(C)F)c2cc(C4CC4)nnc32)n(C)n1]

1-[3-cyclopropyl-5-[(2-fluoro-2-methylpropyl)sulfamoyl]-8,9-dihydro-7H-cyclopenta[h]cinnolin-7-yl]-3-(2,5-dimethylpyrazol-3-yl)thiourea To a stirred suspension of intermediate 82 (42 mg, 0.10 mmol) in dichloromethane (2 mL) was added N,N-diisopropylethylamine (26 mg, 0.20 mmol) and 5-isothiocyanato-1,3-dimethyl-1 h-pyrazole (24 mg, 0.15 mmol). The reaction mixture was stirred at room temperature for 1 hour, diluted with MeOH and concentrated in vacuo. The crude product was purified by column chromatography to afford the title compound (41 mg, 76% Yield). $^1H$ NMR (300 MHz, DMSO-d6) δ 9.43 (s, 1H), 8.58-8.43 (m, 3H), 8.29 (s, 1H), 6.36-6.16 (m, 1H), 5.94 (s, 1H), 3.81-3.60 (m, 1H), 3.55 (s, 3H), 3.49-3.33 (m, 1H), 3.02-2.89 (m, 2H), 2.82-2.70 (m, 1H), 2.24-1.99 (m, 4H), 1.33-1.12 (m, 11H). LCMS $[M+H]^+$ 532.1 RT 2.17 min (Method 3).

Example 24 & 25

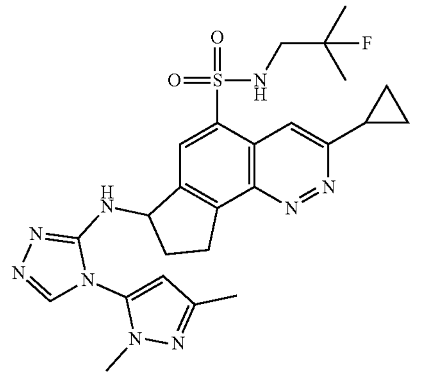

-continued

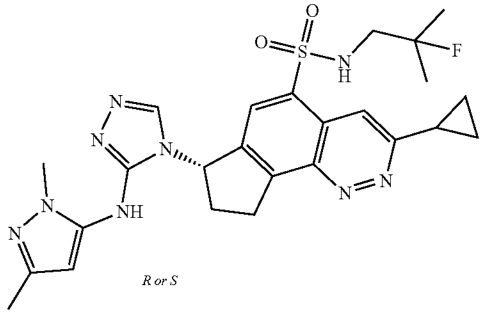

3-cyclopropyl-7-[[4-(2,5-dimethylpyrazol-3-yl)-1,2,4-triazol-3-yl]amino]-N-(2-fluoro-2-methylpropyl)-8,9-dihydro-7H-cyclopenta[h]cinnoline-5-sulfonamide (24)

(7R*)-3-cyclopropyl-7-[3-[(2,5-dimethylpyrazol-3-yl)amino]-1,2,4-triazol-4-yl]-N-(2-fluoro-2-methylpropyl)-8,9-dihydro-7H-cyclopenta[h]cinnoline-5-sulfonamide [* or S] (25)

General Procedure 1 using Example 23 (50 mg, 0.094 mmol) and column chromatography for purification gave Example 24 (21 mg, 41% yield) and the racemic mixture of Example 25 (14 mg, 28% yield). The racemate of Example 25 was purified by chiral HPLC (Column: LUX Cullulose-2 250×21.2 mm, 5 uM, flow rate 10 mL/min, column temp 40° C. Mobile Phase: MeOH+0.1% $NH_4OH$. Run Time: 20 mins) to give Example 25 as the first eluting peak.

Example 24 $^1$H NMR (300 MHz, DMSO-d6) δ 8.56 (s, 1H), 8.45 (s, 1H), 8.26-8.17 (m, 2H), 6.88 (d, J=8.5 Hz, 1H), 6.29 (s, 1H), 5.54 (q, J=7.7 Hz, 1H), 3.78-3.58 (m, 1H), 3.51 (s, 3H), 3.47-3.37 (m, 1H), 2.94-2.67 (m, 3H), 2.30-2.16 (m, 1H), 2.15 (s, 3H), 1.32-1.08 (m, 11H). LCMS $[M+H]^+$540 RT 1.73 min (Method 7).

Example 25 Chiral RT**=2.93 minutes. $^1$H NMR (300 MHz, Methanol-d4) δ 8.75-8.47 (m, 1H), 8.36-8.12 (m, 1H), 8.08-7.89 (m, 1H), 6.11 (t, J=7.0 Hz, 1H), 5.87 (s, 1H), 4.11-3.82 (m, 1H), 3.78-3.47 (m, 4H), 3.18-2.86 (m, 3H), 2.72-2.42 (m, 2H), 2.18 (s, 3H), 1.53-1.24 (m, 4H), 1.24-0.95 (m, 6H). LCMS $[M+H]^+$540, RT 1.65 min (Method 7).

**Chiral analysis was carried out by polar organic mode, using a Lux Cellulose-2 4.6×150 mm, 3 μm column, flow rate 1 mL/min eluting with Methanol (0.1% ammonium hydroxide) using a 10 min run time on an Agilent 1100 UV directed system.

Example 26

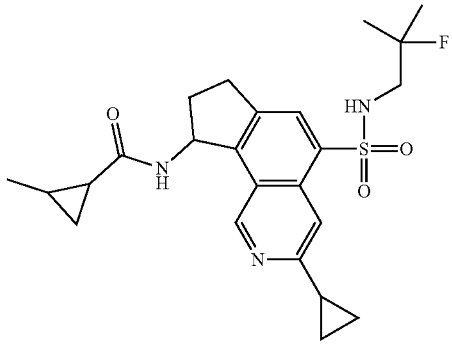 [SMILES: CC1CC1C(=O)NC1CCc2cc(S(=O)(=O)NCC(C)(C)F)c3cc(C4CC4)ncc3c21]

N-[3-cyclopropyl-5-[(2-fluoro-2-methylpropyl)sulfamoyl]-8,9-dihydro-7H-cyclopenta[h]isoquinolin-9-yl]-2-methylcyclopropane-1-carboxamide 2-Methylcyclopropanecarboxylic acid (5.2 mg, 0.05 mmol) was treated with a solution of Intermediate 84 (19 mg, 0.05 mmol) in DMF (0.4 mL). A solution of TBTU (19 mg, 0.05 mmol) in DMF (416 μL) was then added followed by a solution of DIPEA (9 μL, 0.05 mmol) in DMF (50 μL). The resulting mixture was stirred at ambient temperature for 18 hours then purified by preparative HPLC to give the title compound (12.4 mg, 53% Yield). LCMS $[M+H]^+$ 460.5, RT 1.44 minutes (method 13). HRMS $[M+H]^+$ observed 460.2055, calculated $C_{24}H_{31}FN_3O_3S_1$ 460.207.

Example 27

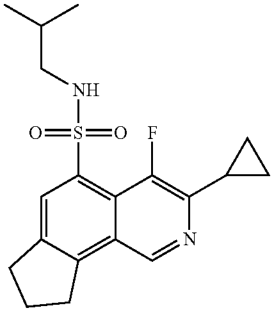 [SMILES: CC(C)CNS(=O)(=O)c1cc2c(c3cnc(C4CC4)c(F)c13)CCC2]

3-cyclopropyl-4-fluoro-N-(2-methylpropyl)-8,9-dihydro-7H-cyclopenta[h]isoquinoline-5-sulfonamide A suspension of Intermediate 120 (22 mg, 0.064 mmol), N-fluorobenzensulphonamide (63 mg, 0.2 mmol) and lithium carbonate (6 mg, 0.08 mmol) in MeCN (0.3 mL) was heated to 75° C. under an argon atmosphere for 3 days, after which time the mixture was filtered and the filtrate purified by preparative HPLC to give the title compound (1.2 mg, 5% yield). $\delta_H$ (500 MHz, DMSO-d6) 9.09 (s, 1H), 8.27 (s, 1H), 7.62 (s, 1H), 3.41-3.35 (m, 2H), 3.13 (t, J=7.5 Hz, 2H), 2.76 (t, J=5.9 Hz, 2H), 2.24 (p, J=7.7 Hz, 2H), 1.69 (hept, J=6.7 Hz, 1H), 1.14-1.07 (m, 5H), 0.80 (d, J=6.7 Hz, 6H). LCMS $[M+H]^+$ 363, RT 3.27 min (Method 15).

Examples 28, 29, 30

Procedure

A solution of intermediate 84 (18.9 mg, 0.05 mmol) and tBuXPhos Pd G3 (6.2 mg, 0.0075 mmol) in dioxane (0.5 mL) was treated with sodium tert-butoxide (14.4 mg, 0.15 mmol) and the appropriate aryl bromide (0.072 mmol, see table below) and the resulting mixture heated to 100° C. under argon for 18 hrs. The products were isolated by preparative HPLC and analysed with LCMS methods 13 () or 14 (*).

| Example | Structure | Name | Reagent | RT | Mass |
|---|---|---|---|---|---|
| 28 | 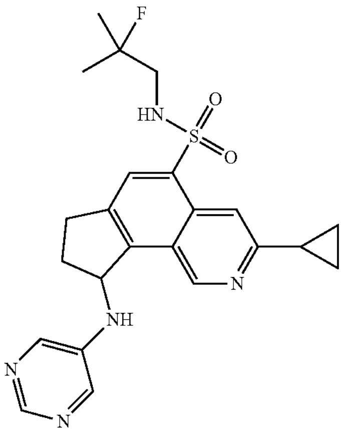 [SMILES: CC(C)(F)CNS(=O)(=O)c1cc2c(c3cnc(C4CC4)cc13)C(Nc1cncnc1)CC2] | 3-cyclopropyl-N-(2-fluoro-2-methylpropyl)-9-(pyrimidin-5-ylamino)-8,9-dihydro-7H-cyclopenta[h]isoquinoline-5-sulfonamide | 5-Bromopyrimidine | 1.24** | 456 |
| 29 | 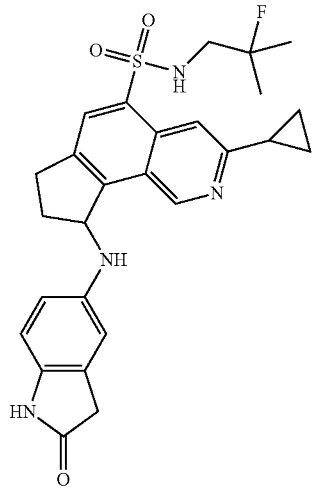 [SMILES: CC(C)(F)CNS(=O)(=O)c1cc2c(c3cnc(C4CC4)cc13)C(Nc1ccc3c(c1)CC(=O)N3)CC2] | 3-cyclopropyl-N-(2-fluoro-2-methylpropyl)-9-[(2-oxo-1,3-dihydroindol-5-yl)amino]-8,9-dihydro-7H-cyclopenta[h]isoquinoline-5-sulfonamide | 5-Bromooxindole | 1.09 *** | 509 |
| 30 | 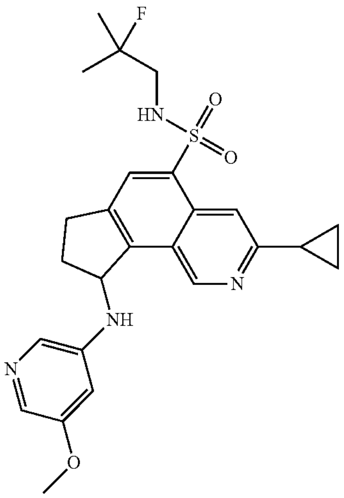 [SMILES: COc1cncc(NC2CCc3cc(S(=O)(=O)NCC(C)(C)F)c4cc(C5CC5)ncc4c32)c1] | 3-cyclopropyl-N-(2-fluoro-2-methylpropyl)-9-[(5-methoxypyridin-3-yl)amino]-8,9-dihydro-7H-cyclopenta[h]isoquinoline-5-sulfonamide | 3-Bromo-5-methoxypyrimidine | 1.42** | 485 |

Example 31

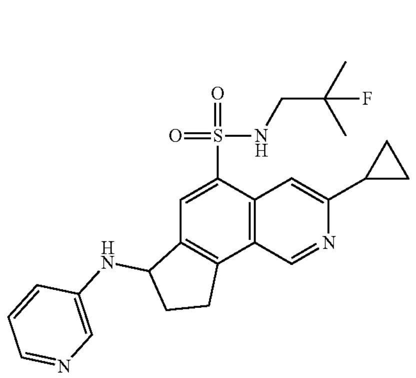 [SMILES: CC(C)(F)CNS(=O)(=O)c1cc2c(c3cnc(C4CC4)cc13)CCC2Nc1cccnc1]

3-cyclopropyl-N-(2-fluoro-2-methylpropyl)-7-(pyridin-3-ylamino)-8,9-dihydro-7H-cyclopenta[h]isoquinoline-5-sulfonamide Intermediate 36 (36.0 mg, 0.0954 mmol), 3-bromopyridine (20 μL, 0.21 mmol), sodium tert-butoxide (18.0 mg, 0.187 mmol), (+/−)-2,2'-bis(diphenylphosphino)-1,1'-binaphthyl (18.0 mg, 0.0280 mmol) and palladium(II) acetate (2.8 mg, 0.012 mmol) were placed in a flask and suspended in toluene (1.5 mL). The flask was sealed, degassed and placed under an atmosphere of nitrogen. The sealed reaction was stirred at 80° C. for 18 hours. The reaction was cooled to room temperature before being diluted with 5% MeOH in DCM (20 mL) and sat. aq. $NaHCO_3$ (20 mL). The layers were separated, and the aq. layer extracted with 5% MeOH in DCM (2×20 mL). The combined organic layers where passed through a phase separator and concentrated in vacuo to give crude product which was purified by basic preparative HPLC to give the title compound (1 mg, 2% Yield). LCMS $[M+H]^+$ 455, RT 2.02 min (Method 3).

Example 32

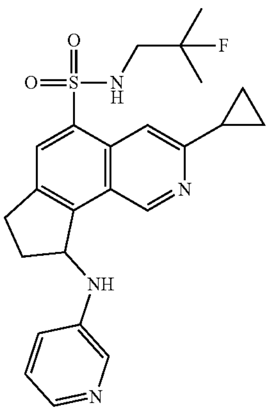 [SMILES: CC(C)(F)CNS(=O)(=O)c1cc2c(c3cnc(C4CC4)cc13)C(Nc1cccnc1)CC2]

3-cyclopropyl-N-(2-fluoro-2-methylpropyl)-9-(pyridin-3-ylamino)-8,9-dihydro-7H-cyclopenta[h]isoquinoline-5-sulfonamide Intermediate 84 (50.0 mg, 0.132 mmol), 3-bromopyridine (0.020 ml, 0.21 mmol), sodium tert-butoxide (27.5 mg, 0.286 mmol), (+/−)-2,2'-bis(diphenylphosphino)-1,1'-binaphthyl (17.0 mg, 0.0265 mmol) and palladium(II) acetate (3.5 mg, 0.016 mmol) were placed in a flask and suspended in toluene (1.7 mL). The flask was sealed, degassed and placed under an atmosphere of nitrogen. The sealed reaction was stirred at 70° C. for 18 hours. The reaction was cooled to room temperature before being diluted with 5% MeOH in DCM (20 mL) and sat. aq. $NaHCO_3$ (20 mL). The layers were separated, and the aq. layer was extracted with 5% MeOH in DCM (2×20 mL). The combined organic layers where passed through a phase separator and concentrated in vacuo to give crude product which was purified by flash column chromatography on silica (gradient elution with 0% to 100% EtOAc in isohexanes) and then basic preparative HPLC to give the title compound (7 mg, 12% Yield). $^1H$ NMR (300 MHz, DMSO-$d_6$) δ 9.27 (s, 1H), 9.27 (d, J=0.9 Hz, 1H), 8.46-8.37 (m, 2H), 8.22 (s, 1H), 8.09 (dd, J=2.5, 1.1 Hz, 1H), 7.83 (dd, J=4.0, 1.9 Hz, 1H), 7.18-7.08 (m, 2H), 6.40 (d, J=8.6 Hz, 1H), 5.68 (dt, J=7.9, 4.2 Hz, 1H), 3.28-3.16 (m, 1H), 3.13-3.01 (m, 1H), 2.96 (d, J=19.8 Hz, 2H), 2.67-2.53 (m, 1H), 2.28 (p, J=6.6 Hz, 1H), 2.11-1.98 (m, 1H), 1.24 (dd, J=21.4, 2.4 Hz, 6H), 1.08-0.94 (m, 4H). LCMS $[M+H]^+$ 455, RT 2.09 min (Method 3).

Example 33

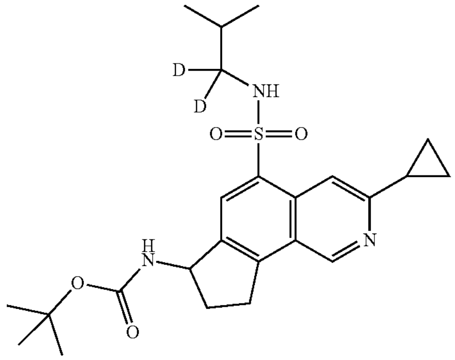 [SMILES: [2H]C([2H])(NS(=O)(=O)c1cc2c(c3cnc(C4CC4)cc13)CCC2NC(=O)OC(C)(C)C)C(C)C]

tert-butyl N-[3-cyclopropyl-5-[(1,1-dideuterio-2-methylpropyl)sulfamoyl]-8,9-dihydro-7H-cyclopenta[h]isoquinolin-7-yl]carbamate To a suspension of intermediate 97 (1.2 g, 2.6 mmol) in toluene (15 mL) was added cyclopropylboronic acid (710 mg, 7.9 mmol), potassium phosphate tribasic (1400 mg, 6.6 mmol), tricyclohexylphosphonium tetrafluoroborate (150 mg, 0.39 mmol), palladium(II) acetate (30 mg, 0.13 mmol) and water (0.15 mL). The mixture was purged with nitrogen before being heated to 115° C. for two hours in a microwave. The mixture was diluted with dichloromethane (20 mL) and washed with water (30 mL). The aqueous was extracted with dichloromethane (2×10 mL). The combined organics were passed through a hydrophobic frit and purified by flash chromatography to give the title compound as a cream solid (1.05 g, 2.27 mmol, 86%). $\delta_H$ (300 MHz, Chloroform-d) δ 9.21 (d, J=0.9 Hz, 1H), 8.33 (s, 1H), 8.25 (d, J=0.9 Hz, 1H), 5.39 (d, J=8.4 Hz, 1H), 4.85 (d, J=8.9 Hz, 1H), 4.66 (s, 1H), 3.49 (ddd, J=17.1, 9.1, 3.5 Hz, 1H), 3.22 (dt, J=16.8, 8.2 Hz, 1H), 2.83 (dd, J=12.6, 7.2 Hz, 1H), 2.29-2.17 (m, 1H), 2.13-1.95 (m, 1H), 1.73-1.62 (m, 1H), 1.51 (s, 9H), 1.19-1.02 (m, 4H), 0.93-0.75 (m, 6H); LCMS $[M+H]^+$ 462, RT 2.64 min (Method 3).

Example 34

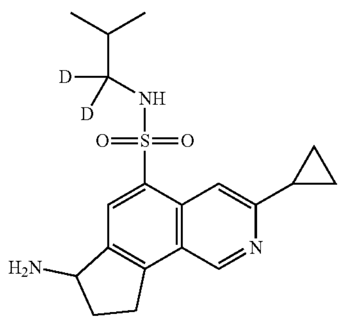 [SMILES: [2H]C([2H])(NS(=O)(=O)c1cc2c(c3cnc(C4CC4)cc13)CCC2N)C(C)C]

7-amino-3-cyclopropyl-N-(1,1-dideuterio-2-methylpropyl)-8,9-dihydro-7H-cyclopenta[h]isoquinoline-5-sulfonamide To Example 33 (15 mg, 0.032 mmol) was added hydrochloric acid (4 mol/L) in 1,4-dioxane (0.2 ml, 0.8 mmol). After 30 minutes hydrochloric acid (4 mol/L) in 1,4-dioxane (0.2 ml, 0.8 mmol) and methanol (50 μL) were added. After 20 minutes the mixture was concentrated under reduced pressure and the residue purified by reverse phase flash chromatography to give the title compound as a white solid (8 mg, 68%). $\delta_H$ (300 MHz, DMSO-d6) δ 9.24 (d, J=0.9 Hz, 1H), 8.38-8.26 (m, 2H), 7.96 (s, 1H), 4.39 (t, J=7.5 Hz, 1H), 3.50-3.37 (m, 1H), 3.18-3.02 (m, 1H), 2.64-2.54 (m, 1H), 2.33-2.22 (m, 1H), 2.15 (br. s, 2H), 1.85-1.69 (m, 1H), 1.64-1.51 (m, 1H), 1.04 (d, J=6.5 Hz, 4H), 0.75 (dd, J=6.7, 1.6 Hz, 6H). LCMS $[M+H]^+$ 362, RT 1.91 min (Method 3).

Example 35

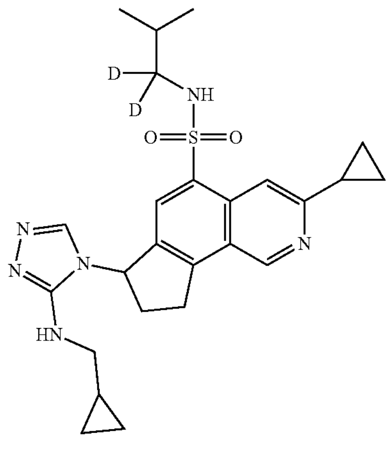 [SMILES: [2H]C([2H])(NS(=O)(=O)c1cc2c(c3cnc(C4CC4)cc13)CCC2n1cnnc1NCC1CC1)C(C)C]

3-cyclopropyl-7-[3-(cyclopropylmethylamino)-1,2,4-triazol-4-yl]-N-(1,1-dideuterio-2-methylpropyl)-8,9-dihydro-7H-cyclopenta[h]isoquinoline-5-sulfonamide To a solution of Intermediate 101 (407 mg, 0.611 mmol) in dichloromethane (50 mL, 780 mmol) cooled in an ice/water bath was added trifluoroacetic acid (5 mL). After 20 minutes saturated sodium bicarbonate solution (20 mL) and water (10 mL) were added to the mixture. The aqueous layer was extracted with dichloromethane (4×20 mL) and dichloromethane:methanol 5:1 (3×10 mL). The combined extracts were passed through a hydrophobic frit, concentrated and the residue purified by reverse phase flash chromatography to give the title compound as a white solid (173 mg, 0.36 mmol, 58%). $\delta_H$ (300 MHz, DMSO-d6) δ 9.36 (d, J=0.9 Hz, 1H), 8.36 (d, J=1.0 Hz, 1H), 8.07 (s, 1H), 7.96 (s, 1H), 6.26 (t, J=5.7 Hz, 1H), 5.92-5.85 (m, 1H), 3.75-3.61 (m, 1H), 3.46-3.36 (m, 1H), 3.18-3.10 (m, 2H), 2.93-2.79 (m, 1H), 2.37-2.23 (m, 3H), 1.51 (p, J=6.6 Hz, 1H), 1.24-1.11 (m, 1H), 1.11-1.02 (m, 4H), 0.71 (d, J=3.6 Hz, 3H), 0.69 (d, J=3.6 Hz, 3H), 0.52-0.44 (m, 2H), 0.30-0.22 (m, 2H); LCMS $[M+H]^+$ 483, RT 2.02 min (Method 3).

Example 36

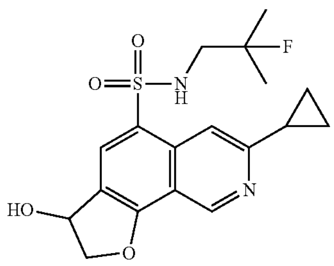 [SMILES: CC(C)(F)CNS(=O)(=O)c1cc2c(c3cnc(C4CC4)cc13)OCC2O]

7-cyclopropyl-N-(2-fluoro-2-methylpropyl)-3-hydroxy-2,3-dihydrofuro[3,2-h]isoquinoline-5-sulfonamide Toluene (0.2 mL) was added to Intermediate 114 (9 mg, 0.016 mmol) followed by palladium(II) acetate (0.4 mg, 0.002 mmol), tricyclohexylphosphonium tetrafluoroborate (1.8 mg, 0.005 mmol) and potassium phosphate tribasic (17 mg, 0.08 mmol), cyclopropylboronic acid (9 mg, 0.1 mmol) and water (2 μL). The mixture was heated to 115° C. in a microwave. After cooling and filtration through Kieselguhr and concentration under reduced pressure, tetrahydrofuran (1 mL) and 1 M tetrabutylammonium fluoride solution in tetrahydrofuran (24 μL, 0.024 mmol, 1 mol/L) were added. After 2.5 hours the mixture was concentrated, diluted with ethyl acetate (10 mL) and washed with 10% ammonium chloride solution (2×5 mL) and water (5 mL). After concentration under reduced pressure, purification by flash chromatography afforded the title compound as a white solid (6.5 mg, 43%). $\delta_H$ (300 MHz, Chloroform-d) δ 9.40 (d, J=0.9 Hz, 1H), 8.44 (s, 1H), 8.19 (d, J=1.0 Hz, 1H), 5.63 (td, J=7.0, 2.7 Hz, 1H), 4.98-4.84 (m, 2H), 4.81 (dd, J=11.0, 2.8 Hz, 1H), 3.03 (dd, J=19.9, 6.6 Hz, 2H), 2.29-2.19 (m, 1H), 2.15 (d, J=7.1 Hz, 1H), 1.34 (d, J=21.5 Hz, 6H), 1.23-1.08 (m, 4H); LCMS $[M+H]^+$ 381, RT 1.97 min (Method 16).

Example 37

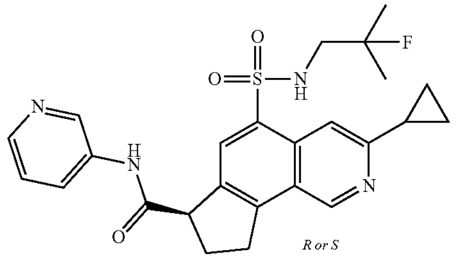 [SMILES: CC(C)(F)CNS(=O)(=O)c1cc2c(c3cnc(C4CC4)cc13)CC[C@H]2C(=O)Nc1cccnc1]

(7R*)-3-cyclopropyl-5-[(2-fluoro-2-methylpropyl) sulfamoyl]-N-pyridin-3-yl-8,9-dihydro-7H-cyclopenta[h]isoquinoline-7-carboxamide [* or S]

Intermediate 85 (70 mg, 0.17 mmol) was dissolved in DCM (3 mL) and HATU (81 mg, 0.20 mmol) was added, followed by triethylamine (0.1 mL, 0.7 mmol). The reaction mixture was stirred at room temperature for 5 min, then 3-aminopyridine (33 mg, 0.34 mmol) was added. After about 1 hour, the crude was diluted with EtOAc and the organic layer washed with water and brine. Purification by column chromatography using a gradient of 0 to 100% EtOAc in hexanes, followed by a gradient of 0 to 10% MeOH in DCM, afforded the title compound as a mixture of enantiomers (34 mg, 41% Yield). The racemate was separated using chiral HPLC (Waters UV prep system, with 2996 PDA. Lux Cellulose-1 21.2x250 mm 5 μm column, flow rate 10 ml/min) to give the title compound (7 mg); Chiral RT**=2.39 min. $^1$H NMR (300 MHz, Chloroform-d) δ 9.20 (s, 1H), 8.59 (d, J=2.6 Hz, 1H), 8.34 (s, 2H), 8.23 (s, 1H), 8.14 (d, J=8.6 Hz, 1H), 7.24 (dd, J=8.4, 4.8 Hz, 1H), 5.54 (s, 1H), 4.30-4.07 (m, 1H), 3.62 (dt, J=15.4, 7.1 Hz, 1H), 3.39-3.24 (m, 1H), 3.05 (dd, J=20.2, 6.1 Hz, 2H), 2.68 (q, J=6.8 Hz, 2H), 2.29-2.17 (m, 1H), 1.40-1.26 (m, 8H), 1.31-1.05 (m, 3H). LCMS [M+H]$^+$ 483, RT 1.78 min (Method 4).

** Chiral analysis used a 100% MeOH (+0.1% NH40H) isocratic method on Lux Cellulose-1 4.6x150 mm, 3 μm column, with a flow rate of 1 ml/min.

Example 38

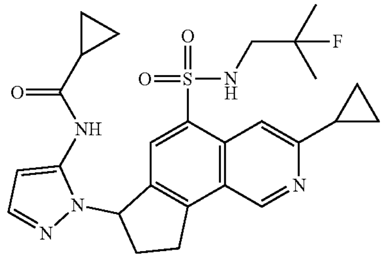 [SMILES: CC(C)(F)CNS(=O)(=O)c1cc2c(c3cnc(C4CC4)cc13)CCC2n1nccc1NC(=O)C1CC1]

N-[2-[3-cyclopropyl-5-[(2-fluoro-2-methylpropyl) sulfamoyl]-8,9-dihydro-7H-cyclopenta[h]isoquinolin-7-yl]pyrazol-3-yl]cyclopropanecarboxamide A mixture of intermediate 88 (105 mg, 0.20 mmol), cyclopropaneboronic acid (56 mg, 0.61 mmol) and palladium (II) acetate (2.3 mg, 0.010 mmol) in 1,4-dioxane (3 mL) was sparged with nitrogen for 5 minutes. Tricyclohexylphosphonium tetrafluoroborate (12 mg, 0.031 mmol) and potassium phosphate tribasic (110 mg, 0.51 mmol) were added and the reaction mixture sparged for 5 min with nitrogen. The reaction was then heated at 120° C. for 2 hours. It was then filtered through celite and the solvent concentrated under reduced pressure. Purification by column chromatography afforded the title compound (38 mg, 36% Yield). $^1$H NMR (300 MHz, Chloroform-d) δ 9.27 (s, 1H), 8.28 (s, 1H), 8.07 (s, 1H), 7.45 (s, 1H), 6.19 (s, 1H), 5.93 (s, 1H), 5.06 (s, 1H), 3.72 (s, 1H), 3.37 (s, 1H), 3.09-2.81 (m, 3H), 2.70 (s, 1H), 2.28 (s, 1H), 1.30 (dd, J=21.5, 15.1 Hz, 6H), 1.24-1.07 (m, 7H), 0.94 (s, 3H). LCMS [M+H]$^+$ 512, RT 2.02 min (Method 4).

Example 39

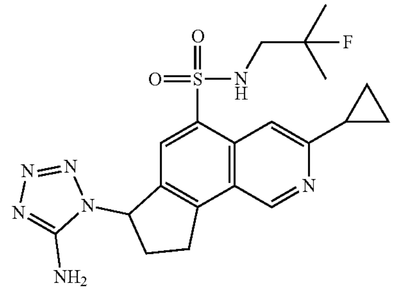 [SMILES: CC(C)(F)CNS(=O)(=O)c1cc2c(c3cnc(C4CC4)cc13)CCC2n1nnnc1N]

7-(5-aminotetrazol-1-yl)-3-cyclopropyl-N-(2-fluoro-2-methylpropyl)-8,9-dihydro-7H-cyclopenta[h]isoquinoline-5-sulfonamide Intermediate 89 (160 mg, 0.31 mmol) was dissolved in DMF (5 mL). Ammonium chloride (42 mg, 0.78 mmol) was added followed by sodium azide (52 mg, 0.80 mmol) and the resulting mixture heated at 80° C. overnight. Volatiles were evaporated and then a DCM/water extraction was performed. Organics were dried with sodium sulfate and evaporated. The crude residue was purified with reverse phase column chromatography using basic conditions to give the title compound (45 mg, 32% Yield). $^1$H NMR (400 MHz, Chloroform-d) δ 9.32 (d, J=0.9 Hz, 1H), 8.29 (d, J=1.0 Hz, 1H), 8.11 (s, 1H), 6.09 (dd, J=8.5, 5.6 Hz, 1H), 5.07 (t, J=6.4 Hz, 1H), 4.47 (s, 2H), 3.81 (ddd, J=17.6, 9.3, 4.9 Hz, 1H), 3.65-3.35 (m, 1H), 3.14-2.84 (m, 3H), 2.66 (ddt, J=14.5, 9.0, 5.9 Hz, 1H), 2.28 (td, J=8.1, 4.1 Hz, 1H), 1.39-1.24 (m, 10H). LCMS [M+H]$^+$ 446, RT 1.64 min (Method 3).

Example 40

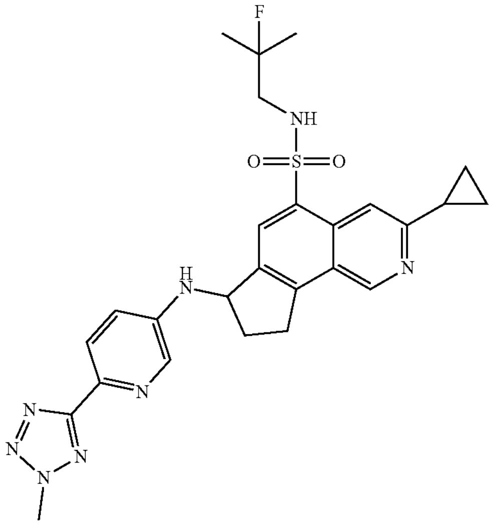 [SMILES: Cn1nnc(-c2ccc(NC3CCc4c3cc(S(=O)(=O)NCC(C)(C)F)c3cc(C5CC5)ncc43)cn2)n1]

3-cyclopropyl-N-(2-fluoro-2-methylpropyl)-7-[[6-(2-methyltetrazol-5-yl)pyridin-3-yl]amino]-8,9-dihydro-7H-cyclopenta[h]isoquinoline-5-sulfonamide Intermediate 36 (35 mg, 0.09272 mmol) and 5-bromo-2-(2-methyl-2H-tetrazol-5-yl)-pyridine (45 mg, 0.1875 mmol) were dissolved in anhydrous 1,4-dioxane (2 mL) under nitrogen. Sodium tert-butoxide (27 mg, 0.28 mmol) and tert-BuXphos-Pd-G3 (6 mg, 0.007 mmol) were then added and the reaction vessel stirred at room temperature overnight. To the reaction mixture was then added sodium tert-butoxide (27 mg, 0.28 mmol) and tert-BuXphos-Pd-G3 (6 mg, 0.007 mmol) and the reaction mixture heated to 80° C. for 4 hrs. Reaction was cooled to room temperature then concentrated in vacuo and purified by column chromatography to yield the title compound (21 mg). $\delta_H$ (400 MHz, d6-DMSO) 9.27 (s, 1H), 8.50 (s, 1H), 8.25 (d, J=2.8 Hz, 1H), 8.12 (s, 1H), 7.89 (d, J=8.6 Hz, 1H), 7.27 (dd, J=8.7, 2.8 Hz, 1H), 6.93 (d, J=8.4 Hz, 1H), 5.35 (d, J=7.7 Hz, 1H), 4.40 (s, 3H), 3.51 (s, 1H), 3.31 (d, J=4.7 Hz, 1H), 2.80 (s, 3H), 2.27 (s, 1H), 2.03 (tt, =14.8, 7.3 Hz, 1H), 1.24 (s, 1H), 1.16 (d, J=21.5 Hz, 6H), 1.05 (d, J=6.7 Hz, 4H). LCMS $[M+H]^+$ 537.0, RT 2.07 min (Method 3).

Example 41

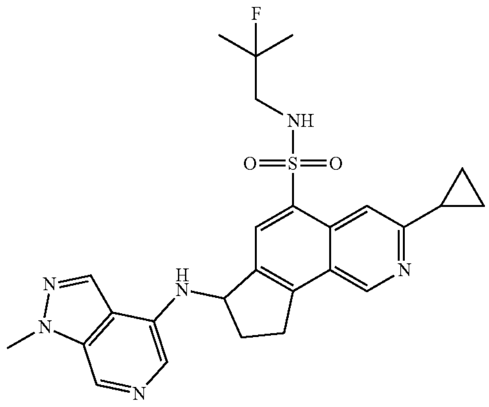 [SMILES: Cn1ncc2c(NC3CCc4c3cc(S(=O)(=O)NCC(C)(C)F)c3cc(C5CC5)ncc43)cncc21]

3-cyclopropyl-N-(2-fluoro-2-methylpropyl)-7-[(1-methylpyrazolo[3,4-c]pyridin-4-yl)amino]-8,9-dihydro-7H-cyclopenta[h]isoquinoline-5-sulfonamide The method described for Example 40, using Intermediate 36 (0.093 mmol) and 4-bromo-1-methyl-1H-pyrazolo[3,4-c]pyridine (41 mg, 0.1854 mmol), afforded the title compound (13 mg, 0.026 mmol). $\delta_H$ (400 MHz, d4-methanol) 9.26 (d, J=0.9 Hz, 1H), 8.41 (d, J=1.0 Hz, 1H), 8.33 (d, J=0.8 Hz, 1H), 8.31 (s, 1H), 8.21 (d, J=0.9 Hz, 1H), 7.70 (s, 1H), 5.58 (t, J=7.0 Hz, 1H), 4.13 (s, 3H), 3.69-3.60 (m, 1H), 3.46-3.36 (m, 1H), 3.01-2.85 (m, 3H), 2.38-2.23 (m, 2H), 1.21 (d, J=5.9 Hz, 3H), 1.16 (d, J=5.8 Hz, 3H), 1.15-1.07 (m, 4H). LCMS $[M+H]^+$ 509.0, RT 1.96 min (Method 3).

Example 42

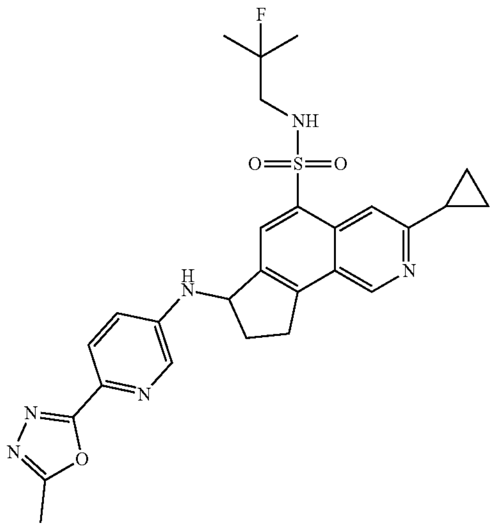 [SMILES: Cc1nnc(-c2ccc(NC3CCc4c3cc(S(=O)(=O)NCC(C)(C)F)c3cc(C5CC5)ncc43)cn2)o1]

3-cyclopropyl-N-(2-fluoro-2-methylpropyl)-7-[[6-(5-methyl-1,3,4-oxadiazol-2-yl)pyridin-3-yl]amino]-8,9-dihydro-7H-cyclopenta[h]isoquinoline-5-sulfonamide The method described for Example 40, using intermediate 36 (0.093 mmol) and 2-(5-bromo-2-pyridyl)-5-methyl-1,3,4-oxadiazole (46 mg, 0.19 mmol), afforded the title compound (13 mg, 0.024 mmol). $\delta_H$ (400 MHz, d4-methanol) 9.26 (d, J=1.0 Hz, 1H), 8.42 (d, J=1.0 Hz, 1H), 8.30 (s, 1H), 8.19 (d, J=2.7 Hz, 1H), 7.97 (d, J=9.0 Hz, 1H), 7.32 (dd, J=8.8, 2.9 Hz, 1H), 5.42 (t, J=6.9 Hz, 1H), 3.68-3.57 (m, 1H), 3.46-3.36 (m, 1H), 2.97 (d, J=19.4 Hz, 2H), 2.94-2.85 (m, 1H), 2.62 (s, 3H), 2.38-2.30 (m, 1H), 2.24-2.13 (m, 1H), 1.23 (s, 3H), 1.17 (s, 3H), 1.16-1.07 (m, 4H). LCMS $[M+H]^+$537.0, RT 1.98 min (Method 3).

Example 43

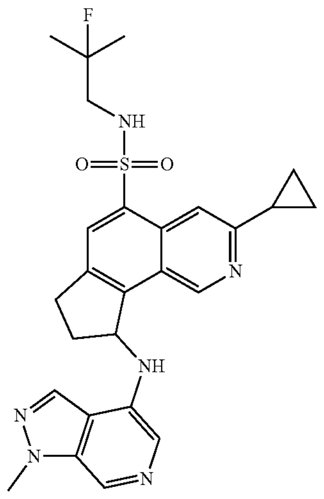 [SMILES: Cn1ncc2c(NC3CCc4cc(S(=O)(=O)NCC(C)(C)F)c5cc(C6CC6)ncc5c43)cncc21]

3-cyclopropyl-N-(2-fluoro-2-methylpropyl)-9-[(1-methylpyrazolo[3,4-c]pyridin-4-yl)amino]-8,9-dihydro-7H-cyclopenta[h]isoquinoline-5-sulfonamide The method described for Example 40, using Intermediate 84 (0.093 mmol) and 4-bromo-1-methyl-1H-pyrazolo[3,4-C]pyridine (41 mg, 0.185 mmol) afforded the title compound (18 mg, 0.032 mmol). $\delta_H$ (400 MHz, d4-methanol) 9.33 (d, J=0.9 Hz, 1H), 8.44 (d, J=1.0 Hz, 1H), 8.36 (s, 1H), 8.34 (d, J=0.8 Hz, 1H), 8.12 (d, J=0.8 Hz, 1H), 7.73 (s, 1H), 5.97 (dd, J=7.8, 3.7 Hz, 1H), 4.12 (s, 3H), 3.42-3.32 (m, 1H), 3.23-3.13 (m, 1H), 3.08-2.97 (m, 2H), 2.89-2.77 (m, 1H), 2.38-2.25 (m, 2H), 1.33-1.27 (m, 3H), 1.24 (d, J=5.0 Hz, 3H), 1.07-1.02 (m, 4H). LCMS $[M+H]^+$ 509.0, RT 1.99 min (Method 3).

Example 44

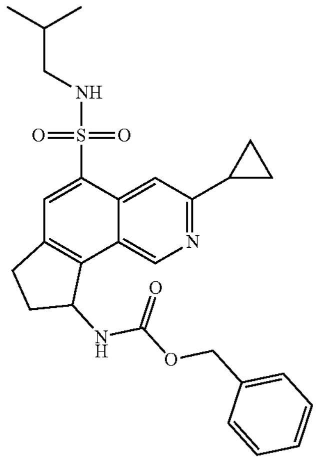 [SMILES: CC(C)CNS(=O)(=O)c1cc2c(c3cnc(C4CC4)cc13)C(NC(=O)OCc1ccccc1)CC2]

benzyl N-[3-cyclopropyl-5-(2-methylpropylsulfamoyl)-8,9-dihydro-7H-cyclopenta[h]isoquinolin-9-yl]carbamate Intermediate 39 (25 mg, 0.07 mmol) was dissolved in DCM (1 mL) and treated with DIPEA (25 μL, 0.143 mmol) at room temperature, and then benzyl chloroformate (12 μL, 0.082 mmol) was added dropwise. The reaction was stirred at room temperature overnight. The reaction mixture was diluted with MeOH (0.5 mL) and NaOH (4N in water, 0.5 mL) and stirred vigorously for 72 hours at room temperature. Then the mixture was warmed to 48° C. for 5 hours. The reaction mixture was diluted with water (5 mL) and DCM (5 mL), stirred vigorously and the layers were separated through a phase separator. The aqueous layer was extracted with DCM (×2) and the combined organic layers dried and concentrated in vacuo. Purification by column chromatography in a gradient of methanol in DCM afforded the title compound (31 mg, 0.026 mmol). $\delta_H$ (400 MHz, d6-DMSO) 9.31 (d, J=0.9 Hz, 1H), 8.34 (d, J=0.9 Hz, 1H), 8.17 (s, 1H), 8.06 (t, J=6.1 Hz, 1H), 8.03 (d, J=9.3 Hz, 1H), 7.36-7.32 (m, 5H), 5.72 (td, J=8.6, 3.6 Hz, 1H), 5.16-5.01 (m, 2H), 3.26-3.17 (m, 1H), 3.03-2.92 (m, 1H), 2.64-2.53 (m, 3H), 2.27 (p, J=6.8 Hz, 1H), 2.10-1.97 (m, 1H), 1.68-1.53 (m, 1H), 1.11-0.96 (m, 4H), 0.77 (d, J=2.5 Hz, 3H), 0.75 (d, J=2.4 Hz, 3H). LCMS $[M+H]^+$ 494.0 RT 2.65 min (Method 3).

Example 45

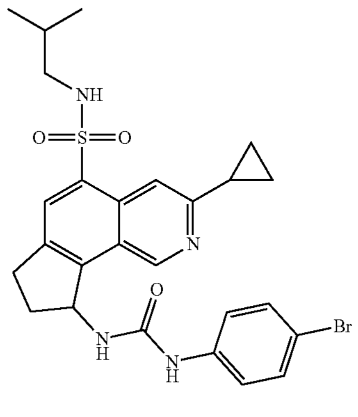 [SMILES: CC(C)CNS(=O)(=O)c1cc2c(c3cnc(C4CC4)cc13)C(NC(=O)Nc1ccc(Br)cc1)CC2]

1-(4-bromophenyl)-3-[3-cyclopropyl-5-(2-methylpropylsulfamoyl)-8,9-dihydro-7H-cyclopenta[h]isoquinolin-9-yl]urea Intermediate 39 (25 mg, 0.07 mmol) was dissolved in DCM (1 mL) at room temperature and treated with DIPEA (25 μL, 0.143 mmol) and 4-bromophenyl-isocyanate (16 mg, 0.081 mmol). The reaction was stirred at room temperature overnight. The reaction mixture was concentrated in vacuo and the crude residue purified by column chromatography in a gradient of methanol in DCM to yield the title compound (32 mg, 0.05 mmol). $\delta_H$ (400 MHz, d6-DMSO) 9.36 (d, J=0.9 Hz, 1H), 8.46 (s, 1H), 8.35 (d, J=1.0 Hz, 1H), 8.20 (s, 1H), 8.08 (t, J=6.0 Hz, 1H), 7.40 (s, 4H), 6.95 (d, J=8.7 Hz, 1H), 5.87 (td, J=8.5, 3.8 Hz, 1H), 3.24 (dt, J=15.7, 7.5 Hz, 1H), 3.03 (ddd, J=16.5, 9.0, 4.4 Hz, 1H), 2.69-2.59 (m, 1H), 2.56 (t, J=6.4 Hz, 2H), 2.30-2.21 (m, 1H), 2.13-2.03 (m, 1H), 1.61 (hept, J=6.7 Hz, 1H), 1.02 (dt, J=8.6, 3.3 Hz, 4H), 0.77 (dd, J=6.7, 2.6 Hz, 6H). LCMS $[M+H]^+$ 557/559, RT 2.66 min (Method 3).

Example 46

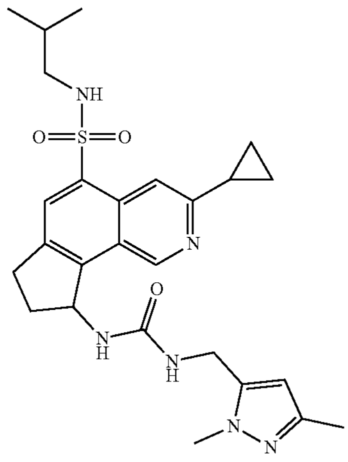 [SMILES: Cc1cc(CNC(=O)NC2CCc3cc(S(=O)(=O)NCC(C)C)c4cc(C5CC5)ncc4c32)n(C)n1]

1-[3-cyclopropyl-5-(2-methylpropylsulfamoyl)-8,9-dihydro-7H-cyclopenta[h]isoquinolin-9-yl]-3-[(2,5-dimethylpyrazol-3-yl)methyl]urea To a solution of (1,3-dimethyl-1H-pyrazol-5-yl)methylamine (10 mg, 0.08 mmol), in acetonitrile (1 mL, 19.1 mmol) under nitrogen was added triethylamine (22 μL, 0.16 mmol) followed by 1,1'-carbonyl-diimidazole (12 mg, 0.074 mmol). The mixture was stirred at room temperature for 1 hour and then intermediate 39 (25 mg, 0.07 mmol) was added. The resulting mixture was stirred at room temperature for 36 hours. The reaction mixture was concentrated and purified by column chromatography in a gradient of methanol in ethyl acetate to yield the title compound (20 mg, 0.28 mmol). $\delta_H$ (400 MHz, d6-DMSO) δ 9.36 (d, J=0.9 Hz, 1H), 8.34 (d, J=1.0 Hz, 1H), 8.17 (s, 1H), 8.06 (t, J=5.9 Hz, 1H), 6.69 (d, J=8.9 Hz, 1H), 6.15 (t, J=5.9 Hz, 1H), 5.88-5.77 (m, 2H), 4.33-4.15 (m, 2H), 3.65 (s, 3H), 3.26-3.12 (m, 1H), 3.06-2.90 (m, 1H), 2.63-2.53 (m, 3H), 2.31-2.20 (m, 1H), 2.06 (s, 3H), 2.03-1.92 (m, 1H), 1.66-1.54 (m, 1H), 1.07-1.01 (m, 4H), 0.77 (d, J=2.6 Hz, 3H), 0.75 (d, J=2.7 Hz, 3H). LCMS $[M+H]^+$ 511.2 RT 1.91 min (Method 3).

Example 47

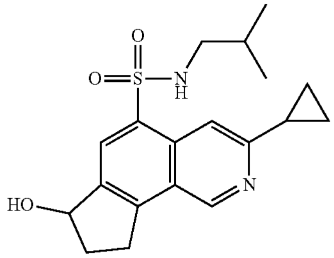 [SMILES: CC(C)CNS(=O)(=O)c1cc2c(c3cnc(C4CC4)cc13)CCC2O]

3-cyclopropyl-7-hydroxy-N-(2-methylpropyl)-8,9-dihydro-7H-cyclopenta[h]isoquinoline-5-sulfonamide To a solution of intermediate 29 (73 mg, 0.15 mmol) in THF (3 mL) at 0° C. was added 1 M tetrabutyl ammonium chloride in THF (0.22 mL, 0.22 mmol). The solution was stirred at 0° C. for 5 minutes then at room temperature for 90 minutes. The solution was diluted with water (10 mL) and EtOAc (15 mL). The organic layer was separated and washed with brine, passed through a phase separator frit. The solvent was removed to give a brown oil which was purified by flash column chromatography (eluting with 0 to 70% of EtOAc in isohexane gradient) to afford the title product as a white solid (53 mg, 96% yield). LCMS $[M+H]^+$ 361, RT 2.19 minutes (Method 3).

Example 48

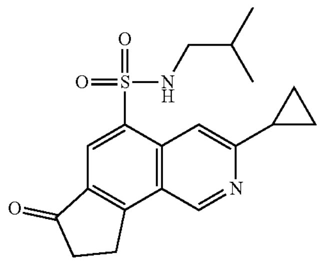 [SMILES: CC(C)CNS(=O)(=O)c1cc2c(c3cnc(C4CC4)cc13)CCC2=O]

3-cyclopropyl-N-(2-methylpropyl)-7-oxo-8,9-dihydrocyclopenta[h]isoquinoline-5-sulfonamide To a solution of Example 47 (60 mg, 0.17 mmol) in DCM (4 mL) at 0° C. was added Dess-Martin periodinane (109 mg, 0.25 mmol). The mixture was stirred for 2.5 hours. A 1:1 mixture of saturated aqueous sodium thiosulfate solution and saturated aqueous $NaHCO_3$ solution (10 mL) was added and the mixture stirred vigorously for 15 minutes. The organic layer was separated and washed further with saturated aqueous $NaHCO_3$ solution (10 mL) and then passed through a phase separator frit. The solvent was removed to give a solid, which was purified by flash column chromatography (eluting with 0 to 70% of EtOAc in iso-hexane gradient) to afford the title product as a white solid (56 mg, 94% yield). $\delta_H$ (400 MHz, Chloroform) 9.45 (d, J=0.9 Hz, 1H), 8.58 (s, 1H), 8.40 (d, J=1.0 Hz, 1H), 4.74 (t, J=6.4 Hz, 1H), 3.58-3.66 (m, 2H), 2.90-2.98 (m, 2H), 2.82 (t, J=6.6 Hz, 2H), 2.31 (tt, J=8.0, 4.8 Hz, 1H), 1.75 (dt, J=13.4, 6.7 Hz, 1H), 1.33-1.22 (m, 4H), 0.87 (d, J=6.7 Hz, 6H). LCMS $[M+H]^+$ 359, RT 2.12 minutes (Method 3).

Example 49

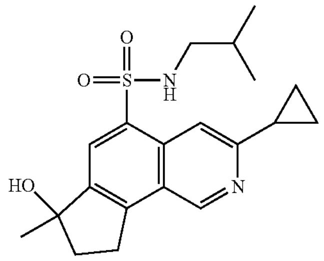 [SMILES: CC(C)CNS(=O)(=O)c1cc2c(c3cnc(C4CC4)cc13)CCC2(C)O]

3-cyclopropyl-7-hydroxy-7-methyl-N-(2-methylpropyl)-8,9-dihydrocyclopenta[h]isoquinoline-5-sulfonamide To a solution of Example 48 (10.5 mg, 0.12 mmol) in THF (1 mL) at 0° C. was added 1 M methyllithium in THF (0.349 ml, 0.35 mmol). The mixture was stirred at 0° C. for 10 minutes then at room temperature for 1 hour. The THF was removed and the residue was partitioned between EtOAc (10 mL) and water (5 mL). The organic layer was passed through a phase separator and the solvent was removed to give a gum, which was purified by flash column chromatography (eluting with 0 to 70% of EtOAc in isohexane gradient) to afford the title product as a white solid (10 mg, 90% yield). $\delta_H$ (400 MHz, Chloroform) 9.26 (d, J=1.0 Hz, 1H), 8.40 (s, 1H), 8.27 (d, J=1.0 Hz, 1H), 4.66 (t, J=6.4 Hz, 1H), 3.45-3.60 (m, 1H), 3.20-3.40 (m, 1H), 2.65-2.87 (m, 2H), 2.35-2.59 (m, 2H), 2.20-2.32 (m, 1H), 1.68-1.83 (m, 4H), 1.04-1.29 (m, 4H), 0.80-1.00 (m, 6H). LCMS $[M+H]^+$ 375, RT 2.08 minutes (Method 3).

Example 50

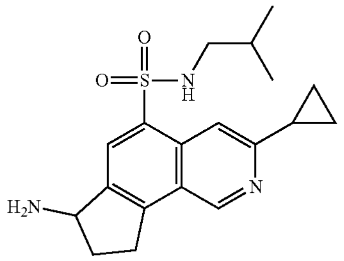 [SMILES: CC(C)CNS(=O)(=O)c1cc2c(c3cnc(C4CC4)cc13)CCC2N]

7-amino-3-cyclopropyl-N-(2-methylpropyl)-8,9-dihydro-7H-cyclopenta[h]isoquinoline-5-sulfonamide Intermediate 13 (308 mg, 0.78 mmol) was suspended in 4 M HCl in dioxane (5 mL, 0.02 mmol) and the mixture stirred for 2 hours. The solvent was removed to give a solid. Purification by SCX column chromatography eluting with 0 to 100% of $NH_3$ in methanol gradient afforded the title product as a brown solid (279 mg, quantitative). $\delta_H$ (300 MHz, DMSO-d6) 9.25 (d, J=0.9 Hz, 1H), 8.29-8.37 (m, 2H), 7.98 (s, 1H), 4.42 (t, J=7.4 Hz, 1H), 3.40-3.55 (m, 1H), 3.11 (dt, J=16.9, 8.5, 1H), 2.62-2.86 (m, 2H), 2.51-2.67 (m, 1H), 2.28 (p, J=6.4 Hz, 1H), 1.73-1.90 (m, 1H), 1.59 (dt, J=13.4, 6.7 Hz, 1H), 1.04 (d, J=6.4 Hz, 4H), 0.75 (dd, J=6.7, 1.6 Hz, 6H). LCMS $[M+H]^+$ 360, RT 2.17 minutes (Method 3).

Example 51

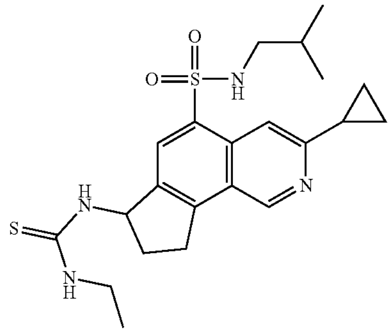 [SMILES: CCNC(=S)NC1CCc2c1cc(S(=O)(=O)NCC(C)C)c1cc(C3CC3)ncc21]

1-[3-cyclopropyl-5-(2-methylpropylsulfamoyl)-8,9-dihydro-7H-cyclopenta[h]isoquinolin-7-yl]-3-ethylthiourea Example 50 (120 mg, 0.33 mmol) was suspended in a mixture of DCM (5 mL) and THF (5 mL). To this suspension was added DIPEA (0.089 mL, 0.50 mmol) and ethyl isothiocyanate (0.044 mL, 0.50 mmol).

The reaction was stirred for 18 hours. The solvent was removed to afford the title product as a white solid (130 mg, 87% yield). $\delta_H$ (300 MHz, Methanol-d4) 9.21 (d, J=1.0 Hz, 1H), 8.38 (s, 2H), 6.23 (s, 1H), 3.45-3.70 (m, 1H), 3.55 (s, 3H), 2.80-2.90 (m, 1H), 2.65-2.75 (m, 2H), 2.31 (tt, J=7.6, 5.5, 1H), 1.99-2.20 (m, 1H), 1.64 (dq, J=13.4, 6.7 Hz, 1H), 1.03-1.35 (m, 7H), 0.81 (dd, J=6.7, 1.9 Hz, 6H). LCMS $[M+H]^+$ 447, RT 2.34 minutes (Method 3).

Example 52

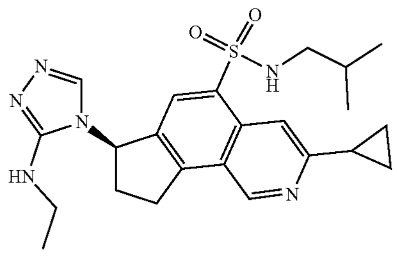

R or S (7R*)-3-cyclopropyl-7-[3-(ethylamino)-1,2,4-triazol-4-yl]-N-(2-methylpropyl)-8,9-dihydro-7H-cyclopenta[h]isoquinoline-5-sulfonamide (* or S)

To a solution of Example 51 (118 mg, 0.26 mmol) in DMF (5 mL) was added formic acid hydrazide (40 mg, 0.67 mmol) followed by mercuric chloride (181 mg, 0.67 mmol). The mixture was stirred for 2 minutes then triethylamine (0.093 mL, 0.67 mmol) was added and the mixture was heated at 80° C. for 18 hours. The reaction was cooled and $CH_3CN$ (10 mL) was added to the mixture which was then filtered through Celite, washing with excess $CH_3CN$ (25 mL). The solvent was removed to give a brown oil. Purification by flash column chromatography followed by reverse phase chromatography afforded the racemic product as a white solid (9 mg, 6% yield). The racemate was purified by chiral SFC to give the title compound as a white solid (2 mg, 1.6% yield). Chiral SFC RT** 6.34 minute (mass found $[M+H]^+$ 455).

**Chiral analysis was carried out by SFC, using a Chiralcel OJ-3 4.6×150 mm, 3 μm column, flow rate 3.5 mL/min eluting with 10-25% Methanol using an 8 min run time on a Waters UPC²-SQD2 system.

Example 53

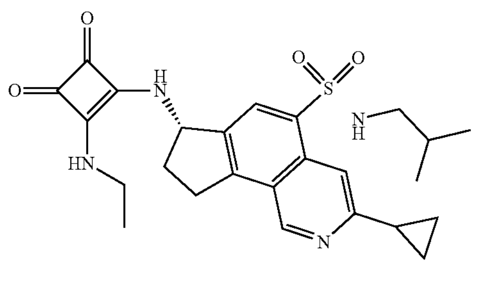

R or S (7R*)-3-cyclopropyl-7-[[2-(ethylamino)-3,4-dioxo-cyclobuten-1-yl]amino]-N-(2-methylpropyl)-8,9-dihydro-7H-cyclopenta[h]isoquinoline-5-sulfonamide (* or S)

To a suspension of Example 50 (45 mg, 0.13 mmol) in DCM (5 mL) was added DIPEA (0.033 mL, 0.19 mmol) and 3,4-dimethoxy-3-cyclobutene-1,2-dione (27 mg, 0.19 mmol). The mixture was stirred for 18 hours. The residue was dissolved in DCM (5 mL) and 2 M ethylamine in THF (3 mL) was added. The mixture was stirred for 1 hour. The solvent was removed and the solid triturated with DCM (3 mL) and filtered to give the racemic product as a white solid (50 mg, 83% yield). The racemate was separated by chiral SFC to give the title product as a white solid (10 mg, 21% yield). LCMS $[M+H]^+$ 483, RT 2.12 minutes (Method 10). Chiral SFC RT**=3.52 minutes.

**Chiral analysis was carried out by SFC, using a Chiralcel OJ-3 4.6×150 mm, 3 μm column, flow rate 3.5 mL/min eluting with 5-20% Methanol (+0.1% $NH_4OH$) using a 6 min run time on a Waters UPC²-SQD2 system.

Example 54

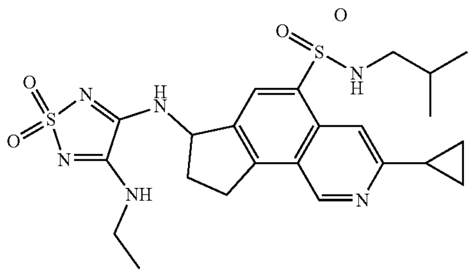

3-cyclopropyl-7-[[4-(ethylamino)-1,1-dioxo-1,2,5-thiadiazol-3-yl]amino]-N-(2-methylpropyl)-8,9-dihydro-7H-cyclopenta[h]isoquinoline-5-sulfonamide To a solution of Example 50 (31 mg, 0.086 mmol) in DCM (10 mL) was added DIPEA (0.023 mL, 0.13 mmol) and 3,4-diethoxy-1,2,5-thiadiazole-1,1-dioxide (0.027 mL, 0.13 mmol). The solution was stirred for 3 hours. 2 M ethylamine in THF (0.085 mL, 0.17 mmol) was added to the solution and this was stirred for 18 hours. The solvent was removed, and the resulting residue was purified by flash column chromatography (eluting with 0 to 100% of EtOAc in isohexane gradient then 0 to 10% methanol in ethyl acetate gradient) to afford the title product as a white solid (35 mg, 80% yield). $\delta_H$ (300 MHz, DMSO-d6) 9.35 (s, 1H), 8.98 (d, J=7.2 Hz, 1H), 8.48 (d, J=5.4 Hz, 1H), 8.38 (d, J=1.0 Hz, 1H), 8.25 (s, 1H), 8.07 (t, J=5.9 Hz, 1H), 5.51 (d, J=6.5 Hz, 1H), 3.48-3.63 (m, 1H), 3.29-3.48 (m, 3H), 2.70-2.90 (m, 1H), 2.50-2.70 (m, 21H), 2.05-2.40 (m, 2H), 1.60 (dt, J=13.3, 6.7 Hz, 1H), 1.18 (t, J=7.3 Hz, 3H), 1.07 (d, J=6.7, 4H), 0.76 (dd, J=6.7, 5.1 Hz, 6H). LCMS $[M+H]^+$ 519, RT 2.09 minutes (Method 3).

Example 55

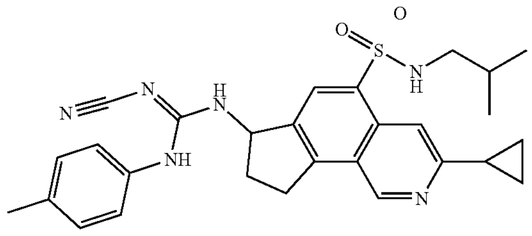

2-cyano-1-[3-cyclopropyl-5-(2-methylpropylsulfamoyl)-8,9-dihydro-7H-cyclopenta[h]isoquinolin-7-yl]-3-(4-methylphenyl)guanidine To a suspension of Example 50 (45 mg, 0.13 mmol) in a mixture of DCM (10 mL) and THF (5 mL) was added DIPEA (0.058 mL, 0.19 mmol) and intermediate 30 (47 mg, 0.19 mmol). The mixture was stirred for 18 hours. The solvent was removed to give a residue which was purified by flash column chromatography (eluting with 0 to 90% of EtOAc in isohexane gradient) to afford the title product as a colourless gum (28 mg, 43% yield). $\delta_H$ (300 MHz, chloroform-d) 9.17 (s, 1H), 8.28 (s, 1H), 8.26 (s, 1H), 7.40 (s, 1H), 7.20 (d, J=7.4 Hz, 2H), 7.15 (d, J=7.4 Hz, 2H), 5.70 (q, J=7.2 Hz, 1H), 5.05 (d, J=3.1 Hz, 1H), 4.00-4.20 (m, 1H), 3.40-3.55 (m, 1H), 3.15-3.35 (m, 1H), 2.65-2.95 (m, 3H), 2.30 (s, 3H), 2.20-2.30 (m, 1H), 1.90-2.05 (m, 1H), 1.50-1.80 (m, 1H), 1.10-1.25 (m, 3H), 0.77-1.00 (m, 6H). LCMS $[M+H]^+$ 517, RT 2.51 minutes (Method 3).

Example 56

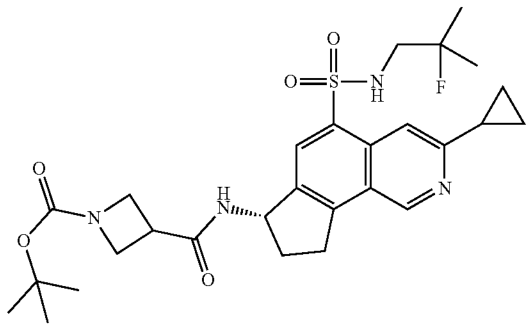

R or S tert-butyl 3-[[(7R*)-3-cyclopropyl-5-[(2-fluoro-2-methylpropyl)sulfamoyl]-8,9-dihydro-7H-cyclopenta[h]isoquinolin-7-yl]carbamoyl]azetidine-1-carboxylate [* or S]

To a solution of intermediate 38 (33 mg, 0.087 mmol) in DMF (2 mL) was added DIPEA (0.046 mL, 0.26 mmol) followed by 1-Boc-azetidine-3-carboxylic acid (21.7 mg, 0.105 mmol) and HATU (41 mg, 0.10 mmol). The mixture was stirred for 18 hours. Water (10 mL) and EtOAc (15 mL) were then added. The organic layer was separated and washed with water (2x10 mL) and brine (10 mL) then passed through a phase separator and the solvent removed to give a brown oil. Purification by flash column chromatography eluting with a gradient of 0 to 100% EtOAc in isohexane followed by 0 to 10% methanol in DCM afforded the title product as a white solid (49 mg, 100% yield). $\delta_H$ (400 MHz, chloroform-d) 9.19 (d, J=0.9 Hz, 1H), 8.21 (t, J=1.1, 2H), 6.03 (d, J=8.6 Hz, 1H), 5.74 (q, J=7.9 Hz, 1H), 5.08 (t, J=6.5 Hz, 1H), 4.04-4.28 (m, 3H), 3.45-3.60 (m, 1H), 3.20-3.35 (m, 2H), 3.10-3.20 (m, 1H), 2.84-3.01 (m, 2H), 2.25 (tt, J=8.1, 4.8 Hz, 1H), 1.98-2.14 (m, 1H), 1.60 (s, 9H), 1.47 (s, 3H), 1.05-1.35 (m, 6H). LCMS $[M+H]^+$ 561, RT 2.29 minutes (Method 3).

Example 57

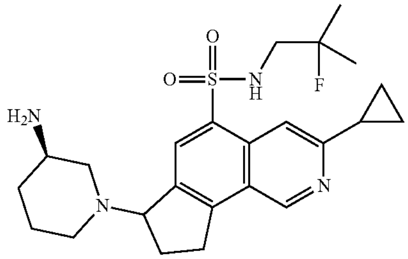 [SMILES: CC(C)(F)CNS(=O)(=O)c1cc2c(c3cnc(C4CC4)cc13)CCC2N1CCC[C@@H](N)C1]

7-[(3R)-3-aminopiperidin-1-yl]-3-cyclopropyl-N-(2-fluoro-2-methylpropyl)-8,9-dihydro-7H-cyclopenta[h]isoquinoline-5-sulfonamide To a solution of intermediate 19 (216 mg, 0.39 mmol) in DCM (2 mL) was added TFA (2 mL). The solution was stirred for 1 hour. The solvent was removed and the excess TFA was azeotroped using 1:1 DCM/iso-hexane (2x10 mL). The brown gum obtained was purified by SCX column chromatography eluting with 0 to 100% of ammonia in methanol gradient to give a brown gum. Further purification by reverse phase column chromatography afforded the title product as a white solid (17 mg, 10% yield). $\delta_H$ (300 MHz, chloroform-d) 9.20 (s, 1H), 8.41 (d, J=12.4 Hz, 1H), 8.31 (d, J=14.7 Hz, 1H), 4.45-4.68 (m, 1H), 2.93-3.51 (m, 5H), 2.06-2.81 (m, 10H), 1.49-2.01 (m, 3H), 1.25-1.40 (m, 6H), 1.00-1.23 (m, 4H). LCMS $[M+H]^+$ 461, RT 1.72 minutes (Method 3).

Example 58

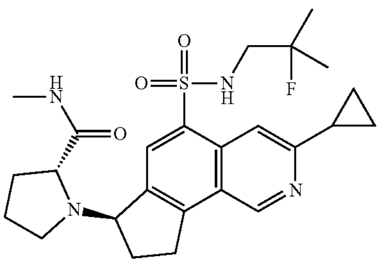

R or S (2R)-1-[(7R*)-3-cyclopropyl-5-[(2-fluoro-2-methylpropyl)sulfamoyl]-8,9-dihydro-7H-cyclopenta[h]isoquinolin-7-yl]-N-methylpyrrolidine-2-carboxamide [* or S]

To a solution of intermediate 20 (96 mg, 0.20 mmol) in a mixture of 1,4-dioxane (3 mL) and toluene (2 mL) was added cyclopropylboronic acid (54 mg, 0.60 mmol) followed by palladium(II) acetate (2.2 mg, 0.010 mmol). Nitrogen gas was bubbled through the mixture for 2 minutes then tricyclohexylphosphonium tetrafluoroborate (11 mg, 0.030 mmol) and potassium phosphate tribasic (106 mg, 0.50 mmol) were added. Nitrogen was bubbled through for 5 minutes then the microwave vial was capped and heated at 130° C. for 18 hours. Saturated aqueous $Na_2CO_3$ solution (10 mL) and EtOAc (10 mL) were added to the mixture. The mixture was filtered through Celite to remove the Pd residues. The organic layer was separated and washed further with sat. aqueous $Na_2CO_3$ solution (15 mL) and brine (10 mL), the solution was then passed through a phase separator. The solvent was removed to give a brown oil. Purification by flash column chromatography eluting with 0 to 100% of EtOAc in isohexane gradient then with 0 to 10% methanol in DCM gradient afforded the product as a mixture of diastereoisomers (42 mg, 43% yield). The mixture was separated by SFC to give the title compound as a single diastereoisomer (4 mg, 13% yield). $\delta_H$ (400 MHz, DMSO-d6) 9.25 (d, J=0.9 Hz, 1H), 8.39 (d, J=1.0 Hz, 1H), 8.33 (d, J=4.0 Hz, 2H), 7.81 (d, J=4.9 Hz, 1H), 4.60 (t, J=6.5 Hz, 1H), 3.37-3.51 (m, 1H), 3.20-3.30 (m, 1H), 2.96 (2×s, 2H), 2.55-2.67 (m, 4H), 1.98-2.46 (m, 6H), 1.61-1.81 (m, 3H), 1.25 (s, 3H), 1.17 (s, 3H), 1.05 (d, J=6.4 Hz, 4H). LCMS $[M+H]^+$489, RT 2.06 minutes (Method 11).

Example 59

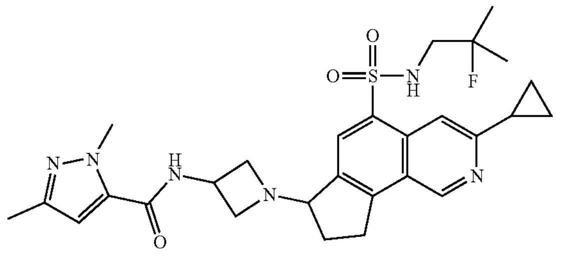 [SMILES: Cc1cc(C(=O)NC2CN(C3CCc4c3cc(S(=O)(=O)NCC(C)(C)F)c3cc(C5CC5)ncc43)C2)n(C)n1]

N-[1-[3-cyclopropyl-5-[(2-fluoro-2-methylpropyl)sulfamoyl]-8,9-dihydro-7H-cyclopenta[h]isoquinolin-7-yl]azetidin-3-yl]-2,5-dimethylpyrazole-3-carboxamide To a solution of intermediate 23 (15 mg, 0.035 mmol) in DMF (1 mL) was added DIPEA (0.018 mL, 0.10 mmol) followed by 1,3-dimethyl-1H-pyrazole-5-carboxylic acid (5.5 mg, 0.042 mmol) and HATU (16.31 mg, 0.042 mmol). The reaction mixture was stirred for 2 hours. Water (10 mL) and EtOAc (15 mL) were added to the mixture. The organic layer was separated and washed further with water (2×10 mL), brine (10 mL) and then was passed through a phase separator. The solvent was removed to give a brown oil. Purification by flash column chromatography eluting with 0 to 10% methanol (containing 7 M $NH_3$) in ethyl acetate gradient afforded the title product as a white solid (7.7 mg, 40% yield). $\delta_H$(400 MHz, DMSO-d6) 9.27 (s, 1H), 8.70 (d, J=6.8 Hz, 1H), 8.38 (s, 2H), 8.15 (s, 1H), 6.66 (s, 1H), 4.40 (d, J=7.1 Hz, 2H), 4.16 (s, 1H), 3.93 (s, 3H), 3.54 (d, J=6.7 Hz, 2H), 3.39 (d, J=8.6 Hz, 1H), 3.12 (s, 1H), 2.80-2.95 (m, 2H), 2.22-2.38 (m, 3H), 2.15 (s, 4H), 1.23 (s, 3H), 1.16 (s, 3H), 1.05 (d, J=6.4 Hz, 4H). LCMS $[M+H]^+$ 555, RT 1.76 minutes (Method 3).

Example 60

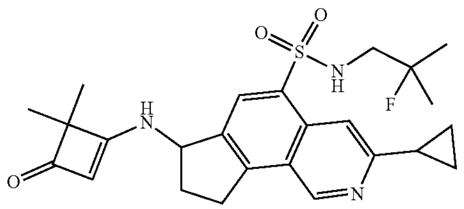 [SMILES: CC(C)(F)CNS(=O)(=O)c1cc2c(c3cnc(C4CC4)cc13)CCC2NC1=CC(=O)C1(C)C]

3-cyclopropyl-7-[(4,4-dimethyl-3-oxocyclobuten-1-yl)amino]-N-(2-fluoro-2-methylpropyl)-8,9-dihydro-7H-cyclopenta[h]isoquinoline-5-sulfonamide To a solution of intermediate 36 (90 mg, 0.24 mmol) in THF (3 mL) was added DIPEA (0.062 mL, 0.36 mmol) followed by 2,2-dimethylcyclobutane-1,3-dione (40 mg, 0.36 mmol). The mixture was stirred at 70° C. for 18 hours. The solvent was removed to give a brown gum. Purification by flash column chromatography eluting with 0 to 100% of EtOAc in isohexane gradient then 0 to 10% methanol in DCM gradient afforded the title product as a pale brown solid (68 mg, 60% yield). $\delta_H$ (400 MHz, chloroform-d) 9.23 (d, J=1.0 Hz, 1H), 8.21-8.31 (m, 2H), 5.79 (d, J=8.0 Hz, 1H), 5.00-5.20 (m, 21H), 4.55 (s, 1H), 3.55-3.65 (m, 1H), 3.25-3.40 (m, 1H), 2.83-3.16 (m, 3H), 2.15-2.40 (m, 2H), 1.25-1.43 (m, 12H), 1.06-1.22 (m, 4H). LCMS $[M+H]^+$ 472, RT 1.88 minutes (Method 3).

Example 61

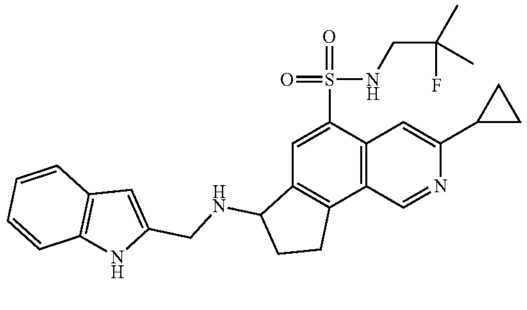 [SMILES: CC(C)(F)CNS(=O)(=O)c1cc2c(c3cnc(C4CC4)cc13)CCC2NCc1cc2ccccc2[nH]1]

3-cyclopropyl-N-(2-fluoro-2-methylpropyl)-7-(1H-indol-2-ylmethylamino)-8,9-dihydro-7H-cyclopenta[h]isoquinoline-5-sulfonamide To a solution of intermediate 24 (95 mg, 0.19 mmol) in a mixture of 1,4-dioxane (3 mL) and toluene (2 mL) was added cyclopropylboronic acid (51 mg, 0.57 mmol) followed by palladium(II) acetate (2.1 mg, 0.0095 mmol). Nitrogen gas was bubbled through the mixture for 2 minutes then tricyclohexylphosphonium tetrafluoroborate (11 mg, 0.028 mmol) and potassium phosphate tribasic (101 mg, 0.47 mmol) were added. Nitrogen was bubbled through for 5 minutes then the microwave vial was capped and heated at 130° C. for 18 hours in a microwave. Saturated aqueous $NaHCO_3$ solution (10 mL) and EtOAc (10 mL) were added to the mixture. The organic layer was separated and passed through a phase separator and the solvent removed to give a green oil. Purification by flash column chromatography eluting with 0 to 100% of EtOAc in isohexane gradient afforded the title product as a brown gum (45 mg, 47% yield). $\delta_H$ (400 MHz, DMSO-d6) 10.98-11.04 (m, 1H), 9.25-9.30 (m, 1H), 8.31-8.44 (m, 3H), 7.45 (d, J=7.7 Hz, 1H), 7.31-7.38 (m, 1H), 6.90-7.07 (m, 2H), 6.35 (s, 1H), 4.35-4.50 (m, 1H), 3.90-4.05 (m, 2H), 3.45-3.55 (m, 1H), 3.15-3.25 (m, 1H), 2.85-3.00 (m, 2H), 2.70-2.85 (m, 1H), 2.30 (q, J=6.5 Hz, 1H), 1.95-2.08 (m, 1H), 1.10-1.30 (m, 6H), 1.00-1.10 (m, 4H). LCMS $[M+H]^+$ 507, RT 2.58 minutes (Method 3).

Example 62

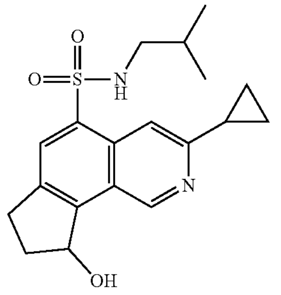 [SMILES: CC(C)CNS(=O)(=O)c1cc2c(c3cnc(C4CC4)cc13)C(O)CC2]

3-cyclopropyl-9-hydroxy-N-(2-methylpropyl)-8,9-dihydro-7H-cyclopenta[h]isoquinoline-5-sulfonamide In a microwave vial, intermediate 26 (53 mg, 0.15 mmol) was dissolved in 1,4-dioxane (2.5 mL) and caesium carbonate (123 mg, 0.37 mmol) and cyclopropylboronic acid (41 mg, 0.45 mmol) were added. The flask was evacuated and placed under a nitrogen atmosphere for 5 minutes. Chloro ($\eta^2$—P,C-tris(2,4-di-tert-butylphenyl)phosphite)(tricyclohexylphosphine)palladium(II) (16 mg, 0.015 mmol) was then added and the flask was again evacuated and placed under a nitrogen atmosphere. The reaction was then heated at 120° C. for 3 hours in a microwave. The mixture was diluted with EtOAc (10 mL) and filtered through Celite. Purification by flash column chromatography eluting with 0 to 50% of EtOAc in isohexane gradient afforded the title product as a white solid (5 mg, 9% yield). $\delta_H$ (400 MHz, chloroform-d) 9.70 (s, 1H), 8.34 (s, 1H), 8.29 (s, 1H), 5.92 (dd, J=7.3, 4.2 Hz, 1H), 4.74 (t, J=6.5 Hz, 1H), 3.27-3.39 (m, 1H), 2.99-3.12 (m, 1H), 2.74 (dq, J=9.4, 6.2 Hz, 3H), 2.25-2.40 (m, 1H), 1.72 (h, J=6.7 Hz, 1H), 1.16-1.30 (m, 3H), 1.09-1.21 (m, 2H), 0.86 (dd, J=5.5, 1.1 Hz, 6H). LCMS $[M+H]^+$361, RT 2.35 minutes (Method 3).

Example 63

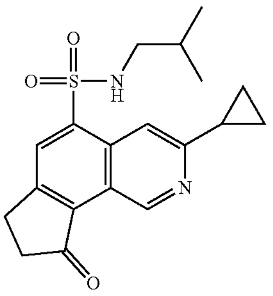 [SMILES: CC(C)CNS(=O)(=O)c1cc2c(c3cnc(C4CC4)cc13)C(=O)CC2]

3-cyclopropyl-N-(2-methylpropyl)-9-oxo-7,8-dihydrocyclopenta[h]isoquinoline-5-sulfonamide To a suspension of Example 62 (44 mg, 0.12 mmol) in DCM (4 mL) at 0° C. was added Dess-Martin periodinane (160 mg, 0.37 mmol). The mixture was stirred for 18 hours. A 1:1 mixture of saturated aqueous sodium thiosulfate solution and saturated aqueous $NaHCO_3$ solution (10 mL) was added and the mixture stirred vigorously for 15 minutes. The organic layer was separated and washed further with saturated aqueous $NaHCO_3$ solution (10 mL) and then passed through a phase separator frit. The solvent was removed to give a solid. Purification by flash column chromatography eluting with 0 to 50% of EtOAc in isohexane gradient afforded the title product as a yellow solid (28 mg, 64% yield). $\delta_H$ (400 MHz, chloroform-d) 10.40 (d, J=0.9 Hz, 1H), 8.45 (s, 1H), 8.28 (d, J=1.0 Hz, 1H), 4.91 (t, J=6.4 Hz, 1H), 3.29-3.37 (m, 2H), 2.87-2.95 (m, 2H), 2.79 (t, J=6.6 Hz, 2H), 2.24 (tt, J=8.2, 4.8 Hz, 1H), 1.73 (dt, J=13.4, 6.7 Hz, 1H), 1.17-1.32 (m, 2H), 1.04-1.14 (m, 2H), 0.86 (d, J=6.7 Hz, 6H). LCMS $[M+H]^+$359, RT 2.25 minutes (Method 3).

Example 64

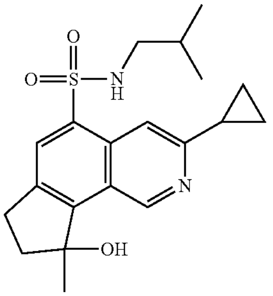 [SMILES: CC(C)CNS(=O)(=O)c1cc2c(c3cnc(C4CC4)cc13)C(C)(O)CC2]

3-cyclopropyl-9-hydroxy-9-methyl-N-(2-methylpropyl)-7,8-dihydrocyclopenta[h]isoquinoline-5-sulfonamide To a solution of Example 63 (18 mg, 0.050 mmol) in THF (1 mL) at 0° C. was added 1 M methyllithium in THF (0.151 mL, 0.15 mmol). The mixture was stirred for 2 hours. The solvent was removed, and the residue was partitioned between $H_2O$ (3 mL) and EtOAc (10 mL). The product went into the organic layer, which was then passed through a phase separator frit. The solvent was removed to give a yellow gum. Purification by flash column chromatography eluting with 0 to 50% of EtOAc in isohexane gradient afforded the title product as a white solid (4 mg, 21% yield). $\delta_H$ (400 MHz, chloroform-d) 10.02 (s, 1H), 8.22-8.29 (m, 2H), 4.65 (t, J=6.4 Hz, 1H), 3.08-3.19 (m, 1H), 2.95-3.05 (m, 1H), 2.65-2.82 (m, 2H), 2.50-2.60 (m, 1H), 2.16-2.43 (m, 3H), 1.46-1.93 (m, 4H), 1.08-1.33 (m, 3H), 1.10 (t, J=3.1 Hz, 1H), 0.83-0.98 (m, 6H). LCMS [M+H]$^+$ 375, RT 2.14 minutes (Method 3).

Example 65

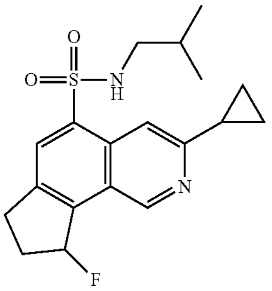 [SMILES: CC(C)CNS(=O)(=O)c1cc2c(c3cnc(C4CC4)cc13)C(F)CC2]

3-cyclopropyl-9-fluoro-N-(2-methylpropyl)-8,9-dihydro-7H-cyclopenta[h]isoquinoline-5-sulfonamide In a microwave vial, Intermediate 27 (43 mg, 0.12 mmol) was suspended in toluene (3 mL) and cyclopropylboronic acid (33 mg, 0.36 mmol) and potassium phosphate tribasic (64 mg, 0.30 mmol) were added. The flask was evacuated and placed under a nitrogen atmosphere for 5 minutes. Tricyclohexylphosphonium tetrafluoroborate (6.8 mg, 0.018 mmol) and palladium (II) acetate (1.35 mg, 0.006 mmol) was then added and the flask was again evacuated and placed under a nitrogen atmosphere. The reaction was then heated at 110° C. for 1 hour 15 minutes in a microwave. The mixture was retreated with cyclopropylboronic acid (33 mg, 0.36 mmol) and potassium phosphate tribasic (64 mg, 0.30 mmol), tricyclohexylphosphonium tetrafluoroborate (6.8 mg, 0.018 mmol) and palladium(II) acetate (1.35 mg, 0.006 mmol). The mixture was sparged with nitrogen and heated at 110° C. for 2 hours. The solvent was removed to give a residue. Purification by flash column chromatography eluting with 0 to 20% of EtOAc in isohexane gradient afforded the title product as an off-white solid (13 mg, 30% yield). $\delta_H$ (300 MHz, chloroform-d) 9.47 (s, 1H), 8.34 (d, J=1.4 Hz, 1H), 8.27 (d, J=1.0 Hz, 1H), 6.63 (ddd, J=56.6, 6.9, 2.9 Hz, 1H), 4.68 (t, J=6.4 Hz, 1H), 3.24-3.53 (m, 1H), 3.00-3.20 (m, 1H), 2.44-2.84 (m, 3H), 2.20-2.35 (m, 1H), 1.65-1.80 (m, 1H), 1.02-1.29 (m, 4H), 0.85 (dd, J=6.7, 1.7 Hz, 6H). LCMS [M+H]$^+$ 363, RT 2.48 minutes (Method 3).

Example 66

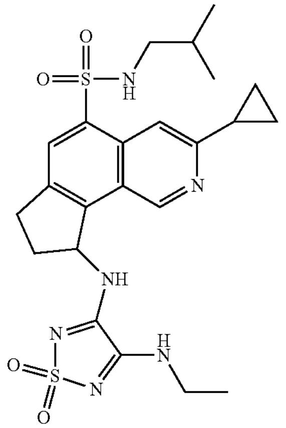 [SMILES: CCNC1=NS(=O)(=O)N=C1NC1CCc2cc(S(=O)(=O)NCC(C)C)c3cc(C4CC4)ncc3c21]

3-cyclopropyl-9-[[4-(ethylamino)-1,1-dioxo-1,2,5-thiadiazol-3-yl]amino]-N-(2-methylpropyl)-8,9-dihydro-7H-cyclopenta[h]isoquinoline-5-sulfonamide Intermediate 39 (55 mg, 0.139 mmol) was dissolved in a mixture of dichloromethane (5 mL) and N,N-diisopropylethylamine (54 mg, 0.417 mmol). 3,4-Diethoxy-1,2,5-thiadiazole-1,1-dioxide (45 mg, 0.208 mmol) was added and the mixture stirred at room temperature for 2 hours. A further (14 mg, 0.070 mmol) of 3,4-diethoxy-1,2,5-thiadiazole-1,1-dioxide and (18 mg, 0.139 mmol) of N,N-diisopropylethylamine were added. The mixture was stirred at room temperature for a further 1 hour. Ethylamine solution (2 M in THF) (2.8 mL, 5.56 mmol) was added and the mixture stirred at room temperature for 1 hour. The solvents were evaporated, and the crude material purified by flash chromatography (eluting with 75-100% EtOAc in hexane followed by 0-15% MeOH in EtOAc) to afford the title compound (63 mg, 87% yield). $S_H$ (300 MHz, d-DMSO), 9.18 (s, 1H), 8.93 (d, J=7.5 Hz, 1H), 8.39 (s, 1H), 8.35-8.31 (m, 1H), 8.29 (s, 1H), 8.18-8.10 (m, 1H), 5.98-5.90 (m, 1H), 3.74-3.63 (m, 1H), 3.53-3.43 (m, 1H), 3.28-3.22 (m, 1H), 3.20-3.08 (m, 1H), 2.74-2.62 (m, 1H), 2.58 (t, J=6.3 Hz, 2H), 2.34-2.21 (m, 2H), 1.71-1.54 (m, 1H), 1.13 (t, J=7.3 Hz, 3H), 1.05 (d, J=6.5 Hz, 4H), 0.79 (dd, J=6.7, 4.0 Hz, 6H). LCMS [M+H]$^+$ 519, RT 2.14 min (Method 3).

Example 67

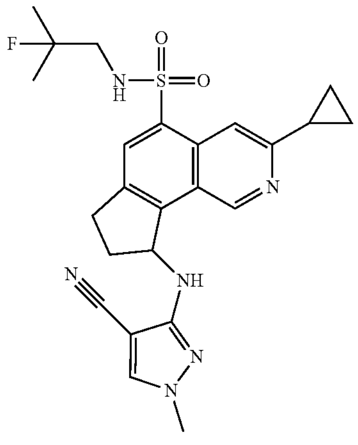 [SMILES: Cn1cc(C#N)c(NC2CCc3cc(S(=O)(=O)NCC(C)(C)F)c4cc(C5CC5)ncc4c32)n1]

9-[(4-cyano-1-methylpyrazol-3-yl)amino]-3-cyclopropyl-N-(2-fluoro-2-methylpropyl)-8,9-dihydro-7H-cyclopenta[h]isoquinoline-5-sulfonamide A mixture of intermediate 84 (50 mg, 0.132 mmol), 3-bromo-1-methyl-1H-pyrazole-4-carbonitrile (37 mg, 0.198 mmol) and sodium tert-butoxide (40 mg, 0.413 mmol) in anhydrous 1,4-dioxane (2 mL) was degassed, vacuum/nitrogen purge (×3). tBuXPhos Pd G3 (17 mg, 0.021 mmol) was added and the mixture degassed again, vacuum/nitrogen purge (×3). The reaction mixture heated at 70° C. for 16 hours then cooled to room temperature and filtered through celite, washing with dioxane. The solvent was evaporated, and the crude material purified by column chromatography to give the title compound (23 mg, 36% yield). $\delta_H$ (300 MHz, d-DMSO), 9.31 (s, 1H), 8.44-8.35 (m, 2H), 8.21-8.14 (m, 2H), 6.82 (d, J=8.9 Hz, 1H), 5.76 (td, J=8.5, 3.8 Hz, 1H), 3.73 (s, 3H), 3.63-3.39 (m, 1H), 3.31-3.11 (m, 1H), 3.06-2.89 (m, 2H), 2.66-2.54 (m, 1H), 2.27 (q, J=6.4 Hz, 1H), 2.17-2.04 (m, 1H), 1.32-1.18 (m, 6H), 1.08-0.97 (m, 4H). LCMS $[M-H]^-$ 481, RT 2.06 min (Method 10).

Example 68

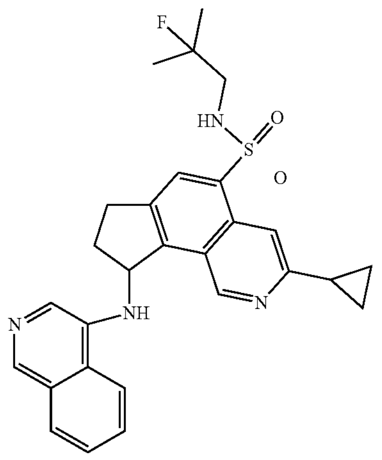

3-cyclopropyl-N-(2-fluoro-2-methylpropyl)-9-(isoquinolin-4-ylamino)-8,9-dihydro-7H-cyclopenta[h]isoquinoline-5-sulfonamide A mixture of intermediate 84 (50 mg, 0.132 mmol), 4-bromoisoquinoline (41 mg, 0.198 mmol) and sodium tert-butoxide (40 mg, 0.413 mmol) in anhydrous 1,4-dioxane (2 mL) was degassed, vacuum/nitrogen purge (×3). tBuXPhos Pd G3 (17 mg, 0.021 mmol) was added and the mixture degassed again, vacuum/nitrogen purge (×3). The reaction mixture was heated at 70° C. for 16 hours then cooled to room temperature and filtered through celite, washing with dioxane. The solvent was evaporated, and the crude material purified by flash column chromatography to give the title compound (25 mg, 37% yield). $\delta_H$ (300 MHz, d-DMSO), 9.32 (d, J=0.9 Hz, 1H), 8.64 (s, 1H), 8.47-8.39 (m, 2H), 8.27 (s, 1H), 8.20-8.07 (m, 2H), 8.03-7.94 (m, 1H), 7.66-7.54 (m, 2H), 6.74 (d, J=8.6 Hz, 1H), 5.97 (td, J=8.2, 4.0 Hz, 1H), 3.28 (d, J=10.3 Hz, 1H), 3.19-3.06 (m, 1H), 3.00 (dd, J=19.9, 6.5 Hz, 2H), 2.87-2.71 (m, 1H), 2.34-2.13 (m, 2H), 1.35-1.18 (m, 6H), 1.03-0.93 (m, 4H). LCMS $[M-H]^-$ 503, RT 1.71 min (Method 10).

Example 69

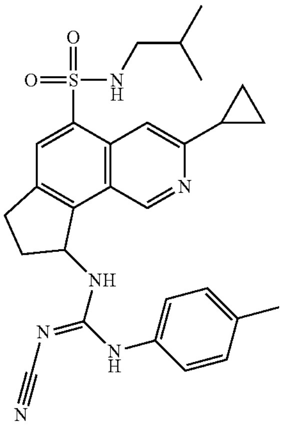 [SMILES: Cc1ccc(N/C(=N\C#N)NC2CCc3cc(S(=O)(=O)NCC(C)C)c4cc(C5CC5)ncc4c32)cc1]

2-cyano-1-[3-cyclopropyl-5-(2-methylpropylsulfamoyl)-8,9-dihydro-7H-cyclopenta[h]isoquinolin-9-yl]-3-(4-methylphenyl)guanidine Intermediate 39 (43 mg, 0.109 mmol) was dissolved in a mixture of dichloromethane (10 mL) and N,N-diisopropylethylamine (42 mg, 0.326 mmol). Intermediate 30 (41 mg, 0.163 mmol) was then added and the mixture stirred at 120° C. in the microwave for 4 hours. The solvent was evaporated, and the crude material purified by flash column chromatography to give the title compound (28 mg, 50% yield). $\delta_H$ (300 MHz, d-DMSO), 9.32 (d, J=0.9 Hz, 1H), 9.16 (s, 1H), 8.35 (d, J=1.1 Hz, 1H), 8.15 (s, 1H), 8.07 (t, J=5.9 Hz, 1H), 7.75 (d, J=8.7 Hz, 1H), 7.08 (d, J=8.3 Hz, 2H), 7.02 (d, J=8.4 Hz, 2H), 6.04 (td, J=8.6, 4.1 Hz, 1H), 3.27-3.12 (m, 1H), 3.04-2.90 (m, 1H), 2.70-2.53 (m, 3H), 2.35-2.25 (m, 1H), 2.22 (s, 3H), 2.19-2.02 (m, 1H), 1.66-1.54 (m, 1H), 1.12-0.99 (m, 4H), 0.80-0.72 (m, 6H). LCMS $[M+H]^+$ 517, RT 2.53 min (Method 3).

Example 70

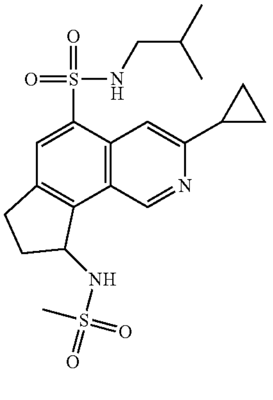 [SMILES: CC(C)CNS(=O)(=O)c1cc2c(c3cnc(C4CC4)cc13)C(NS(C)(=O)=O)CC2]

3-cyclopropyl-9-(methanesulfonamido)-N-(2-methylpropyl)-8,9-dihydro-7H-cyclopenta[h]isoquinoline-5-sulfonamide Intermediate 39 (16 mg, 0.040 mmol) was dissolved in dichloromethane (2 mL) and N,N-diisopropylethylamine (68 mg, 0.527 mmol). Methanesulfonyl chloride (31 mg, 0.274 mmol) was added. The mixture was stirred at room temperature for 1 hour. The crude material was purified by flash chromatography (eluting with 30-100% EtOAc in hexane) to give the title compound (8.5 mg, 48% yield). $\delta_H$ (300 MHz, d-DMSO), 9.59 (d, J=0.9 Hz, 1H), 8.35 (d, J=0.9 Hz, 1H), 8.18 (s, 1H), 8.11-8.01 (m, 1H), 7.82-7.65 (m, 1H), 5.59-5.43 (m, 1H), 3.29-3.17 (m, 1H), 3.10 (s, 3H), 3.07-2.91 (m, 1H), 2.75-2.61 (m, 1H), 2.56 (d, J=6.9 Hz, 2H), 2.33-2.11 (m, 2H), 1.68-1.51 (m, 1H), 1.10-0.98 (m, 4H), 0.80-0.68 (m, 6H). LCMS $[M+H]^+$438, RT 2.11 min (Method 3).

Example 71

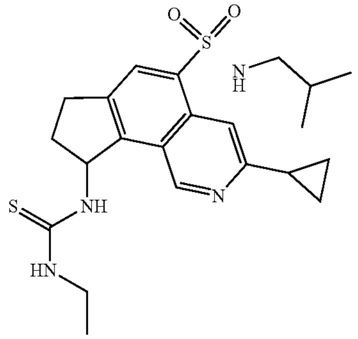

1-[3-cyclopropyl-5-(2-methylpropylsulfamoyl)-8,9-dihydro-7H-cyclopenta[h]isoquinolin-9-yl]-3-ethylthiourea Intermediate 39 (129 mg, 0.326 mmol) was dissolved in a mixture of dichloromethane (5 mL) and N,N-diisopropylethylamine (63 mg, 0.489 mmol). Ethyl isothiocyanate (86 mg, 0.978 mmol) was added and the mixture stirred at room temperature for 20 hours and then at 45° C. for 2 hours. The crude material was purified by flash chromatography (eluting with 30-100% EtOAc in hexane and then 0-10% MeOH in EtOAc) to give the title compound (93 mg, 64% yield). $\delta_H$ (300 MHz, d-DMSO), 9.33 (s, 1H), 8.35 (d, J=1.0 Hz, 1H), 8.19 (s, 1H), 8.10-8.03 (m, 1H), 7.98 (d, J=9.0 Hz, 1H), 7.49-7.10 (m, 1H), 6.71-6.52 (m, 1H), 3.54-3.33 (m, 2H), 3.28-3.14 (m, 1H), 3.09-2.94 (m, 1H), 2.70-2.53 (m, 3H), 2.33-2.19 (m, 1H), 2.07-1.91 (m, 1H), 1.69-1.54 (m, 1H), 1.10-0.97 (m, 7H), 0.81-0.72 (m, 6H). LCMS $[M-H]^-$ 445, RT 2.29 min (Method 10).

Examples 72 & 73

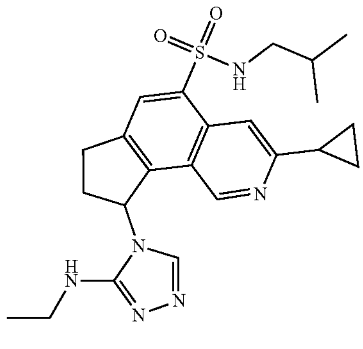

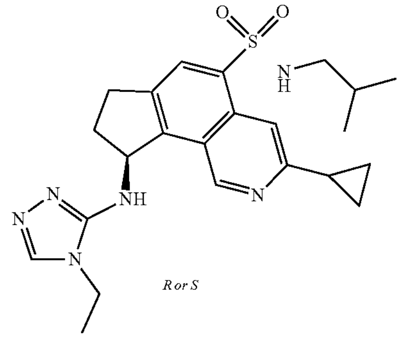

R or S 3-cyclopropyl-9-[3-(ethylamino)-1,2,4-triazol-4-yl]-N-(2-methylpropyl)-8,9-dihydro-7H-cyclopenta[h]isoquinoline-5-sulfonamide (72)

(9R*)-3-cyclopropyl-9-[(4-ethyl-1,2,4-triazol-3-yl)amino]-N-(2-methylpropyl)-8,9-dihydro-7H-cyclopenta[h]isoquinoline-5-sulfonamide [* or S] (73)

Example 71 (105 mg, 0.235 mmol) was dissolved in N,N-dimethylformamide (5 mL). Formic acid hydrazide (47 mg, 0.705 mmol) and mercuric chloride (128 mg, 0.470 mmol) were added. The mixture was stirred at room temperature for 5 mins. Triethylamine (72 mg, 0.705 mmol) was the added and the mixture was stirred at 90° C. for 3 h. The reaction mixture was diluted with MeCN (10 mL) and filtered through a pad of celite washing with MeCN (3×10 mL). The filtrate was evaporated, and the crude material purified by flash column chromatography followed by SFC to give Example 72 and the racemic mixture of Example 73.

Example 72 (11 mg, 10% yield). $\delta_H$ (400 MHz, d-DMSO), 8.79 (d, J=0.9 Hz, 1H), 8.39 (d, J=0.9 Hz, 1H), 8.28 (s, 1H), 8.18-8.08 (m, 1H), 7.48 (s, 1H), 6.35 (t, J=5.5 Hz, 1H), 6.24 (dd, J=8.6, 3.7 Hz, 1H), 3.47-3.34 (m, 3H), 3.21-3.10 (m, 1H), 2.86-2.73 (m, 1H), 2.66-2.55 (m, 2H), 2.30-2.22 (m, 1H), 2.21-2.10 (m, 1H), 1.65-1.54 (m, 1H), 1.26 (t, J=7.2 Hz, 3H), 1.06-0.95 (m, 4H), 0.80-0.70 (m, 6H).

The racemic mixture of Example 73 (38 mg, 36% yield) was separated using chiral SFC to give the title compound as a single isomer (11 mg, 29% yield). Chiral SFC RT**=2.24 minutes; $\delta_H$ (400 MHz, d-DMSO), 9.38 (s, 1H), 8.37 (s, 1H), 8.20 (s, 1H), 8.13-8.04 (m, 1H), 8.03 (s, 1H), 6.65 (d, J=8.8 Hz, 1H), 5.93-5.84 (m, 1H), 3.72 (q, J=7.2 Hz, 2H), 3.31-3.21 (m, 1H), 3.08-2.98 (m, 1H), 2.73-2.62 (m, 1H), 2.59-2.54 (m, 2H), 2.25 (p, J=6.5 Hz, 1H), 2.19-2.10 (m, 1H), 1.63 (hept, J=6.8 Hz, 1H), 1.16 (t, J=7.2 Hz, 3H), 1.06-0.94 (m, 4H), 0.83-0.73 (m, 6H). LCMS $[M+H]^+$ 455, RT 2.08 min (Method 16).

**Chiral analysis was carried out by SFC, using a Chiralcel OJ-3 4.6×150 mm, 3 μm column, flow rate 3.5 mL/min eluting with an isocratic 10% methanol method, using a 5 min run time on a Waters UPC$^2$-SQD2 system.

Example 74

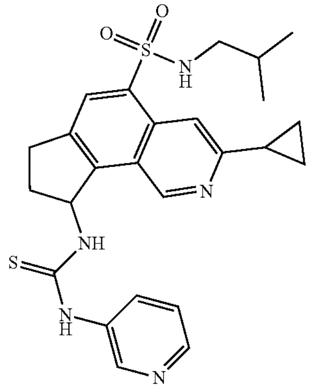 [SMILES: CC(C)CNS(=O)(=O)c1cc2c(c3cnc(C4CC4)cc13)C(NC(=S)Nc1cccnc1)CC2]

1-[3-cyclopropyl-5-(2-methylpropylsulfamoyl)-8,9-dihydro-7H-cyclopenta[h]isoquinolin-9-yl]-3-pyridin-3-ylthiourea Intermediate 39 (100 mg, 0.278 mmol) was dissolved in a mixture of dichloromethane (5 mL) and N,N-diisopropylethylamine (54 mg, 0.417 mmol). 3-Pyridyl isothiocyanate (60 mg, 0.417 mmol) was added and the mixture stirred at room temperature overnight. The crude material was purified by flash chromatography eluting with 60-100% EtOAc in hexane and then 0-20% MeOH in EtOAc, to give the title compound (104 mg, 75% yield). $\delta_H$ (400 MHz, d-DMSO), 9.54 (s, 1H), 9.37 (s, 1H), 8.68 (d, J=8.6 Hz, 1H), 8.54 (s, 1H), 8.38 (d, J=1.0 Hz, 1H), 8.29 (d, J=4.8 Hz, 1H), 8.22 (s, 1H), 8.10 (t, J=6.0 Hz, 1H), 7.95 (dt, J=8.2, 2.1 Hz, 1H), 7.34 (dd, J=8.2, 4.7 Hz, 1H), 6.72-6.63 (m, 1H), 3.29-3.21 (m, 1H), 3.12-3.02 (m, 1H), 2.74-2.67 (m, 1H), 2.58 (t, J=6.4 Hz, 2H), 2.32-2.23 (m, 1H), 2.18-2.08 (m, 1H), 1.68-1.57 (m, 1H), 1.10-0.99 (m, 4H), 0.81-0.73 (m, 6H). LCMS $[M+H]^+$ 496, RT 2.39 min (Method 3).

Example 75

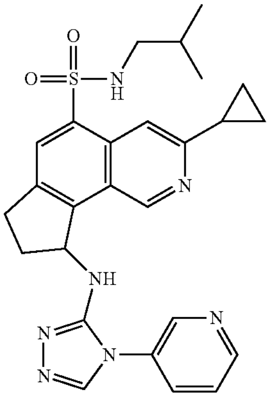 [SMILES: CC(C)CNS(=O)(=O)c1cc2c(c3cnc(C4CC4)cc13)C(Nc1nncn1-c1cccnc1)CC2]

3-cyclopropyl-N-(2-methylpropyl)-9-[(4-pyridin-3-yl-1,2,4-triazol-3-yl)amino]-8,9-dihydro-7H-cyclopenta[h]isoquinoline-5-sulfonamide Example 74 (102 mg, 0.206 mmol) was dissolved in N,N-dimethylformamide (5 mL). Formic acid hydrazide (41 mg, 0.618 mmol) and mercuric chloride (112 mg, 0.412 mmol) were added. The mixture was stirred at room temperature for 5 mins. Triethylamine (63 mg, 0.618 mmol) was added. The mixture was stirred at 90° C. for 5 hours and then allowed to cool to room temperature. The reaction mixture was then diluted with MeCN (10 mL) and filtered through a pad of celite washing with MeCN (3×10 mL). The filtrate was evaporated. The crude material was purified by reverse phase flash column chromatography to give the title compound (9 mg, 9% yield). $\delta_H$ (400 MHz, d-DMSO), 9.44 (d, J=0.9 Hz, 1H), 8.63 (d, J=2.5 Hz, 1H), 8.60 (dd, J=4.8, 1.5 Hz, 1H), 8.35-8.30 (m, 2H), 8.17 (s, 1H), 8.10-8.03 (m, 1H), 7.87 (ddd, J=8.2, 2.6, 1.5 Hz, 1H), 7.53 (dd, J=8.1, 4.8 Hz, 1H), 6.85 (d, J=8.7 Hz, 1H), 5.96-5.89 (m, 1H), 3.29-3.20 (m, 1H), 3.06-2.95 (m, 1H), 2.74-2.62 (m, 1H), 2.61-2.54 (m, 2H), 2.31-2.15 (m, 2H), 1.67-1.57 (m, 1H), 1.07-0.99 (m, 4H), 0.82-0.73 (m, 6H). LCMS $[M+H]^+$ 504, RT 1.48 min (Method 10).

Example 76

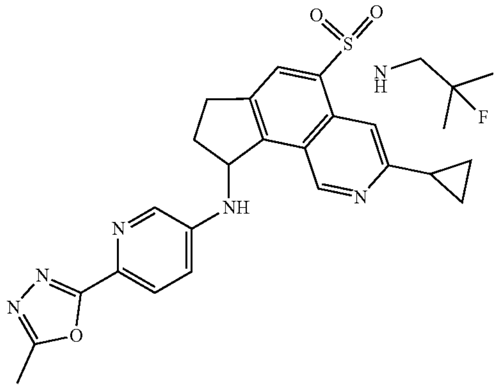

3-cyclopropyl-N-(2-fluoro-2-methylpropyl)-9-[[6-(5-methyl-1,3,4-oxadiazol-2-yl)pyridin-3-yl]amino]-8,9-dihydro-7H-cyclopenta[h]isoquinoline-5-sulfonamide A mixture of intermediate 84 (52 mg, 0.138 mmol), 2-(5-bromo-2-pyridyl)-5-methyl-1,3,4-oxadiazole (50 mg, 0.207 mmol) and sodium tert-butoxide (40 mg, 0.413 mmol) in anhydrous 1,4-dioxane (2 mL) was degassed, vacuum/nitrogen purge (×3). tBuXPhos Pd G3 (17 mg, 0.021 mmol) was added and the mixture degassed again, vacuum/nitrogen purge (×3). The reaction mixture heated at 70° C. for 16 hours. Cooled to room temperature and filtered through celite, washing with dioxane. The solvent was evaporated, and the crude material purified by flash column chromatography to give the title compound (11 mg, 15% yield). $\delta_H$ (300 MHz, d-DMSO), 9.25 (d, J=0.8 Hz, 1H), 8.50-8.40 (m, 2H), 8.26 (s, 1H), 8.20 (d, J=2.7 Hz, 1H), 7.92 (d, J=8.7 Hz, 1H), 7.29 (dd, J=8.8, 2.8 Hz, 1H), 7.21 (d, J=8.2 Hz, 1H), 5.87-5.76 (m, 1H), 3.29-3.20 (m, 1H), 3.18-3.04 (m, 1H), 3.02 (d, J=6.4 Hz, 1H), 2.96 (d, J=6.4 Hz, 1H), 2.76-2.61 (m, 1H), 2.57 (s, 3H), 2.36-2.22 (m, 1H), 2.15-2.02 (m, 1H), 1.32-1.18 (m, 6H), 1.03 (d, J=7.5 Hz, 4H). LCMS $[M+H]^+$ 537, RT 1.97 min (Method 3).

Example 77

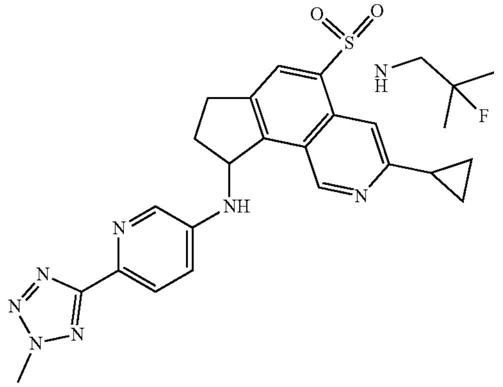

3-cyclopropyl-N-(2-fluoro-2-methylpropyl)-9-[[6-(2-methyltetrazol-5-yl)pyridin-3-yl]amino]-8,9-dihydro-7H-cyclopenta[h]isoquinoline-5-sulfonamide A mixture of intermediate 84 (52 mg, 0.138 mmol), 5-bromo-2-(2-methyl-2H-tetrazol-5-yl)-pyridine (50 mg, 0.207 mmol) and sodium tert-butoxide (40 mg, 0.413 mmol) in anhydrous 1,4-dioxane (2 mL) was degassed, vacuum/nitrogen purge (×3). tBuXPhos Pd G3 (17 mg, 0.021 mmol) was added and the mixture degassed again, vacuum/nitrogen purge (×3). The reaction mixture heated at 70° C. for 16 hours then cooled to room temperature and filtered through celite, washing with dioxane. The solvent was evaporated, and the crude material purified by flash column chromatography to give the title compound (16 mg, 22% yield). $\delta_H$ (300 MHz, d-DMSO), 9.28 (d, J=0.9 Hz, 1H), 8.48-8.40 (m, 2H), 8.26 (s, 1H), 8.21 (d, J=2.7 Hz, 1H), 7.92 (d, J=8.6 Hz, 1H), 7.28 (dd, J=8.7, 2.8 Hz, 1H), 6.96 (d, J=8.3 Hz, 1H), 5.86-5.74 (m, 1H), 4.41 (s, 3H), 3.31-3.19 (m, 1H), 3.17-3.05 (m, 1H), 3.02 (d, J=6.4 Hz, 1H), 2.96 (d, J=6.4 Hz, 1H), 2.75-2.59 (m, 1H), 2.29 (p, J=6.6 Hz, 1H), 2.15-2.03 (m, 1H), 1.32-1.18 (m, 6H), 1.07-0.97 (m, 4H). LCMS $[M+H]^+$ 537, RT 2.09 min (Method 3).

Example 78

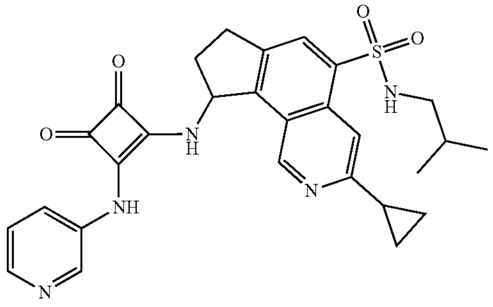 [SMILES: CC(C)CNS(=O)(=O)c1cc2c(c3cnc(C4CC4)cc13)C(Nc1c(Nc3cccnc3)c(=O)c1=O)CC2]

3-cyclopropyl-9-[[3,4-dioxo-2-(pyridin-3-ylamino)cyclobuten-1-yl]amino]-N-(2-methylpropyl)-8,9-dihydro-7H-cyclopenta[h]isoquinoline-5-sulfonamide 3-Methoxy-4-(3-pyridylamino)cyclobut-3-ene-1,2-dione (43 mg, 0.209 mmol) was suspended in dichloromethane (3 mL). N,N-Diisopropylethylamine (27 mg, 0.209 mmol) and methanol (2 mL) added. Intermediate 39 (50 mg, 0.139 mmol) was then added and the mixture was stirred at room temperature for 18 hours. The precipitate that formed was filtered off and washed with DCM to give the title compound (5.7 mg, 8% yield). $\delta_H$ (400 MHz, d-DMSO), 9.54 (s, 1H), 9.33 (s, 1H), 8.51 (d, J=2.8 Hz, 1H), 8.41 (s, 1H), 8.30 (s, 1H), 8.25-8.12 (m, 3H), 7.94-7.85 (m, 1H), 7.36 (dd, J=8.4, 4.7 Hz, 1H), 6.35-6.25 (m, 1H), 3.36-3.27 (m, 1H), 3.20-3.09 (m, 1H), 2.80-2.70 (m, 1H), 2.63-2.55 (m, 2H), 2.37-2.23 (m, 2H), 1.68-1.57 (m, 1H), 1.09-1.01 (m, 4H), 0.82-0.74 (m, 6H). LCMS $[M+H]^+$ 532, RT 2.07 min (Method 3).

Example 79

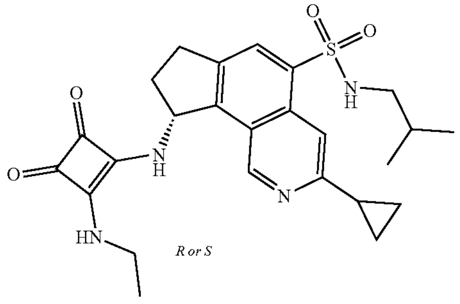 [SMILES: CCNc1c(N[C@@H]2CCc3cc(S(=O)(=O)NCC(C)C)c4cc(C5CC5)ncc4c32)c(=O)c1=O]

(9R*)-3-cyclopropyl-9-[[2-(ethylamino)-3,4-dioxo-cyclobuten-1-yl]amino]-N-(2-methylpropyl)-8,9-dihydro-7H-cyclopenta[h]isoquinoline-5-sulfonamide [* or S]

Intermediate 39 (43 mg, 0.109 mmol) was dissolved in a mixture of dichloromethane (10 mL) and N,N-diisopropylethylamine (21 mg, 0.163 mmol). 3,4-dimethoxy-3-cyclobutene-1,2-dione (23 mg, 0.163 mmol) was added and the mixture stirred at room temperature for 16 hours. Ethylamine solution (2 M in THF, 2.17 mL, 4.34 mmol) was added and the mixture stirred at room temperature for 1 hour. The solvent was evaporated and the crude material purified by flash column chromatography to give the title compound as a racemic mixture (26.5 mg, 51% Yield). The racemate was separated using chiral HPLC in polar organic mode to provide the title compound as a single isomer (6.2 mg, 23% yield). $\delta_H$ (300 MHz, d-DMSO), 9.26 (s, 1H), 8.39 (d, J=0.9 Hz, 1H), 8.25 (s, 1H), 8.17-8.09 (m, 1H), 8.07-7.85 (brs, 1H), 7.30-7.00 (brs, 1H), 6.24 (s, 1H), 3.50 (s, 3H), 3.29-3.19 (m, 1H), 3.14-3.01 (m, 1H), 2.72-2.62 (m, 1H), 2.60-2.53 (m, 2H), 2.33-2.12 (m, 1H), 1.67-1.54 (m, 1H), 1.12 (t, J=7.1 Hz, 3H), 1.08-0.97 (m, 4H), 0.81-0.70 (m, 6H). LCMS $[M+H]^+$ 483, RT 1.94 min (Method 3). Chiral RT**=2.76 minutes (Peak 2).

**Analysis was carried out in polar organic mode, using a Lux Cellulose-4, 4.6×150 mm, 3 μm column, flow rate 1 mL/min eluting with 100% methanol using a 10 min run time on a UV directed Agilent 1100 system.

Example 80

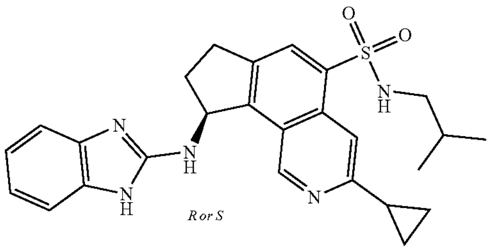 [SMILES: CC(C)CNS(=O)(=O)c1cc2c(c3cnc(C4CC4)cc13)[C@@H](Nc1nc3ccccc3[nH]1)CC2]

(9R*)-9-(1H-benzimidazol-2-ylamino)-3-cyclopropyl-N-(2-methylpropyl)-8,9-dihydro-7H-cyclopenta[h]isoquinoline-5-sulfonamide [* or S]

intermediate 39 (50 mg, 0.139 mmol), 2-chlorobenzimidazole (32 mg, 0.209 mmol) and 1-butanol (3 mL) were charged into a microwave tube. 4 M Hydrochloric acid in dioxane (0.03 mL, 0.14 mmol) was added. The sealed reaction mixture was heated in the microwave at 160° C. for 4.5 hours and cooled to room temperature. The solvent was evaporated, and the residue portioned between DCM and aqueous saturated $NaHCO_3$ solution. The organic phase was washed with brine, passed through a phase separator cartridge and evaporated. The crude material was purified by flash chromatography to give the title compound as a racemic mixture (26 mg, 39% Yield). The racemate (20 mg) was then separated by chiral SFC, to provide the title compound as a single isomer (4 mg, 20% yield from chiral separation, peak 1). Chiral SFC RT**=6.36 minutes; $\delta_H$ (300 MHz, d-DMSO), 10.85-10.65 (m, 1H), 9.37 (s, 1H), 8.36 (s, 1H), 8.21 (s, 1H), 8.15-8.00 (m, 1H), 7.41-7.32 (m, 1H), 7.27-7.10 (m, 2H), 6.98-6.83 (m, 2H), 6.17-6.06 (m, 1H), 3.31-3.22 (m, 1H), 3.11-2.97 (m, 1H), 2.78-2.63 (m, 1H), 2.57 (d, J=6.9 Hz, 2H), 2.30-2.09 (m, 2H), 1.69-1.55 (m, 1H), 1.03-0.91 (m, 4H), 0.81-0.73 (m, 6H). LCMS $[M+H]^+$ 476, RT 2.50 min (Method 16).

**Chiral analysis was carried out by SFC, using a Chiralcel OJ-3 4.6×150 mm, 3 μm column, flow rate 3.5 mL/min eluting with 5-15% Methanol (+0.1% $NH_4OH$) using a 9 min run time on a Waters $UPC^2$-SQD2 system.

Example 81

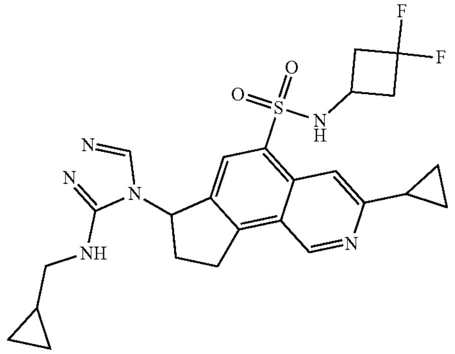 [SMILES: N=CN(C(=N)NCC1CC1)C1CCc2c1cc(S(=O)(=O)NC1CC(F)(F)C1)c1cc(C3CC3)ncc21]

3-cyclopropyl-7-[3-(cyclopropylmethylamino)-1,2,4-triazol-4-yl]-N-(3,3-difluorocyclobutyl)-8,9-dihydro-7H-cyclopenta[h]isoquinoline-5-sulfonamide Intermediate 119 (35 mg, 0.026 mmol, 50% purity) was stirred in DCM (3 mL) and TFA (30.2 μl, 0.39 mmol) was add. Reaction stirred for 30 minutes at room temperature. The orange suspension was quenched with saturated aq. $NaHCO_3$ (10 mL), organic layer separated and aq. layer was extracted with further DCM (3×20 mL). Organics layers were combined, dried over sodium sulphate and concentrated under vacuum. The orange residue was purified by acidic prep HPLC to afford the title compound (1 mg, 7% Yield) as a white solid. $\delta_H$ (500 MHz, Methanol-d4) 9.31 (s, 1H), 8.41 (s, 1H), 8.12 (s, 1H), 7.79 (s, 1H), 5.96-5.90 (m, 1H), 3.80-3.71 (m, 1H), 3.59-3.46 (m, 2H), 3.28-3.19 (m, 2H), 3.06-2.95 (m, 1H), 2.66-2.51 (m, 2H), 2.47-2.38 (m, 1H), 2.37-2.25 (m, 3H), 1.25-1.19 (m, 1H), 1.18-1.10 (m, 4H), 0.60-0.53 (m, 2H), 0.34-0.26 (m, 2H). LCMS $[M+H]^+$ 515, RT 2.20 min (Method 12).

Example 82

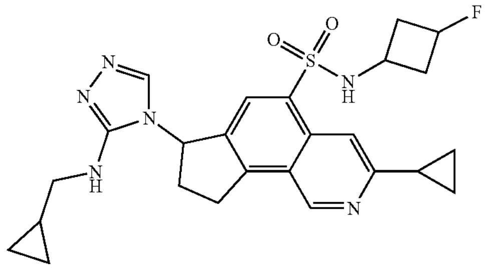 [SMILES: O=S(=O)(NC1CC(F)C1)c1cc2c(c3cnc(C4CC4)cc13)CCC2n1cnnc1NCC1CC1]

3-cyclopropyl-7-[3-(cyclopropylmethylamino)-1,2,4-triazol-4-yl]-N-(3-fluorocyclobutyl)-8,9-dihydro-7H-cyclopenta[h]isoquinoline-5-sulfonamide Intermediate 113 (46 mg, 0.034 mmol) was stirred in DCM (4 mL) and TFA (39 μl, 0.51 mmol) was added. Reaction stirred for 30 minutes at room temperature. The orange suspension was quenched with saturated aq. $NaHCO_3$ (15 mL), organic layer separated, and aq. layer extracted with further DCM (3×20 mL). Organics layers were combined, dried over sodium sulphate and concentrated under vacuum. The orange residue was purified by HPLC (basic conditions) to afford title compound (4.1 mg, 24% Yield) as an approx. 7:3 mixture of diastereoisomers (observed by NMR). $\delta_H$ (500 MHz, Methanol-d4) 9.31 (s, 1H), 8.41-8.37 (m, 1H), 8.12 (s, 1H, isomer 2), 8.10 (s, 1H, isomer 1), 7.79 (s, 1H), 5.98-5.89 (m, 1H), 5.08-4.87 (m, 1H, isomer 2), 4.67-4.44 (m, 1H, isomer 1), 3.96-3.85 (m, 1H, isomer 2), 3.83-3.70 (m, 1H), 3.60-3.43 (m, 1H), 3.29-3.15 (m, 2H+isomer 1, 1H), 3.08-2.92 (m, 1H), 2.54-2.01 (m, 5H), 1.99-1.77 (m, 1H), 1.28-1.19 (m, 1H), 1.18-1.06 (m, 4H), 0.62-0.52 (m, 2H), 0.36-0.23 (m, 2H). LCMS $[M+H]^+$ 497, RT 2.13 min (Method 12).

Example 83

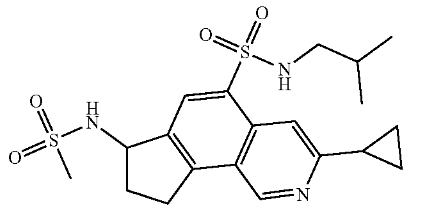 [SMILES: CC(C)CNS(=O)(=O)c1cc2c(c3cnc(C4CC4)cc13)CCC2NS(C)(=O)=O]

3-cyclopropyl-7-(methanesulfonamido)-N-(2-methylpropyl)-8,9-dihydro-7H-cyclopenta[h]isoquinoline-5-sulfonamide A mixture of intermediate 58 (255 mg, 0.59 mmol), cyclopropylboronic acid (152 mg, 1.77 mmol) and caesium carbonate (385 mg, 1.18 mmol) in anhydrous 1,4-dioxane (1.5 mL) was degassed by sonicating under a flow of nitrogen for 5 minutes. Bedford Catalyst: (2-{[bis(2,4-di-tert-butylphenoxy)phosphanyl]oxy}-3,5-di-tert-butylphenyl)(chloro)palladium-tricyclohexylphosphine (1:1) (63.06 mg, 0.06 mmol) was then added, the tube sealed and the mixture heated to 120° C. with stirring in a microwave reactor for 2 h. More Bedford Catalyst (63.06 mg, 0.06 mmol) and cyclopropylboronic acid (152 mg, 1.77 mmol) were then added and the mixture sealed and heated to 120° C. with stirring in a microwave reactor for 1 hour more. The mixture was then concentrated in vacuo. The residue obtained was taken in EtOAc (5 mL) and washed with water (5 mL). An emulsion formed, and the mixture was passed through a plug of Kieselguhr. The solid removed was washed with EtOAc (5 mL). The two phases present in the filtrate were separated and the aqueous phase extracted with EtOAc (5 mL). The combined organic extracts were washed with brine (5 mL), dried over $MgSO_4$, filtered and concentrated in vacuo. The crude material was purified by preparative HPLC under basic conditions to give title compound (28 mg, 16.3% Yield) as a white solid. $\delta_H$ (500 MHz, Chloroform-d) 9.23 (s, 1H), 8.39 (s, 1H), 8.28 (s, 1H), 5.20 (app. q, J=7.6 Hz, 1H), 4.76-4.62 (m, 2H), 3.55 (ddd, J=17.0, 8.9, 3.3 Hz, 1H), 3.32-3.21 (m, 1H), 3.15 (s, 3H), 2.98-2.90 (m, 1H), 2.84-2.72 (m, 2H), 2.31-2.23 (m, 1H), 2.23-2.15 (m, 1H), 1.77-1.68 (m, 1H), 1.20-1.15 (m, 2H), 1.14-1.07 (m, 2H), 0.86 (dd, J=6.7, 3.5 Hz, 6H). LCMS $[M+H]^+$ 438, RT 2.90 min (Method 12).

Example 84

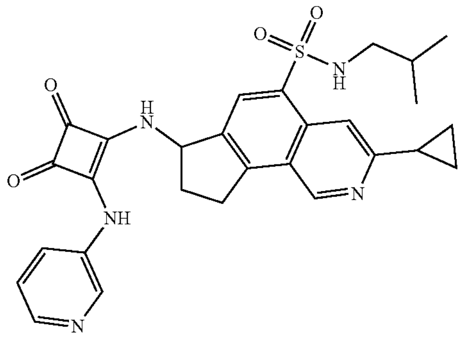 [SMILES: CC(C)CNS(=O)(=O)c1cc2c(c3cnc(C4CC4)cc13)CCC2Nc1c(Nc2cccnc2)c(=O)c1=O]

3-cyclopropyl-7-[[3,4-dioxo-2-(pyridin-3-ylamino)cyclobuten-1-yl]amino]-N-(2-methylpropyl)-8,9-dihydro-7H-cyclopenta[h]isoquinoline-5-sulfonamide To a stirred suspension of intermediate 99 (45 mg, 0.22 mmol) in dichloromethane (3 mL) was added N,N-diisopropylethylamine (0.04 mL, 0.2 mmol) followed by methanol (2 mL) to solubilise the mixture. Example 50 (50 mg, 0.14 mmol) was added and the resulting mixture stirred at room temperature for 17 hours. The reaction mixture was evaporated under vacuum and the residue purified via column chromatography, using a gradient of 0-100% ethyl acetate in iso-hexane followed by 1-20% methanol in ethyl acetate to afford the title compound (62 mg, 84% Yield). $\delta_H$ (300 MHz, d6-DMSO) 9.77 (s, 1H), 9.35 (d, J=0.9 Hz, 1H), 8.55 (d, J=2.8 Hz, 1H), 8.37 (d, J=0.9 Hz, 1H), 8.25-8.21 (m, 1H), 8.20 (s, 1H), 8.11 (m, 1H), 7.91 (m, 1H), 7.37 (dd, J=8.4, 4.7 Hz, 1H), 5.83 (m, 1H), 3.59 (m, 1H), 2.83 (m, 1H), 2.54 (m, 2H), 2.25 (m, 2H), 1.56 (dq, J=13.5, 6.7 Hz, 1H), 1.14-0.98 (m, 4H), 0.73 (dd, J=6.7, 4.7 Hz, 6H). One $CH_2$ proton obscured under water peak. One $NH_2$ proton missing. LCMS $[M+H]^+$ 532, RT 2.12 min (Method 16).

Example 85

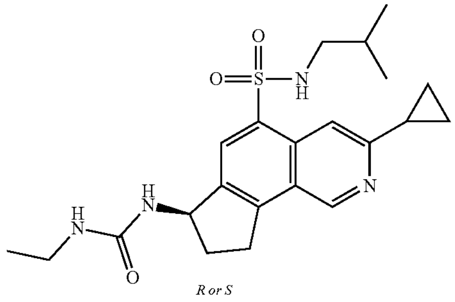 [SMILES: CCNC(=O)N[C@@H]1CCc2c1cc(S(=O)(=O)NCC(C)C)c1cc(C3CC3)ncc21]

1-ethyl-3-[(7R*)-3-cyclopropyl-5-(2-methylpropylsulfamoyl-8,9-dihydro-7H-cyclopenta[h]isoquinolin-7-yl]urea [* or S]

A mixture of Example 50 (60 mg, 0.15 mmol) and ethyl isocyanate (33 µL, 0.41 mmol) in dichloromethane (3 mL)

was stirred at room temperature for 3 hours. The reaction mixture was quenched by the addition of methanol (1.5 mL) and evaporated under vacuum. The residue was purified via column chromatography, using a gradient of 0-100% ethyl acetate in iso-hexane to afford product (51 mg) as a mixture of enantiomers. Purified via chiral chromatography to afford the title compound (14 mg, 29% Yield). Chiral SFC*RT=4.01 min. $\delta_H$ (300 MHz, d6-DMSO) 9.26 (d, J=0.9 Hz, 1H), 8.34 (s, 1H), 8.12 (s, 1H), 8.02 (s, 1H), 6.39 (d, J=8.4 Hz, 1H), 5.85 (t, J=5.6 Hz, 1H), 5.32 (q, J=8.0 Hz, 1H), 3.57-3.38 (m, 1H), 3.25-3.00 (m, 3H), 2.61 (m, 1H), 2.56-2.52 (m, 2H), 2.27 (m, 1H), 1.90 (m, 1H), 1.58 (m, 1H), 1.09-0.99 (m, 7H), 0.75 (m, 6H). LCMS $[M+H]^+$ 431, RT 2.25 min (Method 16).

* Chiral analysis was carried out using a Chiralpak IB-3 4.6×150 mm, 3 μm column, flow rate 3.5 mL/min eluting with 10-25% Methanol (0.1% ammonium hydroxide) using a 6 min run time on a Waters UPC$^2$-SQD2 system.

Example 86

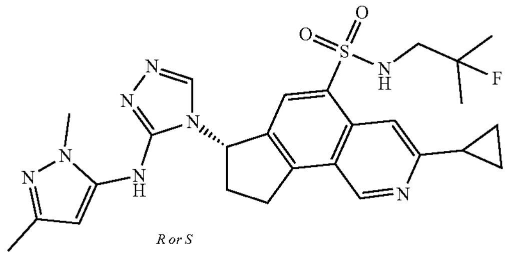 [SMILES: Cc1cc(Nc2nncn2[C@H]2CCc3c2cc(S(=O)(=O)NCC(C)(C)F)c2cc(C4CC4)ncc32)n(C)n1]

(7R*)-3-cyclopropyl-7-[3-[(2,5-dimethylpyrazol-3-yl)amino]-1,2,4-triazol-4-yl]-N-(2-fluoro-2-methyl-propyl)-8,9-dihydro-7H-cyclopenta[h]isoquinoline-5-sulfonamide [* or S]

The title compound was prepared according to general procedure 2 with intermediate 116 (410 mg, 0.77 mmol), formic acid hydrazide (150 mg, 2.2 mmol), mercuric chloride (420 mg, 1.5 mmol), N,N-dimethylformamide (15 mL) and triethylamine (0.32 mL, 2.3 mmol). Purified via chromatography, using a gradient of 0-15% methanol in dichloromethane followed by reverse-phase column chromatography, using a gradient of 0-100% acetonitrile in water (+0.1% ammonia) to afford the title compound (229 mg) as a mixture of enantiomers. Sample purified via chiral SFC to afford the title compound as a single isomer (8 mg). Chiral SFC RT**=6.62 min. $\delta_H$ (300 MHz, d6-DMSO) 9.34 (s, 1H), 8.55 (s, 0.5H, rotameric), 8.43 (s, 1H), 8.03 (s, 1H), 7.92 (s, 1H), 6.08-5.93 (m, 1H), 5.83 (s, 1H), 3.66 (m, 1H), 3.41 (m, 4H), 2.87 (m, 1.5H, rotameric), 2.80 (m, 1.5H, rotameric), 2.36-2.24 (m, 2H), 2.05 (s, 3H), 1.17 (d, J=2.5 Hz, 3H), 1.10 (d, J=2.5 Hz, 3H), 1.06 (m, 4H). Compound partially rotameric. Rotameric 0.5 proton missing. One NH proton missing. LCMS $[M+H]^+$ 539, RT 1.92 min (Method 6).

** Chiral analysis was carried out by SFC, using a Chiralcel OJ-3 4.6×150 mm, 3 μm column, flow rate 3.5 mL/min eluting with 5-15% Methanol (0.1% ammonium hydroxide) using an 8 min run time on a Waters UPC$^2$-SQD2 system.

Example 87 & 88

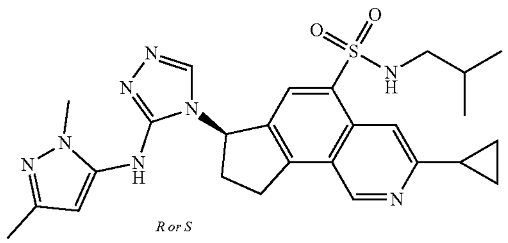

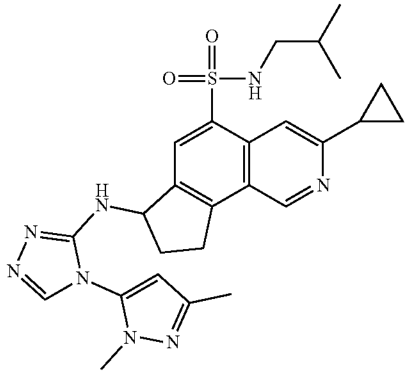

(7R*)-3-cyclopropyl-7-[3-[(2,5-dimethylpyrazol-3-yl)amino]-1,2,4-triazol-4-yl]-N-(2-methylpropyl)-8,9-dihydro-7H-cyclopenta[h]isoquinoline-5-sulfonamide [* or S] (87)

3-cyclopropyl-7-[[4-(2,5-dimethylpyrazol-3-yl)-1,2,4-triazol-3-yl]amino]-N-(2-methylpropyl)-8,9-dihydro-7H-cyclopenta[h]isoquinoline-5-sulfonamide (88)

The title compound was prepared according to general procedure 5 with intermediate 117 (145 mg, 0.28 mmol), formic acid hydrazide (60 mg, 0.90 mmol), mercuric chloride (155 mg, 0.57 mmol), N,N-dimethylformamide (5 mL) and triethylamine (0.12 mL, 0.86 mmol). Purified via reverse-phase column chromatography, using a gradient of 0-100% acetonitrile in water (+0.1% formic acid) followed by column chromatography, using a gradient of 0-100% ethyl acetate in iso-hexane and then 1-50% methanol in ethyl acetate to afford the title compounds.

Example 87 (23 mg) was obtained as a mixture of enantiomers which were separated via chiral chromatography to give the title compound (6 mg) as a single isomer. Chiral HPLC RT**=2.60 min. $\delta_H$ (300 MHz, d6-DMSO) 9.36 (d, J=0.9 Hz, 1H), 8.36 (d, J=0.9 Hz, 1H), 8.02 (m, 3H), 6.09-5.94 (m, 1H), 5.82 (s, 1H), 3.81-3.63 (m, 1H), 3.45 (m, 4H), 2.86 (m, 1H), 2.46 (m, 3H partially obscured under DMSO), 2.35-2.24 (m, 1H), 2.06 (s, 3H), 1.49 (dt, J=13.3, 6.7 Hz, 1H), 1.12-1.02 (m, 4H), 0.67 (dd, J=6.6, 2.3 Hz, 6H). One NH proton missing. LCMS $[M-H]^-$ 519, RT 1.84 min (Method 3).

**Chiral analysis was carried out by polar organic mode, using a Lux Cellulose-2 4.6×150 mm, 3 μm column, flow rate 1 ml/min eluting with Methanol (0.1% ammonium hydroxide) using a 10 min run time on an Agilent 1100 UV directed system.

Example 88 (34 mg, 23% Yield); $\delta_H$ (300 MHz, d6-DMSO) 9.28 (d, J=0.9 Hz, 1H), 8.39 (s, 1H), 8.32 (d, J=0.9 Hz, 1H), 8.22 (s, 1H), 8.18 (s, 1H), 6.81 (d, J=8.5 Hz, 1H), 6.28 (s, 1H), 5.46 (q, J=7.7 Hz, 1H), 3.54 (m, 1H partially obscured under water), 3.50 (s, 3H partially obscured under water), 3.46 (m, 1H partially obscured under water), 3.26 (m, 2H partially obscured under water), 2.70 (m, 1H), 2.32-2.23 (m, 1H), 2.15 (m, 4H), 1.56 (dq, J=13.4, 6.7 Hz, 1H), 1.05 (m, 4H), 0.74 (dd, J=6.6, 2.0 Hz, 6H). LCMS $[M+H]^+$ 521, RT 2.22 min (Method 16).

Example 89

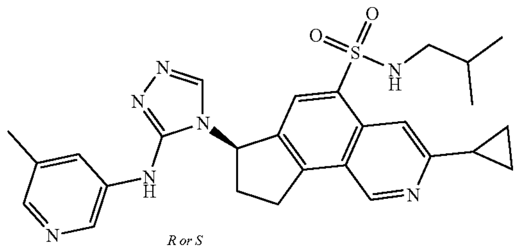 [SMILES: Cc1cncc(Nc2nncn2[C@@H]2CCc3c2cc(S(=O)(=O)NCC(C)C)c2cc(C4CC4)ncc32)c1]

(7R*)-3-cyclopropyl-N-(2-methylpropyl)-7-[3-[(5-methylpyridin-3-yl)amino]-1,2,4-triazol-4-yl]-8,9-dihydro-7H-cyclopenta[h]isoquinoline-5-sulfonamide [* or S]

The title compound was prepared according to general procedure 5 with intermediate 118 (135 mg, 0.26 mmol), formic acid hydrazide (55 mg, 0.82 mmol), mercuric chloride (145 mg, 0.53 mmol), N,N-dimethylformamide (5 mL) and triethylamine (0.11 mL, 0.79 mmol). Purified via reverse-phase column chromatography, using a gradient of 0-100% acetonitrile in water (+0.1% formic acid) to afford the title compound (61 mg) as a mixture of enantiomers. Purified via chiral chromatography to afford the title compound as a single isomer (17 mg). Chiral HPLC RT**=2.13 min. $\delta_H$ (300 MHz, d6-DMSO) 9.38 (d, J=0.9 Hz, 1H), 9.04 (s, 1H), 8.54 (d, J=2.5 Hz, 1H), 8.37 (d, J=0.9 Hz, 1H), 8.08 (t, J=5.9 Hz, 1H), 8.02 (s, 1H), 8.00 (s, 1H), 7.97 (d, J=1.9 Hz, 1H), 7.94 (t, J=2.1 Hz, 1H), 6.18-6.06 (m, 1H), 3.81-3.64 (m, 1H), 3.52-3.37 (m, 1H), 3.03-2.85 (m, 1H), 2.48-2.39 (m, 2H), 2.38-2.24 (m, 5H), 1.51 (dq, J=13.4, 6.6 Hz, 1H), 1.08 (m, 4H), 0.68 (dd, J=6.7, 3.4 Hz, 6H). LCMS $[M+H]^+$ 518, RT 2.14 min (Method 16).

**Chiral analysis was carried out by polar organic mode, using a Lux Cellulose-2 4.6×150 mm, 3 μm column, flow rate 1 mL/min eluting with Methanol using a 10 min run time on an Agilent 1100 UV directed system.

Examples 90 & 91

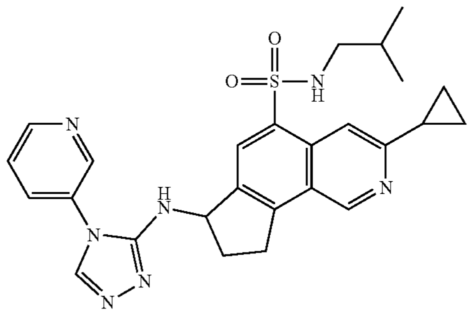

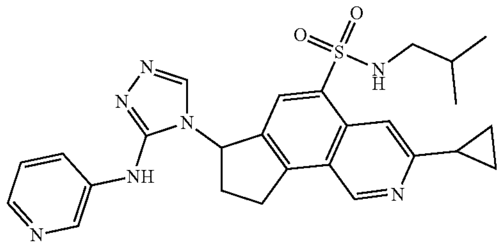

3-cyclopropyl-N-(2-methylpropyl)-7-[(4-pyridin-3-yl-1,2,4-triazol-3-yl)amino]-8,9-dihydro-7H-cyclopenta[h]isoquinoline-5-sulfonamide (90)

3-cyclopropyl-N-(2-methylpropyl)-7-[3-(pyridin-3-ylamino)-1,2,4-triazol-4-yl]-8,9-dihydro-7H-cyclopenta[h]isoquinoline-5-sulfonamide (91)

The title compounds were prepared according to general procedure 5 with Example 95 (105 mg, 0.21 mmol), formic acid hydrazide (42 mg, 0.63 mmol), mercuric chloride (115 mg, 0.42 mmol), N,N-dimethylformamide (5 mL) and triethylamine (0.09 mL, 0.60 mmol). Purified via reverse-phase column chromatography, using a gradient of 0-100% acetonitrile in water (+0.1% ammonia) to afford product (115 mg) as a mixture. A sample was purified by SFC to afford the title compounds:

Example 90 (4 mg); $\delta_H$ (300 MHz, d6-DMSO) 9.28 (s, 1H), 8.71 (dd, J=2.6, 0.7 Hz, 1H), 8.64 (dd, J=4.8, 1.5 Hz, 1H), 8.36 (s, 1H), 8.34 (s, 1H), 8.26 (s, 1H), 8.10-7.87 (m, 2H), 7.57 (ddd, J=8.2, 4.8, 0.8 Hz, 1H), 6.71 (d, J=8.5 Hz, 1H), 5.46 (q, J=7.7 Hz, 1H), 3.50 (m, 1H), 3.23 (m, 1H), 2.84-2.64 (m, 1H), 2.35-2.09 (m, 2H), 1.56 (dq, J=13.7, 6.9 Hz, 1H), 1.04 (m, 4H), 0.74 (dd, J=6.6, 3.7 Hz, 6H). Two $CH_2$ protons obscured under DMSO peak. LCMS $[M+H]^+$ 504, RT 2.04 min (Method 16).

Example 91 (10 mg); $\delta_H$ (300 MHz, d6-DMSO) 9.38 (d, J=0.9 Hz, 1H), 9.20-8.99 (m, 1H), 8.81-8.71 (m, 1H), 8.37 (d, J=0.9 Hz, 1H), 8.18-8.03 (m, 3H), 8.01 (d, J=2.4 Hz, 2H), 7.33 (ddd, J=8.4, 4.7, 0.7 Hz, 1H), 6.20-6.05 (m, 1H), 3.81-3.62 (m, 1H), 3.53-3.36 (m, 1H), 3.03-2.86 (m, 1H), 2.59-2.51 (m, 1H), 2.34 (m, 3H), 1.50 (dt, J=13.4, 6.7 Hz, 1H), 1.13-1.03 (m, 4H), 0.68 (dd, J=6.7, 3.3 Hz, 6H). LCMS $[M+H]^+$ 504, RT 2.11 min (Method 16).

Example 92

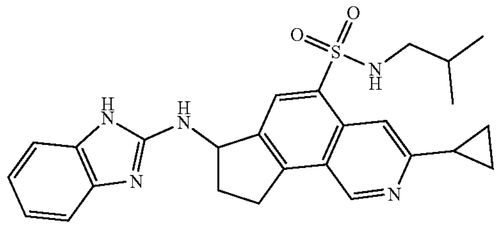 [SMILES: CC(C)CNS(=O)(=O)c1cc2c(c3cnc(C4CC4)cc13)CCC2Nc1nc2ccccc2[nH]1]

7-(1H-benzimidazol-2-ylamino)-3-cyclopropyl-N-(2-methylpropyl)-8,9-dihydro-7H-cyclopenta[h]isoquinoline-5-sulfonamide Example 50 (50 mg, 0.14 mmol), 2-chlorobenzimidazole (32 mg, 0.21 mmol) and 1-butanol (3 mL) was charged into a microwave tube. 4 M Hydrochloric acid solution in dioxane (0.03 mL, 0.1 mmol) was added and the sealed mixture was heated in the microwave at 160° C. for 2 hours. Further 2-chlorobenzimidazole (10 mg, 0.07 mmol) and 4 M hydrochloric acid solution in dioxane (2 drops) were added and the mixture heated in the microwave at 160° C. for 1 hour. The cooled reaction mixture was quenched with 25% aqueous ammonia solution (2 mL), partitioned between dichloromethane (10 mL) and saturated sodium bicarbonate solution (10 mL). The aqueous layer was separated and further extracted into dichloromethane (10 mL), combined organic extracts washed with brine (10 mL), dried over sodium sulfate and evaporated down under vacuum. The residue was purified via column chromatography, using a gradient of 0-100% ethyl acetate in iso-hexane followed by 1-30% methanol in ethyl acetate and then by reverse-phase column chromatography, using a gradient of 0-100% acetonitrile in water (+0.1% ammonia) to afford the title compound (12 mg, 18% Yield). $\delta_H$ (300 MHz, d6-DMSO) 11.72 (broad s, 1H), 9.33 (d, J=0.9 Hz, 1H), 8.35 (d, J=0.9 Hz, 1H), 8.26 (s, 1H), 8.04 (t, J=6.0 Hz, 1H), 7.25 (m, 2H), 7.02 (m, 2H), 5.58 (q, J=7.8 Hz, 1H), 3.67-3.48 (m, 1H), 3.26 (m, 1H), 2.93-2.73 (m, 1H), 2.51 (m, 2H), 2.37-2.24 (m, 1H), 2.16 (dq, J=15.6, 7.8 Hz, 1H), 1.54 (dt, J=13.4, 6.7 Hz, 1H), 1.06 (m, 4H), 0.70 (dd, J=6.7, 2.6 Hz, 6H). One NH proton partially observed. LCMS $[M+H]^+$476, RT 2.43 min (Method 16).

Example 93

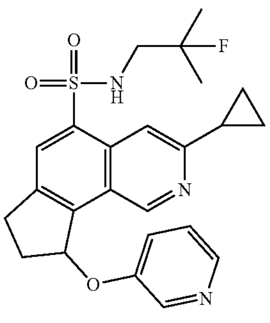 [SMILES: CC(C)(F)CNS(=O)(=O)c1cc2c(c3cnc(C4CC4)cc13)C(Oc1cccnc1)CC2]

3-cyclopropyl-N-(2-fluoro-2-methylpropyl)-9-pyridin-3-yloxy-8,9-dihydro-7H-cyclopenta[h]isoquinoline-5-sulfonamide Synthesised in the same manner as Example 94 using Intermediate 91 (36 mg, 0.08 mmol) and comparable stoichiometries of reagents. Purification by reverse phase HPLC (basic conditions) gave the title compound (0.4 mg, 1% Yield). $\delta_H$ (400 MHz, Methanol-d4) 9.22 (d, J=1.0 Hz, 1H), 8.45 (d, J=1.0 Hz, 1H), 8.37-8.34 (m, 2H), 8.23 (dd, J=4.6, 1.2 Hz, 1H), 7.64 (ddd, J=8.6, 3.0, 1.2 Hz, 1H), 7.47 (dd, J=8.5, 4.8 Hz, 1H), 6.59 (dd, J=7.1, 2.9 Hz, 1H), 3.42-3.32 (m, 1H), 3.20 (ddd, J=16.8, 9.0, 4.2 Hz, 1H), 3.06 (d, J=19.6 Hz, 2H), 2.95-2.83 (m, 1H), 2.45-2.28 (m, 2H), 1.24 (dd, J=21.1, 1.6 Hz, 6H), 1.12-1.05 (m, 4H). LCMS $[M+H]^+$ 456, RT 2.14 minutes (Method 3).

Example 94

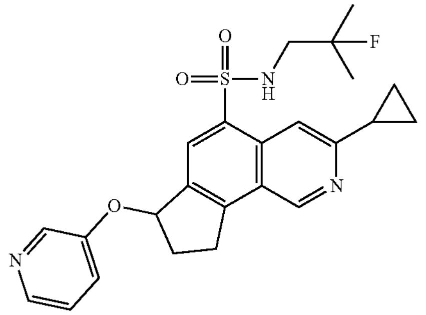 [SMILES: CC(C)(F)CNS(=O)(=O)c1cc2c(c3cnc(C4CC4)cc13)CCC2Oc1cccnc1]

3-cyclopropyl-N-(2-fluoro-2-methylpropyl)-7-pyridin-3-yloxy-8,9-dihydro-7H-cyclopenta[h]isoquinoline-5-sulfonamide To a solution of Intermediate 90 (25 mg, 0.056 mmol) in 1,4-dioxane (2 mL) were added cyclopropylboronic acid (22 mg, 0.2433 mmol) and caesium carbonate (66 mg, 0.20 mmol). The mixture was degassed, chloro($\eta^2$—P,C-tris(2,4-di-tert-butylphenyl)phosphite)(tricyclohexylphosphine) palladium(II) (9 mg, 0.01 mmol) added and then purged with $N_2$ for 5 min. The resultant mixture was heated at 100° C. for 10 hours. The reaction mixture was then filtered through celite (30 mL DCM washings). The solution was diluted with $H_2O$ (50 mL) and the phases separated. The aqueous was extracted with DCM (2×30 mL), the combined organics dried (phase separator) and concentrated in vacuo. Purification by revers phase HPLC (basic conditions) gave the title compound (0.6 mg, 2% Yield). $\delta_H$ (400 MHz, Methanol-d4) 9.28 (d, J=1.0 Hz, 1H), 8.44 (d, J=1.0 Hz, 1H), 8.38-8.33 (m, 21H), 8.20 (d, J=4.4 Hz, 1H), 7.63 (ddd, J=8.6, 3.0, 1.3 Hz, 1H), 7.44 (dd, J=8.5, 4.8 Hz, 1H), 6.14 (dd, J=6.9, 3.6 Hz, 1H), 3.69-3.59 (m, 1H), 3.53-3.42 (m, 1H), 3.00 (dd, J=19.4, 1.3 Hz, 2H), 2.95-2.86 (m, 1H), 2.37 (dddd, J=15.6, 13.3, 8.7, 4.8 Hz, 2H), 1.28-1.18 (m, 6H), 1.17-1.08 (m, 4H). LCMS $[M+H]^+$ 456, RT 2.14 minutes (Method 3).

Example 95

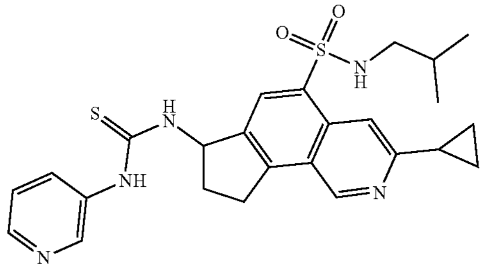 [SMILES: CC(C)CNS(=O)(=O)c1cc2c(c3cnc(C4CC4)cc13)CCC2NC(=S)Nc1cccnc1]

1-[3-cyclopropyl-5-(isobutylsulfamoyl)-8,9-dihydro-7H-cyclopenta[h]isoquinolin-7-yl]-3-(3-pyridyl) thiourea The title compound was prepared according to general procedure 4 with Example 50 (100 mg, 0.28 mmol), 3-pyridyl isothiocyanate (0.05 mL, 0.42 mmol), N,N-diisopropylethylamine (0.07 mL, 0.4 mmol) and dichloromethane (10 mL). Purified via column chromatography, using a gradient of 0-100% ethyl acetate in iso-hexane followed by 1-20% methanol in ethyl acetate to afford the title compound (120 mg, 87% Yield). $\delta_H$ (300 MHz, d6-DMSO) 9.70 (s, 1H), 9.30 (d, J=0.9 Hz, 1H), 8.66-8.49 (m, 2H), 8.35 (d, J=0.9 Hz, 1H), 8.30 (m, 2H), 8.08 (t, J=5.9 Hz, 1H), 7.97 (ddd, J=8.3, 2.6, 1.5 Hz, 1H), 7.36 (ddd, J=8.2, 4.7, 0.7 Hz, 1H), 6.17 (m, 1H), 3.53 (dd, J=16.4, 7.9 Hz, 1H), 3.30-3.18 (m, 1H), 2.76 (dq, J=12.7, 4.6, 4.1 Hz, 1H), 2.61-2.53 (m, 2H), 2.29 (p, J=6.5 Hz, 1H), 2.11 (m, 1H), 1.60 (dq, J=13.2, 6.6 Hz, 1H), 1.11-0.99 (m, 4H), 0.76 (dd, J=6.6, 3.3 Hz, 6H). LCMS $[M+H]^+$ 496, RT 2.40 min (Method 16).

In Vitro Biochemical Assay

Protocol for Preparation of IRE-Tb Reagent 86 nmoles of IgE-Fc(N265Q, N371Q) (Young et al., 1995) at 172 μM in 100 mM $NaHCO_3$, pH 9.5 was added to 1 mg of LanthaScreen™ Amine Reactive Tb Chelate (ThermoFisher catalogue number PV3583) and incubated for 16 hours at 20° C. The material was then buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Tb conjugation determined by measuring the absorption at 280 nm and 343 nm.

The integrity of the conjugated material was determined by analytical size exclusion chromatography on a 5200 HR 10×300 column (GE Healthcare). Typical conjugation ratios were 4:1 Tb:IgE-Fc.

Young R J., Owens, R J., MacKay G A., Chan C M W., Shi J., Hide M., Francis D M., Henry A J., Sutton B J., and Gould H J (1995) Protein Engineering 8:193-199

Protocol for Preparation of sFcεR1α-Y131A-AF488 Reagent 400 nmoles FcεR1α (Y131A mutant) (Cook et al., 1997) at 400 μM in 100 mM NaOAc pH 5.5 was reacted with 1 mM final concentration sodium periodate (in 100 mM NaOAc, pH 5.5) for 60 minutes at 22° C. Oxidation was quenched with the addition of 40 μL of ethanediol and incubation for 60 minutes at 22° C. The protein was buffer exchanged in to conjugation buffer (50 mM $NaHCO_3$, 150 mM NaCl, pH 9.5) and concentrated to 750 μM.

175 nmoles of protein was added to 1 mg of Alexa Fluor™ 488 hydrazide (Invitrogen) and incubated for 16 hours at 22° C. Sodium cyanoborohydride (at 100 mM in conjugation buffer) was added to a final concentration of 1 mM and incubated for 60 minutes on ice. The protein was buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Alexa Fluor™ 488 conjugation determined by measuring the absorption at 280 nm and 495 nm.

The integrity of the conjugated material was determined by analytical size exclusion chromatography on a S200 HR 10×300 column (GE Healthcare). Typical conjugation ratios were 2:1 Alexa Fluor™ 488: sFcεR1α

Cook J P D., Henry A J., McDonnell J M., Owens R J., Sutton B J., and Gould H J (1997) Biochemistry 36:15579-15588

The aim was to measure binding of IgE-Tb to receptor, and the inhibition thereof by compounds, using an in vitro Fluorescence Resonance Energy Transfer (FRET) Assay.

Reagents

FRET reagents used were IgE labelled with Terbium (FRET donor), and soluble IgE receptor FcεR1α with a Y131A mutation, labelled with Alexa Fluor™ 488 (FRET acceptor). Unlabelled FcεR1α was also used to generate a background control. The assay buffer consisted of 20 mM Tris pH7.2, 150 mM NaCl, and 0.002% Tween, 1% DMSO.

Assay Reaction

The assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by IgE-Tb diluting 10-fold in assay buffer. For the assay, 5 μl of diluted compound was added to 10 μl of IgE-Tb, followed by addition of 10 μl FcεR1α-Y131A-AF488. FRET reagents FACs were 5 nM IgE-Tb, 25 nM FcεR1α-Y131A-AF488. Usually the top FAC of compound in the assay was 10 μM. The final DMSO concentration was 2%. The minimum signal (MIN) was measured by adding 5 μl unlabelled FcεR1α at 1 μM (FAC=200 nM) to the FRET reagents. The maximum FRET signal (MAX) was measured in wells containing FRET reagents but no compound.

The assay was incubated for 2 hours at room temperature, protected from light and evaporation, and with gentle agitation.

FRET Measurement

Measurement of FRET for each well was carried out by exciting at 330 nm and measuring emission at 495/520 nm using an Envision plate reader (Perkin Elmer). FRET ratio was calculated as follows:

Emission at 520/Emission at 495×1000.

The FRET ratio was used for the data analysis.

Data Analysis

Z' was calculated as follows (σ=standard deviation and μ=mean):

$$1-((3\times\sigma_{MAX})+(3\times\sigma_{MIN}))/(\mu_{MAX}-\mu_{MIN})$$

Z' above 0.5 was considered a good assay.

Background signal (MIN) was subtracted from all wells. Using the background subtracted values, the percent inhibition by compound in each test-well was calculated as follows:

100−Test-well FRET ratio/MAX FRET ratio×100.

Percent inhibition was plotted against compound concentration. IC50 values for each compound were determined using four parameter logistic fit model using the XLFIT5 software package.

Compounds show an IC50 value ranging from 4 nM to 3602 nM.

The table below shows the range of IC50 values for each example:

| Example Number | FRET $IC_{50}$ range |
|---|---|
| 40, 42, 89 | 1-10 nanomolar |
| 18, 21, 23, 24, 30, 31, 35, 36, 41, 52, 53, 73, 75, 79, 80, 84, 85, 87, 91, 92, 95 | 10-50 nanomolar |
| 2, 22, 25, 28, 32, 77, 78, 86 | 50-100 nanomolar |
| 1, 3, 4, 5, 6, 7, 8, 9, 10, 11, 12, 13, 14, 15, 16, 17, 19, 20, 26, 27, 29, 33, 34, 37, 38, 39, 43, 44, 45, 46, 47, 48, 49, 50, 51, 54, 55, 56, 57, 58, 59, 60, 61, 62, 63, 64, 65, 66, 67, 68, 69, 70, 71, 72, 74, 76, 81, 82, 83, 88, 90, 93, 94 | 0.1-2 micromolar |

The invention claimed is:

1. A compound of general formula (I) or a pharmaceutically acceptable salt thereof, (I)

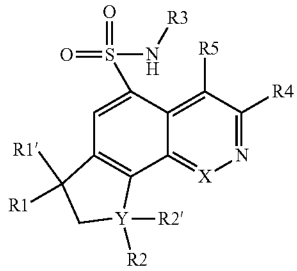

Wherein:

X is C or N,

Y is C or O,

When Y is O, R1 is hydrogen or hydroxy, R1' is hydrogen and R2 and R2' are absent;

R1 represents

Hydrogen;

Hydroxy;

An oxo group;

Amino;

C1-6-alkyl;

C1-6-alkylamino;

C(O)OH;

C(O)NH-Heteroaryl;

—NH—C1-6-alkyl-C3-6-cycloalkyl;

—NH—C1-6-alkyl-C(O)OH optionally substituted with an amino group;

—NH-cycloalkyl optionally substituted with one or more groups which are independently halogen; oxo; C1-6-alkyl; C1-6-alkylamino; C1-6-alkyl-C1-4-alkylamino; C3-8-cycloalkyl-C1-6-alkylamino; heteroaryl; or heteroarylamino optionally substituted with one or more C1-6-alkyl;

Heteroaryl optionally substituted with one or more groups which are independently Halogen; hydroxy; oxo; amino; cyano; —C(O)—C1-6-alkyl; C1-6-alkyl; C1-6-alkylamino; C1-6-alkoxy; —NH—(C1-6-alkyl)-heterocycloalkyl; —NH—(C1-6-alkyl)-heteroaryl optionally substituted with one or more C1-6-alkyl; —NH—C1-6-alkyl-cycloalkyl; —NH—C(O)-cycloalkyl; —NH-heteroaryl substituted with one or more C1-6-alkyl; or —NH—C1-6-alkyl-C(O)OH;

Heteroaryl substituted with heteroarylamino optionally substituted with C1-6-alkyl; C1-6-alkoxy; C3-6-cycloalkyl; C1-6-haloalkoxy, C1-6-haloalkyl; CN, halogen; C(O)OH, or —C(O)O—C1-6-alkyl;

—NH—C(S)—NH—$Ra^1$;

—NH—SO2-$Rb^1$;

—NH-heteroaryl optionally substituted with one or more groups which are independently oxo; C1-6-alkyl; C1-6-alkylamino; heteroaryl optionally substituted with one or more oxo; C1-6-alkyl; —C(O)—NHNH—C(O)CH3; aryl; heteroarylamino; C1-6-alkoxy; C3-6-cycloalkyl; C1-6-haloalkoxy, C1-6-haloalkyl; CN, halogen; C(O)OH, or —C(O)O—C1-6-alkyl;

—NH-heterocycloalkyl optionally substituted with one or more groups which are independently Halogen; C1-6-alkyl; oxo; heteroaryl; C(O)O$Rb^1$; C1-6-alkyl-N$Rb^1Rb^1$; NHC(O)-aryl; or NHC(O)-heteroaryl;

—NH—C1-6-Alkyl substituted with one heteroaryl group optionally substituted with one or more groups which are independently C1-6-alkyl or amino;

—NH—C(O)O—$Rb^1$;

NH—C(NCN)—NH—$Ra^1$;

—NH—C(NCN)—NH-Heteroaryl;

—NH—C(O)—C3-8-heterocycloalkyl-C(O)O—$Rb^1$;

—C(O)NH—C1-6-alkyl;

—NH—C(O)NH—C1-6-alkyl optionally substituted with one or more C3-8-heterocyclolakyl;

—NH—C(O)NH-heterocycloalkyl-C1-6-alkyl;

—NH—C1-6-alkyl-C(O)—C1-6-alkylamino;

Heteroaryloxy;

—NH—C(O)-aryl;

—NH—C(O)-heteroaryl;

—NH—C(O)-heterocycloalkyl;

—NH—C(O)—C1-6-alkyl optionally substituted with one or more amino group;

—NH—C(O)—C1-6-alkyl-C(O)O$Rb^1$ optionally substituted with amino; —NH—C(O)O$Rb^1$ Heterocycloalkyl optionally substituted with one or more groups which are independently amino; —C(O)NH—$Rb^1$; —C(O)O$Rb^1$; —NHC(O)-heteroaryl optionally substituted with one or more C1-6-alkyl; —NHC(O)—C1-6-alkyl optionally substituted with an amino group; or —NHC(O)O—C1-6-alkyl; —NH—C(O)$Rb^1$; or —C2-6-alkene group optionally substituted with one or more groups which are halogen; or =NH group;

$Ra^1$ represents

C1-6-alkyl;

Aryl optionally substituted with one or more C1-6-alkyl; or

Heteroaryl optionally substituted with one or more C1-6-alkyl;

$Rb^1$ represents

Hydrogen;

C1-6-alkyl; or

Aryl optionally substituted with one or more halogen; C1-6-alkyl; or hydroxy;

R1' represents hydrogen; or hydroxy;

R2 represents hydrogen;

Halogen;

A hydroxy group;

An oxo group;

C1-6-alkyl;

C3-8-heterocycloalkyl optionally substituted with one or more hydroxy; Halogen; amino; amino-C-1-6-alkyl; C1-6-alkyl; C(O)O—C1-6-alkyl; or C(O) NH2;

Heteroaryl optionally substituted with one or more groups which are independently C1-6-alkylamino; heteroaryl optionally substituted with one or more C1-6-alkyl; halogen;

Heteroaryl optionally substituted with —NH-heteroaryl optionally substituted with one or more C1-6-alkyl; halogen; cyano; —C(O)OH; —C(O) O—C1-6-alkyl, C1-6-haloalkyl; C1-6-alkoxy; C1-6-haloalkoxy; or C3-6-cycloalkyl;

—NH-cycloalkyl optionally substituted with one or more groups which are independently halogen; oxo; C1-6-alkyl; C1-6-alkylamino; C1-6-alkyl-C1-4-alkylamino; C3-8-cycloalkyl-C1-6-alkylamino; aryl; heteroaryl; or heteroarylamino optionally substituted with one or more C1-6-alkyl;

—NH-heteroaryl optionally substituted with one or more groups which are independently hydroxy; halogen; oxo; C1-6-alkyl; C1-6-alkoxy; heteroaryl optionally substituted with one or more hydroxy; Halogen; oxo; C1-6-alkyl; C(O)O—C1-6-alkyl; C(O)OH; C1-6-haloalkyl; C1-6-alkoxy; C1-6-haloalkoxy; C3-6-cycloalkyl; C1-6-alkylamino; cyano; or heterocycloalkyl substituted with one or more hydroxy Halogen; oxo group;

—NH—C1-6-Alkyl substituted with one heteroaryl group optionally substituted with one or more independently selected C1-6-alkyl groups;

—NH—SO2-Heteroaryl optionally substituted with one or more halogen;

—NHC(O)—C1-6-alkyl optionally substituted with one or more halogen; C1-6-alkoxy; amino; C3-8-cycloalkyl; C3-8-heterocycloalkyl; or heteroaryl;

—NHC(O)-heteroaryl optionally substituted with one or more groups which are independently halogen; hydroxy; oxo; C1-6-alkyl; heteroaryl; C1-6-alkylamino; S(O)2-C1-3-alkyl; or —NHC(O)—C1-6-alkyl;

—NHC(O)—C3-8-heterocycloalkyl optionally substituted with one or more oxo; or C1-6-alkyl;

—NHC(O)O—C1-6-alkyl;

—NHC(O)O—C1-6-alkyl-$Ra^2$;

—NHC(O)O-aryl;

—NHC(O)NH—$Ra^2$;

—NHC(O)NH—C1-6-alkyl-$Ra^2$;

—NH—C(NCN)—NH—$Ra^1$;

—NHC(O)—C3-8-cycloalkyl;

—NH—$SO_2$—$Rb^2$;

—NH—C(S)—NH—$Rb^2$;

—NH—C3-8-heterocycloalkyl optionally substituted with one or more groups which are independently oxo; or C1-6-alkyl;

An Aryloxy group; or

Heteroaryloxy group;

$Ra^2$ represents

Hydrogen;

Aryl optionally substituted with one or more groups which are independently halogen; hydroxy; oxo; or C1-6-alkyl;

Heteroaryl optionally substituted with one or more groups which are independently halogen; hydroxy; oxo; or C1-6-alkyl;

$Rb^2$ represents

C1-6-alkyl; or

Heteroaryl;

R2' represents hydrogen; or hydroxy;

R3 represents

C1-6-alkyl optionally substituted with one or more independently selected $R3^a$ groups;

C1-3-alkanediyl-C3-6-cycloalkyl optionally substituted with one or more independently selected $R3^a$ groups;

C1-3-alkanediyl-C3-6-heterocycloalkyl optionally substituted with one or more independently selected $R3^a$ groups;

C3-6-heterocycloalkyl optionally substituted with one or more independently selected $R3^a$ groups; or C3-6-cycloalkyl optionally substituted with one or more independently selected $R3^a$ groups;

$R3^a$ represents hydrogen; Halogen; C1-2-alkyl; hydroxy; or C1-2-alkoxy;

R4 represents:

C3-6-cycloalkyl optionally substituted with one or more $R4^a$ group; or C1-6-alkanediyl-C3-6-cycloalkyl optionally substituted with one or more $R4^a$ group; or C1-6-alkanediyl-C3-6-heterocycloalkyl optionally substituted with one or more $R4^a$ group;

$R4^a$ represents a group which are independently hydroxy; Halogen; or C1-2-alkyl; and R5 represents Hydrogen, methyl or halogen;

With the proviso that:

when R1' is hydroxy, then R1 is pyridyl or C1-6-alkyl;

when R2' is hydroxy, then R2 is pyridyl or C1-6-alkyl;

when R1 is different than hydrogen, then R2 and R2' are hydrogen;

when R2 is different than hydrogen, then R1 and R1' are hydrogen;

when R1 is oxo, R1' is absent; and when R2 is oxo, R2' is absent.

2. A compound of general formula (I) according to claim 1, wherein

R4 represents cyclopropyl or spiro[2.2]pentanyl; each of which is optionally substituted with one or more groups which are independently hydroxy; chloro, fluoro, bromo; or methyl.

3. A compound of general formula (I) according to claim 1, wherein R4 represents cyclopropyl.

4. A compound of general formula (I) according to claim 1, wherein

R1 represents:

Hydrogen; methoxyimidazopyridinyl; carboxy group; cyclopropyl-methyl-carbamoyl-amino; pyridine-carbonylamino; hydroxy(pyridyl); [(fluorocarbonimidoyl) propenyl]; [(cyclopropylmethylamino)imidazolyl]; [[(cyclopropylmethyl)imidazolyl]amino]; [(dimethylpyrazolyl)carbamothioylamino]; [[(dimethylpyrazolyl)-triazolyl]amino]; (pyridylamino); (tert-butoxycarbonylamino); Amino; [(cyclopropylmethylamino)- triazolyl]; pyridylcarbamoyl; [(cyclopropanecarbonylamino)pyrazolyl]; (aminotetrazolyl); [[(methyltetrazolyl)pyridyl]amino]; [(methylpyrazolopyridinyl)amino]; [[(methyl-oxadiazolyl)-pyridyl]amino]; Oxo; hydroxy(methyl); ethylcarbamothioylamino); [(ethylamino)-triazolyl]; [[(ethylamino)-dioxo-cyclobutenyl]amino]; [[(ethylamino)-dioxo-thiadiazolyl]amino]; [[N'-cyano-N-(p-tolyl)carbamimidoyl]amino]; [(tert-butoxycarbonylazetidine-carbonyl)amino]; [aminopiperidyl]; [(methylcarbamoyl)pyrrolidinyl]; [[(dimethylpyrazolearbonyl)amino]azetidinyl]; [(dimethyl-oxo-cyclobutenyl)amino]; (indolylmethylamino); Methanesulfonamido; [[dioxo(pyridylamino)cyclobutenyl]amino]; ethylcarbamoylamino; [[(dimethylpyrazolyl)amino]-triazolyl]; [[(methyl-pyridyl)amino]-triazolyl]; [[(pyridyl)-triazolyl]amino]; [(pyridylamino)-triazolyl]; (benzimidazolylamino); pyridyloxy; (pyridylcarbamothioylamino).

5. A compound of general formula (I) according to claim 1, wherein

R2 represents:

Hydrogen; [(methylbenzotriazolyl)-triazolyl]methyl; [[(methylpyrazolyl)-triazolyl]amino]; [[(methylpyrazolyl)amino]-triazolyl]; [[(fluoro-pyridyl)-triazolyl]amino]; [[(fluoro-pyridyl)amino]-triazolyl]; (pyridylmethylamino); (pyridylsulfonylamino); [(fluoro-indolecarbonyl)amino]; [(methylbenzimidazolyl)amino]; [(methoxycarbonyl-pyridyl)amino]; [(carboxypyridyl)amino]; [(methyl-pyrazole-carbonyl)amino]; (pyridine-carbonylamino); [(methylcyclopropanecarbonyl)amino]; (pyrimidinylamino); [(oxoindolinyl)amino]; [(methoxypyridyl)amino]; (pyridylamino); [(methylpyrazolopyridinyl)amino]; Benzyloxycarbonylamino; [(bromophenyl)carbamoylamino]; [(dimethylpyrazolyl)methylcarbamoylamino]; Hydroxy; Oxo; Methyl; Fluorine; [[(ethylamino)-dioxo-thiadiazolyl]amino]; [(cyanomethylpyrazolyl)amino]; (isoquinolylamino); [[N'-cyano-N-(p-tolyl)carbamimidoyl]amino]; Methanesulfonamido; Ethylcarbamothioylamino; [(ethylamino)-triazolyl]; [(ethyl-triazolyl)amino]; (pyridylcarbamothioylamino); [[(pyridyl)-triazolyl]amino]; [[(methyltetrazolyl)-pyridyl]amino]; [[dioxo-(pyridylamino)cyclobutenyl]amino]; [[(ethylamino)-dioxo-cyclobutenyl]amino]; (benzimidazolylamino); pyridyloxy.

6. A compound of formula (I) according to claim 1 wherein

R1 represents

Hydrogen; (7-methoxyimidazo[4,5-b]pyridin-3-yl); Carboxy group; cyclopropyl-methyl-carbamoyl-amino; pyridine-3-carbonylamino; hydroxy(3-pyridyl); [1-(fluorocarbonimidoyl)prop-1-enyl]; [2-(cyclopropylmethylamino)imidazol-1-yl]; [[1-(cyclopropylmethyl)imidazol-2-yl]amino]; [(2,5-dimethylpyrazol-3-yl)carbamothioylamino]; [[4-(2,5-dimethylpyrazol-3-yl)-1,2,4-triazol-3-yl]amino]; (3-pyridylamino); (tert-butoxycarbonylamino); Amino; [3-(cyclopropylmethylamino)-1,2,4-triazol-4-yl]; 3-pyridylcarbamoyl; [5-(cyclopropanecarbonylamino)pyrazol-1-yl]; (5-aminotetrazol-1-yl); [[6-(2-methyltetrazol-5-yl)-3-pyridyl]amino]; [(1-methylpyrazolo[3,4-c]pyridin-4-yl)amino]; [[6-(5-methyl-1,3,4-oxadiazol-2-yl)-3-pyridyl]amino]; oxo; hydroxy(methyl); (ethylcarbamothioylamino); [3-(ethylamino)-1,2,4-triazol-4-yl]; [[2-(ethylamino)-3,4-dioxo-cyclobuten-1-yl]amino]; [[4-(ethylamino)-1,1-dioxo-1,2,5-thiadiazol-3-yl]amino]; [[N'-cyano-N-(p-tolyl)carbamimidoyl]amino]; [(1-tert-butoxycarbonylazetidine-3-carbonyl)amino]; [3-amino-1-piperidyl]; [(2R)-2-(methylcarbamoyl)pyrrolidin-1-yl]; [3-[(2,5-dimethylpyrazole-3-carbonyl)amino]azetidin-1-yl]; [(4,4-dimethyl-3-oxo-cyclobuten-1-yl)amino]; (1H-indol-2-ylmethylamino); Methanesulfonamido; [[3,4-dioxo-2-(3-pyridylamino)cyclobuten-1-yl]amino]; ethylcarbamoylamino; [3-[(2,5-dimethylpyrazol-3-yl)amino]-1,2,4-triazol-4-yl]; [3-[(5-methyl-3-pyridyl)amino]-1,2,4-triazol-4-yl]; [[4-(3-pyridyl)-1,2,4-triazol-3-yl]amino]; [3-(3-pyridylamino)-1,2,4-triazol-4-yl]; (1H-benzimidazol-2-ylamino); 3-pyridyloxy; (3-pyridylcarbamothioylamino).

7. A compound of general formula (I) according claim 1 wherein

R2 represents

Hydrogen; [4-(1-methylbenzotriazol-4-yl)-1,2,4-triazol-3-yl]methyl; [[4-(2-methylpyrazol-3-yl)-1,2,4-triazol-3-yl]amino]; [3-[(2-methylpyrazol-3-yl)amino]-1,2,4-triazol-4-yl]; [[4-(5-fluoro-3-pyridyl)-1,2,4-triazol-3-yl]amino]; [3-[(5-fluoro-3-pyridyl)amino]-1,2,4-triazol-4-yl]; (3-pyridylmethylamino); (3-pyridylsulfonylamino); [(6-fluoro-1H-indole-3-carbonyl)amino]; [(1-methylbenzimidazol-2-yl)amino]; [(6-methoxycarbonyl-3-pyridyl)amino]; [(6-carboxy-3-pyridyl)amino]; [(5-methyl-1H-pyrazole-3-carbonyl)amino]; (pyridine-3-carbonylamino); [(2-methylcyclopropanecarbonyl)amino]; (pyrimidin-5-ylamino); (2-oxoindolin-5-yl)amino; [(5-methoxy-3-pyridyl)amino]; (3-pyridylamino); [(1-methylpyrazolo[3,4-c]pyridin-4-yl)amino]; Benzyloxycarbonylamino; [(4-bromophenyl)carbamoylamino]; [(2,5-dimethylpyrazol-3-yl)methylcarbamoylamino]; Hydroxy oxo; Methyl; fluorine; [[4-(ethylamino)-1,1-dioxo-1,2,5-thiadiazol-3-yl]amino]; [(4-cyano-1-methyl-pyrazol-3-yl)amino]; (4-isoquinolylamino); [[N'-cyano-N-(p-tolyl)carbamimidoyl]amino]; Methanesulfonamido; Ethylcarbamothioylamino; [3-(ethylamino)-1,2,4-triazol-4-yl]; [(4-ethyl-1,2,4-triazol-3-yl)amino]; (3-pyridylcarbamothioylamino); [[4-(3-pyridyl)-1,2,4-triazol-3-yl]amino]; [[6-(2-methyltetrazol-5-yl)-3-pyridyl]amino]; [[3,4-dioxo-2-(3-pyridylamino)cyclobuten-1-yl]amino]; [[2-(ethylamino)-3,4-dioxo-cyclobuten-1-yl]amino]; (1H-benzimidazol-2-ylamino); 3-pyridyloxy.

8. A compound of general formula (I) according to claim 1 which is 3-cyclopropyl-N-(2-fluoro-2-methylpropyl)-7-(7-methoxyimidazo[4,5-b]pyridin-3-yl)-8,9-dihydro-7H-cyclopenta[h]isoquinoline-5-sulfonamide;

3-cyclopropyl-N-isobutyl-9-[[4-(1-methylbenzotriazol-4-yl)-1,2,4-triazol-3-yl]amino]-8,9-dihydro-7H-cyclopenta[h]isoquinoline-5-sulfonamide;

3-cyclopropyl-N-isobutyl-9-[[4-(2-methylpyrazol-3-yl)-1,2,4-triazol-3-yl]amino]-8,9-dihydro-7H-cyclopenta[h]isoquinoline-5-sulfonamide;

3-cyclopropyl-N-isobutyl-9-[3-[(2-methylpyrazol-3-yl)amino]-1,2,4-triazol-4-yl]-8,9-dihydro-7H-cyclopenta[h]isoquinoline-5-sulfonamide;

3-cyclopropyl-9-[[4-(5-fluoro-3-pyridyl)-1,2,4-triazol-3-yl]amino]-N-isobutyl-8,9-dihydro-7H-cyclopenta[h]isoquinoline-5-sulfonamide;

3-cyclopropyl-9-[3-[(5-fluoro-3-pyridyl)amino]-1,2,4-triazol-4-yl]-N-isobutyl-8,9-dihydro-7H-cyclopenta[h]isoquinoline-5-sulfonamide;

3-cyclopropyl-5-[(2-fluoro-2-methylpropyl)sulfamoyl]-8,9-dihydro-7H-cyclopenta[h]isoquinoline-7-carboxylic acid;

1-(cyclopropylmethyl)-3-[(7R*)-3-cyclopropyl-5-[(2-fluoro-2-methylpropyl)sulfamoyl]-8,9-dihydro-7H-cyclopenta[h]isoquinolin-7-yl]urea [* or S];

N-[(7R*)-3-cyclopropyl-5-[(2-fluoro-2-methylpropyl)sulfamoyl]-8,9-dihydro-7H-cyclopenta[h]isoquinolin-7-yl]pyridine-3-carboxamide [* or S];

3-cyclopropyl-N-(2-fluoro-2-methylpropyl)-7-hydroxy-7-pyridin-3-yl-8,9-dihydrocyclopenta[h]isoquinoline-5-sulfonamide;

3-cyclopropyl-N-(2-fluoro-2-methylpropyl)-7-(2-fluoropyridin-3-yl)-8,9-dihydro-7H-cyclopenta[h]isoquinoline-5-sulfonamide;

(7R*)-3-cyclopropyl-7-[2-(cyclopropylmethylamino)imidazol-1-yl]-N-(2-fluoro-2-methylpropyl)-8,9-dihydro-7H-cyclopenta[h]isoquinoline-5-sulfonamide [* or S];

(7R*)-3-cyclopropyl-7-[[1-(cyclopropylmethyl)imidazol-2-yl]amino]-N-(2-fluoro-2-methylpropyl)-8,9-dihydro-7H-cyclopenta[h]isoquinoline-5-sulfonamide [* or S];

3-cyclopropyl-N-(2-methylpropyl)-9-(pyridin-3-ylmethylamino)-8,9-dihydro-7H-cyclopenta[h]isoquinoline-5-sulfonamide;

3-cyclopropyl-N-(2-methylpropyl)-9-(pyridin-3-ylsulfonylamino)-8,9-dihydro-7H-cyclopenta[h]isoquinoline-5-sulfonamide;

6-fluoro-N-[(9R*)-3-cyclopropyl-5-[(2-fluoro-2-methylpropyl)sulfamoyl]-8,9-dihydro-7H-cyclopenta[h]isoquinolin-9-yl]-1H-indole-3-carboxamide [* or S];

3-cyclopropyl-N-(2-fluoro-2-methylpropyl)-9-[(1-methylbenzimidazol-2-yl)amino]-8,9-dihydro-7H-cyclopenta[h]isoquinoline-5-sulfonamide;

methyl 5-[[3-cyclopropyl-5-(2-methylpropylsulfamoyl)-8,9-dihydro-7H-cyclopenta[h]isoquinolin-9-yl]amino]pyridine-2-carboxylate;

5-[[3-cyclopropyl-5-(2-methylpropylsulfamoyl)-8,9-dihydro-7H-cyclopenta[h]isoquinolin-9-yl]amino]pyridine-2-carboxylic acid;

5-methyl-N-[(9R*)-3-cyclopropyl-5-(2-methylpropylsulfamoyl)-8,9-dihydro-7H-cyclopenta[h]isoquinolin-9-yl]-1H-pyrazole-3-carboxamide [* or S];

N-[(9R*)-3-cyclopropyl-5-(2-methylpropylsulfamoyl)-8,9-dihydro-7H-cyclopenta[h]isoquinolin-9-yl]pyridine-3-carboxamide [* or S];

3-cyclopropyl-N-(2-methylpropyl)-8,9-dihydro-7H-cyclopenta[h]cinnoline-5-sulfonamide;

1-[3-cyclopropyl-5-[(2-fluoro-2-methylpropyl)sulfamoyl]-8,9-dihydro-7H-cyclopenta[h]cinnolin-7-yl]-3-(2,5-dimethylpyrazol-3-yl)thiourea;

3-cyclopropyl-7-[[4-(2,5-dimethylpyrazol-3-yl)-1,2,4-triazol-3-yl]amino]-N-(2-fluoro-2-methylpropyl)-8,9-dihydro-7H-cyclopenta[h]cinnoline-5-sulfonamide;

(7R*)-3-cyclopropyl-7-[3-[(25-dimethylpyrazol-3-yl)amino]-1,2,4-triazol-4-yl]-N-(2-fluoro-2-methylpropyl)-8,9-dihydro-7H-cyclopenta[h]cinnoline-5-sulfonamide [* or S];

N-[3-cyclopropyl-5-[(2-fluoro-2-methylpropyl)sulfamoyl]-8,9-dihydro-7H-cyclopenta[h]isoquinolin-9-yl]-2-methylcyclopropane-1-carboxamide;

3-cyclopropyl-4-fluoro-N-(2-methylpropyl)-8,9-dihydro-7H-cyclopenta[h]isoquinoline-5-sulfonamide;

3-cyclopropyl-N-(2-fluoro-2-methylpropyl)-9-(pyrimidin-5-ylamino)-8,9-dihydro-7H-cyclopenta[h]isoquinoline-5-sulfonamide;

3-cyclopropyl-N-(2-fluoro-2-methylpropyl)-9-[(2-oxo-1,3-dihydroindol-5-yl)amino]-8,9-dihydro-7H-cyclopenta[h]isoquinoline-5-sulfonamide;

3-cyclopropyl-N-(2-fluoro-2-methylpropyl)-9-[(5-methoxypyridin-3-yl)amino]-8,9-dihydro-7H-cyclopenta[h]isoquinoline-5-sulfonamide;

3-cyclopropyl-N-(2-fluoro-2-methylpropyl)-7-(pyridin-3-ylamino)-8,9-dihydro-7H-cyclopenta[h]isoquinoline-5-sulfonamide;

3-cyclopropyl-N-(2-fluoro-2-methylpropyl)-9-(pyridin-3-ylamino)-8,9-dihydro-7H-cyclopenta[h]isoquinoline-5-sulfonamide;

tert-butyl N-[3-cyclopropyl-5-[(1,1-dideuterio-2-methylpropyl)sulfamoyl]-8,9-dihydro-7H-cyclopenta[h]isoquinolin-7-yl]carbamate;

7-amino-3-cyclopropyl-N-(1,1-dideuterio-2-methylpropyl)-8,9-dihydro-7H-cyclopenta[h]isoquinoline-5-sulfonamide;

3-cyclopropyl-7-[3-(cyclopropylmethylamino)-1,2,4-triazol-4-yl]-N-(1,1-dideuterio-2-methylpropyl)-8,9-dihydro-7H-cyclopenta[h]isoquinoline-5-sulfonamide;

7-cyclopropyl-N-(2-fluoro-2-methylpropyl)-3-hydroxy-2,3-dihydrofuro[3,2-h]isoquinoline-5-sulfonamide;

(7R*)-3-cyclopropyl-5-[(2-fluoro-2-methylpropyl)sulfamoyl]-N-pyridin-3-yl-8,9-dihydro-7H-cyclopenta[h]isoquinoline-7-carboxamide [* or S];

N-[2-[3-cyclopropyl-5-[(2-fluoro-2-methylpropyl)sulfamoyl]-8,9-dihydro-7H-cyclopenta[h]isoquinolin-7-yl]pyrazol-3-yl]cyclopropanecarboxamide;

7-(5-aminotetrazol-1-yl)-3-cyclopropyl-N-(2-fluoro-2-methylpropyl)-8,9-dihydro-7H-cyclopenta[h]isoquinoline-5-sulfonamide;

3-cyclopropyl-N-(2-fluoro-2-methylpropyl)-7-[[6-(2-methyltetrazol-5-yl)pyridin-3-yl]amino]-8,9-dihydro-7H-cyclopenta[h]isoquinoline-5-sulfonamide;

3-cyclopropyl-N-(2-fluoro-2-methylpropyl)-7-[(1-methylpyrazolo[3,4-c]pyridin-4-yl)amino]-8,9-dihydro-7H-cyclopenta[h]isoquinoline-5-sulfonamide;

3-cyclopropyl-N-(2-fluoro-2-methylpropyl)-7-[[6-(5-methyl-1,3,4-oxadiazol-2-yl)pyridin-3-yl]amino]-8,9-dihydro-7H-cyclopenta[h]isoquinoline-5-sulfonamide;

3-cyclopropyl-N-(2-fluoro-2-methylpropyl)-9-[(1-methylpyrazolo[3,4-c]pyridin-4-yl)amino]-8,9-dihydro-7H-cyclopenta[h]isoquinoline-5-sulfonamide;

benzyl N-[3-cyclopropyl-5-(2-methylpropylsulfamoyl)-8,9-dihydro-7H-cyclopenta[h]isoquinolin-9-yl]carbamate;

1-(4-bromophenyl)-3-[3-cyclopropyl-5-(2-methylpropylsulfamoyl)-8,9-dihydro-7H-cyclopenta[h]isoquinolin-9-yl]urea;

1-[3-cyclopropyl-5-(2-methylpropylsulfamoyl)-8,9-dihydro-7H-cyclopenta[h]isoquinolin-9-yl]-3-[(2,5-dimethylpyrazol-3-yl)methyl]urea;

3-cyclopropyl-7-hydroxy-N-(2-methylpropyl)-8,9-dihydro-7H-cyclopenta[h]isoquinoline-5-sulfonamide;

3-cyclopropyl-N-(2-methylpropyl)-7-oxo-8,9-dihydrocyclopenta[h]isoquinoline-5-sulfonamide;

3-cyclopropyl-7-hydroxy-7-methyl-N-(2-methylpropyl)-8,9-dihydrocyclopenta[h]isoquinoline-5-sulfonamide;

7-amino-3-cyclopropyl-N-(2-methylpropyl)-8,9-dihydro-7H-cyclopenta[h]isoquinoline-5-sulfonamide;

1-[3-cyclopropyl-5-(2-methylpropylsulfamoyl)-8,9-dihydro-7H-cyclopenta[h]isoquinolin-7-yl]-3-ethylthiourea;

(7R*)-3-cyclopropyl-7-[3-(ethylamino)-1,2,4-triazol-4-yl]-N-(2-methylpropyl)-8,9-dihydro-7H-cyclopenta[h]isoquinoline-5-sulfonamide (* or S);

(7R*)-3-cyclopropyl-7-[[2-(ethylamino)-3,4-dioxocyclobuten-1-yl]amino]-N-(2-methylpropyl)-8,9-dihydro-7H-cyclopenta[h]isoquinoline-5-sulfonamide (* or S);

3-cyclopropyl-7-[[4-(ethylamino)-1,1-dioxo-1,2,5-thiadiazol-3-yl]amino]-N-(2-methylpropyl)-8,9-dihydro-7H-cyclopenta[h]isoquinoline-5-sulfonamide;

2-cyano-1-[3-cyclopropyl-5-(2-methylpropylsulfamoyl)-8,9-dihydro-7H-cyclopenta[h]isoquinolin-7-yl]-3-(4-methylphenyl)guanidine;

tert-butyl 3-[[(7R*)-3-cyclopropyl-5-[(2-fluoro-2-methylpropyl)sulfamoyl]-8,9-dihydro-7H-cyclopenta[h]isoquinolin-7-yl]carbamoyl]azetidine-1-carboxylate [* or S];

7-[(3R)-3-aminopiperidin-1-yl]-3-cyclopropyl-N-(2-fluoro-2-methylpropyl)-8,9-dihydro-7H-cyclopenta[h]isoquinoline-5-sulfonamide;

(2R)-1-[(7R*)-3-cyclopropyl-5-[(2-fluoro-2-methylpropyl)sulfamoyl]-8,9-dihydro-7H-cyclopenta[h]isoquinolin-7-yl]-N-methylpyrrolidine-2-carboxamide [* or S];

N-[1-[3-cyclopropyl-5-[(2-fluoro-2-methylpropyl)sulfamoyl]-8,9-dihydro-7H-cyclopenta[h]isoquinolin-7-yl]azetidin-3-yl]-2,5-dimethylpyrazole-3-carboxamide;

3-cyclopropyl-7-[(4,4-dimethyl-3-oxocyclobuten-1-yl)amino]-N-(2-fluoro-2-methylpropyl)-8,9-dihydro-7H-cyclopenta[h]isoquinoline-5-sulfonamide;

3-cyclopropyl-N-(2-fluoro-2-methylpropyl)-7-(1H-indol-2-ylmethylamino)-8,9-dihydro-7H-cyclopenta[h]isoquinoline-5-sulfonamide;

3-cyclopropyl-9-hydroxy-N-(2-methylpropyl)-8,9-dihydro-7H-cyclopenta[h]isoquinoline-5-sulfonamide;

3-cyclopropyl-N-(2-methylpropyl)-9-oxo-7,8-dihydrocyclopenta[h]isoquinoline-5-sulfonamide;

3-cyclopropyl-9-hydroxy-9-methyl-N-(2-methylpropyl)-7,8-dihydrocyclopenta[h]isoquinoline-5-sulfonamide;

3-cyclopropyl-9-fluoro-N-(2-methylpropyl)-8,9-dihydro-7H-cyclopenta[h]isoquinoline-5-sulfonamide;

3-cyclopropyl-9-[[4-(ethylamino)-1,1-dioxo-1,2,5-thiadiazol-3-yl]amino]-N-(2-methylpropyl)-8,9-dihydro-7H-cyclopenta[h]isoquinoline-5-sulfonamide;

9-[(4-cyano-1-methylpyrazol-3-yl)amino]-3-cyclopropyl-N-(2-fluoro-2-methylpropyl)-8,9-dihydro-7H-cyclopenta[h]isoquinoline-5-sulfonamide;

3-cyclopropyl-N-(2-fluoro-2-methylpropyl)-9-(isoquinolin-4-ylamino)-8,9-dihydro-7H-cyclopenta[h]isoquinoline-5-sulfonamide;

2-cyano-1-[3-cyclopropyl-5-(2-methylpropylsulfamoyl)-8,9-dihydro-7H-cyclopenta[h]isoquinolin-9-yl]-3-(4-methylphenyl)guanidine;

3-cyclopropyl-9-(methanesulfonamido)-N-(2-methylpropyl)-8,9-dihydro-7H-cyclopenta[h]isoquinoline-5-sulfonamide;

1-[3-cyclopropyl-5-(2-methylpropylsulfamoyl)-8,9-dihydro-7H-cyclopenta[h]isoquinolin-9-yl]-3-ethylthiourea;

3-cyclopropyl-9-[3-(ethylamino)-1,2,4-triazol-4-yl]-N-(2-methylpropyl)-8,9-dihydro-7H-cyclopenta[h]isoquinoline-5-sulfonamide;

(9R*)-3-cyclopropyl-9-[(4-ethyl-1,2,4-triazol-3-yl)amino]-N-(2-methylpropyl)-8,9-dihydro-7H-cyclopenta[h]isoquinoline-5-sulfonamide [* or S];

1-[3-cyclopropyl-5-(2-methylpropylsulfamoyl)-8,9-dihydro-7H-cyclopenta[h]isoquinolin-9-yl]-3-pyridin-3-ylthiourea;

3-cyclopropyl-N-(2-methylpropyl)-9-[(4-pyridin-3-yl-1,2,4-triazol-3-yl)amino]-8,9-dihydro-7H-cyclopenta[h]isoquinoline-5-sulfonamide;

3-cyclopropyl-N-(2-fluoro-2-methylpropyl)-9-[[6-(5-methyl-1,3,4-oxadiazol-2-yl)pyridin-3-yl]amino]-8,9-dihydro-7H-cyclopenta[h]isoquinoline-5-sulfonamide;

3-cyclopropyl-N-(2-fluoro-2-methylpropyl)-9-[[6-(2-methyltetrazol-5-yl)pyridin-3-yl]amino]-8,9-dihydro-7H-cyclopenta[h]isoquinoline-5-sulfonamide;

3-cyclopropyl-9-[[3,4-dioxo-2-(pyridin-3-ylamino)cyclobuten-1-yl]amino]-N-(2-methylpropyl)-8,9-dihydro-7H-cyclopenta[h]isoquinoline-5-sulfonamide;

(9R*)-3-cyclopropyl-9-[[2-(ethylamino)-3,4-dioxocyclobuten-1-yl]amino]-N-(2-methylpropyl)-8,9-dihydro-7H-cyclopenta[h]isoquinoline-5-sulfonamide [* or S];

(9R*)-9-(1H-benzimidazol-2-ylamino)-3-cyclopropyl-N-(2-methylpropyl)-8,9-dihydro-7H-cyclopenta[h]isoquinoline-5-sulfonamide [* or S];

3-cyclopropyl-7-[3-(cyclopropylmethylamino)-1,2,4-triazol-4-yl]-N-(3,3-difluorocyclobutyl)-8,9-dihydro-7H-cyclopenta[h]isoquinoline-5-sulfonamide;

3-cyclopropyl-7-[3-(cyclopropylmethylamino)-1,2,4-triazol-4-yl]-N-(3-fluorocyclobutyl)-8,9-dihydro-7H-cyclopenta[h]isoquinoline-5-sulfonamide;

3-cyclopropyl-7-(methanesulfonamido)-N-(2-methylpropyl)-8,9-dihydro-7H-cyclopenta[h]isoquinoline-5-sulfonamide;

3-cyclopropyl-7-[[3,4-dioxo-2-(pyridin-3-ylamino)cyclobuten-1-yl]amino]-N-(2-methylpropyl)-8,9-dihydro-7H-cyclopenta[h]isoquinoline-5-sulfonamide;

1-ethyl-3-[(7R*)-3-cyclopropyl-5-(2-methylpropylsulfamoyl)-8,9-dihydro-7H-cyclopenta[h]isoquinolin-7-yl]urea [* or S];

(7R*)-3-cyclopropyl-7-[3-[(25-dimethylpyrazol-3-yl)amino]-1,2,4-triazol-4-yl]-N-(2-fluoro-2-methylpropyl)-8,9-dihydro-7H-cyclopenta[h]isoquinoline-5-sulfonamide [* or S];

(7R*)-3-cyclopropyl-7-[3-[(25-dimethylpyrazol-3-yl)amino]-1,2,4-triazol-4-yl]-N-(2-methylpropyl)-8,9-dihydro-7H-cyclopenta[h]isoquinoline-5-sulfonamide [* or S];

3-cyclopropyl-7-[[4-(2,5-dimethylpyrazol-3-yl)-1,2,4-triazol-3-yl]amino]-N-(2-methylpropyl)-8,9-dihydro-7H-cyclopenta[h]isoquinoline-5-sulfonamide;

(7R*)-3-cyclopropyl-N-(2-methylpropyl)-7-[3-[(5-methyl pyridin-3-yl)amino]-12,4-triazol-4-yl]-8,9-dihydro-7H-cyclopenta[h]isoquinoline-5-sulfonamide [* or S];

3-cyclopropyl-N-(2-methylpropyl)-7-[(4-pyridin-3-yl-1,2,4-triazol-3-yl)amino]-8,9-dihydro-7H-cyclopenta[h]isoquinoline-5-sulfonamide;

3-cyclopropyl-N-(2-methylpropyl)-7-[3-(pyridin-3-ylamino)-1,2,4-triazol-4-yl]-8,9-dihydro-7H-cyclopenta[h]isoquinoline-5-sulfonamide;

7-(1H-benzimidazol-2-ylamino)-3-cyclopropyl-N-(2-methylpropyl)-8,9-dihydro-7H-cyclopenta[h]isoquinoline-5-sulfonamide;

3-cyclopropyl-N-(2-fluoro-2-methylpropyl)-9-pyridin-3-yloxy-8,9-dihydro-7H-cyclopenta[h]isoquinoline-5-sulfonamide;

3-cyclopropyl-N-(2-fluoro-2-methylpropyl)-7-pyridin-3-yloxy-8,9-dihydro-7H-cyclopenta[h]isoquinoline-5-sulfonamide; or 1-[3-cyclopropyl-5-(isobutylsulfamoyl)-8,9-dihydro-7H-cyclopenta[h]isoquinolin-7-yl]-3-(3-pyridyl)thiourea.

9. A method for the treatment or prevention of disorders caused by IgE comprising administration to a patient in need thereof a compound according to claim 1 or a pharmaceutically acceptable salt thereof.

10. A method for the treatment or prevention of allergy, non-allergic mast cell responses, type 1 hypersensitivity, urticaria, or familiar sinus inflammation comprising administration to a patient in need thereof a compound according to claim 1 or a pharmaceutically acceptable salt thereof.

11. A method for the treatment or prevention of airway constriction in asthma, local inflammation in eczema, increased mucus secretion in allergic rhinitis, urticaria, or increased vascular permeability comprising administration to a patient in need thereof a compound according to claim 1 or a pharmaceutically acceptable salt thereof.

12. A method for the treatment or prevention of eosinophilic granulomatosis with polyangiitis, aspirin exacerbated respiratory disease, or cutaneous T-cell lymphoma comprising administration to a patient in need thereof a compound according to claim 1 or a pharmaceutically acceptable salt thereof.

13. A pharmaceutical composition comprising a compound of formula (I) according to claim 1 or a pharmaceutically acceptable salt thereof and a pharmaceutically acceptable carrier.

14. A method for the treatment or prevention of allergy, non-allergic mast cell responses, type 1 hypersensitivity, urticaria, familiar sinus inflammation, eosinophilic granulomatosis with polyangiitis, aspirin exacerbated respiratory disease, or cutaneous T-cell lymphoma, which comprises the administration of a compound according to claim 1 or a pharmaceutically acceptable salt thereof in a therapeutically effective amount to a patient.

15. A compound of general formula (I) according to claim 1, wherein R4 represents cyclopropyl.

16. A compound of general formula (I) according to claim 1, wherein

R1 represents:

Hydrogen; methoxyimidazopyridinyl; carboxy group; cyclopropyl-methyl-carbamoyl-amino; pyridine-carbonylamino; hydroxy(pyridyl); [(fluorocarbonimidoyl) propenyl]; [(cyclopropylmethylamino)imidazolyl]; [[(cyclopropylmethyl)imidazolyl]amino]; [(dimethylpyrazolyl)carbamothioylamino]; [[(dimethylpyrazolyl)-triazolyl]amino]; (pyridylamino); (tert-butoxycarbonylamino); Amino; [(cyclopropylmethylamino)-triazolyl]; pyridylcarbamoyl; [(cyclopropanecarbonylamino)pyrazolyl]; (aminotetrazolyl); [[(methyltetrazolyl)pyridyl]amino]; [(methylpyrazolopyridinyl)amino]; [[(methyl-oxadiazolyl)-pyridyl]amino]; Oxo; hydroxy(methyl); ethylcarbamothioylamino); [(ethylamino)-triazolyl]; [[(ethylamino)-dioxo-cyclobutenyl]amino]; [[(ethylamino)-dioxo-thiadiazolyl]amino]; [[N'-cyano-N-(p-tolyl)carbamimidoyl]amino]; [(tert-butoxycarbonylazetidine-carbonyl)amino]; [aminopiperidyl]; [(methylcarbamoyl)pyrrolidinyl]; [[(dimethylpyrazolearbonyl)amino]azetidinyl]; [(dimethyl-oxo-cyclobutenyl)amino]; (indolylmethylamino); Methanesulfonamido; [[dioxo(pyridylamino)cyclobutenyl]amino]; ethylcarbamoylamino; [[(dimethylpyrazolyl)amino]-triazolyl]; [[(methyl-pyridyl)amino]-triazolyl]; [[(pyridyl)-triazolyl]amino]; [(pyridylamino)-triazolyl]; (benzimidazolylamino); pyridyloxy; (pyridylcarbamothioylamino).

17. A compound of general formula (I) according to claim 1, wherein

R2 represents:

Hydrogen; [(methylbenzotriazolyl)-triazolyl]methyl; [[(methylpyrazolyl)-triazolyl]amino]; [[(methylpyrazolyl)amino]-triazolyl]; [[(fluoro-pyridyl)-triazolyl] amino]; [[(fluoro-pyridyl)amino]-triazolyl]; (pyridylmethylamino); (pyridylsulfonylamino); [(fluoro-indolecarbonyl)amino]; [(methylbenzimidazolyl) amino]; [(methoxycarbonyl-pyridyl)amino]; [(carboxypyridyl)amino]; [(methyl-pyrazole-carbonyl) amino]; (pyridine-carbonylamino); [(methylcyclopropanecarbonyl)amino]; (pyrimidinylamino); [(oxoindolinyl)amino]; [(methoxypyridyl)amino]; (pyridylamino); [(methylpyrazolopyridinyl)amino]; Benzyloxycarbonylamino; [(bromophenyl)carbamoylamino]; [(dimethylpyrazolyl)methylcarbamoylamino]; Hydroxy; Oxo; Methyl; Fluorine; [[(ethylamino)-dioxo-thiadiazolyl]amino]; [(cyanomethylpyrazolyl)amino]; (isoquinolylamino); [[N'-cyano-N-(p-tolyl)carbamimidoyl]amino]; Methanesulfonamido; Ethylcarbamothioylamino; [(ethylamino)-triazolyl]; [(ethyl-triazolyl)amino]; (pyridylcarbamothioylamino); [[(pyridyl)-triazolyl]amino]; [[(methyltetrazolyl)-pyridyl]amino]; [[dioxo-(pyridylamino)cyclobutenyl]amino]; [[(ethylamino)-dioxo-cyclobutenyl]amino]; (benzimidazolylamino); pyridyloxy.

18. A compound of formula (I) according to claim 1 wherein

R1 represents

Hydrogen; (7-methoxyimidazo[4,5-b]pyridin-3-yl); Carboxy group; cyclopropyl-methyl-carbamoyl-amino; pyridine-3-carbonylamino; hydroxy(3-pyridyl); [1-(fluorocarbonimidoyl)prop-1-enyl]; [2-(cyclopropylmethylamino)imidazol-1-yl]; [[1-(cyclopropylmethyl) imidazol-2-yl]amino]; [(2,5-dimethylpyrazol-3-yl) carbamothioylamino]; [[4-(2,5-dimethylpyrazol-3-yl)-1,2,4-triazol-3-yl]amino]; (3-pyridylamino); (tert-butoxycarbonylamino); Amino; [3-(cyclopropylmethylamino)-1,2,4-triazol-4-yl]; 3-pyridylcarbamoyl; [5-(cyclopropanecarbonylamino) pyrazol-1-yl]; (5-aminotetrazol-1-yl); [[6-(2-methyltetrazol-5-yl)-3-pyridyl]amino]; [(1-methylpyrazolo[3,4-c]pyridin-4-yl)amino]; [[6-(5-methyl-1,3,4-oxadiazol-2-yl)-3-pyridyl]amino]; oxo; hydroxy(methyl); (ethylcarbamothioylamino); [3-(ethylamino)-1,2,4-triazol-4-yl]; [[2-(ethylamino)-3,4-dioxo-cyclobuten-1-yl]amino]; [[4-(ethylamino)-1,1-dioxo-1,2,5-thiadiazol-3-yl]amino]; [[N'-cyano-N-(p-tolyl) carbamimidoyl]amino]; [(1-tert-butoxycarbonylazetidine-3-carbonyl)amino]; [3-amino-1-piperidyl]; [(2R)-2-(methylcarbamoyl)pyrrolidin-1-yl]; [3-[(2,5-dimethylpyrazole-3-carbonyl) amino]azetidin-1-yl]; [(4,4-dimethyl-3-oxo-cyclobuten-1-yl)amino]; (1H-indol-2-ylmethylamino); Methanesulfonamido; [[3,4-dioxo-2-(3-pyridylamino) cyclobuten-1-yl]amino]; ethylcarbamoylamino; [3-[(2,5-dimethylpyrazol-3-yl)amino]-1,2,4-triazol-4-yl]; [3-[(5-methyl-3-pyridyl)amino]-1,2,4-triazol-4-yl]; [[4-(3-pyridyl)-1,2,4-triazol-3-yl]amino]; [3-(3-pyridylamino)-1,2,4-triazol-4-yl]; (1H-benzimidazol-2-ylamino); 3-pyridyloxy; (3-pyridylcarbamothioylamino).

19. A compound of general formula (I) according claim 1 wherein

R2 represents

Hydrogen; [4-(1-methylbenzotriazol-4-yl)-1,2,4-triazol-3-yl]methyl; [[4-(2-methylpyrazol-3-yl)-1,2,4-triazol-3-yl]amino]; [3-[(2-methylpyrazol-3-yl)amino]-1,2,4-triazol-4-yl]; [[4-(5-fluoro-3-pyridyl)-1,2,4-triazol-3-yl]amino]; [3-[(5-fluoro-3-pyridyl)amino]-1,2,4-triazol-4-yl]; (3-pyridylmethylamino); (3-pyridylsulfonylamino); [(6-fluoro-1H-indole-3-carbonyl)amino]; [(1-methylbenzimidazol-2-yl)amino]; [(6-methoxycarbonyl-3-pyridyl)amino]; [(6-carboxy-3-pyridyl)amino]; [(5-methyl-1H-pyrazole-3-carbonyl) amino]; (pyridine-3-carbonylamino); [(2-methylcyclopropanecarbonyl)amino]; (pyrimidin-5-ylamino); (2-oxoindolin-5-yl)amino; [(5-methoxy-3-pyridyl) amino]; (3-pyridylamino); [(1-methylpyrazolo[3,4-c] pyridin-4-yl)amino]; Benzyloxycarbonylamino; [(4-bromophenyl)carbamoylamino]; [(2,5-dimethylpyrazol-3-yl)methylcarbamoylamino]; Hydroxy oxo; Methyl; fluorine; [[4-(ethylamino)-1,1-dioxo-1,2,5-thiadiazol-3-yl]amino]; [(4-cyano-1-methyl-pyrazol-3-yl)amino]; (4-isoquinolylamino); [[N'-cyano-N-(p-tolyl)carbamimidoyl]amino]; Methanesulfonamido; Ethylcarbamothioylamino; [3-(ethylamino)-1,2,4-triazol-4-yl]; [(4-ethyl-1,2,4-triazol-3-yl) amino]; (3-pyridylcarbamothioylamino); [[4-(3-pyridyl)-1,2,4-triazol-3-yl]amino]; [[6-(2-methyltetrazol-5-yl)-3-pyridyl]amino]; [[3,4-dioxo-2-(3-pyridylamino)cyclobuten-1-yl]amino]; [[2-(ethylamino)-3,4-dioxo-cyclobuten-1-yl]amino]; (1H-benzimidazol-2-ylamino); 3-pyridyloxy.

* * * * *